US008106055B2

(12) United States Patent
Oberboersch et al.

(10) Patent No.: US 8,106,055 B2
(45) Date of Patent: Jan. 31, 2012

(54) SUBSTITUTED AMIDE COMPOUNDS

(75) Inventors: Stefan Oberboersch, Aachen (DE); Melanie Reich, Aachen (DE); Bernd Sundermann, Friedrichsdorf (DE); Utz-Peter Jagusch, Aachen (DE); Beatrix Merla, Aachen (DE); Stefan Schunk, Aachen (DE); Werner Englberger, Stolberg (DE); Timo Struenker, Cologne (DE); Hagen-Heinrich Hennies, Simmerath (DE); Edward Bijsterveld, Ge Nijmegen (NL); Fritz Theil, Berlin (DE); Heinz Graubaum, Berlin (DE)

(73) Assignee: Gruenenthal GmbH, Aachen (DE)

( * ) Notice: Subject to any disclaimer, the term of this patent is extended or adjusted under 35 U.S.C. 154(b) by 624 days.

(21) Appl. No.: 12/112,406

(22) Filed: Apr. 30, 2008

(65) Prior Publication Data

US 2008/0306084 A1 Dec. 11, 2008

(30) Foreign Application Priority Data

Apr. 30, 2007 (DE) ......................... 10 2007 020 493

(51) Int. Cl.
*A61K 31/497* (2006.01)
*A61K 31/47* (2006.01)
*C07D 401/12* (2006.01)
*C07D 215/08* (2006.01)
(52) U.S. Cl. .................. 514/253.01; 514/312; 544/360; 546/153
(58) Field of Classification Search ............. 514/253.01, 514/312; 544/360; 546/153
See application file for complete search history.

(56) References Cited

U.S. PATENT DOCUMENTS

2008/0249128 A1* 10/2008 Oberboersch et al. ........ 514/309

FOREIGN PATENT DOCUMENTS

| WO | WO 2004/092164 A1 | 10/2004 |
| WO | WO 2007/079930 A1 | 7/2007 |

OTHER PUBLICATIONS

Giselle F. Passos et al., "Kinin B₁ Receptor Up-Regulation after Lipopolysaccharide Administration: Role of Proinflammatory Cytokines and Neutrophil Influx[1]", The Journal of Immunology, 2004, pp. 1839-1847, vol. 172, The American Association of Immunologists, Inc.
L.M. Fredrik Leeb-Lundberg et al., "International Union of Pharmacology. XLV. Classification of the Kinin Receptor Family: from Molecular Mechanisms to Pathophysiological Consequences", Pharmacological Reviews, 2005, pp. 27-77, vol. 57, No. 1, The American Society for Pharmacology and Experimental Therapeutics, USA.
R. Hayashi et al., "Bradykinin Stimulates IL-6 and IL-8 Production by Human Lung Fibroblasts Through ERK-and p38 MAPK-dependent Mechanisms", European Respiratory Journal, 2000, pp. 452-458, vol. 16, ISSN: 0903-1936.
E. G. Gray, et al., "The Isolation of Nerve Endings From Brain: an Electron-Microscopic Study of Cell Fragments Derived by Homogenization and Centrifugation", Journal of Anatomy, pp. 79-98, vol. 96, Part I No date provided.
Bichoy H. Gabra et al., "The Kinin System Mediates Hyperalgesia through the Inducible Bradykinin B1 Receptor Subtype: Evidence in Various Experimental Animal Models of Type 1 and Type 2 Diabetic Neuropathy", Biol. Chem., Feb. 2006, pp. 127-143, vol. 387.
Martin CH. Frink, et al., "Influence of Tramadol on Neurotransmitter Systems of the Rat Brain", Arzneim-Forsh/Drug Res., 1996, pp. 1029-1036, vol. 46 (H), No. 11.
Joao B. Calixto et al., "Kinin $B_1$ Receptors: Key G-protein-coupled Receptors and their Role in Inflammatory and Painful Processes", British Journal of Pharmacology, 2004, pp. 803-818, vol. 143, 2004 Nature Publishing Group.
H. Buschmann, et al., "NA and 5-HT Reuptake Inhibitors and $\alpha_2$ agonists", pp. 265-284, 2002 Wiley-VHC Verlag GmbH & Co., KGaA, Weinheim, ISBN: 3-527-30403-7.
Sara H. Bengtson et al., "Kinin Receptor Expression During Staphylococcus Aureus Infection", Blood, Sep. 15, 2006, pp. 2055-2063, vol. 108, No. 6, The American Society of Hematology.
Antoni Stadnicki et al., "Immunolocalization and Expression of Kinin $B_1$ R and $B_2$R Receptors in Human Inflammatory Bowel Disease", Am. J. Physiol. Gastrointest. Liver Physiol, Mar. 31, 2005, pp. G361-G366, vol. 289, American Physiological Society.
Joao B. Pesquero et al., "Genetically Altered Animal Models in the Kallikrein-Kinin System", Biol. Chem., Feb. 2006, pp. 119-126, vol. 387.
Joao B. Pesquero et al., "Hypoalgesia and Altered Inflammatory Responses in Mice Lacking Kinin B1 Receptors", PNAS, Jul. 5, 2000, pp. 8140-8145, vol. 97, No. 14. A. Prat et al., "Bradykinin $B_1$ Receptor Expression and Function on T Lymphocytes in Active Multiple Sclerosis", Neurology, Dec. 10, 1999, pp. 2087-2092, vol. 53, No. 9, 1999 American Academy of Neurology, ISSN: 0028-3878.
International Search Report with partial translation dated Feb. 4, 2009 (Five (5) pages).
PCT/ISA/237 (Six (6) pages) No date provided.

* cited by examiner

*Primary Examiner* — James O Wilson
*Assistant Examiner* — Ebenezer O Sackey
(74) *Attorney, Agent, or Firm* — Crowell & Moring LLP

(57) ABSTRACT

Substituted amide compounds corresponding to formula I:

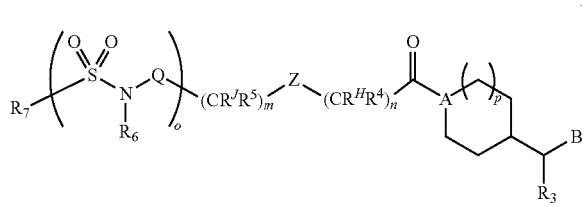

processes for preparing them, pharmaceutical compositions containing these compounds, and the use of substituted amide derivatives for the preparation of medicaments for the treatment of pain and various other conditions.

29 Claims, No Drawings

SUBSTITUTED AMIDE COMPOUNDS

BACKGROUND OF THE INVENTION

The present invention relates to substituted amide derivatives, processes for the preparation thereof, medicaments containing these compounds and the use of substituted amide derivatives for the preparation of medicaments and the treatment of pain and other conditions.

Treatment of chronic and non-chronic states of pain is of great importance in medicine. There is a worldwide need for pain therapies which are highly effective. The urgent need for action for targeted treatment of chronic and non-chronic states of pain appropriate for the patient, by which is to be understood successful and satisfactory pain treatment for the patient, is documented in the large number of scientific works which have been published recently in the field of applied analgesics and of basic research into nociception.

Conventional opioids, such as morphine, have a good action in the therapy of severe to very severe pain. However, their use is limited by the known side effects, e.g. respiratory depression, vomiting, sedation, constipation and development of tolerance. Furthermore, they are less active on neuropathic or incidental pain, from which tumour patients in particular suffer.

In contrast to the constitutive expression of the bradykinin 2 receptor (B2R), in most tissues the bradykinin 1 receptor (B1R) is not expressed or expressed only weakly. Nevertheless, expression of B1R can be induced on various cells. For example, in the course of inflammation reactions a rapid and pronounced induction of B1R takes place on neuronal cells, but also various peripheral cells, such as fibroblasts, endothelial cells, granulocytes, macrophages and lymphocytes. In the course of inflammation reactions, a switch from a B2R to a B1R dominance thus occurs on the cells involved. The cytokines interleukin-1 (IL-1) and tumour necrosis factor alpha (TNFα) are involved to a considerable degree in this upwards regulation of B1R (Passos et al. J. Immunol. 2004, 172, 1839-1847). After activation with specific ligands, B1R-expressing cells can then themselves secrete inflammation-promoting cytokines such as IL-6 and IL-8 (Hayashi et al., Eur. Respir. J. 2000, 16, 452-458). This leads to inwards migration of further inflammation cells, e.g. neutrophilic granulocytes (Pesquero et al., PNAS 2000, 97, 8140-8145). The bradykinin B1R system can contribute towards chronification of diseases via these mechanisms. This is demonstrated by a large number of animal studies (overviews in Leeb-Lundberg et al., Pharmacol. Rev. 2005, 57, 27-77 and Pesquero et al., Biol. Chem. 2006, 387, 119-126). On humans too, an enhanced expression of B1R, e.g. on enterocytes and macrophages, in the affected tissue of patients with inflammatory intestinal diseases (Stadnicki et al., Am. J. Physiol. Gastrointest. Liver Physiol. 2005, 289, G361-366) and on T lymphocytes in patients with multiple sclerosis (Prat 1999), or an activation of the bradykinin B2R-B1R system in the course of infections with *Staphylococcus aureus* (Bengtson et al., Blood 2006, 108, 2055-2063) is found. Infections with *Staphylococcus* are responsible for syndromes such as superficial infections of the skin up to septic shock.

SUMMARY OF THE INVENTION

Based on the described pathophysiological relationships, there is a great therapeutic potential for the use of B1R antagonists on acute and, in particular, chronically inflammatory diseases. These include diseases of the respiratory tract (bronchial asthma, allergies, COPD/chronic obstructive pulmonary disease, cystic fibrosis etc.), inflammatory intestinal diseases (ulcerative colitis, CD/Crohn's disease etc.), neurological diseases (multiple sclerosis, neurodegeneration etc.), inflammations of the skin (atopic dermatitis, psoriasis, bacterial infections etc.) and mucous membranes (Behcet's disease, pelvitis, prostatitis etc.), rheumatic diseases (rheumatoid arthritis, osteoarthritis etc.), septic shock and reperfusion syndrome (following cardiac infarction, stroke).

The bradykinin (receptor) system is moreover also involved in regulation of angiogenesis (potential as an angiogenesis inhibitor in cancer cases and macular degeneration on the eye, and B1R knockout mice are protected from induction of overweight by a particularly fat-rich diet (Pesquero et al., Biol. Chem. 2006, 387, 119-126). B1R antagonists are therefore also suitable for treatment of obesity.

B1R antagonists are suitable in particular for treatment of pain, in particular inflammation pain and neuropathic pain (Calixto et al., Br. J. Pharmacol. 2004, 1-16), and here in particular diabetic neuropathy (Gabra et al., Biol. Chem. 2006, 387, 127-143).

One object on which the invention is based was to provide novel compounds which are preferably suitable as pharmacological active compounds, in particular novel substances having an analgesic action which are suitable for pain therapy—in particular also chronic and neuropathic pain.

The invention therefore provides substituted compounds corresponding to formula I:

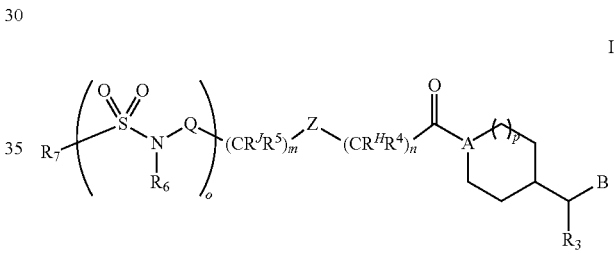

wherein
m represents 0, 1, 2 or 3
n represents 1 or 2
o represents 0 or 1
p represents 0, 1 or 2
A represents N, CH—NH—, CH—CH$_2$—NH—, CH—CH$_2$—CH$_2$—NH— or CH—CH$_2$—CH$_2$—CH$_2$—NH—, wherein individual H atoms can also be replaced by C$_{1-5}$-alkyl,
B represents NR$^1$R$^2$ or CN
R$^1$ and R$^2$ independently of one another denote H; C$_{1-6}$-alkyl, in each case saturated or unsaturated, branched or unbranched, unsubstituted or mono- or polysubstituted; or aryl, linked via a C$_{1-3}$-alkyl chain and unsubstituted or mono- or polysubstituted, wherein R$^1$ and R$^2$ do not simultaneously denote H, or
R$^1$ and R$^2$ together denote CH$_2$CH$_2$OCH$_2$CH$_2$, CH$_2$CH$_2$NR$^8$CH$_2$CH$_2$ or (CH$_2$)$_{3-6}$, wherein
R$^8$ denotes H; C$_{1-6}$-alkyl, in each case saturated or unsaturated, branched or unbranched, unsubstituted or mono- or polysubstituted; aryl, heteroaryl, in each case unsubstituted or mono- or polysubstituted, or aryl or heteroaryl, linked via a C$_{1-3}$-alkyl chain and in each case unsubstituted or mono- or polysubstituted;
R$^3$ represents C$_{1-8}$-alkyl, in each case saturated or unsaturated, branched or unbranched, unsubstituted or mono- or polysubstituted; aryl or heteroaryl, in each case unsubstituted or mono- or polysubstituted; or aryl or heteroaryl, linked via a $C_{1-3}$-alkyl chain and in each case unsubstituted or mono- or polysubstituted;

$R^4$ represents H, $C_{1-6}$-alkyl, in each case saturated or unsaturated, branched or unbranched, unsubstituted or mono- or polysubstituted; aryl, in each case unsubstituted or mono- or polysubstituted; or aryl, linked via a $C_{1-3}$-alkyl chain and in each case unsubstituted or mono- or polysubstituted;

$R^H$ represents H, or $R^4$ and $R^H$ together denote =O;

Z represents O or NH;

$R^5$ represents H; or $C_{1-6}$-alkyl, in each case saturated or unsaturated, branched or unbranched, unsubstituted or mono- or polysubstituted;

$R^J$ represents H, or $R^5$ and $R^J$ together denote =O;

Q denotes a single bond, —$CH_2$—, —$CH_2$—$CH_2$—, or

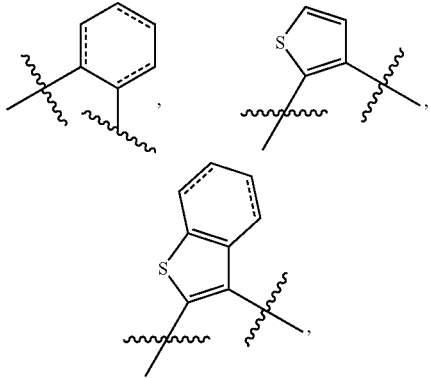

wherein ---- represents a single bond or a double bond;

$R^6$ represents H; $C_{1-6}$-alkyl, in each case saturated or unsaturated, branched or unbranched, unsubstituted or mono- or polysubstituted; $C_{3-8}$-cycloalkyl, saturated or unsaturated, unsubstituted or mono- or polysubstituted; aryl or heteroaryl, unsubstituted or mono- or polysubstituted; aryl or $C_{3-8}$-cycloalkyl, linked via a $C_{1-3}$-alkyl chain; or $R^6$ together with Q, including the adjacent nitrogen, forms a four-, five-, six- or seven-membered carbocyclic radical, which can be saturated or unsaturated and can contain a further hetero atom O, S or N and on to which a further five- or six-membered ring, saturated or unsaturated, can be fused; wherein, in the case of the common ring closure, Q represents

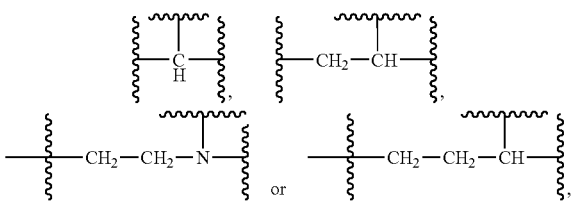

and the ring can be substituted independently of one another in any position by phenyl, =O, OH; $OR^N$ where $R^N$=$C_{1-3}$-alkyl; F, Cl, $CF_3$, or $C_{1-6}$-alkyl; and $R^7$ represents aryl or heteroaryl, in each case unsubstituted or mono- or polysubstituted; $SO_2$-aryl, $SO_2$-heteroaryl, aryl or heteroaryl, linked via a $C_{1-3}$-alkyl group and in each case unsubstituted or mono- or polysubstituted;

in the form of the racemate; of the enantiomers, diastereomers, mixtures of the enantiomers or diastereomers or of an individual enantiomer or diastereomer; of the bases and/or salts of physiologically acceptable acids.

The compounds preferably have an affinity for the μ opioid receptor and preferably inhibit the reuptake of serotonin. They furthermore influence the B1 receptor.

If the group A in the compounds of the general formula I represents CH—NH—, CH—$CH_2$—NH—, CH—$CH_2$—$CH_2$—NH— or CH—$CH_2$—$CH_2$—$CH_2$—NH—, the C chain end is always bonded into the ring and the N chain end linked to the carbonyl group.

In the context of this invention, the expressions "$C_{1-3}$-alkyl", "$C_{1-6}$-alkyl and "$C_{1-8}$-alkyl" include acyclic saturated or unsaturated hydrocarbon radicals, which can be branched- or straight-chain and unsubstituted or mono- or polysubstituted, having 1 to 3 C atoms or 1 to 6 C atoms or 1 to 8 C atoms respectively, i.e. $C_{1-3}$-alkanyls, $C_{2-3}$-alkenyls and $C_{2-3}$-alkynyls, or $C_{1-6}$-alkanyls, $C_{2-6}$-alkenyls and $C_{2-6}$-alkynyls, or $C_{1-8}$-alkanyls, $C_{2-8}$-alkenyls and $C_{2-8}$-alkynyls. In this context, alkenyls have at least one C—C double bond and alkynyls have at least one C—C triple bond. Alkyl is advantageously chosen from the group which includes methyl, ethyl, n-propyl, 2-propyl, n-butyl, iso-butyl, sec-butyl, tert-butyl, n-pentyl, iso-pentyl, neo-pentyl, hexyl, heptyl, octyl, ethylenyl (vinyl), ethynyl, propenyl (—$CH_2CH$=$CH_2$, —CH=CH—$CH_3$, —C(=$CH_2$)—$CH_3$), propynyl (—CH—C≡CH, —C≡C—$CH_3$), butenyl, butynyl, pentenyl, pentynyl, hexenyl and hexynyl. Methyl, ethyl and n-propyl are particularly advantageous.

In the context of this invention, the expression "aryl" denotes aromatic hydrocarbons, inter alia phenyls and naphthyls. The aryl radicals can also be fused with further saturated, (partially) unsaturated or aromatic ring systems. Each aryl radical can be unsubstituted or mono- or polysubstituted, wherein the substituents on the aryl can be identical or different and can be in any desired and possible position of the aryl. Aryl is advantageously chosen from the group which contains phenyl, 1-naphthyl, 2-naphthyl, which can in each case be unsubstituted or mono- or polysubstituted. The phenyl radical is particularly advantageous.

The expression "heteroaryl" represents a 5-, 6- or 7-membered cyclic aromatic radical which contains at least 1, if appropriate also 2, 3, 4 or 5 hetero atoms, wherein the hetero atoms are identical or different and the heterocyclic ring can be unsubstituted or mono- or polysubstituted; in the case of substitution on the heterocyclic ring, the substituents can be identical or different and can be in any desired and possible position of the heteroaryl. The heterocyclic ring can also be part of a bi- or polycyclic system. Preferred hetero atoms are nitrogen, oxygen and sulfur. It is preferable for the heteroaryl radical to be chosen from the group which contains pyrrolyl, indolyl, furyl (furanyl), benzofuranyl, thienyl (thiophenyl), benzothienyl, benzothiadiazolyl, benzothiazolyl, benzotriazolyl, benzodioxolanyl, benzodioxanyl, phthalazinyl, pyrazolyl, imidazolyl, thiazolyl, oxadiazolyl, isoxazolyl, pyridyl, pyridazinyl, pyrimidinyl, pyrazinyl, pyranyl, indazolyl, purinyl, indolizinyl, quinolinyl, isoquinolinyl, quinazolinyl, carbazolyl, phenazinyl, phenothiazinyl or oxadiazolyl, wherein bonding to the compounds of the general structure I can take place via any desired and possible ring member of the heteroaryl radical. Thienyl, oxadiazolyl and pyridyl are particularly preferred.

For the purposes of the present invention, the expression "aryl or heteroaryl bonded via $C_{1-3}$-alkyl" means that $C_{1-3}$-alkyl and aryl or, respectively, heteroaryl have the meanings defined above and the aryl or heteroaryl radical is bonded to the compound of the general structure I via a $C_{1-3}$-alkyl group. Phenyl, benzyl and phenethyl are particularly advantageous in the context of this invention.

In connection with "alkyl" and "cycloalkyl", in the context of this invention the term "substituted" is understood as meaning replacement of a hydrogen radical by F, Cl, Br, I, —CN, $NH_2$, NH—$C_{1-6}$-alkyl, NH—$C_{1-6}$-alkyl-OH, $C_{1-6}$-alkyl, N($C_{1-6}$-alkyl)$_2$, N($C_{1-6}$-alkyl-OH)$_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl or benzyl, where polysubstituted radicals are to be understood as meaning those radicals which are substituted several times, e.g. two or three times, either on different or on the same atoms, for example three times on the same C atom, as in the case of $CF_3$ or —$CH_2CF_3$, or at different places, as in the case of —CH(OH)—CH=CH—$CHCl_2$. Polysubstitution can be with the same or with different substituents.

With respect to "aryl" and "heteroaryl", in the context of this invention "mono- or polysubstituted" is understood as meaning the replacement, once or several times, e.g. two, three or four times, of one or more hydrogen atoms of the ring system by F, Cl, Br, I, CN, $NH_2$, NH—$C_{1-6}$-alkyl, NH—$C_{1-6}$-alkyl-OH, N($C_{1-6}$-alkyl)$_2$, N($C_{1-6}$-alkyl-OH)$_2$, $NO_2$, SH, S—$C_{1-6}$-alkyl, OH, O—$C_{1-6}$-alkyl, O—$C_{1-6}$-alkyl-OH, C(=O)$C_{1-6}$-alkyl, $CO_2H$, $CH_2SO_2$-phenyl, $CO_2$—$C_{1-6}$-alkyl, $OCF_3$, $CF_3$,

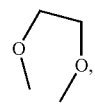

$C_{1-6}$-alkyl, phenyl, pyridyl, thienyl or furyl; on one or optionally different atoms, where a substituent can optionally be substituted in its turn. In this context, polysubstitution is by the same or by different substituents. For "aryl", in this context preferred substituents are —F, —Cl, tert-butyl, $CF_3$, $OCF_3$,

$CH_3$ or $OCH_3$. For "heteroaryl", particularly preferred substituents are —F, —Cl, 2-thienyl, $CH_2SO_2$-phenyl, 2-pyridyl or phenyl, unsubstituted or mono- or polysubstituted by methyl, F, Cl, methoxy, tert-butyl, $CF_3$ or

In the context of this invention, the term salt formed with a physiologically acceptable acid is understood as meaning salts of the particular active compound with inorganic or organic acids, which are physiologically acceptable—in particular when used on humans and/or mammals. The hydrochloride is particularly preferred. Examples of physiologically acceptable acids include hydrochloric acid, hydrobromic acid, sulfuric acid, methanesulfonic acid, formic acid, acetic acid, oxalic acid, succinic acid, tartaric acid, mandelic acid, fumaric acid, maleic acid, lactic acid, citric acid, glutamic acid, 1,1-dioxo-1,2-dihydro1$\lambda^6$-benzo[d]isothiazol-3-one (saccharic acid), monomethylsebacic acid, 5-oxo-proline, hexane-1-sulfonic acid, nicotinic acid, 2-, 3- or 4-aminobenzoic acid, 2,4,6-trimethylbenzoic acid, α-liponic acid, acetylglycine, hippuric acid, phosphoric acid and/or aspartic acid. Citric acid and hydrochloric acid are particularly preferred.

The term $(CH_2)_{3-6}$ or $(CH_2)_{4-5}$ is to be understood as meaning —$CH_2$—$CH_2$—$CH_2$—, —$CH_2$—$CH_2$—$CH_2$—$CH_2$—, —$CH_2$—$CH_2$—$CH_2$—$CH_2$—$CH_2$— and —$CH_2$—$CH_2$—$CH_2$—$CH_2$—$CH_2$—$CH_2$—, or, respectively, —$CH_2$—$CH_2$—$CH_2$—$CH_2$— and —$CH_2$—$CH_2$—$CH_2$—$CH_2$—$CH_2$—.

Preferred substituted amide derivatives of the general formula I are those wherein the radicals or groups $R^1$-$R^8$, $R^H$, $R^J$, A, B, Z and Q and m, n, o and p have the abovementioned meaning, wherein "alkyl substituted" and "cycloalkyl substituted" means the replacement of one or more hydrogen radicals independently of one another by F, Cl, Br, I, —CN, $NH_2$, NH—$C_{1-6}$-alkyl, NH—$C_{1-6}$-alkyl-OH, $C_{1-6}$-alkyl, N($C_{1-6}$-alkyl)$_2$, N($C_{1-6}$-alkyl-OH)$_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl or benzyl, "aryl substituted" and "heteroaryl substituted" means the replacement, once or several times, e.g. two, three or four times, of one or more hydrogen atoms of the ring system independently of one another by F, Cl, Br, I, CN, $NH_2$, NH—$C_{1-6}$-alkyl, NH—$C_{1-6}$-alkyl-OH, N($C_{1-6}$-alkyl)$_2$, N($C_{1-6}$-alkyl-OH)$_2$, $NO_2$, SH, S—$C_{1-6}$-alkyl, OH, O—$C_{1-6}$-alkyl, O—$C_{1-6}$-alkyl-OH, C(=O)$C_{1-6}$-alkyl, $CO_2H$, $CH_2SO_2$-phenyl, $CO_2$—$C_{1-6}$-alkyl, $OCF_3$, $CF_3$,

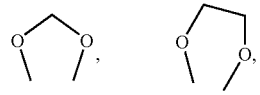

$C_{1-6}$-alkyl, phenyl, pyridyl, thienyl or furyl, in the form of the racemate; of the enantiomers, diastereomers, mixtures of the enantiomers or diastereomers or of an individual enantiomer or diastereomer; of the bases and/or salts of physiologically acceptable acids.

The radicals and groups or substituents described as preferred in the following can be combined in the compounds according to the invention with the broadest meaning of the remaining radicals, but also with preferred meanings of other radicals and groups or substituents.

Substituted amide derivatives which are preferred in the context of this invention are those wherein A represents CH—NH—, CH—$CH_2$—NH—, CH—$CH_2$—$CH_2$—NH— or CH—$CH_2$—$CH_2$—$CH_2$—NH—, wherein individual H atoms can also be replaced by $C_{1-5}$-alkyl.

Substituted amide derivatives which are furthermore preferred in the context of this invention are those wherein B represents $NR^1R^2$.

Substituted amide derivatives which are particularly preferred are those wherein $R^1$ and $R^2$ independently of one another denote H; $CH_3$; or phenyl linked via a $C_{1-3}$-alkyl chain, wherein $R^1$ and $R^2$ do not simultaneously denote H, or $R^1$ and $R^2$ together denote $CH_2CH_2OCH_2CH_2$, $CH_2CH_2NR^8CH_2CH_2$ or $(CH_2)_{4-5}$.

Substituted amide derivatives which are preferred in the context of this invention are also those wherein $R^3$ represents aryl or heteroaryl, in each case unsubstituted or mono- or polysubstituted; or aryl, linked via a $C_{1-3}$-alkyl chain and in each case unsubstituted or mono- or polysubstituted. In particular, the aryl can be substituted by one or more F or Cl radicals.

Substituted amide derivatives which are particularly preferred are those wherein $R^3$ represent 2-thienyl, 4-fluorophenyl, 3-fluorophenyl, 4-chlorophenyl, phenethyl, phenyl or benzyl.

Substituted amide derivatives which are preferred are also those wherein $R^4$ and $R^H$ represent H.

Substituted amide derivatives which are furthermore preferred are those wherein Z represents O.

Substituted amide derivatives which are moreover preferred are those wherein $R^5$ and $R^J$ represent H.

Substituted amide derivatives which are preferred are also those wherein $R^6$ represents methyl, ethyl, cyclopropyl or benzyl and Q represents a single bond.

Substituted amide derivatives which are furthermore preferred are those wherein

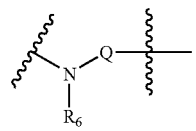

represents

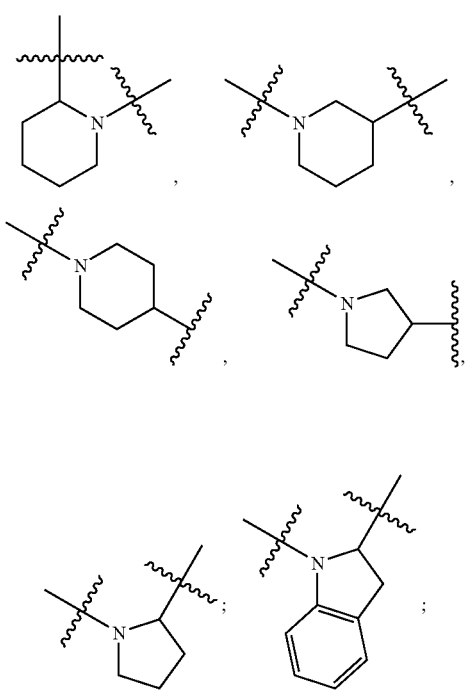

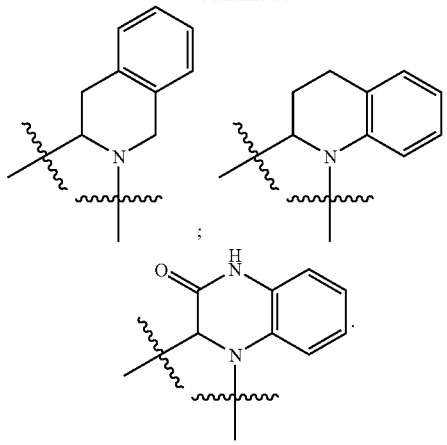

Substituted amide derivatives which are preferred are also those wherein Q denotes

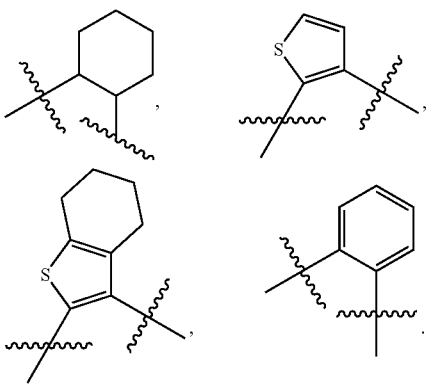

Substituted amide derivatives which are preferred are also those wherein o represents 0 and $R^7$ denotes substituted oxadiazole.

In this context, in compounds wherein o represents 0, $R^7$ represents 1,2,4-oxadiazole substituted by 2-thienyl, 2-methyl-5-fluorophenyl, 2,4-dichlorophenyl, 3,5-dichlorophenyl, 3,4-dimethoxyphenyl, 2,6-dichlorophenyl, benzo[1,3]dioxole, 2-pyridyl, 2-methoxyphenyl, 4-tert.-butylphenyl, 4-trifluoromethylphenyl, 2,4,6-trimethylphenyl, $CH_2$—$SO_2$-phenyl, 2,4,6-trichlorophenyl, 2,4-dichloro-6-methylphenyl.

Substituted amide derivatives which are preferred are also those wherein $R^7$ represents phenyl, unsubstituted or mono- or polysubstituted.

Substituted amide derivatives which are particularly preferred are those wherein $R^7$ represents 2-methyl-5-fluorophenyl, 2,4-dichlorophenyl, 3,5-dichlorophenyl, 3,4-dimethoxyphenyl, 2,6-dichlorophenyl, benzo[1,3]dioxole, 4-tert-butylphenyl, 4-trifluoromethylphenyl, 2,4,6-trimethylphenyl, 2,4,6-trichlorophenyl, 2,4-dichloro-6-methylphenyl, 4-methoxyphenyl, 3-trifluoromethylphenyl, 4-methylphenyl, 2,3,6-trimethyl-4-methoxyphenyl, pentafluorophenyl, 2-methoxyphenyl, 2,6-dimethyl-4-methoxyphenyl, 4-fluorophenyl, 4-chlorophenyl, 3,4-dichlorophenyl, 2,4-dimethoxyphenyl or 2,3-dichlorophenyl.

Substituted amide derivatives which are particularly preferred are also those according to the general formula I wherein o represents 1 and $R^7$ represents aryl or heteroaryl, in each case unsubstituted or mono- or polysubstituted.

Substituted amide derivatives which are particularly preferred are also those according to the general formula I wherein
o represents 1;
Z represents O;
m represents 1 or 2;
$R^J$ and $R^5$ each represent H;
n represents 1; and
$R^H$ and $R^4$ each represent H.

Substituted amide derivatives which are particularly preferred are also those according to the general formula I wherein
o represents 1;
and the group

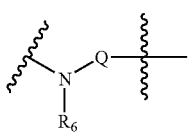

represents

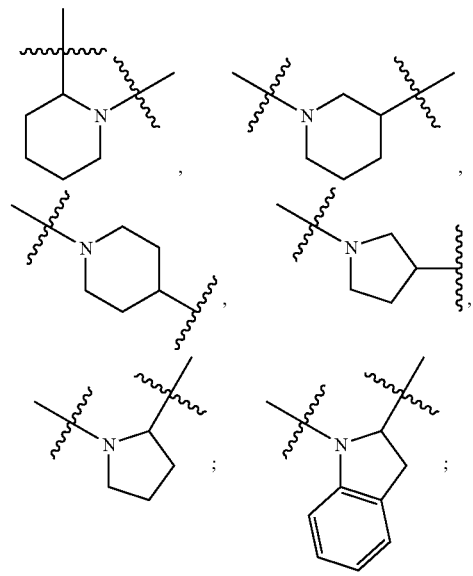

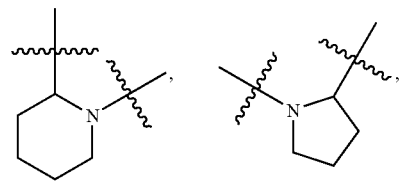

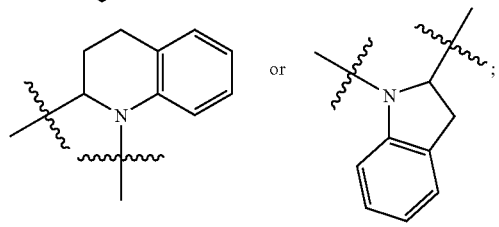

or in the group

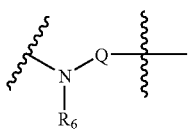

Q represents a single bond or —CH$_2$—; and
$R^6$ represents $C_{1-6}$-alkyl, in particular methyl, ethyl or $C_{3-8}$-cycloalkyl, in particular cyclopropyl.

Amide derivatives which are also preferred are those according to the general formula I in which
o represents 1;
m represents 1 or 2;
$R^J$ and $R^5$ each represent H;
Z represents O;
n represents 1;
$R^H$ and $R^4$ each represent H;
the group

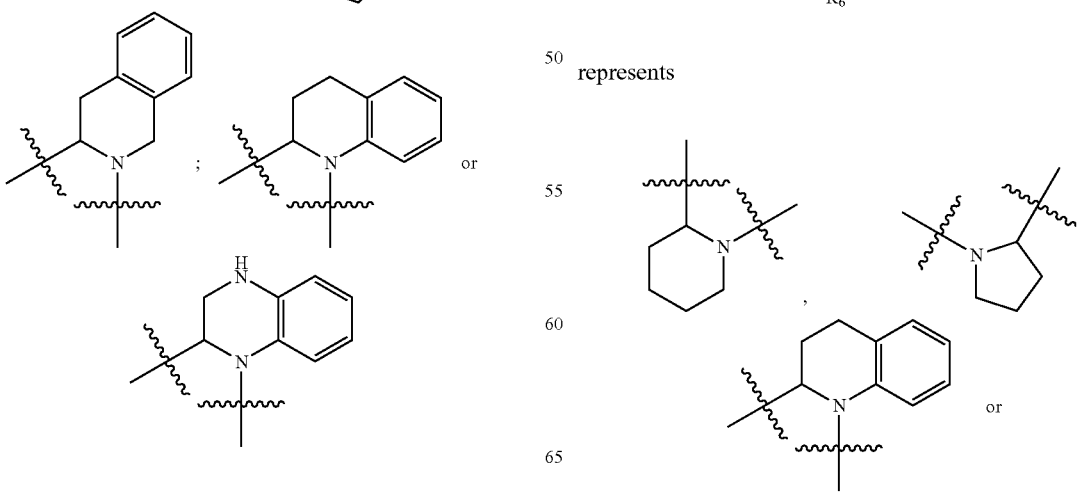

represents

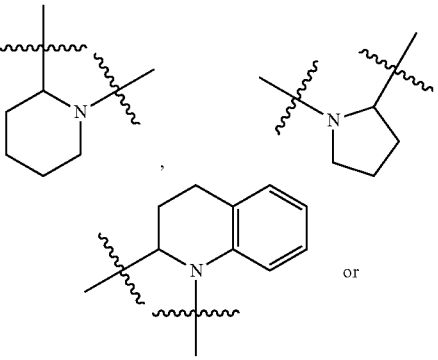

in particular represents

-continued

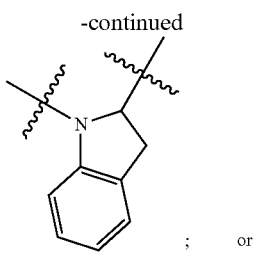

; or in the group

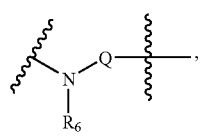

Q represents a single bond and $R^6$ represents $C_{1-6}$-alkyl, in particular methyl, ethyl or $C_{3-8}$-cycloalkyl, in particular cyclopropyl; and (i) A represents CH—CH$_2$—NH— or CH—CH$_2$—CH$_2$—NH, wherein individual H atoms can also be replaced by $C_{1-5}$-alkyl, in particular methyl, B represents NR$^1$R$^2$, wherein R$^1$ and R$^2$ independently of one another denote H; $C_{1-6}$-alkyl, in each case saturated or unsaturated, branched or unbranched, unsubstituted or mono- or polysubstituted, in particular methyl, and wherein R$^1$ and R$^2$ do not simultaneously denote H, or the radicals R$^1$ and R$^2$ together denote (CH$_2$)$_{3-6}$, in particular (CH$_2$)$_2$ and (CH$_2$)$_3$, and R$^3$ represents aryl or heteroaryl, in each case unsubstituted or mono- or polysubstituted, in particular phenyl, 2-thienyl, 4-fluorophenyl, 3-fluorophenyl, 4-chlorophenyl; 2-, 3- or 4-pyridinyl; or R$^3$ represents an aryl linked via a $C_{1-3}$-alkyl chain, in each case unsubstituted or mono- or polysubstituted, in particular phenethyl or benzyl; or (ii) A represents N, B represents NR$^1$R$^2$, wherein R$^1$ and R$^2$ together form CH$_2$CH$_2$NR$^8$CH$_2$CH$_2$ and R$^8$ represents $C_{1-6}$-alkyl, in particular methyl; and R$^3$ represents aryl or heteroaryl, in each case unsubstituted or mono- or polysubstituted, in particular phenyl, 4-fluorophenyl, 3-fluorophenyl; 2-, 3- or 4-pyridinyl; or R$^3$ represents an aryl linked via a $C_{1-3}$-alkyl chain, in each case unsubstituted or mono- or polysubstituted, in particular benzyl or phenethyl.

Substituted amide derivatives which are very particularly preferred are those selected from the group consisting of:

(1) N-(4-((dimethylamino)(thiophen-2-yl)methyl)cyclohexyl)-2-(1-(4-methoxy-2,3,6-trimethylphenylsulfonyl) piperidin-4-yloxy)acetamide
(2) N-((4-((dimethylamino)(thiophen-2-yl)methyl)cyclohexyl)methyl)-2-phenoxypropanamide
(3) N-(4-((dimethylamino)(phenyl)methyl)cyclohexyl)-2-(2-(1-(4-methoxyphenylsulfonyl)piperidin-2-yl)ethoxy) acetamide
(4) N-((4-((dimethylamino)(thiophen-2-yl)methyl)cyclohexyl)methyl)-2-(2-(N,4-dimethylphenylsulfonamido) ethoxy)acetamide
(5) N-(4-((dimethylamino)(thiophen-2-yl)methyl)cyclohexyl)-2-(2-(1-(4-methoxy-2,3,6-trimethylphenylsulfonyl)piperidin-4-yl)ethoxy)acetamide
(6) N-(4-((dimethylamino)(thiophen-2-yl)methyl)cyclohexyl)-2-(2-(1-(4-methoxyphenylsulfonyl)piperidin-2-yl) ethoxy)acetamide
(7) N-((4-((dimethylamino)(thiophen-2-yl)methyl)cyclohexyl)methyl)-2-((2-(4-methoxyphenylsulfonyl)-1,2,3,4-tetrahydroisoquinolin-3-yl)methoxy)acetamide
(8) 2-(2-(2,4-dichloro-N-methylphenylsulfonamido) ethoxy)-N-((4-((dimethylamino)(thiophen-2-yl)methyl) cyclohexyl)methyl)acetamide
(9) 2-(2-(2,4-dichloro-N-methylphenylsulfonamido) ethoxy)-N-(2-(4-((dimethylamino) (thiophen-2-yl)methyl)cyclohexyl)ethyl)acetamide
(10) N-(4-((dimethylamino)(thiophen-2-yl)methyl)cyclohexyl)-2-(2-(4-fluoro-N-methylphenylsulfonamido) ethoxy)acetamide
(11) N-(4-((dimethylamino)(thiophen-2-yl)methyl)cyclohexyl)-2-(1-(3-(trifluoromethyl)phenylsulfonyl)pyrrolidin-3-yloxy)acetamide
(12) N-(4-((dimethylamino)(thiophen-2-yl)methyl)cyclohexyl)-2-(1-(mesitylsulfonyl)pyrrolidin-3-yloxy)acetamide
(13) 2-(2-(2,6-dichloro-N-methylphenylsulfonamido) ethoxy)-N-((4-((dimethylamino)(phenyl)methyl)cyclohexyl)methyl)acetamide
(14) N-((4-((dimethylamino)(phenyl)methyl)cyclohexyl) methyl)-2-(2-(2,4,6-trichloro-N-methylphenylsulfonamido)ethoxy)acetamide
(15) 2-(2-(N-benzylphenylsulfonamido)ethoxy)-N-((4-((dimethylamino)(phenyl)methyl)cyclohexyl)methyl)acetamide
(16) N-((4-((dimethylamino)(thiophen-2-yl)methyl)cyclohexyl)methyl)-2-(2-(N-ethyl-4-methoxy-2,3,6-trimethylphenylsulfonamido)ethoxy)acetamide
(17) 2-((1-(3,4-dichlorophenylsulfonyl)piperidin-2-yl)methoxy)-N-((4-((dimethylamino)(phenyl)methyl)cyclohexyl) methyl)acetamide
(18) 2-((1-(3,4-dichlorophenylsulfonyl)pyrrolidin-2-yl) methoxy)-N-((4-((dimethylamino)(phenyl)methyl)cyclohexyl)methyl)acetamide
(19) N-((4-((dimethylamino)(phenyl)methyl)cyclohexyl) methyl)-2-((2-(4-methoxyphenylsulfonyl)-1,2,3,4-tetrahydroisoquinolin-3-yl)methoxy)acetamide
(20) N-(4-((dimethylamino)(phenyl)methyl)cyclohexyl)-2-(2-(4-(4-methoxy-2,3,6-trimethylphenylsulfonyl)piperazin-1-yl)ethoxy)acetamide
(21) 2-(1-(2,4-dichlorophenylsulfonyl)pyrrolidin-3-yloxy)-N-(2-(4-((dimethylamino)(thiophen-2-yl)methyl)cyclohexyl)ethyl)acetamide
(22) 2-(1-(3,4-dimethoxyphenylsulfonyl)pyrrolidin-3-yloxy)-N-((4-((dimethylamino)(phenyl)methyl)cyclohexyl)methyl)acetamide
(23) 2-(1-(3,4-dimethoxyphenylsulfonyl)pyrrolidin-3-yloxy)-N-((4-((dimethylamino)(thiophen-2-yl)methyl) cyclohexyl)methyl)acetamide
(24) 2-((1-(2,3-dichlorophenylsulfonyl)piperidin-2-yl)methoxy)-N-(4-((dimethylamino)(phenyl)methyl)cyclohexyl) acetamide
(25) N-((4-((dimethylamino)(thiophen-2-yl)methyl)cyclohexyl)methyl)-2-(1-(3-(trifluoromethyl)phenylsulfonyl) pyrrolidin-3-yloxy)acetamide
(26) N-((4-((dimethylamino)(phenyl)methyl)cyclohexyl) methyl)-2-(1-(mesitylsulfonyl)pyrrolidin-3-yloxy)acetamide
(27) N-((4-((dimethylamino)(thiophen-2-yl)methyl)cyclohexyl)methyl)-2-(1-(mesitylsulfonyl)pyrrolidin-3-yloxy) acetamide

(28) N-(4-(((dimethylamino)(thiophen-2-yl)methyl)cyclohexyl)-2-(1-(4-fluorophenylsulfonyl)pyrrolidin-3-yloxy)acetamide
(29) N-((4-((dimethylamino)(phenyl)methyl)cyclohexyl)methyl)-2-(1-(4-methoxy-2,3,6-trimethylphenylsulfonyl)piperidin-3-yloxy)acetamide
(30) N-(2-(4-((dimethylamino)(thiophen-2-yl)methyl)cyclohexyl)ethyl)-2-((1-(4-methoxyphenylsulfonyl)piperidin-2-yl)methoxy)acetamide
(31) 2-(2-(3,4-dichloro-N-methylphenylsulfonamido)cyclohexyloxy)-N-((4-((dimethylamino)(thiophen-2-yl)methyl)cyclohexyl)methyl)acetamide
(32) N-(2-(4-((dimethylamino)(thiophen-2-yl)methyl)cyclohexyl)ethyl)-2-(2-(N-methyl-3-(trifluoromethyl)phenylsulfonamido)ethoxy)acetamide
(33) 2-(2-(2,4-dichloro-N-methylphenylsulfonamido)ethoxy)-N-(4-((dimethylamino)(phenyl)methyl)cyclohexyl)acetamide
(34) N-(4-((dimethylamino)(phenyl)methyl)cyclohexyl)-2-(2-(2,4,6-trichloro-N-methylphenylsulfonamido)ethoxy)acetamide
(35) N-((4-((dimethylamino)(thiophen-2-yl)methyl)cyclohexyl)methyl)-2-(2-(4-methoxy-N,2,3,6-tetramethylphenylsulfonamido)ethoxy)acetamide
(36) N-((4-((dimethylamino)(thiophen-2-yl)methyl)cyclohexyl)methyl)-2-(1-(phenylsulfonyl)pyrrolidin-3-yloxy)acetamide
(37) 2-(2-(4-chloro-N-methylphenylsulfonamido)ethoxy)-N-(2-(4-((dimethylamino)(thiophen-2-yl)methyl)cyclohexyl)ethyl)acetamide
(38) N-(4-((dimethylamino)(phenyl)methyl)cyclohexyl)-2-((2-(4-methoxyphenylsulfonyl)-1,2,3,4-tetrahydroisoquinolin-3-yl)methoxy)acetamide
(39) 2-(2-(3,4-dichloro-N-methylphenylsulfonamido)cyclohexyloxy)-N-(4-((dimethylamino)(phenyl)methyl)cyclohexyl)acetamide
(40) N-((4-((dimethylamino)(phenyl)methyl)cyclohexyl)methyl)-2-(2-(4-methoxy-N,2,3,6-tetramethylphenylsulfonamido)ethoxy)acetamide
(41) 2-(2-(2,6-dichloro-N-methylphenylsulfonamido)ethoxy)-N-(2-(4-((dimethylamino)(3-fluorophenyl)methyl)cyclohexyl)ethyl)acetamide
(42) N-(4-((dimethylamino)(thiophen-2-yl)methyl)cyclohexyl)-2-(1-(phenylsulfonyl)piperidin-3-yloxy)acetamide
(43) N-(4-((dimethylamino)(thiophen-2-yl)methyl)cyclohexyl)-2-(1-(4-methoxy-2,3,6-trimethylphenylsulfonyl)pyrrolidin-3-yloxy)acetamide
(44) N-((4-((dimethylamino)(phenyl)methyl)cyclohexyl)methyl)-2-(1-(4-methoxy-2,3,6-trimethylphenylsulfonyl)pyrrolidin-3-yloxy)acetamide
(45) N-((4-((dimethylamino)(thiophen-2-yl)methyl)cyclohexyl)methyl)-2-((1-(4-methoxyphenylsulfonyl)piperidin-2-yl)methoxy)acetamide
(46) N-(2-(4-((dimethylamino)(thiophen-2-yl)methyl)cyclohexyl)ethyl)-2-(1-(4-methoxyphenylsulfonyl)piperidin-2-yl)ethoxy)acetamide
(47) N-(4-((dimethylamino)(thiophen-2-yl)methyl)cyclohexyl)-2-((2-(4-methoxyphenylsulfonyl)-1,2,3,4-tetrahydroisoquinolin-3-yl)methoxy)acetamide
(48) N-(2-(4-((dimethylamino)(thiophen-2-yl)methyl)cyclohexyl)ethyl)-2-((2-(4-methoxyphenylsulfonyl)-1,2,3,4-tetrahydroisoquinolin-3-yl)methoxy)acetamide
(49) 2-((1-(2,4-dimethoxyphenylsulfonyl)piperidin-2-yl)methoxy)-N-((4-((dimethylamino)(thiophen-2-yl)methyl)cyclohexyl)methyl)acetamide
(50) N-((4-((dimethylamino)(phenyl)methyl)cyclohexyl)methyl)-2-phenoxypropanamide
(51) 2-(2-(N-benzylphenylsulfonamido)ethoxy)-N-(4-((dimethylamino)(phenyl)methyl)cyclohexyl)acetamide
(52) N-(2-(4-((dimethylamino)(thiophen-2-yl)methyl)cyclohexyl)ethyl)-2-(2-(4-methoxy-N,2,3,6-tetramethylphenylsulfonamido)ethoxy)acetamide
(53) N-((4-((dimethylamino)(phenyl)methyl)cyclohexyl)methyl)-2-(2-(N-methyl-4-(trifluoromethoxy)phenylsulfonamido)ethoxy)acetamide
(54) 2-(1-(4-chlorophenylsulfonyl)pyrrolidin-3-yloxy)-N-((4-((dimethylamino)(thiophen-2-yl)methyl)cyclohexyl)methyl)acetamide
(55) 2-(2-(4-chloro-N-methylphenylsulfonamido)ethoxy)-N-((4-((dimethylamino)(thiophen-2-yl)methyl)cyclohexyl)methyl)acetamide
(56) N-((4-((dimethylamino)(thiophen-2-yl)methyl)cyclohexyl)methyl)-2-(2-(4-fluoro-N-methylphenylsulfonamido)ethoxy)acetamide
(57) N-((4-((dimethylamino)(thiophen-2-yl)methyl)cyclohexyl)methyl)-2-(2-(N,2,4,6-tetramethylphenylsulfonamido)ethoxy)acetamide
(58) N-((4-((dimethylamino)(thiophen-2-yl)methyl)cyclohexyl)methyl)-2-(1-(4-methoxy-2,3,6-trimethylphenylsulfonyl)pyrrolidin-3-yloxy)acetamide
(59) N-(4-((dimethylamino)(thiophen-2-yl)methyl)cyclohexyl)-2-(2-(N-ethyl-4-methoxy-2,3,6-trimethylphenylsulfonamido)ethoxy)acetamide
(60) N-((4-((dimethylamino)(thiophen-2-yl)methyl)cyclohexyl)methyl)-2-(1-(4-methoxy-2,3,6-trimethylphenylsulfonyl)piperidin-3-yloxy)acetamide
(61) N-((4-((dimethylamino)(phenyl)methyl)cyclohexyl)methyl)-2-(2-(4-(4-methoxy-2,3,6-trimethylphenylsulfonyl)piperazin-1-yl)ethoxy)acetamide
(62) N-(4-((dimethylamino)(3-fluorophenyl)methyl)cyclohexyl)-2-(2-(1-(4-methoxyphenylsulfonyl)piperidin-2-yl)ethoxy)acetamide
(63) N-(4-((dimethylamino)(phenyl)methyl)cyclohexyl)-2-(2-(N,2,4,6-tetramethylphenylsulfamido)ethoxy)acetamide
(64) N-(4-((dimethylamino)(phenyl)methyl)cyclohexyl)-2-(1-(mesitylsulfonyl)pyrrolidin-3-yloxy)acetamide
(65) N-(2-(4-((dimethylamino)(thiophen-2-yl)methyl)cyclohexyl)ethyl)-2-(2-(N-methyl-4-(trifluoromethoxy)phenylsulfonamido)ethoxy)acetamide
(66) 2-(1-(4-chlorophenylsulfonyl)pyrrolidin-3-yloxy)-N-(2-(4-((dimethylamino)(thiophen-2-yl)methyl)cyclohexyl)ethyl)acetamide
(67) 2-(1-(2,4-dichlorophenylsulfonyl)pyrrolidin-3-yloxy)-N-((4-((dimethylamino)(phenyl)methyl)cyclohexyl)methyl)acetamide
(68) N-((4-((dimethylamino)(thiophen-2-yl)methyl)cyclohexyl)methyl)-2-(1-tosylpyrrolidin-3-yloxy)acetamide
(69) N-((4-((dimethylamino)(thiophen-2-yl)methyl)cyclohexyl)methyl)-2-(2-(4-methoxy-N,2,6-trimethylphenylsulfonamido)ethoxy)acetamide
(70) 2-(2-(2,4-dichloro-N-methylphenylsulfonamido)ethoxy)-N-((4-((dimethylamino)(3-fluorophenyl)methyl)cyclohexyl)methyl)acetamide
(71) N-(2-(4-((dimethylamino)(thiophen-2-yl)methyl)cyclohexyl)ethyl)-2-(1-(mesitylsulfonyl)pyrrolidin-3-yloxy)acetamide
(72) 2-(2-(2,6-dichloro-N-methylphenylsulfonamido)ethoxy)-N-((4-((dimethylamino)(3-fluorophenyl)methyl)cyclohexyl)methyl)acetamide
(73) N-(4-((dimethylamino)(thiophen-2-yl)methyl)cyclohexyl)-2-(2-(4-methoxy-N-methylphenylsulfonamido)ethoxy)acetamide

(74) N-(2-(4-((dimethylamino)(thiophen-2-yl)methyl)cyclohexyl)ethyl)-2-(1-(4-methoxy-2,3,6-trimethylphenylsulfonyl)pyrrolidin-3-yloxy)acetamide
(75) N-(2-(4-((dimethylamino)(thiophen-2-yl)methyl)cyclohexyl)ethyl)-2-(2-(1-(4-methoxy-2,3,6-trimethylphenylsulfonyl)piperidin-4-yl)ethoxy)acetamide
(76) N-(4-((dimethylamino)(3-fluorophenyl)methyl)cyclohexyl)-2-(2-(4-(4-methoxy-2,3,6-trimethylphenylsulfonyl)piperazin-1-yl)ethoxy)acetamide
(77) N-(2-(4-((dimethylamino)(thiophen-2-yl)methyl)cyclohexyl)ethyl)-2-((1-(4-methoxyphenyl sulfonyl)pyrrolidin-2-yl)methoxy)acetamide
(78) 2-(2-(3,4-dichloro-N-methylphenylsulfonamido)cyclohexyloxy)-N-((4-((dimethylamino)(phenyl)methyl)cyclohexyl)methyl)acetamide
(79) N-((4-((dimethylamino)(3-fluorophenyl)methyl)cyclohexyl)methyl)-2-phenoxypropanamide
(80) N-(4-((dimethylamino) (phenyl)methyl)cyclohexyl)-2-(2-(4-methoxy-N,2,3,6-tetramethylphenylsulfonamido)ethoxy)acetamide
(81) 2-(1-(4-chlorophenylsulfonyl)pyrrolidin-3-yloxy)-N-((4-((dimethylamino)(phenyl)methyl)cyclohexyl)methyl)acetamide
(82) N-(2-(4-((dimethylamino)(thiophen-2-yl)methyl)cyclohexyl)ethyl)-2-(2-(N,4-dimethylphenylsulfonamido)ethoxy)acetamide
(83) 2-(2-(4-chloro-N-methylphenylsulfonamido)ethoxy)-N-(4-((dimethylamino) (thiophen-2-yl)methyl)cyclohexyl)acetamide
(84) N-(2-(4-((dimethylamino)(thiophen-2-yl)methyl)cyclohexyl)ethyl)-2-(2-(4-methoxy-N,2,6-trimethylphenylsulfonamido)ethoxy)acetamide
(85) N-(2-(4-((dimethylamino)(thiophen-2-yl)methyl)cyclohexyl)ethyl)-2-(2-(4-fluoro-N-methylphenylsulfonamido)ethoxy)acetamide
(86) N-((4-((dimethylamino)(thiophen-2-yl)methyl)cyclohexyl)methyl)-2-(1-(4-methoxy-2,6-dimethylphenylsulfonyl)pyrrolidin-3-yloxy)acetamide
(87) 2-((1-(3,4-dichlorophenylsulfonyl)piperidin-2-yl)methoxy)-N-((4-((dimethylamino)(3-fluorophenyl)methyl)cyclohexyl)methyl)acetamide
(88) N-((4-((dimethylamino)(phenyl)methyl)cyclohexyl)methyl)-2-((1-(4-methoxyphenyl sulfonyl)piperidin-2-yl)methoxy)acetamide
(89) N-((4-((dimethylamino)(phenyl)methyl)cyclohexyl)methyl)-2-(2-(1-(4-methoxyphenyl sulfonyl)piperidin-2-yl)ethoxy)acetamide
(90) N-((4-((dimethylamino)(thiophen-2-yl)methyl)cyclohexyl)methyl)-2-(2-(1-(4-methoxyphenylsulfonyl)piperidin-2-yl)ethoxy)acetamide
(91) N-((4-((dimethylamino)(phenyl)methyl)cyclohexyl)methyl)-2-(2-(N-methyl-3-(trifluoromethyl)phenylsulfonamido)ethoxy)acetamide
(92) N-((4-((dimethylamino)(thiophen-2-yl)methyl)cyclohexyl)methyl)-2-(2-(N-methyl-3-(trifluoromethyl)phenylsulfonamido)ethoxy)acetamide
(93) N-((4-((dimethylamino)(thiophen-2-yl)methyl)cyclohexyl)methyl)-2-(2-(N-methyl-4-(trifluoromethoxy)phenylsulfonamido)ethoxy)acetamide
(94) 2-(1-(3,4-dimethoxyphenylsulfonyl)pyrrolidin-3-yloxy)-N-(2-(4-((dimethylamino)(thiophen-2-yl)methyl)cyclohexyl)ethyl)acetamide
(95) 2-((1-(4-chlorophenylsulfonyl)piperidin-2-yl)methoxy)-N-(4-((dimethylamino)(phenyl)methyl)cyclohexyl)acetamide
(96) N-(2-(4-((dimethylamino)(thiophen-2-yl)methyl)cyclohexyl)ethyl)-2-(1-(3-(trifluoromethyl)phenylsulfonyl)pyrrolidin-3-yloxy)acetamide
(97) N-((4-((dimethylamino)(thiophen-2-yl)methyl)cyclohexyl)methyl)-2-(1-(4-fluorophenylsulfonyl)pyrrolidin-3-yloxy)acetamide
(98) N-(4-((dimethylamino)(thiophen-2-yl)methyl)cyclohexyl)-2-(1-(4-methoxy-2,6-dimethylphenylsulfonyl)pyrrolidin-3-yloxy)acetamide
(99) N-(2-(4-((dimethylamino)(thiophen-2-yl)methyl)cyclohexyl)ethyl)-2-(2-(4-(phenylsulfonyl)piperazin-1-yl)ethoxy)acetamide
(100) N-(2-(4-((dimethylamino)(thiophen-2-yl)methyl)cyclohexyl)ethyl)-2-(1-(phenylsulfonyl)piperidin-3-yloxy)acetamide
(101) N-((4-((dimethylamino)(thiophen-2-yl)methyl)cyclohexyl)methyl)-2-((1-(phenylsulfonyl)piperidin-3-yl)methoxy)acetamide
(102) 2-(2-(N-benzylphenylsulfonamido)ethoxy)-N-((4-((dimethylamino)(thiophen-2-yl)methyl)cyclohexyl)methyl)acetamide
(103) N-(2-(4-((dimethylamino)(thiophen-2-yl)methyl)cyclohexyl)ethyl)-2-(2-(N-ethyl-4-methoxy-2,3,6-trimethylphenylsulfonamido)ethoxy)acetamide
(104) N-((4-((dimethylamino)(thiophen-2-yl)methyl)cyclohexyl)methyl)-2-(1-(4-methoxy-2,3,6-trimethylphenylsulfonyl)piperidin-4-yloxy)acetamide
(105) N-((4-((dimethylamino)(thiophen-2-yl)methyl)cyclohexyl)methyl)-2-((1-(4-methoxyphenylsulfonyl)pyrrolidin-2-yl)methoxy)acetamide
(106) 2-((1-(2,4-dimethoxyphenylsulfonyl)piperidin-2-yl)methoxy)-N-((4-((dimethylamino)(phenyl)methyl)cyclohexyl)methyl)acetamide
(107) 2-((1-(2,4-dimethoxyphenylsulfonyl)piperidin-2-yl)methoxy)-N-(2-(4-((dimethylamino)(thiophen-2-yl)methyl)cyclohexyl)ethyl)acetamide
(108) N-((4-((dimethylamino)(3-fluorophenyl)methyl)cyclohexyl)methyl)-2-phenoxypropanamide
(109) N-(4-((dimethylamino)(phenyl)methyl)cyclohexyl)-2-(1-(phenylsulfonyl)piperidin-3-yloxy)acetamide
(110) 2-(2-(4-chloro-N-methylphenylsulfonamido)ethoxy)-N-((4-((dimethylamino) (phenyl)methyl)cyclohexyl)methyl)acetamide
(111) N-(2-(4-((dimethylamino)(thiophen-2-yl)methyl)cyclohexyl)ethyl)-2-(2-(4-methoxy-N,2,6-trimethylphenylsulfonamido)ethoxy)acetamide
(112) N-((4-((dimethylamino)(phenyl)methyl)cyclohexyl)methyl)-2-(2-(4-fluoro-N-methylphenylsulfonamido)ethoxy)acetamide
(113) N-((4-((dimethylamino)(phenyl)methyl)cyclohexyl)methyl)-2-(1-(3-(trifluoromethyl)phenylsulfonyl)pyrrolidin-3-yloxy)acetamide
(114) N-((4-((dimethylamino)(phenyl)methyl)cyclohexyl)methyl)-2-(1-(phenylsulfonyl)piperidin-3-yloxy)acetamide
(115) N-(2-(4-((dimethylamino)(thiophen-2-yl)methyl)cyclohexyl)ethyl)-2-((1-(phenylsulfonyl)piperidin-3-yl)methoxy)acetamide
(116) 2-(2-(N-benzylphenylsulfonamido)ethoxy)-N-(2-(4-((dimethylamino)(thiophen-2-yl)methyl)cyclohexyl)ethyl)acetamide
(117) N-((4-((dimethylamino)(3-fluorophenyl)methyl)cyclohexyl)methyl)-2-(2-(N-ethyl-4-methoxy-2,3,6-trimethylphenylsulfonamido)ethoxy)acetamide
(118) N-(4-((dimethylamino)(3-fluorophenyl)methyl)cyclohexyl)-2-(2-(1-(4-methoxy-2,3,6-trimethylphenylsulfonyl)piperidin-4-yl)ethyl)acetamide (119) 2-((1-(3,4-dichlorophenylsulfonyl)pyrrolidin-2-yl)methoxy)-N-((4-((dimethylamino)(3-fluorophenyl)methyl)cyclohexyl)methyl)acetamide
(120) 2-((1-(3,4-dimethoxyphenylsulfonyl)piperidin-2-yl)methoxy)-N-(2-(4-((dimethylamino)(thiophen-2-yl)methyl)cyclohexyl)ethyl)acetamide
(121) N-(4-((dimethylamino)(3-fluorophenyl)methyl)cyclohexyl)-2-phenoxypropanamide
(122) N-((4-((dimethylamino)(3-fluorophenyl)methyl)cyclohexyl)methyl)-2-phenoxypropanamide
(123) N-(4-((dimethylamino)(phenyl)methyl)cyclohexyl)-2-(1-tosylpyrrolidin-3-yloxy)acetamide
(124) N-(4-((dimethylamino)(phenyl)methyl)cyclohexyl)-2-(2-(1-(phenylsulfonyl)piperidin-4-yl)ethoxy)acetamide
(125) N-((4-((dimethylamino)(phenyl)methyl)cyclohexyl)methyl)-2-(1-tosylpyrrolidin-3-yloxy)acetamide
(126) 2-(2-(2,4-dichloro-N-methylphenylsulfonamido)ethoxy)-N-(2-(4-((dimethylamino)(3-fluorophenyl)methyl)cyclohexyl)ethyl)acetamide
(127) 2-(2-(3,4-Dimethoxy-N-methylphenylsulfonamido)ethoxy)-N-((4-((dimethylamino)(thiophen-2-yl)methyl)cyclohexyl)methyl)acetamide
(128) N-(2-(4-((dimethylamino)(thiophen-2-yl)methyl)cyclohexyl)ethyl)-2-(2-(4-methoxy-N-methylphenylsulfonamido)ethoxy)acetamide
(129) N((4((dimethylamino)(phenyl)methyl)cyclohexyl)methyl)-2-((1-(phenylsulfonyl)piperidin-3-yl)methoxy)acetamide
(130) N-(2-(4-((dimethylamino)(thiophen-2-yl)methyl)cyclohexyl)ethyl)-2-(1-(4-methoxy-2,3,6-trimethylphenylsulfonyl)piperidin-3-yloxy)acetamide
(131) N-((4-((dimethylamino)(thiophen-2-yl)methyl)cyclohexyl)methyl)-2-(2-(1-(4-methoxy-2,3,6-trimethylphenylsulfonyl)piperidin-4-yl)ethoxy)acetamide
(132) 2-(2-(3,4-dichloro-N-methylphenylsulfonamido)cyclohexyloxy)-N-(4-((dimethylamino)(3-fluorophenyl)methyl)cyclohexyl)acetamide
(133) 2-((1-(3,4-Dimethoxyphenylsulfonyl)piperidin-2-yl)methoxy)-N-((4-((dimethylamino)(thiophen-2-yl)methyl)cyclohexyl)methyl)acetamide
(134) 2-(benzyloxy)-N-(2-(4-((dimethylamino)(phenyl)methyl)cyclohexyl)ethyl)acetamide
(135) 2-(2-(2,6-dichloro-N-methylphenylsulfonamido)ethoxy)-N-(4-((dimethylamino)(phenyl)methyl)cyclohexyl)acetamide
(136) N-(4-((dimethylamino)(phenyl)methyl)cyclohexyl)-2-(2-(2,3,4,5,6-pentafluoro-N-methylphenylsulfonamido)ethoxy)acetamide
(137) N-((4-((dimethylamino)(phenyl)methyl)cyclohexyl)methyl)-2-(2-(4-methoxy-N,2,6-trimethylphenylsulfonamido)ethoxy)acetamide
(138) N-(2-(4-((dimethylamino)(thiophen-2-yl)methyl)cyclohexyl)ethyl)-2-(1-(4-fluorophenylsulfonyl)pyrrolidin-3-yloxy)acetamide
(139) N-(4-((dimethylamino)(3-fluorophenyl)methyl)cyclohexyl)-2-(1-(3-(trifluoromethyl)phenylsulfonyl)pyrrolidin-3-yloxy)acetamide
(140) N-(4-((dimethylamino)(3-fluorophenyl)methyl)cyclohexyl)-2-(1-(mesitylsulfonyl)pyrrolidin-3-yloxy)acetamide
(141) N-((4-((dimethylamino)(3-fluorophenyl)methyl)cyclohexyl)methyl)-2-(1-(mesitylsulfonyl)pyrrolidin-3-yloxy)acetamide
(142) N-((4-((dimethylamino)(thiophen-2-yl)methyl)cyclohexyl)methyl)-2-(2-(4-methoxy-N-methylphenylsulfonamido)ethoxy)acetamide
(143) N-((4-((dimethylamino)(phenyl)methyl)cyclohexyl)methyl)-2-(1-(4-methoxy-2,3,6-trimethylphenylsulfonyl)piperidin-4-yloxy)acetamide
(144) N-((4-((dimethylamino)(thiophen-2-yl)methyl)cyclohexyl)-2-(1-(4-methoxy-2,3,6-trimethylphenylsulfonyl)piperidin-3-yloxy)acetamide
(145) N-((4-((dimethylamino)(3-fluorophenyl)methyl)cyclohexyl)methyl)-2-(1-(4-methoxy-2,3,6-trimethylphenylsulfonyl)piperidin-3-yloxy)acetamide
(146) N-((4-((dimethylamino)(phenyl)methyl)cyclohexyl)methyl)-2-(2-(1-(4-methoxy-2,3,6-trimethylphenylsulfonyl)piperidin-4-yl)ethoxy)acetamide
(147) 2-((1-(3,4-dichlorophenylsulfonyl)piperidin-2-yl)methoxy)-N-(2-(4-((dimethylamino)(3-fluorophenyl)methyl)cyclohexyl)ethyl)acetamide
(148) 2-(2-(N-benzyl-4-methoxy-2,6-dimethylphenylsulfonamido)ethoxy)-N-((4-((dimethylamino)(phenyl)methyl)cyclohexyl)methyl)acetamide
(149) 2-(2-(N-benzyl-4-methoxy-2,6-dimethylphenylsulfonamido)ethoxy)-N-(2-(4-((dimethylamino) (thiophen-2-yl)methyl)cyclohexyl)ethyl)acetamide
(150) 2-((1-(3,4-Dimethoxyphenylsulfonyl)piperidin-2-yl)methoxy)-N-((4-((dimethylamino)(phenyl)methyl)cyclohexyl)methyl)acetamide
(151) 2-((1-(2,4-dimethoxyphenylsulfonyl)piperidin-2-yl)methoxy)-N-((4-((dimethylamino)(3-fluorophenyl)methyl)cyclohexyl)methyl)acetamide
(152) N-(4-((dimethylamino)(thiophen-2-yl)methyl)cyclohexyl)-2-(2-(N-methyl-3-(trifluoromethyl)phenylsulfonamido)ethoxy)acetamide
(153) N-(4-((dimethylamino)(3-fluorophenyl)methyl)cyclohexyl)-2-phenoxypropanamide
(154) N-(4-((dimethylamino)(phenyl)methyl)cyclohexyl)-2-((1-(4-methoxyphenylsulfonyl)piperidin-2-yl)methoxy)acetamide
(155) 2-(1-(3,4-dimethoxyphenylsulfonyl)pyrrolidin-3-yloxy)-N-(4-((dimethylamino)(thiophen-2-yl)methyl)cyclohexyl)acetamide
(156) N-(4-((dimethylamino)(thiophen-2-yl)methyl)cyclohexyl)-2-(1-tosylpyrrolidin-3-yloxy)acetamide
(157) N-((4-((dimethylamino) (phenyl)methyl)cyclohexyl)methyl)-2-(2-(N,4-dimethylphenylsulfonamido)ethoxy)acetamide
(158) 2-(2-(4-chloro-N-methylphenylsulfonamido)ethoxy)-N-((4-((dimethylamino)(3-fluorophenyl)methyl)cyclohexyl)methyl)acetamide
(159) N-(4-((dimethylamino)(3-fluorophenyl)methyl)cyclohexyl)-2-(2-(4-methoxy-N,2,3,6-tetramethylphenylsulfonamido)ethoxy)acetamide
(160) N-((4-((dimethylamino)(3-fluorophenyl)methyl)cyclohexyl)methyl)-2-(2-(4-methoxy-N,2,3,6-tetramethylphenylsulfonamido)ethoxy)acetamide
(161) 2-(2-(N-benzylphenylsulfonamido)ethoxy)-N-(4-((dimethylamino)(thiophen-2-yl)methyl)cyclohexyl)acetamide
(162) N-(4-((dimethylamino)(thiophen-2-yl)methyl)cyclohexyl)-2-((1-(4-methoxyphenylsulfonyl)pyrrolidin-2-yl)methoxy)acetamide
(163) N-((4-((dimethylamino)(3-fluorophenyl)methyl)cyclohexyl)methyl)-2-((2-(4-methoxyphenylsulfonyl)-1,2,3,4-tetrahydroisoquinolin-3-yl)methoxy)acetamide
(164) 2-(2-(3,4-dichloro-N-methylphenylsulfonamido)cyclohexyloxy)-N-((4-((dimethylamino)(3-fluorophenyl)methyl)cyclohexyl)methyl)acetamide
(165) N-(4-((dimethylamino)(phenyl)methyl)cyclohexyl)-2-(1-(4-methoxy-2,6-dimethylphenylsulfonyl)pyrrolidin-3-yloxy)acetamide (166) 2-(2-(3,4-dichloro-N-methylphenylsulfonamido)phenoxy)-N-(4-((dimethylamino)(phenyl)methyl)cyclohexyl)acetamide
(167) N-(4-((dimethylamino)(3-fluorophenyl)methyl)cyclohexyl)-2-(1-tosylpyrrolidin-3-yloxy)acetamide
(168) N-(4-((dimethylamino) (thiophen-2-yl)methyl)cyclohexyl)-2-(2-(N,4-dimethylphenylsulfamido)ethoxy)acetamide
(169) 2-(2-(3,4-dimethoxy-N-methylphenylsulfonamido)ethoxy)-N-((4-((dimethylamino)(phenyl)methyl)cyclohexyl)methyl)acetamide
(170) N-((4-((dimethylamino)(3-fluorophenyl)methyl)cyclohexyl)methyl)-2-(1-(3-(trifluoromethyl)phenylsulfonyl)pyrrolidin-3-yloxy)acetamide
(171) 2-(2-(2,6-dichloro-N-methylphenylsulfonamido)ethoxy)-N-(4-((dimethylamino)(3-fluorophenyl)methyl)cyclohexyl)acetamide
(172) N-(4-((dimethylamino)(3-fluorophenyl)methyl)cyclohexyl)-2-(1-(4-fluorophenylsulfonyl)pyrrolidin-3-yloxy)acetamide
(173) N-((4-((dimethylamino)(phenyl)methyl)cyclohexyl)methyl)-2-(1-(4-methoxy-2,6-dimethylphenylsulfonyl)pyrrolidin-3-yloxy)acetamide
(174) N-(2-(4-((dimethylamino)(3-fluorophenyl)methyl)cyclohexyl)ethyl)-2-(2-(2,4,6-trichloro-N-methylphenylsulfonamido)ethoxy)acetamide
(175) 2-(2-(N-benzylphenylsulfonamido)ethoxy)-N-(4-((dimethylamino)(3-fluorophenyl)methyl)cyclohexyl)acetamide
(176) N-(4-((dimethylamino)(3-fluorophenyl)methyl)cyclohexyl)-2-(2-(N-ethyl-4-methoxy-2,3,6-trimethylphenylsulfonamido)ethoxy)acetamide
(177) N-(2-(4-((dimethylamino)(thiophen-2-yl)methyl)cyclohexyl)ethyl)-2-(1-(4-methoxy-2,3,6-trimethylphenylsulfonyl)piperidin-4-yloxy)acetamide
(178) N-(4-((dimethylamino)(4-fluorophenyl)methyl)cyclohexyl)-2-(2-(1-(4-methoxy-2,3,6-trimethylphenylsulfonyl)piperidin-4-yl)ethoxy)acetamide
(179) N-((4-((dimethylamino)(3-fluorophenyl)methyl)cyclohexyl)methyl)-2-((1-(4-methoxyphenylsulfonyl)piperidin-2-yl)methoxy)acetamide
(180) N-(2-(4-((dimethylamino)(3-fluorophenyl)methyl)cyclohexyl)ethyl)-2-((1-(4-methoxyphenylsulfonyl)piperidin-2-yl)methoxy)acetamide
(181) N-(4-((dimethylamino)(phenyl)methyl)cyclohexyl)-2-phenoxypropanamide
(182) N-(4-((dimethylamino)(phenyl)methyl)cyclohexyl)-2-((1-(4-methoxyphenylsulfonyl)pyrrolidin-2-yl)methoxy)acetamide
(183) N-(2-(4-((dimethylamino)(3-fluorophenyl)methyl)cyclohexyl)ethyl)-2-(2-(4-methoxy-N,2,3,6-tetramethylphenylsulfonamido)ethoxy)acetamide
(184) 2-(1-(3,4-dimethoxyphenylsulfonyl)pyrrolidin-3-yloxy)-N-((4-((dimethylamino)(3-fluorophenyl)methyl)cyclohexyl)methyl)acetamide
(185) N-((4-((dimethylamino)(3-fluorophenyl)methyl)cyclohexyl)methyl)-2-(1-tosylpyrrolidin-3-yloxy)acetamide
(186) 2-(2-(4-chloro-N-methylphenylsulfonamido)ethoxy)-N-(2-(4-((dimethylamino)(3-fluorophenyl)methyl)cyclohexyl)ethyl)acetamide
(187) 2-((1-(2,4-dimethoxyphenylsulfonyl)piperidin-2-yl)methoxy)-N-(4-((dimethylamino)(phenyl)methyl)cyclohexyl)acetamide
(188) N-((4-((dimethylamino)(3-fluorophenyl)methyl)cyclohexyl)methyl)-2-(2-(2,4,6-trichloro-N-methylphenylsulfonamido)ethoxy)acetamide
(189) N-(4-((dimethylamino)(3-fluorophenyl)methyl)cyclohexyl)-2-(1-(4-methoxy-2,3,6-trimethylphenylsulfonyl)pyrrolidin-3-yloxy)acetamide
(190) N-(2-(4-((dimethylamino) (3-fluorophenyl)methyl)cyclohexyl)ethyl)-2-((2-(4-methoxy phenylsulfonyl)-1,2,3,4-tetrahydroisoquinolin-3-yl)methoxy)acetamide
(191) 2-((1-(3,4-dimethoxyphenylsulfonyl)piperidin-2-yl)methoxy)-N-(2-(4-((dimethylamino)(3-fluorophenyl)methyl)cyclohexyl)ethyl)acetamide
(192) N-(2-(4-((dimethylamino)(3-fluorophenyl)methyl)cyclohexyl)ethyl)-2-(2-(N-methyl-3-(trifluoromethyl)phenylsulfonamido)ethoxy)acetamide
(193) 2-(2-(N-benzyl-4-methoxy-2,3,6-trimethylphenylsulfonamido)ethoxy)-N-(4-((dimethylamino) (phenyl)methyl)cyclohexyl)acetamide
(194) N-(4-((dimethylamino)(thiophen-2-yl)methyl)cyclohexyl)-2-(1-(phenylsulfonyl)pyrrolidin-3-yloxy)acetamide
(195) N-((4-((dimethylamino)(phenyl)methyl)cyclohexyl)methyl)-2-(1-(phenylsulfonyl)pyrrolidin-3-yloxy)acetamide
(196) 2-(2-(4-chloro-N-methylphenylsulfonamido)ethoxy)-N-(4-((dimethylamino)(3-fluorophenyl)methyl)cyclohexyl)acetamide
(197) N-(2-(4-((dimethylamino)(3-fluorophenyl)methyl)cyclohexyl)ethyl)-2-(2-(4-methoxy-N,2,6-trimethylphenylsulfonamido)ethoxy)acetamide
(198) 2-((1-(3,4-dimethoxyphenylsulfonyl)piperidin-2-yl)methoxy)-N-(4-((dimethylamino)(phenyl)methyl)cyclohexyl)acetamide
(199) N-(2-(4-((dimethylamino)(thiophen-2-yl)methyl)cyclohexyl)ethyl)-2-(1-(4-methoxy-2,6-dimethylphenylsulfonyl)pyrrolidin-3-yloxy)acetamide
(200) N-(2-(4-((dimethylamino)(3-fluorophenyl)methyl)cyclohexyl)ethyl)-2-(2-(4-(4-methoxy-2,3,6-trimethylphenylsulfonyl)piperazin-1-yl)ethoxy)acetamide
(201) 2-(2-(N-benzyl-4-methoxy-2,3,6-trimethylphenylsulfonamido)ethoxy)-N-((4-((dimethylamino)(phenyl)methyl)cyclohexyl)methyl)acetamide
(202) 2-((1-(3,4-dichlorophenylsulfonyl)pyrrolidin-2-yl)methoxy)-N-(2-(4-((dimethylamino)(3-fluorophenyl)methyl)cyclohexyl)ethyl)acetamide
(203) N-((4-((dimethylamino)(3-fluorophenyl)methyl)cyclohexyl)methyl)-2-(2-(1-(4-methoxyphenylsulfonyl)piperidin-2-yl)ethoxy)acetamide
(204) 2-(1-(4-chlorophenylsulfonyl)pyrrolidin-3-yloxy)-N-(4-((dimethylamino)(3-fluorophenyl)methyl)cyclohexyl)acetamide
(205) N-(4-((dimethylamino)(3-fluorophenyl)methyl)cyclohexyl)-2-(2-(4-fluoro-N-methylphenylsulfamido)ethoxy)acetamide
(206) 2-(2-(3,4-dimethoxy-N-methylphenylsulfonamido)ethoxy)-N-(4-((dimethylamino)(thiophen-2-yl)methyl)cyclohexyl)acetamide
(207) N-((4-((4-chlorophenyl)(dimethylamino)methyl)cyclohexyl)methyl)-2-(2-(2,6-dichloro-N-methylphenylsulfonamido)ethoxy)acetamide
(208) N-(4-((dimethylamino)(3-fluorophenyl)methyl)cyclohexyl)-2-(2-(2,4,6-trichloro-N-methylphenylsulfonamido)ethoxy)acetamide
(209) N-(2-(4-((dimethylamino)(3-fluorophenyl)methyl)cyclohexyl)ethyl)-2-(2-(N-ethyl-4-methoxy-2,3,6-trimethylphenylsulfonamido)ethoxy)acetamide
(210) 2-((1-(3,4-dichlorophenylsulfonyl)piperidin-2-yl)methoxy)-N-(4-((dimethylamino)(3-fluorophenyl)methyl)cyclohexyl)acetamide (211) 2-((1-(3,4-dichlorophenylsulfonyl)pyrrolidin-2-yl)methoxy)-N-(4-((dimethylamino)(3-fluorophenyl)methyl)cyclohexyl)acetamide
(212) N-(4-((dimethylamino)(4-fluorophenyl)methyl)cyclohexyl)-2-(2-(1-(4-methoxyphenylsulfonyl)piperidin-2-yl)ethoxy)acetamide
(213) N-(2-(4-((dimethylamino)(3-fluorophenyl)methyl)cyclohexyl)ethyl)-2-(2-(1-(4-methoxyphenylsulfonyl)piperidin-2-yl)ethoxy)acetamide
(214) 2-(2-(3,4-dichloro-N-methylphenylsulfonamido)cyclohexyloxy)-N-(2-(4-((dimethylamino) (thiophen-2-yl)methyl)cyclohexyl)ethyl)acetamide
(215) N-(2-(4-((dimethylamino)(3-fluorophenyl)methyl)cyclohexyl)ethyl)-2-(2-(N-methyl-4-(trifluoromethoxy)phenylsulfonamido)ethoxy)acetamide
(216) N-(2-(4-((dimethylamino)(3-fluorophenyl)methyl)cyclohexyl)ethyl)-2-(1-tosylpyrrolidin-3-yloxy)acetamide
(217) 2-(2-(2,4-dichloro-N-methylphenylsulfonamido)ethoxy)-N-(4-((dimethylamino)(3-fluorophenyl)methyl)cyclohexyl)acetamide
(218) N-(2-(4-((dimethylamino)(3-fluorophenyl)methyl)cyclohexyl)ethyl)-2-(2-(4-fluoro-N-methylphenylsulfonamido)ethoxy)acetamide
(219) N-((4-((dimethylamino)(phenyl)methyl)cyclohexyl)methyl)-2-(1-(4-fluorophenylsulfonyl)pyrrolidin-3-yloxy)acetamide
(220) N-((4-((dimethylamino)(3-fluorophenyl)methyl)cyclohexyl)methyl)-2-((1-(phenylsulfonyl)piperidin-3-yl)methoxy)acetamide
(221) N-(2-(4-((dimethylamino) (3-fluorophenyl)methyl)cyclohexyl)ethyl)-2-(1-(4-methoxy-2,3,6-trimethylphenylsulfonyl)piperidin-3-yloxy)acetamide
(222) N-(4-((dimethylamino)(4-fluorophenyl)methyl)cyclohexyl)-2-(2-(4-(4-methoxy-2,3,6-trimethylphenylsulfonyl)piperazin-1-yl)ethoxy)acetamide
(223) N-((4-((dimethylamino)(3-fluorophenyl)methyl)cyclohexyl)methyl)-2-(2-(4-(4-methoxy-2,3,6-trimethylphenylsulfonyl)piperazin-1-yl)ethoxy)acetamide
(224) N-(2-(4-((dimethylamino)(3-fluorophenyl)methyl)cyclohexyl)ethyl)-2-((1-(4-methoxyphenylsulfonyl)pyrrolidin-2-yl)methoxy)acetamide
(225) 2-(1-(2,4-dichlorophenylsulfonyl)pyrrolidin-3-yloxy)-N-((4-((dimethylamino)(3-fluorophenyl)methyl)cyclohexyl)methyl)acetamide
(226) N-(4-((dimethylamino)(3-fluorophenyl)methyl)cyclohexyl)-2-(2-(N,4-dimethylphenylsulfamido)ethoxy)acetamide
(227) N-((4-((dimethylamino)(3-fluorophenyl)methyl)cyclohexyl)methyl)-2-(2-(N,4-dimethylphenylsulfonamido)ethoxy)acetamide
(228) N-(4-((dimethylamino)(3-fluorophenyl)methyl)cyclohexyl)-2-(2-(4-methoxy-N,2,6-trimethylphenylsulfonamido)ethoxy)acetamide
(229) N-((4-((dimethylamino)(3-fluorophenyl)methyl)cyclohexyl)methyl)-2-(2-(4-fluoro-N-methylphenylsulfonamido)ethoxy)acetamide
(230) N-(2-(4-((dimethylamino)(thiophen-2-yl)methyl)cyclohexyl)ethyl)-2-(1-(phenylsulfonyl)piperidin-4-yloxy)acetamide
(231) N-((4-((dimethylamino)(phenyl)methyl)cyclohexyl)methyl)-2-(2-(N-ethyl-4-methoxy-2,3,6-trimethylphenylsulfonamido)ethoxy)acetamide
(232) N-(2-(4-((dimethylamino)(3-fluorophenyl)methyl)cyclohexyl)ethyl)-2-(1-(4-methoxy-2,3,6-trimethylphenylsulfonyl)piperidin-4-yloxy)acetamide
(233) 2-((1-(3,4-dichlorophenylsulfonyl)piperidin-2-yl)methoxy)-N-((4-((dimethylamino)(4-fluorophenyl)methyl)cyclohexyl)methyl)acetamide
(234) N-(4-((dimethylamino)(4-fluorophenyl)methyl)cyclohexyl)-2-((2-(4-methoxyphenylsulfonyl)-1,2,3,4-tetrahydroisoquinolin-3-yl)methoxy)acetamide
(235) N-(4-((dimethylamino)(thiophen-2-yl)methyl)cyclohexyl)-2-(2-(N,2,4,6-tetramethylphenylsulfonamido)ethoxy)acetamide
(236) N-((4-((dimethylamino)(4-fluorophenyl)methyl)cyclohexyl)methyl)-2-phenoxypropanamide
(237) N-((4-((4-chlorophenyl)(dimethylamino)methyl)cyclohexyl)methyl)-2-phenoxypropanamide
(238) N-((4-((4-chlorophenyl)(dimethylamino)methyl)cyclohexyl)methyl)-2-phenoxypropanamide
(239) N-(4-((dimethylamino)(phenyl)methyl)cyclohexyl)-2-(2-(4-methoxy-N,2,6-trimethylphenylsulfonamido)ethoxy)acetamide
(240) N-(2-(4-((dimethylamino)(3-fluorophenyl)methyl)cyclohexyl)ethyl)-2-(2-(N,4-dimethylphenylsulfonamido)ethoxy)acetamide
(241) N-(2-(4-((4-chlorophenyl)(dimethylamino)methyl)cyclohexyl)ethyl)-2-(2-(4-fluoro-N-methylphenylsulfonamido)ethoxy)acetamide
(242) N-((4-((dimethylamino)(phenyl)methyl)cyclohexyl)methyl)-2-(2-(4-methoxy-N-methylphenylsulfonamido)ethoxy)acetamide
(243) N-(4-((dimethylamino)(thiophen-2-yl)methyl)cyclohexyl)-2-((1-(4-methoxyphenylsulfonyl)piperidin-2-yl)methoxy)acetamide
(244) 2-(2-(3,4-dichloro-N-methylphenylsulfonamido)cyclohexyloxy)-N-(2-(4-((dimethylamino)(4-fluorophenyl)methyl)cyclohexyl)ethyl)acetamide
(245) 2-(benzyloxy)-N-(4-((dimethylamino)(phenyl)methyl)cyclohexyl)acetamide
(246) N-(4-((dimethylamino)(3-fluorophenyl)methyl)cyclohexyl)-2-(N-methyl-4-(trifluoromethoxy)phenylsulfonamido)ethoxy)acetamide
(247) 2-(1-(4-chlorophenylsulfonyl)pyrrolidin-3-yloxy)-N-(2-(4-((dimethylamino)(3-fluorophenyl)methyl)cyclohexyl)ethyl)acetamide
(248) N-((4-((dimethylamino)(3-fluorophenyl)methyl)cyclohexyl)methyl)-2-(2-(4-methoxy-N,2,6-trimethylphenylsulfonamido)ethoxy)acetamide
(249) 2-(2-(2,4-dichloro-N-methylphenylsulfonamido)ethoxy)-N-((4-((dimethylamino)(4-fluorophenyl)methyl)cyclohexyl)methyl)acetamide
(250) N-(4-((dimethylamino)(3-fluorophenyl)methyl)cyclohexyl)-2-(2-(4-methoxy-N-methylphenylsulfonamido)ethoxy)acetamide
(251) N-(4-((dimethylamino)(3-fluorophenyl)methyl)cyclohexyl)-2-(1-(4-methoxy-2,6-dimethylphenylsulfonyl)pyrrolidin-3-yloxy)acetamide
(252) N-((4-((dimethylamino)(3-fluorophenyl)methyl)cyclohexyl)methyl)-2-(1-(4-methoxy-2,3,6-trimethylphenylsulfonyl)pyrrolidin-3-yloxy)acetamide
(253) N-(2-(4-((dimethylamino)(3-fluorophenyl)methyl)cyclohexyl)ethyl)-2-(1-(4-methoxy-2,3,6-trimethylphenylsulfonyl)pyrrolidin-3-yloxy)acetamide
(254) 2-(2-(N-benzyl-4-methoxy-2,3,6-trimethylphenylsulfonamido)ethoxy)-N-(2-(4-((dimethylamino)(thiophen-2-yl)methyl)cyclohexyl)ethyl)acetamide
(255) N-(4-((dimethylamino)(3-fluorophenyl)methyl)cyclohexyl)-2-((1-(4-methoxyphenylsulfonyl)piperidin-2-yl)methoxy)acetamide (256) 2-(2-(3,4-dichloro-N-methylphenylsulfonamido)cyclohexyloxy)-N-(4-((dimethylamino)(4-fluorophenyl)methyl)cyclohexyl)acetamide
(257) N-(4-((dimethylamino)(phenyl)methyl)cyclohexyl)-2-(1-(phenylsulfonyl)piperidin-4-yloxy)acetamide
(258) 2-(1-(4-chlorophenylsulfonyl)pyrrolidin-3-yloxy)-N-((4-((dimethylamino)(3-fluorophenyl)methyl)cyclohexyl)methyl)acetamide
(259) 2-(1-(2,4-dichlorophenylsulfonyl)pyrrolidin-3-yloxy)-N-(2-(4-((dimethylamino)(3-fluorophenyl)methyl)cyclohexyl)ethyl)acetamide
(260) N-((4-((4-chlorophenyl)(dimethylamino)methyl)cyclohexyl)methyl)-2-(1-(3,4-dimethoxyphenylsulfonyl)pyrrolidin-3-yloxy)acetamide
(261) 2-((1-(3,4-dimethoxyphenylsulfonyl)piperidin-2-yl)methoxy)-N-(4-((dimethylamino)(thiophen-2-yl)methyl)cyclohexyl)acetamide
(262) 2-(1-(3,4-dimethoxyphenylsulfonyl)pyrrolidin-3-yloxy)-N-(2-(4-((dimethylamino)(3-fluorophenyl)methyl)cyclohexyl)ethyl)acetamide
(263) N-((4-((4-chlorophenyl)(dimethylamino)methyl)cyclohexyl)methyl)-2-(2-(4-fluoro-N-methylphenylsulfonamido)ethoxy)acetamide
(264) N-(2-(4-((dimethylamino)(3-fluorophenyl)methyl)cyclohexyl)ethyl)-2-(1-(mesitylsulfonyl)pyrrolidin-3-yloxy)acetamide
(265) N-((4-((dimethylamino)(3-fluorophenyl)methyl)cyclohexyl)methyl)-2-(1-(4-methoxy-2,6-dimethylphenylsulfonyl)pyrrolidin-3-yloxy)acetamide
(266) N-(4-((dimethylamino)(3-fluorophenyl)methyl)cyclohexyl)-2-((1-(phenylsulfonyl)piperidin-3-yl)methoxy)acetamide
(267) 2-((1-(3,4-dichlorophenylsulfonyl)pyrrolidin-2-yl)methoxy)-N-((4-((dimethylamino)(4-fluorophenyl)methyl)cyclohexyl)methyl)acetamide
(268) N-(4-((dimethylamino)(3-fluorophenyl)methyl)cyclohexyl)-2-((1-(4-methoxyphenylsulfonyl)pyrrolidin-2-yl)methoxy)acetamide
(269) N-((4-((4-chlorophenyl)(dimethylamino)methyl)cyclohexyl)methyl)-2-(2-(3,4-dichloro-N-methylphenylsulfonamido)cyclohexyloxy)acetamide
(270) N-(2-(4-((dimethylamino)(phenyl)methyl)cyclohexyl)ethyl)-2-phenoxypropanamide
(271) N-(4-((dimethylamino)(3-fluorophenyl)methyl)cyclohexyl)-2-(1-(phenylsulfonyl)pyrrolidin-3-yloxy)acetamide
(272) N-(2-(4-((dimethylamino)(thiophen-2-yl)methyl)cyclohexyl)ethyl)-2-(1-tosylpyrrolidin-3-yloxy)acetamide
(273) N-((4-((4-chlorophenyl)(dimethylamino)methyl)cyclohexyl)methyl)-2-(2-(N,4-dimethylphenylsulfonamido)ethoxy)acetamide
(274) N-(2-(4-((4-chlorophenyl)(dimethylamino)methyl)cyclohexyl)ethyl)-2-(2-(2,6-dichloro-N-methylphenylsulfonamido)ethoxy)acetamide
(275) N-((4-((dimethylamino)(3-fluorophenyl)methyl)cyclohexyl)methyl)-2-(1-(4-fluorophenylsulfonyl)pyrrolidin-3-yloxy)acetamide
(276) N-((4-((dimethylamino)(thiophen-2-yl)methyl)cyclohexyl)methyl)-2-(1-(phenylsulfonyl)piperidin-4-yloxy)acetamide
(277) N-(4-((dimethylamino)(3-fluorophenyl)methyl)cyclohexyl)-2-(1-(phenylsulfonyl)piperidin-3-yloxy)acetamide
(278) 2-(2-(N-benzylphenylsulfonamido)ethoxy)-N-(2-(4-((dimethylamino)(3-fluorophenyl)methyl)cyclohexyl)ethyl)acetamide
(279) N-(4-((dimethylamino)(3-fluorophenyl)methyl)cyclohexyl)-2-(1-(4-methoxy-2,3,6-trimethylphenylsulfonyl)piperidin-3-yloxy)acetamide
(280) N-((4-((4-chlorophenyl)(dimethylamino)methyl)cyclohexyl)methyl)-2-((1-(2,4-dimethoxyphenylsulfonyl)piperidin-2-yl)methoxy)acetamide
(281) 2-((1-(2,4-dimethoxyphenylsulfonyl)piperidin-2-yl)methoxy)-N-(2-(4-((dimethylamino)(3-fluorophenyl)methyl)cyclohexyl)ethyl)acetamide
(282) N-(4-((dimethylamino)(thiophen-2-ylmethyl)cyclohexyl)-2-(2-(N-methyl-4-(trifluoromethoxy)phenylsulfonamido)ethoxy)acetamide
(283) 2-(1-(2,4-dichlorophenylsulfonyl)pyrrolidin-3-yloxy)-N-(4-((dimethylamino)(3-fluorophenyl)methyl)cyclohexyl)acetamide
(284) 2-(2-(4-chloro-N-methylphenylsulfonamido)ethoxy)-N-((4-((4-chlorophenyl)(dimethylamino)methyl)cyclohexyl)methyl)acetamide
(285) 2-(2-(2,6-dichloro-N-methylphenylsulfonamido)ethoxy)-N-(2-(4-((dimethylamino)(4-fluorophenyl)methyl)cyclohexyl)ethyl)acetamide
(286) N-(4-((dimethylamino)(3-fluorophenyl)methyl)cyclohexyl)-2-(1-(4-methoxy-2,3,6-trimethylphenylsulfonyl)piperidin-4-yloxy)acetamide
(287) N-((4-((dimethylamino)(3-fluorophenyl)methyl)cyclohexyl)methyl)-2-(1-(4-methoxy-2,3,6-trimethylphenylsulfonyl)piperidin-4-yloxy)acetamide
(288) N-((4-((dimethylamino)(4-fluorophenyl)methyl)cyclohexyl)methyl)-2-((2-(4-methoxyphenylsulfonyl)-1,2,3,4-tetrahydroisoquinolin-3-yl)methoxy)acetamide
(289) N-(2-(4-((4-chlorophenyl)(dimethylamino)methyl)cyclohexyl)ethyl)-2-(2-(N-methyl-3-(trifluoromethyl)phenylsulfonamido)ethoxy)acetamide
(290) 2-(1-(2,4-dichlorophenylsulfonyl)pyrrolidin-3-yloxy)-N-(4-((dimethylamino)(4-fluorophenyl)methyl)cyclohexyl)acetamide
(291) N-(2-(4-((4-chlorophenyl)(dimethylamino)methyl)cyclohexyl)ethyl)-2-(2-(2,4-dichloro-N-methylphenylsulfonamido)ethoxy)acetamide
(292) N-(2-(4-((dimethylamino)(3-fluorophenyl)methyl)cyclohexyl)ethyl)-2-(2-(4-methoxy-N-methylphenylsulfonamido)ethoxy)acetamide
(293) 2-(2-(3,4-dimethoxy-N-methylphenylsulfonamido)ethoxy)-N-(2-(4-((dimethylamino)(3-fluorophenyl)methyl)cyclohexyl)ethyl)acetamide
(294) N-((4-((4-chlorophenyl)(dimethylamino)methyl)cyclohexyl)methyl)-2-((1-(phenylsulfonyl)piperidin-3-yl)methoxy)acetamide
(295) N-(2-(4-((dimethylamino)(3-fluorophenyl)methyl)cyclohexyl)ethyl)-2-((1-(phenylsulfonyl)piperidin-3-yl)methoxy)acetamide
(296) 2-(2-(N-benzylphenylsulfonamido)ethoxy)-N-((4-((dimethylamino)(3-fluorophenyl)methyl)cyclohexyl)methyl)acetamide
(297) N-(4-((dimethylamino)(3-fluorophenyl)methyl)cyclohexyl)-2-(2-(N-methyl-3-(trifluoromethyl)phenylsulfonamido)ethoxy)acetamide
(298) N-((4-((4-chlorophenyl)(dimethylamino)methyl)cyclohexyl)methyl)-2-(2-(4-methoxy-N,2,3,6-tetramethylphenylsulfonamido)ethoxy)acetamide
(299) N-((4-((4-chlorophenyl)(dimethylamino)methyl)cyclohexyl)methyl)-2-(1-(phenylsulfonyl)pyrrolidin-3-yloxy)acetamide
(300) N-((4-((dimethylamino)(phenyl)methyl)cyclohexyl)methyl)-2-(1-(phenylsulfonyl)piperidin-4-yloxy)acetamide (301) N-((4-((4-chlorophenyl)(dimethylamino)methyl)cyclohexyl)methyl)-2-(1-(phenylsulfonyl)piperidin-3-yloxy)acetamide
(302) N-((4-((dimethylamino)(3-fluorophenyl)methyl)cyclohexyl)methyl)-2-(2-(N-methyl-3-(trifluoromethyl)phenylsulfonamido)ethoxy)acetamide
(303) N-((4-((dimethylamino)(3-fluorophenyl)methyl)cyclohexyl)methyl)-2-(2-(N-methyl-4-(trifluoromethoxy)phenylsulfonamido)ethoxy)acetamide
(304) N-((4-((4-chlorophenyl)(dimethylamino)methyl)cyclohexyl)methyl)-2-(1-tosylpyrrolidin-3-yloxy)acetamide
(305) N-(2-(4-((4-chlorophenyl)(dimethylamino)methyl)cyclohexyl)ethyl)-2-(1-tosylpyrrolidin-3-yloxy)acetamide
(306) N-(2-(4-((4-chlorophenyl)(dimethylamino)methyl)cyclohexyl)ethyl)-2-(2-(N,4-dimethylphenylsulfonamido)ethoxy)acetamide
(307) N-(2-(4-((dimethylamino)(3-fluorophenyl)methyl)cyclohexyl)ethyl)-2-(1-(4-methoxy-2,6-dimethylphenylsulfonyl)pyrrolidin-3-yloxy)acetamide
(308) N-((4-((dimethylamino)(3-fluorophenyl)methyl)cyclohexyl)methyl)-2-(2-(4-(phenylsulfonyl)piperazin-1-yl)ethoxy)acetamide
(309) N-((4-((dimethylamino)(3-fluorophenyl)methyl)cyclohexyl)methyl)-2-(1-(phenylsulfonyl)piperidin-3-yloxy)acetamide
(310) N-((4-((4-chlorophenyl)(dimethylamino)methyl)cyclohexyl)methyl)-2-(2-(N-ethyl-4-methoxy-2,3,6-trimethylphenylsulfonamido)ethoxy)acetamide
(311) N-(2-(4-((4-chlorophenyl)(dimethylamino)methyl)cyclohexyl)ethyl)-2-((1-(4-methoxyphenylsulfonyl)piperidin-2-yl)methoxy)acetamide
(312) N-((4-((4-chlorophenyl)(dimethylamino)methyl)cyclohexyl)methyl)-2-(2-(1-(4-methoxyphenylsulfonyl)piperidin-2-yl)ethoxy)acetamide
(313) N-((4-((dimethylamino)(3-fluorophenyl)methyl)cyclohexyl)methyl)-2-((1-(4-methoxyphenylsulfonyl)pyrrolidin-2-yl)methoxy)acetamide
(314) N-((4-((4-chlorophenyl)(dimethylamino)methyl)cyclohexyl)methyl)-2-(2-(N-methyl-3-(trifluoromethyl)phenylsulfonamido)ethoxy)acetamide
(315) N-(2-(4-((dimethylamino)(thiophen-2-yl)methyl)cyclohexyl)ethyl)-2-phenoxypropanamide
(316) 2-(4-chlorophenoxy)-N-(4-(((dimethylamino)(phenyl)methyl)cyclohexyl)acetamide
(317) N-(2-(4-((4-chlorophenyl)(dimethylamino)methyl)cyclohexyl)ethyl)-2-(2-(4-methoxy-N,2,3,6-tetramethylphenylsulfonamido)ethoxy)acetamide
(318) N-((4-((4-chlorophenyl)(dimethylamino)methyl)cyclohexyl)methyl)-2-(2-(2,4,6-trichloro-N-methylphenylsulfonamido)ethoxy)acetamide
(319) N-((4-((dimethylamino)(3-fluorophenyl)methyl)cyclohexyl)methyl)-2-(2-(1-(4-methoxy-2,3,6-trimethylphenylsulfonyl)piperidin-4-yl)ethoxy)acetamide
(320) N-(2-(4-((4-chlorophenyl)(dimethylamino)methyl)cyclohexyl)ethyl)-2-(2-(4-(4-methoxy-2,3,6-trimethylphenylsulfonyl)piperazin-1-yl)ethoxy)acetamide
(321) N-((4-((4-chlorophenyl)(dimethylamino)methyl)cyclohexyl)methyl)-2-((1-(4-methoxyphenylsulfonyl)piperidin-2-yl)methoxy)acetamide
(322) 2-((1-(2,4-dimethoxyphenylsulfonyl)piperidin-2-yl)methoxy)-N-(4-((dimethylamino)(3-fluorophenyl)methyl)cyclohexyl)acetamide
(323) 2-(1-(3,4-dimethoxyphenylsulfonyl)pyrrolidin-3-yloxy)-N-((4-((dimethylamino)(3-fluorophenyl)methyl)cyclohexyl)acetamide
(324) N-((4-((4-chlorophenyl)(dimethylamino)methyl)cyclohexyl)methyl)-2-(2-(4-methoxy-N-methylphenylsulfonamido)ethoxy)acetamide
(325) N-(2-(4-((dimethylamino)(3-fluorophenyl)methyl)cyclohexyl)ethyl)-2-(2-(4-(phenylsulfonyl)piperazin-1-yl)ethoxy)acetamide
(326) N-(2-(4-((dimethylamino)(3-fluorophenyl)methyl)cyclohexyl)ethyl)-2-(1-(phenylsulfonyl)piperidin-3-yloxy)acetamide
(327) N-((4-((dimethylamino)(4-fluorophenyl)methyl)cyclohexyl)methyl)-2-(2-(N-ethyl-4-methoxy-2,3,6-trimethylphenylsulfonamido)ethoxy)acetamide
(328) 2-((1-(3,4-dichlorophenylsulfonyl)piperidin-2-yl)methoxy)-N-(4-((dimethylamino)(4-fluorophenyl)methyl)cyclohexyl)acetamide
(329) 2-((1-(3,4-dimethoxyphenylsulfonyl)piperidin-2-yl)methoxy)-N-((4-((dimethylamino)(3-fluorophenyl)methyl)cyclohexyl)methyl)acetamide
(330) N-(4-((dimethylamino)(4-fluorophenyl)methyl)cyclohexyl)-2-(1-(3-(trifluoromethyl)phenylsulfonyl)pyrrolidin-3-yloxy)acetamide
(331) N-((4-((4-chlorophenyl)(dimethylamino)methyl)cyclohexyl)methyl)-2-(1-(3-(trifluoromethyl)phenylsulfonyl)pyrrolidin-3-yloxy)acetamide
(332) N-(4-((dimethylamino)(4-fluorophenyl)methyl)cyclohexyl)-2-(1-(mesitylsulfonyl)pyrrolidin-3-yloxy)acetamide
(333) N-((4-((dimethylamino)(3-fluorophenyl)methyl)cyclohexyl)methyl)-2-(2-(1-(phenylsulfonyl)piperidin-4-yl)ethoxy)acetamide
(334) 2-(2-(2,6-dichloro-N-methylphenylsulfonamido)ethoxy)-N-((4-((dimethylamino)(4-fluorophenyl)methyl)cyclohexyl)methyl)acetamide
(335) N-(4-((dimethylamino)(3-fluorophenyl)methyl)cyclohexyl)-2-(1-(phenylsulfonyl)piperidin-4-yloxy)acetamide
(336) 2-(2-(N-benzylphenylsulfonamido)ethoxy)-N-(4-((dimethylamino)(4-fluorophenyl)methyl)cyclohexyl)acetamide
(337) 2-((1-(3,4-dichlorophenylsulfonyl)piperidin-2-yl)methoxy)-N-(2-(4-((dimethylamino)(4-fluorophenyl)methyl)cyclohexyl)ethyl)acetamide
(338) N-(2-(4-((4-chlorophenyl)(dimethylamino)methyl)cyclohexyl)ethyl)-2-(1-(3,4-dimethoxyphenylsulfonyl)pyrrolidin-3-yloxy)acetamide
(339) N-(2-(4-((4-chlorophenyl)(dimethylamino)methyl)cyclohexyl)ethyl)-2-(2-(3,4-dimethoxy-N-methylphenylsulfonamido)ethoxy)acetamide
(340) N-((4-((dimethylamino)(3-fluorophenyl)methyl)cyclohexyl)methyl)-2-(2-(4-methoxy-N-methylphenylsulfonamido)ethoxy)acetamide
(341) N-(4-((dimethylamino)(thiophen-2-yl)methyl)cyclohexyl)-2-(2-(4-(phenylsulfonyl)piperazin-1-yl)ethoxy)acetamide
(342) 2-(2-(N-benzylphenylsulfonamido)ethoxy)-N-((4-((dimethylamino)(4-fluorophenyl)methyl)cyclohexyl)methyl)acetamide
(343) 2-(2-(N-benzylphenylsulfonamido)ethoxy)-N-((4-((4-chlorophenyl)(dimethylamino)methyl)cyclohexyl)methyl)acetamide
(344) 2-((1-(3,4-dichlorophenylsulfonyl)pyrrolidin-2-yl)methoxy)-N-(4-((dimethylamino)(4-fluorophenyl)methyl)cyclohexyl)acetamide
(345) N-((4-((dimethylamino)(4-fluorophenyl)methyl)cyclohexyl)methyl)-2-((1-(4-methoxyphenylsulfonyl)piperidin-2-yl)methoxy)acetamide (346) N-(2-(4-((4-chlorophenyl)(dimethylamino)methyl)cyclohexyl)ethyl)-2-((1-(4-methoxyphenylsulfonyl)pyrrolidin-2-yl)methoxy)acetamide
(347) 2-(2-(4-chloro-N-methylphenylsulfonamido)ethoxy)-N-(2-(4-((4-chlorophenyl)(dimethylamino)methyl)cyclohexyl)ethyl)acetamide
(348) N-((4-((4-chlorophenyl)(dimethylamino)methyl)cyclohexyl)methyl)-2-(2-(4-methoxy-N,2,6-trimethylphenylsulfonamido)ethoxy)acetamide
(349) N-(2-(4-((dimethylamino)(4-fluorophenyl)methyl)cyclohexyl)ethyl)-2-((1-(4-methoxyphenylsulfonyl)piperidin-2-yl)methoxy)acetamide
(350) N-((4-((dimethylamino)(4-fluorophenyl)methyl)cyclohexyl)methyl)-2-(2-(1-(4-methoxyphenylsulfonyl)piperidin-2-yl)ethoxy)acetamide
(351) N-((4-((4-chlorophenyl)(dimethylamino)methyl)cyclohexyl)methyl)-2-((1-(4-methoxyphenylsulfonyl)pyrrolidin-2-yl)methoxy)acetamide
(352) 2-((1-(3,4-dimethoxyphenylsulfonyl)piperidin-2-yl)methoxy)-N-(4-((dimethylamino)(3-fluorophenyl)methyl)cyclohexyl)acetamide
(353) 2-(benzyloxy)-N-(4-((dimethylamino)(3-fluorophenyl)-methyl)cyclohexyl)acetamide
(354) N-(2-(4-((dimethylamino)(4-fluorophenyl)methyl)cyclohexyl)ethyl)-2-(2-(4-methoxy-N,2,3,6-tetramethylphenylsulfonamido)ethoxy)acetamide
(355) N-((4-((dimethylamino)(3-fluorophenyl)methyl)cyclohexyl)methyl)-2-(1-(phenylsulfonyl)pyrrolidin-3-yloxy)acetamide
(356) 2-(2-(2,4-dichloro-N-methylphenylsulfonamido)ethoxy)-N-(4-((dimethylamino)(4-fluorophenyl)methyl)cyclohexyl)acetamide
(357 N-(4-((dimethylamino)(4-fluorophenyl)methyl)cyclohexyl)-2-(2-(4-fluoro-N-methylphenylsulfonamido)ethoxy)acetamide
(358) 2-(2-(N-benzyl-4-methoxy-2,6-dimethylphenylsulfonamido)ethoxy)-N-(2-(4-((dimethylamino)(3-fluorophenyl)methyl)cyclohexyl)ethyl)acetamide
(359) 2-(2-(3,4-dichloro-N-methylphenylsulfonamido)cyclohexyloxy)-N-((4-((dimethylamino)(4-fluorophenyl)methyl)cyclohexyl)methyl)acetamide
(360) 2-((4-((4-chlorophenyl)(dimethylamino)methyl)cyclohexyl)methylamino)-2-oxo-1-phenylethyl acetate
(361) N-(4-((dimethylamino)(4-fluorophenyl)methyl)cyclohexyl)-2-(2-(N-methyl-4-(trifluoromethoxy)phenylsulfonamido)ethoxy)acetamide
(362) N-((4-((dimethylamino)(4-fluorophenyl)methyl)cyclohexyl)methyl)-2-(2-(N,4-dimethylphenylsulfonamido)ethoxy)acetamide
(363) 2-(2-(2,6-dichloro-N-methylphenylsulfonamido)ethoxy)-N-(4-((dimethylamino) (4-fluorophenyl)methyl)cyclohexyl)acetamide
(364) N-(4-((dimethylamino)(3-fluorophenyl)methyl)cyclohexyl)-2-(2-(4-(phenylsulfonyl)piperazin-1-yl)ethoxy)acetamide
(365) N-(4-((dimethylamino)(4-fluorophenyl)methyl)cyclohexyl)-2-(1-(4-methoxy-2,3,6-trimethylphenylsulfonyl)pyrrolidin-3-yloxy)acetamide
(366) N-((4-((dimethylamino)(4-fluorophenyl)methyl)cyclohexyl)methyl)-2-(2-(4-(4-methoxy-2,3,6-trimethylphenylsulfonyl)piperazin-1-yl)ethoxy)acetamide
(367) N-((4-((4-chlorophenyl)(dimethylamino)methyl)cyclohexyl)methyl)-2-((1-(3,4-dimethoxyphenylsulfonyl)piperidin-2-yl)methoxy)acetamide
(368) N-(2-(4-((dimethylamino)(4-fluorophenyl)methyl)cyclohexyl)ethyl)-2-(2-(N-methyl-3-(trifluoromethyl)phenylsulfonamido)ethoxy)acetamide
(369) 2-((2-(3,4-dichloro-N-methylphenylsulfonamido)-4,5,6,7-tetrahydrobenzo[b]thiophen-3-yl)methoxy)-N-(4-((dimethylamino) (phenyl)methyl)cyclohexyl)acetamide
(370) 2-(1-(4-chlorophenylsulfonyl)pyrrolidin-3-yloxy)-N-(4-((dimethylamino)(4-fluorophenyl)methyl)cyclohexyl)acetamide
(371) N-(4-((dimethylamino)(4-fluorophenyl)methyl)cyclohexyl)-2-(1-tosylpyrrolidin-3-yloxy)acetamide
(372) 2-(2-(N-benzyl-4-methoxy-2,6-dimethylphenylsulfonamido)ethoxy)-N-(4-((dimethylamino)(3-fluorophenyl)methyl)cyclohexyl)acetamide
(373) N-((4-(1-(dimethylamino)-3-phenylpropyl)cyclohexyl)methyl)-2-((2-(4-methoxyphenylsulfonyl)-1,2,3,4-tetrahydroisoquinolin-3-yl)methoxy)acetamide
(374) N-(2-(4-((4-chlorophenyl)(dimethylamino)methyl)cyclohexyl)ethyl)-2-((2-(4-methoxyphenylsulfonyl)-1,2,3,4-tetrahydroisoquinolin-3-yl)methoxy)acetamide
(375) N-(2-(4-((4-chlorophenyl)(dimethylamino)methyl)cyclohexyl)ethyl)-2-(1-(phenylsulfonyl)pyrrolidin-3-yloxy)acetamide
(376) N-(2-(4-((dimethylamino)(3-fluorophenyl)methyl)cyclohexyl)ethyl)-2-(1-(phenylsulfonyl)pyrrolidin-3-yloxy)acetamide
(377) 2-(2-(4-chloro-N-methylphenylsulfonamido)ethoxy)-N-(2-(4-((dimethylamino)(4-fluorophenyl)methyl)cyclohexyl)ethyl)acetamide
(378) N-(2-(4-((4-chlorophenyl)(dimethylamino)methyl)cyclohexyl)ethyl)-2-(2-(4-methoxy-N,2,6-trimethylphenylsulfonamido)ethoxy)acetamide
(379) N-((4-((4-chlorophenyl)(dimethylamino)methyl)cyclohexyl)methyl)-2-(2-(3,4-dimethoxy-N-methylphenylsulfonamido)ethoxy)acetamide
(380) N-(4-((dimethylamino)(4-fluorophenyl)methyl)cyclohexyl)-2-(2-(4-methoxy-N,2,3,6-tetramethylphenylsulfonamido)ethoxy)acetamide
(381) N-(4-((dimethylamino)(4-fluorophenyl)methyl)cyclohexyl)-2-(1-(4-fluorophenylsulfonyl)pyrrolidin-3-yloxy)acetamide
(382) N-(4-((dimethylamino)(4-fluorophenyl)methyl)cyclohexyl)-2-(2-(2,4,6-trichloro-N-methylphenylsulfonamido)ethoxy)acetamide
(383) N-(2-(4-((4-chlorophenyl)(dimethylamino)methyl)cyclohexyl)ethyl)-2-(2-(1-(4-methoxyphenylsulfonyl)piperidin-2-yl)ethoxy)acetamide
(384) N-((4-((4-chlorophenyl)(dimethylamino)methyl)cyclohexyl)methyl)-2-(1-(4-chlorophenylsulfonyl)pyrrolidin-3-yloxy)acetamide
(385) N-(2-(4-((dimethylamino)(thiophen-2-yl)methyl)cyclohexyl)ethyl)-2-(2-(N,2,4,6-tetramethylphenylsulfonamido)ethoxy)acetamide
(386) N-(2-(4-((dimethylamino)(4-fluorophenyl)methyl)cyclohexyl)ethyl)-2-(2-(2,4,6-trichloro-N-methylphenylsulfonamido)ethoxy)acetamide
(387) N-(2-(4-((dimethylamino)(4-fluorophenyl)methyl)cyclohexyl)ethyl)-2-(2-(4-(4-methoxy-2,3,6-trimethylphenylsulfonyl)piperazin-1-yl)ethoxy)acetamide
(388) 2-(2-(N-benzyl-4-methoxy-2,6-dimethylphenylsulfonamido)ethoxy)-N-((4-((dimethylamino)(3-fluorophenyl)methyl)cyclohexyl)methyl)acetamide
(389) N-(2-(4-((dimethylamino)(4-fluorophenyl)methyl)cyclohexyl)ethyl)-2-((2-(4-methoxyphenylsulfonyl)-1,2,3,4-tetrahydroisoquinolin-3-yl)methoxy)acetamide
(390) N-((4-((dimethylamino)(4-fluorophenyl)methyl)cyclohexyl)methyl)-2-(2-(N-methyl-3-(trifluoromethyl)phenylsulfonamido)ethoxy)acetamide (391) 2-(1-(2,4-dichlorophenylsulfonyl)pyrrolidin-3-yloxy)-N-((4-((dimethylamino)(4-fluorophenyl)methyl)cyclohexyl)methyl)acetamide
(392) N-(2-(4-((dimethylamino)(4-fluorophenyl)methyl)cyclohexyl)ethyl)-2-(2-(4-methoxy-N,2,6-trimethylphenylsulfonamido)ethoxy)acetamide
(393) N-((4-((4-chlorophenyl)(dimethylamino)methyl)cyclohexyl)methyl)-2-(1-(mesitylsulfonyl)pyrrolidin-3-yloxy)acetamide
(394) N-((4-((4-chlorophenyl)(dimethylamino)methyl)cyclohexyl)methyl)-2-(1-(4-fluorophenylsulfonyl)pyrrolidin-3-yloxy)acetamide
(395) N-(2-(4-((4-chlorophenyl)(dimethylamino)methyl)cyclohexyl)ethyl)-2-(1-(phenylsulfonyl)piperidin-3-yloxy)acetamide
(396) N-(4-((dimethylamino)(4-fluorophenyl)methyl)cyclohexyl)-2-(2-(N-ethyl-4-methoxy-2,3,6-trimethylphenylsulfonamido)ethoxy)acetamide
(397) N-(2-(4-((dimethylamino)(3-fluorophenyl)methyl)cyclohexyl)ethyl)-2-(2-(1-(4-methoxy-2,3,6-trimethylphenylsulfonyl)piperidin-4-yl)ethoxy)acetamide
(398) N-(2-(4-((dimethylamino)(4-fluorophenyl)methyl)cyclohexyl)ethyl)-2-(2-(1-(4-methoxyphenylsulfonyl)piperidin-2-yl)ethoxy)acetamide
(399) 2-(2-(4-chloro-N-methylphenylsulfonamido)ethoxy)-N-((4-((dimethylamino)(4-fluorophenyl)methyl)cyclohexyl)methyl)acetamide
(400) N-((4-((dimethylamino)(4-fluorophenyl)methyl)cyclohexyl)methyl)-2-(2-(4-fluoro-N-methylphenylsulfonamido)ethoxy)acetamide
(401) 2-(2-(3,4-dimethoxy-N-methylphenylsulfonamido)ethoxy)-N-(4-((dimethylamino)(3-fluorophenyl)methyl)cyclohexyl)acetamide
(402) N-((4-((dimethylamino)(4-fluorophenyl)methyl)cyclohexyl)methyl)-2-(1-(3-(trifluoromethyl)phenylsulfonyl)pyrrolidin-3-yloxy)acetamide
(403) N-((4-((4-chlorophenyl)(dimethylamino)methyl)cyclohexyl)methyl)-2-(1-(4-methoxy-2,6-dimethylphenylsulfonyl)pyrrolidin-3-yloxy)acetamide
(404) N-((4-((dimethylamino)(4-fluorophenyl)methyl)cyclohexyl)methyl)-2-(2-(2,4,6-trichloro-N-methylphenylsulfonamido)ethoxy)acetamide
(405) 2-((1-(2,4-dimethoxyphenylsulfonyl)piperidin-2-yl)methoxy)-N-((4-((dimethylamino)(4-fluorophenyl)methyl)cyclohexyl)methyl)acetamide
(406) 2-(2-(4-chloro-N-methylphenylsulfonamido)ethoxy)-N-(4-((dimethylamino)(4-fluorophenyl)methyl)cyclohexyl)acetamide
(407) N-(2-(4-((dimethylamino)(3-fluorophenyl)methyl)cyclohexyl)ethyl)-2-(1-(4-fluorophenylsulfonyl)pyrrolidin-3-yloxy)acetamide
(408) N-(4-((dimethylamino)(4-fluorophenyl)methyl)cyclohexyl)-2-(1-(phenylsulfonyl)piperidin-4-yloxy)acetamide
(409) N-(2-(4-((dimethylamino)(4-fluorophenyl)methyl)cyclohexyl)ethyl)-2-((1-(4-methoxyphenylsulfonyl)pyrrolidin-2-yl)methoxy)acetamide
(410) N-(2-(4-((4-chlorophenyl)(dimethylamino)methyl)cyclohexyl)ethyl)-2-(2-(3,4-dichloro-N-methylphenylsulfonamido)cyclohexyloxy)acetamide
(411) N-((4-((4-chlorophenyl)(dimethylamino)methyl)cyclohexyl)methyl)-2-(2-(N-methyl-4-(trifluoromethoxy)phenylsulfonamido)ethoxy)acetamide
(412) N-(2-(4-((4-chlorophenyl)(dimethylamino)methyl)cyclohexyl)ethyl)-2-(1-(4-methoxy-2,3,6-trimethylphenylsulfonyl)pyrrolidin-3-yloxy)acetamide
(413) N-(2-(4-((dimethylamino)(4-fluorophenyl)methyl)cyclohexyl)ethyl)-2-(2-(N-ethyl-4-methoxy-2,3,6-trimethylphenylsulfonamido)ethoxy)acetamide
(414) 2-(2-(N-benzyl-4-methoxy-2,3,6-trimethylphenylsulfonamido)ethoxy)-N-((4-((dimethylamino)(3-fluorophenyl)methyl)cyclohexyl)methyl)acetamide
(415) 2-((1-(3,4-dichlorophenylsulfonyl)pyrrolidin-2-yl)methoxy)-N-((4-(1-(dimethylamino)-3-phenylpropyl)cyclohexyl)methyl)acetamide
(416) N-(2-(4-((4-chlorophenyl)(dimethylamino)methyl)cyclohexyl)ethyl)-2-(2-(N,2,4,6-tetramethylphenylsulfonamido)ethoxy)acetamide
(417) N-(2-(4-((dimethylamino)(4-fluorophenyl)methyl)cyclohexyl)ethyl)-2-(2-(N,2,4,6-tetramethylphenylsulfonamido)ethoxy)acetamide
(418) N-((4-((dimethylamino)(4-fluorophenyl)methyl)cyclohexyl)methyl)-2-(1-(4-methoxy-2,3,6-trimethylphenylsulfonyl)piperidin-3-yloxy)acetamide
(419) 2-(2-(N-benzyl-4-methoxy-2,3,6-trimethylphenylsulfonamido)ethoxy)-N-(4-((dimethylamino)(3-fluorophenyl)methyl)cyclohexyl)acetamide
(420) 2-((1-(2,4-dimethoxyphenylsulfonyl)piperidin-2-yl)methoxy)-N-((4-(1-(dimethylamino)-3-phenylpropyl)cyclohexyl)methyl)acetamide
(421) ethyl 2-((4-(1-(dimethylamino)-3-phenylpropyl)cyclohexyl)methylamino)-2-oxoacetate
(422) N-(4-((dimethylamino)(4-fluorophenyl)methyl)cyclohexyl)-2-(2-(4-methoxy-N,2,6-trimethylphenylsulfonamido)ethoxy)acetamide
(423) N-(4-((dimethylamino)(4-fluorophenyl)methyl)cyclohexyl)-2-(1-(phenylsulfonyl)piperidin-3-yloxy)acetamide
(424) N-((4-((dimethylamino)(4-fluorophenyl)methyl)cyclohexyl)methyl)-2-((1-(phenylsulfonyl)piperidin-3-yl)methoxy)acetamide
(425) N-(2-(4-((4-chlorophenyl)(dimethylamino)methyl)cyclohexyl)ethyl)-2-((1-(phenylsulfonyl)piperidin-3-yl)methoxy)acetamide
(426) 2-(2-(N-benzylphenylsulfonamido)ethoxy)-N-(2-(4-((4-chlorophenyl)(dimethylamino)methyl)cyclohexyl)ethyl)acetamide
(427) N-((4-((dimethylamino)(4-fluorophenyl)methyl)cyclohexyl)methyl)-2-(1-(4-methoxy-2,3,6-trimethylphenylsulfonyl)pyrrolidin-3-yloxy)acetamide
(428) N-((4-((4-chlorophenyl)(dimethylamino)methyl)cyclohexyl)methyl)-2-(1-(4-methoxy-2,3,6-trimethylphenylsulfonyl)pyrrolidin-3-yloxy)acetamide
(429) N-((4-((4-chlorophenyl)(dimethylamino)methyl)cyclohexyl)methyl)-2-(2-(4-(4-methoxy-2,3,6-trimethylphenylsulfonyl)piperazin-1-yl)ethoxy)acetamide
(430) 2-(1-(3,4-dimethoxyphenylsulfonyl)pyrrolidin-3-yloxy)-N-(2-(4-((dimethylamino)(4-fluorophenyl)methyl)cyclohexyl)ethyl)acetamide
(431) N-(2-(4-((4-chlorophenyl)(dimethylamino)methyl)cyclohexyl)ethyl)-2-(1-(3-(trifluoromethyl)phenylsulfonyl)pyrrolidin-3-yloxy)acetamide
(432) N-((4-((dimethylamino)(4-fluorophenyl)methyl)cyclohexyl)methyl)-2-(1-(mesitylsulfonyl)pyrrolidin-3-yloxy)acetamide
(433) N-((4-((dimethylamino)(4-fluorophenyl)methyl)cyclohexyl)methyl)-2-(2-(4-(phenylsulfonyl)piperazin-1-yl)ethoxy)acetamide
(434) N-(2-(4-((4-chlorophenyl)(dimethylamino)methyl)cyclohexyl)ethyl)-2-(2-(N-ethyl-4-methoxy-2,3,6-trimethylphenylsulfonamido)ethoxy)acetamide
(435) N-(4-((dimethylamino)(4-fluorophenyl)methyl)cyclohexyl)-2-(1-(4-methoxy-2,3,6-trimethylphenylsulfonyl)piperidin-3-yloxy)acetamide (436) 2-(2-(N-benzyl-4-methoxy-2,3,6-trimethylphenylsulfonamido)ethoxy)-N-(2-(4-(((dimethylamino)(3-fluorophenyl)methyl)cyclohexyl)ethyl)acetamide
(437) 2-((1-(3,4-dichlorophenylsulfonyl)piperidin-2-yl)methoxy)-N-((4-(1-(dimethylamino)-3-phenylpropyl)cyclohexyl)methyl)acetamide
(438) N-(4-((dimethylamino)(4-fluorophenyl)methyl)cyclohexyl)-2-(2-(N-methyl-3-(trifluoromethyl)phenylsulfonamido)ethoxy)acetamide
(439) N-((4-((dimethylamino)(4-fluorophenyl)methyl)cyclohexyl)methyl)-2-(2-(N-methyl-4-(trifluoromethoxy)phenylsulfonamido)ethoxy)acetamide
(440) N-(2-(4-((4-chlorophenyl)(dimethylamino)methyl)cyclohexyl)ethyl)-2-(1-(4-fluorophenylsulfonyl)pyrrolidin-3-yloxy)acetamide
(441) N-(4-((dimethylamino)(4-fluorophenyl)methyl)cyclohexyl)-2-(1-(4-methoxy-2,6-dimethylphenylsulfonyl)pyrrolidin-3-yloxy)acetamide
(442) N-(2-(4-((4-chlorophenyl)(dimethylamino)methyl)cyclohexyl)ethyl)-2-(2-(2,4,6-trichloro-N-methylphenylsulfonamido)ethoxy)acetamide
(443) N-(2-(4-((4-chlorophenyl)(dimethylamino)methyl)cyclohexyl)ethyl)-2-(1-(phenylsulfonyl)piperidin-4-yloxy)acetamide
(444) N-(2-(4-((dimethylamino)(3-fluorophenyl)methyl)cyclohexyl)ethyl)-2-(1-(phenylsulfonyl)piperidin-4-yloxy)acetamide
(445) 2-(2-(4-chloro-N-methylphenylsulfonamido)ethoxy)-N-((4-(1-(dimethylamino)-3-phenylpropyl)cyclohexyl)methyl)acetamide
(446) N-(2-(4-((dimethylamino)(4-fluorophenyl)methyl)cyclohexyl)ethyl)-2-(2-(N-methyl-4-(trifluoromethoxy)phenylsulfonamido)ethoxy)acetamide
(447) N-((4-((dimethylamino)(4-fluorophenyl)methyl)cyclohexyl)methyl)-2-(1-tosylpyrrolidin-3-yloxy)acetamide
(448) N-(4-((dimethylamino)(4-fluorophenyl)methyl)cyclohexyl)-2-(2-(N,4-dimethylphenylsulfamido)ethoxy)acetamide
(449) N-((4-((4-chlorophenyl)(dimethylamino)methyl)cyclohexyl)methyl)-2-(1-(4-methoxy-2,3,6-trimethylphenylsulfonyl)piperidin-3-yloxy)acetamide
(450) N-(4-((dimethylamino)(4-fluorophenyl)methyl)cyclohexyl)-2-((1-(4-methoxyphenyl sulfonyl)piperidin-2-yl)methoxy)acetamide
(451) 2-(2-(3,4-dichloro-N-methylphenylsulfonamido)cyclohexyloxy)-N-((4-(1-(dimethylamino)-3-phenylpropyl)cyclohexyl)methyl)acetamide
(452) N-((4-(1-(dimethylamino)-3-phenylpropyl)cyclohexyl)methyl)-2-(2-(N,4-dimethylphenylsulfonamido)ethoxy)acetamide
(453) N-((4-(1-(dimethylamino)-3-phenylpropyl)cyclohexyl)methyl)-2-(2-(4-methoxy-N,2,3,6-tetramethylphenylsulfonamido)ethoxy)acetamide
(454) N-(4-((dimethylamino)(4-fluorophenyl)methyl)cyclohexyl)-2-(1-(4-methoxy-2,3,6-trimethylphenylsulfonyl)piperidin-4-yloxy)acetamide
(455) N-(2-(4-((dimethylamino)(4-fluorophenyl)methyl)cyclohexyl)ethyl)-2-phenoxypropanamide
(456) 2-(1-(2,4-dichlorophenylsulfonyl)pyrrolidin-3-yloxy)-N-(2-(4-((dimethylamino)(4-fluorophenyl)methyl)cyclohexyl)ethyl)acetamide
(457) N-(2-(4-((dimethylamino) (4-fluorophenyl)methyl)cyclohexyl)ethyl)-2-(2-(N,4-dimethylphenylsulfonamido)ethoxy)acetamide
(458) N-((4-((dimethylamino)(4-fluorophenyl)methyl)cyclohexyl)methyl)-2-(2-(4-methoxy-N,2,6-trimethylphenylsulfonamido)ethoxy)acetamide
(459) N-((4-((4-chlorophenyl)(dimethylamino)methyl)cyclohexyl)methyl)-2-(2-(2,4-dichloro-N-methylphenylsulfonamido)ethoxy)acetamide
(460) N-(2-(4-((4-chlorophenyl)(dimethylamino)methyl)cyclohexyl)ethyl)-2-(2-(4-methoxy-N-methylphenylsulfonamido)ethoxy)acetamide
(461) N-(4-((dimethylamino)(4-fluorophenyl)methyl)cyclohexyl)-2-((1-(4-methoxyphenylsulfonyl)pyrrolidin-2-yl)methoxy)acetamide
(462) 2-((1-(3,4-dimethoxyphenylsulfonyl)piperidin-2-yl)methoxy)-N-(2-(4-((dimethylamino)(4-fluorophenyl)methyl)cyclohexyl)ethyl)acetamide
(463) N-(4-((dimethylamino)(4-fluorophenyl)methyl)cyclohexyl)-2-(1-(phenylsulfonyl)pyrrolidin-3-yloxy)acetamide
(464) 2-(1-(4-chlorophenylsulfonyl)pyrrolidin-3-yloxy)-N-(2-(4-((dimethylamino)(4-fluorophenyl)methyl)cyclohexyl)ethyl)acetamide
(465) N-(2-(4-((dimethylamino)(thiophen-2-yl)methyl)cyclohexyl)ethyl)-2-(2-(2,3,4,5,6-pentafluoro-N-methylphenylsulfonamido)ethoxy)acetamide
(466) N-(2-(4-((dimethylamino)(4-fluorophenyl)methyl)cyclohexyl)ethyl)-2-(1-(3-(trifluoromethyl)phenylsulfonyl)pyrrolidin-3-yloxy)acetamide
(467) N-(2-(4-((dimethylamino)(4-fluorophenyl)methyl)cyclohexyl)ethyl)-2-(1-(4-methoxy-2,3,6-trimethylphenylsulfonyl)pyrrolidin-3-yloxy)acetamide
(468) N-(2-(4-((dimethylamino)(4-fluorophenyl)methyl)cyclohexyl)ethyl)-2-(1-(4-methoxy-2,3,6-trimethylphenylsulfonyl)piperidin-3-yloxy)acetamide
(469) N-((4-(1-(dimethylamino)-3-phenylpropyl)cyclohexyl)methyl)-2-((1-(4-methoxyphenylsulfonyl)piperidin-2-yl)methoxy)acetamide
(470) N-(2-(4-((dimethylamino)(4-fluorophenyl)methyl)cyclohexyl)ethyl)-2-(2-(1-(phenylsulfonyl)piperidin-4-yl)ethoxy)acetamide
(471) N-((4-((4-chlorophenyl)(dimethylamino)methyl)cyclohexyl)methyl)-2-(1-(phenylsulfonyl)piperidin-4-yloxy)acetamide
(472) N-(2-(4-((4-chlorophenyl)(dimethylamino)methyl)cyclohexyl)ethyl)-2-(1-(4-methoxy-2,3,6-trimethylphenylsulfonyl)piperidin-4-yloxy)acetamide
(473) 2-(2-(N-benzyl-4-methoxy-2,6-dimethylphenylsulfonamido)ethoxy)-N-((4-((4-chlorophenyl)(dimethylamino)methyl)cyclohexyl)methyl)acetamide
(474) N-(2-(4-((4-chlorophenyl)(dimethylamino)methyl)cyclohexyl)ethyl)-2-((1-(2,4-dimethoxyphenylsulfonyl)piperidin-2-yl)methoxy)acetamide
(475) N-((4-(1-(dimethylamino)-3-phenylpropyl)cyclohexyl)methyl)-2-(1-(mesitylsulfonyl)pyrrolidin-3-yloxy)acetamide
(476) 2-(2-(2,6-dichloro-N-methylphenylsulfonamido)ethoxy)-N-((4-(1-(dimethylamino)-3-phenylpropyl)cyclohexyl)methyl)acetamide
(477) N-((4-((dimethylamino)(3-fluorophenyl)methyl)cyclohexyl)methyl)-2-(1-(phenylsulfonyl)piperidin-4-yloxy)acetamide
(478) N-(4-((dimethylamino)(4-fluorophenyl)methyl)cyclohexyl)-2-((1-(phenylsulfonyl)piperidin-3-yl)methoxy)acetamide
(479) N-(2-(4-((dimethylamino)(4-fluorophenyl)methyl)cyclohexyl)ethyl)-2-((1-(phenylsulfonyl)piperidin-3-yl)methoxy)acetamide
(480) N-(2-(4-((dimethylamino)(4-fluorophenyl)methyl)cyclohexyl)ethyl)-2-(1-(4-methoxy-2,3,6-trimethylphenylsulfonyl)piperidin-4-yloxy)acetamide (481) N-((4-((dimethylamino)(4-fluorophenyl)methyl)cyclohexyl)methyl)-2-(2-(1-(4-methoxy-2,3,6-trimethylphenylsulfonyl)piperidin-4-yl)ethoxy)acetamide
(482) 2-(benzyloxy)-N-(2-(4-((4-chlorophenyl)-(dimethylamino)methyl)cyclohexyl)ethyl)acetamide
(483) 2-(2-(N-benzyl-4-methoxy-2,6-dimethylphenylsulfonamido)ethoxy)-N-(4-((dimethylamino)(phenyl)methyl)cyclohexyl)acetamide
(484) 2-(2-(3,4-dimethoxy-N-methylphenylsulfonamido)ethoxy)-N-(2-(4-((dimethylamino)(4-fluorophenyl)methyl)cyclohexyl)ethyl)acetamide
(485) N-(2-(4-((4-chlorophenyl)(dimethylamino)methyl)cyclohexyl)ethyl)-2-(1-(4-methoxy-2,3,6-trimethylphenylsulfonyl)piperidin-3-yloxy)acetamide
(486) 2-((1-(2,4-dimethoxyphenylsulfonyl)piperidin-2-yl)methoxy)-N-((4-(1-(dimethylamino)-3-phenylpropyl)cyclohexyl)methyl)acetamide
(487) N-(2-(4-((dimethylamino)(4-fluorophenyl)methyl)cyclohexyl)ethyl)-2-(2-(4-fluoro-N-methylphenylsulfonamido)ethoxy)acetamide
(488) N-((4-((dimethylamino)(4-fluorophenyl)methyl)cyclohexyl)methyl)-2-(1-(phenylsulfonyl)piperidin-3-yloxy)acetamide
(489) 2-(2-(N-benzylphenylsulfonamido)ethoxy)-N-(2-(4-((dimethylamino)(4-fluorophenyl)methyl)cyclohexyl)ethyl)acetamide
(490) N-(4-((dimethylamino)(4-fluorophenyl)methyl)cyclohexyl)-2-(2-(N,2,4,6-tetramethylphenylsulfonamido)ethoxy)acetamide
(491) N-(2-(4-((dimethylamino)(4-fluorophenyl)methyl)cyclohexyl)ethyl)-2-(1-tosylpyrrolidin-3-yloxy)acetamide
(492) N-(2-(4-((4-chlorophenyl)(dimethylamino)methyl)cyclohexyl)ethyl)-2-(1-(4-methoxy-2,6-dimethylphenylsulfonyl)pyrrolidin-3-yloxy)acetamide
(493) N-(2-(4-((dimethylamino)(4-fluorophenyl)methyl)cyclohexyl)ethyl)-2-(2-(4-(phenylsulfonyl)piperazin-1-yl)ethoxy)acetamide
(494) 2-(2-(N-benzyl-4-methoxy-2,6-dimethylphenylsulfonamido)ethoxy)-N-((4-((dimethylamino)(4-fluorophenyl)methyl)cyclohexyl)methyl)acetamide
(495) N-((4-(1-(dimethylamino)-3-phenylpropyl)cyclohexyl)methyl)-2-phenoxypropanamide
(496) 2-(1-(2,4-dichlorophenylsulfonyl)pyrrolidin-3-yloxy)-N-((4-(1-(dimethylamino)-3-phenylpropyl)cyclohexyl)methyl)acetamide
(497) 2-(1-(3,4-dimethoxyphenylsulfonyl)pyrrolidin-3-yloxy)-N-((4-((dimethylamino)(4-fluorophenyl)methyl)cyclohexyl)methyl)acetamide
(498) N-((4-((4-chlorophenyl)(dimethylamino)methyl)cyclohexyl)methyl)-2-(1-(4-methoxy-2,3,6-trimethylphenylsulfonyl)piperidin-4-yloxy)acetamide
(499) N-((4-((4-chlorophenyl)(dimethylamino)methyl)cyclohexyl)methyl)-2-(2-(1-(4-methoxy-2,3,6-trimethylphenylsulfonyl)piperidin-4-yl)ethoxy)acetamide
(500) 2-((1-(2,4-dimethoxyphenylsulfonyl)piperidin-2-yl)methoxy)-N-(2-(4-((dimethylamino)(4-fluorophenyl)methyl)cyclohexyl)ethyl)acetamide
(501) N-(2-(4-((dimethylamino)(4-fluorophenyl)methyl)cyclohexyl)ethyl)-2-(1-(mesitylsulfonyl)pyrrolidin-3-yloxy)acetamide
(502) N-(4-((dimethylamino)(4-fluorophenyl)methyl)cyclohexyl)-2-(2-(4-(phenylsulfonyl)piperazin-1-yl)ethoxy)acetamide
(503) N-((4-(1-(dimethylamino)-3-phenylpropyl)cyclohexyl)methyl)-2-(1-(4-methoxy-2,3,6-trimethylphenylsulfonyl)pyrrolidin-3-yloxy)acetamide
(504) 2-(2-(N-benzyl-4-methoxy-2,6-dimethylphenylsulfonamido)ethoxy)-N-(4-((dimethylamino)(4-fluorophenyl)methyl)cyclohexyl)acetamide
(505) 2-(4-chlorophenoxy)-N-(4-((dimethylamino)(3-fluorophenyl)methyl)cyclohexyl)acetamide
(506) N-(2-(4-((4-chlorophenyl)(dimethylamino)methyl)cyclohexyl)ethyl)-2-(1-(mesitylsulfonyl)pyrrolidin-3-yloxy)acetamide
(507) N-((4-((dimethylamino)(phenyl)methyl)cyclohexyl)methyl)-2-(2-(1-(phenylsulfonyl)piperidin-4-yl)ethoxy)acetamide
(508) N-((4-((dimethylamino)(4-fluorophenyl)methyl)cyclohexyl)methyl)-2-(2-(4-methoxy-N-methylphenylsulfonamido)ethoxy)acetamide
(509) N-(2-(4-((dimethylamino)(4-fluorophenyl)methyl)cyclohexyl)ethyl)-2-(1-(4-methoxy-2,6-dimethylphenylsulfonyl)pyrrolidin-3-yloxy)acetamide
(510) N-(2-(4-((dimethylamino)(4-fluorophenyl)methyl)cyclohexyl)ethyl)-2-(2-(1-(4-methoxy-2,3,6-trimethylphenylsulfonyl)piperidin-4-yl)ethoxy)acetamide
(511) N-((4-((dimethylamino)(4-fluorophenyl)methyl)cyclohexyl)methyl)-2-((1-(4-methoxyphenylsulfonyl)pyrrolidin-2-yl)methoxy)acetamide
(512) 2-(1-(3,4-dimethoxyphenylsulfonyl)pyrrolidin-3-yloxy)-N-(4-((dimethylamino)(4-fluorophenyl)methyl)cyclohexyl)acetamide
(513) 2-(2-(2,4-dichloro-N-methylphenylsulfonamido)ethoxy)-N-((4-(1-(dimethylamino)-3-phenylpropyl)cyclohexyl)methyl)acetamide
(514) 2-(2-(3,4-dimethoxy-N-methylphenylsulfonamido)ethoxy)-N-((4-((dimethylamino)(4-fluorophenyl)methyl)cyclohexyl)methyl)acetamide
(515) N-((4-(1-(dimethylamino)-3-phenylpropyl)cyclohexyl)methyl)-2-(2-(2,4,6-trichloro-N-methylphenylsulfonamido)ethoxy)acetamide
(516) N-(4-((dimethylamino)(4-fluorophenyl)methyl)cyclohexyl)-2-phenoxypropanamide
(517) 2-(1-(4-chlorophenylsulfonyl)pyrrolidin-3-yloxy)-N-((4-((dimethylamino)(4-fluorophenyl)methyl)cyclohexyl)methyl)acetamide
(518) N-(2-(4-((dimethylamino)(4-fluorophenyl)methyl)cyclohexyl)ethyl)-2-(1-(4-fluorophenylsulfonyl)pyrrolidin-3-yloxy)acetamide
(519) N-(2-(4-((dimethylamino)(4-fluorophenyl)methyl)cyclohexyl)ethyl)-2-(2-(4-methoxy-N-methylphenylsulfonamido)ethoxy)acetamide
(520) N-(2-(4-((dimethylamino)(4-fluorophenyl)methyl)cyclohexyl)ethyl)-2-(1-(phenylsulfonyl)piperidin-3-yloxy)acetamide
(521) N-((4-(1-(dimethylamino)-3-phenylpropyl)cyclohexyl)methyl)-2-(2-(1-(4-methoxy-2,3,6-trimethylphenylsulfonyl)piperidin-4-yl)ethoxy)acetamide
(522) N-((4-((dimethylamino)(4-fluorophenyl)methyl)cyclohexyl)methyl)-2-(1-(4-fluorophenylsulfonyl)pyrrolidin-3-yloxy)acetamide
(523) 2-(2-(N-benzyl-4-methoxy-2,3,6-trimethylphenylsulfonamido)ethoxy)-N-(4-((dimethylamino)(4-fluorophenyl)methyl)cyclohexyl)acetamide
(524) 2-((1-(2,4-dimethoxyphenylsulfonyl)piperidin-2-yl)methoxy)-N-(4-((dimethylamino)(4-fluorophenyl)methyl)cyclohexyl)acetamide
(525) N-((4-(1-(dimethylamino)-3-phenylpropyl)cyclohexyl)methyl)-2-(2-(4-methoxy-N,2,6-trimethylphenylsulfonamido)ethoxy)acetamide
(526) N-((4-(1-(dimethylamino)-3-phenylpropyl)cyclohexyl)methyl)-2-(2-(4-(phenylsulfonyl)piperazin-1-yl)ethoxy)acetamide (527) N-((4-((dimethylamino)(4-fluorophenyl)methyl)cyclohexyl)methyl)-2-(1-(4-methoxy-2,3,6-trimethylphenylsulfonyl)piperidin-4-yloxy)acetamide
(528) N-((4-(1-(dimethylamino)-3-phenylpropyl)cyclohexyl)methyl)-2-(2-(4-(4-methoxy-2,3,6-trimethylphenylsulfonyl)piperazin-1-yl)ethoxy)acetamide
(529) 2-(benzyloxy)-N-(4-((dimethylamino)(4-fluorophenyl)-methyl)cyclohexyl)acetamide
(530) N-(2-(4-((dimethylamino)(4-fluorophenyl)methyl)cyclohexyl)ethyl)-2-(1-(phenylsulfonyl)pyrrolidin-3-yloxy)acetamide
(531) N-(2-(4-((4-chlorophenyl)(dimethylamino)methyl)cyclohexyl)ethyl)-2-(2-(1-(phenylsulfonyl)piperidin-4-yl)ethoxy)acetamide
(532) N-((4-((dimethylamino)(4-fluorophenyl)methyl)cyclohexyl)methyl)-2-(1-(phenylsulfonyl)pyrrolidin-3-yloxy)acetamide
(533) 2-(2-(N-benzylphenylsulfonamido)ethoxy)-N-((4-(1-(dimethylamino)-3-phenylpropyl)cyclohexyl)methyl)acetamide
(534) 2-((1-(3,4-dimethoxyphenylsulfonyl)piperidin-2-yl)methoxy)-N-((4-((dimethylamino)(4-fluorophenyl)methyl)cyclohexyl)methyl)acetamide
(535) N-((4-(1-(dimethylamino)-3-phenylpropyl)cyclohexyl)methyl)-2-(2-(1-(4-methoxyphenylsulfonyl)piperidin-2-yl)ethoxy)acetamide
(536) N-((4-(1-(dimethylamino)-3-phenylpropyl)cyclohexyl)methyl)-2-(2-(N-ethyl-4-methoxy-2,3,6-trimethylphenylsulfonamido)ethoxy)acetamide
(537) 2-((1-(3,4-dimethoxyphenylsulfonyl)piperidin-2-yl)methoxy)-N-((4-((dimethylamino)(4-fluorophenyl)methyl)cyclohexyl)methyl)acetamide
(538) N-((4-(1-(dimethylamino)-3-phenylpropyl)cyclohexyl)methyl)-2-(1-tosylpyrrolidin-3-yloxy)acetamide
(539) N-((4-(1-(dimethylamino)-3-phenylpropyl)cyclohexyl)methyl)-2-(2-(4-fluoro-N-methylphenylsulfonamido)ethoxy)acetamide
(540) N-(2-(4-((4-chlorophenyl)(dimethylamino)methyl)cyclohexyl)ethyl)-2-((1-(3,4-dimethoxyphenylsulfonyl)piperidin-2-yl)methoxy)acetamide
(541) N-((4-((dimethylamino)(4-fluorophenyl)methyl)cyclohexyl)methyl)-2-(1-(4-methoxy-2,6-dimethylphenylsulfonyl)pyrrolidin-3-yloxy)acetamide
(542) 2-(2-(N-benzyl-4-methoxy-2,6-dimethylphenylsulfonamido)ethoxy)-N-((4-(1-(dimethylamino)-3-phenylpropyl)cyclohexyl)methyl)acetamide
(543) N-(2-(4-((dimethylamino)(3-fluorophenyl)methyl)cyclohexyl)ethyl)-2-(2-(1-(phenylsulfonyl)piperidin-4-yl)ethoxy)acetamide
(544) N-((4-(1-(dimethylamino)-3-phenylpropyl)cyclohexyl)methyl)-2-((1-(phenylsulfonyl)piperidin-3-yl)methoxy)acetamide
(545) N-(4-(1-(dimethylamino)-3-phenylpropyl)cyclohexyl)-2-phenoxypropanamide
(546) N-((4-(1-(dimethylamino)-3-phenylpropyl)cyclohexyl)methyl)-2-(1-(4-methoxy-2,3,6-trimethylphenylsulfonyl)piperidin-4-yloxy)acetamide
(547) 2-(2-(N-benzyl-4-methoxy-2,6-dimethylphenylsulfonamido)ethoxy)-N-(2-(4-((dimethylamino)(4-fluorophenyl)methyl)cyclohexyl)ethyl)acetamide
(548) 2-(2-(3,4-dimethoxy-N-methylphenylsulfonamido)ethoxy)-N-(4-((dimethylamino)(4-fluorophenyl)methyl)cyclohexyl)acetamide
(549) N-(4-((dimethylamino)(4-fluorophenyl)methyl)cyclohexyl)-2-(2-(4-methoxy-N-methylphenylsulfonamido)ethoxy)acetamide
(550) N-((4-(1-(dimethylamino)-3-phenylpropyl)cyclohexyl)methyl)-2-(2-(4-methoxy-N-methylphenylsulfonamido)ethoxy)acetamide
(551) N-((4-(1-(dimethylamino)-3-phenylpropyl)cyclohexyl)methyl)-2-(1-(4-methoxy-2,3,6-trimethylphenylsulfonyl)piperidin-3-yloxy)acetamide
(552) N-((4-(1-(dimethylamino)-3-phenylpropyl)cyclohexyl)methyl)-2-(1-(3-(trifluoromethyl)phenylsulfonyl)pyrrolidin-3-yloxy)acetamide
(553) N-(2-(4-((dimethylamino)(4-fluorophenyl)methyl)cyclohexyl)ethyl)-2-(1-(phenylsulfonyl)piperidin-4-yloxy)acetamide
(554) 2-(2-(N-benzyl-4-methoxy-2,3,6-trimethylphenylsulfonamido)ethoxy)-N-(2-(4-((dimethylamino)(4-fluorophenyl)methyl)cyclohexyl)ethyl)acetamide
(555) 2-((1-(3,4-dimethoxyphenylsulfonyl)piperidin-2-yl)methoxy)-N-(4-((dimethylamino)(4-fluorophenyl)methyl)cyclohexyl)acetamide
(556) N-((4-(1-(dimethylamino)-3-phenylpropyl)cyclohexyl)methyl)-2-(2-(N-methyl-3-(trifluoromethyl)phenylsulfonamido)ethoxy)acetamide
(557) 2-(1-(4-chlorophenylsulfonyl)pyrrolidin-3-yloxy)-N-((4-(1-(dimethylamino)-3-phenylpropyl)cyclohexyl)methyl)acetamide
(558) N-((4-(1-(dimethylamino)-3-phenylpropyl)cyclohexyl)methyl)-2-(1-(phenylsulfonyl)piperidin-3-yloxy)acetamide
(559) 2-((1-(3,4-dimethoxyphenylsulfonyl)piperidin-2-yl)methoxy)-N-((4-(1-(dimethylamino)-3-phenylpropyl)cyclohexyl)methyl)acetamide
(560) 2-(2-(N-benzyl-4-methoxy-2,3,6-trimethylphenylsulfonamido)ethoxy)-N-((4-((4-chlorophenyl)(dimethylamino)methyl)cyclohexyl)methyl)acetamide
(561) N-(2-(4-((4-chlorophenyl)(dimethylamino)methyl)cyclohexyl)ethyl)-2-(2-(1-(4-methoxy-2,3,6-trimethylphenylsulfonyl)piperidin-4-yl)ethoxy)acetamide
(562) 2-(2-(N-benzyl-4-methoxy-2,3,6-trimethylphenylsulfonamido)ethoxy)-N-((4-(1-(dimethylamino)-3-phenylpropyl)cyclohexyl)methyl)acetamide
(563) 2-(2-(N-benzyl-4-methoxy-2,3,6-trimethylphenylsulfonamido)ethoxy)-N-((4-((dimethylamino)(4-fluorophenyl)methyl)cyclohexyl)methyl)acetamide
(564) 2-(4-chlorophenoxy)-N-(4-(1-(dimethylamino)-3-phenylpropyl)cyclohexyl)acetamide
(565) N-((4-(1-(dimethylamino)-3-phenylpropyl)cyclohexyl)methyl)-2-(1-(4-methoxy-2,6-dimethylphenylsulfonyl)pyrrolidin-3-yloxy)acetamide
(566) 2-(1-(3,4-dimethoxyphenylsulfonyl)pyrrolidin-3-yloxy)-N-((4-(1-(dimethylamino)-3-phenylpropyl)cyclohexyl)methyl)acetamide
(567) N-((4-(1-(dimethylamino)-3-phenylpropyl)cyclohexyl)methyl)-2-(2-(N-methyl-4-(trifluoromethoxy)phenylsulfonamido)ethoxy)acetamide
(568) N-((4-((dimethylamino)(4-fluorophenyl)methyl)cyclohexyl)methyl)-2-(1-(phenylsulfonyl)piperidin-4-yloxy)acetamide
(569) 2-(2-(N-benzyl-4-methoxy-2,6-dimethylphenylsulfonamido)ethoxy)-N-(2-(4-((4-chlorophenyl)(dimethylamino)methyl)cyclohexyl)ethyl)acetamide
(570) 2-((1-(3,4-dimethoxyphenylsulfonyl)piperidin-2-yl)methoxy)-N-((4-(1-(dimethylamino)-3-phenylpropyl)cyclohexyl)methyl)acetamide
(571) 2-(2-(3,4-dimethoxy-N-methylphenylsulfonamido)ethoxy)-N-((4-(1-(dimethylamino)-3-phenylpropyl)cyclohexyl)methyl)acetamide (572) N-((4-(1-(dimethylamino)-3-phenylpropyl)cyclohexyl)methyl)-2-((1-(4-methoxyphenylsulfonyl)pyrrolidin-2-yl)methoxy)acetamide
(573) N-((4-(1-(dimethylamino)-3-phenylpropyl)cyclohexyl)methyl)-2-(1-(phenylsulfonyl)pyrrolidin-3-yloxy)acetamide
(574) N-((4-(1-(dimethylamino)-3-phenylpropyl)cyclohexyl)methyl)-2-(1-(4-fluorophenylsulfonyl)pyrrolidin-3-yloxy)acetamide
(575) N-(2-(4-((4-chlorophenyl)(dimethylamino)methyl)cyclohexyl)ethyl)-2-(2-(N-methyl-4-(trifluoromethoxy)phenylsulfonamido)ethoxy)acetamide
(576) 2-(2-(N-benzyl-4-methoxy-2,3,6-trimethylphenylsulfonamido)ethoxy)-N-(2-(4-((4-chlorophenyl)(dimethylamino)methyl)cyclohexyl)ethyl)acetamide
(577) N-(4-(1-(dimethylamino)-3-phenylpropyl)cyclohexyl)-2-phenoxypropanamide
(578) N-((4-(1-(dimethylamino)-3-phenylpropyl)cyclohexyl)methyl)-2-(1-(phenylsulfonyl)piperidin-4-yloxy)acetamide
(579) methyl 2-(2-(4-((dimethylamino)(phenyl)methyl)cyclohexyl)ethylamino)-2-oxoacetate
(580) 2-(2-(2,6-dichloro-N-methylphenylsulfonamido)ethoxy)-N-((4-(1-(dimethylamino)-3-phenylpropyl)cyclohexyl)methyl)acetamide
(581) 2-((1-(3,4-dimethoxyphenylsulfonyl)piperidin-2-yl)methoxy)-N-(2-(4-((dimethylamino)(3-fluorophenyl)methyl)cyclohexyl)ethyl)acetamide
(582) 2-(benzyloxy)-N-(4-(1-(dimethylamino)-3-phenylpropyl)cyclohexyl)acetamide
(583) N-((4-((dimethylamino)(4-fluorophenyl)methyl)cyclohexyl)methyl)-2-(2-(1-(phenylsulfonyl)piperidin-4-yl)ethoxy)acetamide
(584) N-((4-((4-chlorophenyl)(dimethylamino)methyl)cyclohexyl)methyl)-2-(2-(1-(phenylsulfonyl)piperidin-4-yl)ethoxy)acetamide
(585) N-(4-((dimethylamino)(phenyl)methyl)cyclohexyl)-2-(2-(4-fluoro-N-methylphenylsulfonamido)ethoxy)acetamide
(586) 2-(2-(2,4-dichloro-N-methylphenylsulfonamido)ethoxy)-N-(2-(4-((dimethylamino)(4-fluorophenyl)methyl)cyclohexyl)ethyl)acetamide
(587) N-(2-(4-((dimethylamino)(3-fluorophenyl)methyl)cyclohexyl)ethyl)-2-(2-(N,2,4,6-tetramethylphenylsulfonamido)ethoxy)acetamide
(588) N-(4-((dimethylamino)(phenyl)methyl)cyclohexyl)-2-(2-(N-methylphenylsulfonamido)ethoxy)acetamide
(589) 2-(2-(4-chloro-N-methylphenylsulfonamido)ethoxy)-N-(4-((dimethylamino)(phenyl)methyl)cyclohexyl)acetamide
(590) N-(4-((dimethylamino)(phenyl)methyl)cyclohexyl)-2-(2-(4-methoxy-N-methylphenylsulfonamido)ethoxy)acetamide
(591) N-(4-((dimethylamino)(phenyl)methyl)cyclohexyl)-2-(1-(4-fluorophenylsulfonyl)pyrrolidin-3-yloxy)acetamide
(592) 2-(2-(3,4-dimethoxy-N-methylphenylsulfonamido)ethoxy)-N-(4-((dimethylamino)(phenyl)methyl)cyclohexyl)acetamide
(593) N-(4-((dimethylamino)(phenyl)methyl)cyclohexyl)-2-(2-(N-methyl-3-(trifluoromethyl)phenylsulfonamido)ethoxy)acetamide
(594) N-(4-((dimethylamino)(phenyl)methyl)cyclohexyl)-2-(2-(N-methyl-4-(trifluoromethoxy)phenylsulfonamido)ethoxy)acetamide
(595) N-(4-((dimethylamino)(phenyl)methyl)cyclohexyl)-2-(1-(phenylsulfonyl)pyrrolidin-3-yloxy)acetamide
(596) 2-(1-(2,4-dichlorophenylsulfonyl)pyrrolidin-3-yloxy)-N-(4-((dimethylamino)(phenyl)methyl)cyclohexyl)acetamide
(597) N-[4-(dimethylaminophenylmethyl)-cyclohexyl]-2-{2-[(4-methoxy-2,3,6-trimethylbenzenesulfonyl)-methylamino]-ethoxy}-acetamide
(598) N-[4-(dimethylaminophenylmethyl)-cyclohexyl]-2-{2-[methyl-(2,4,6-trichlorobenzenesulfonyl)-amino]-ethoxy}-acetamide
(599) N-{4-[(benzylmethylamino)-phenylmethyl]-cyclohexyl}-2-{2-[methyl-(2,4,6-trichlorobenzenesulfonyl)-amino]-ethoxy}-acetamide
(600) 2-{2-[cyclopropyl-(2,4,6-trichlorobenzenesulfonyl)-amino]-ethoxy}-N-[4-(dimethylaminophenylmethyl)-cyclohexyl]-acetamide
(601) 2-{2-[methyl-(2,4,6-trichlorobenzenesulfonyl)-amino]-ethoxy}-N-[4-(phenylpiperidin-1-yl-methyl)-cyclohexyl]-acetamide
(602) 2-{2-[cyclopropyl-(2,4,6-trichlorobenzenesulfonyl)-amino]-ethoxy}-N-[4-(phenylpiperidin-1-ylmethyl)-cyclohexyl]-acetamide
(603) 2-{2-[cyclopropyl-(2,4,6-trichlorobenzenesulfonyl)-amino]-ethoxy}-N-[4-(phenylpyrrolidin-1-ylmethyl)-cyclohexyl]-acetamide
(604) N-{4-[(benzylmethylamino)-phenylmethyl]-cyclohexyl}-2-{2-[cyclopropyl-(2,4,6-trichlorobenzenesulfonyl)-amino]-ethoxy}-acetamide
(605) 2-{2-[cyclopropyl-(2,4,6-trichlorobenzenesulfonyl)-amino]-ethoxy}-N-[4-(morpholin-4-yl-phenylmethyl)-cyclohexyl]-acetamide
(606) 2-{2-[methyl-(2,4,6-trichlorobenzenesulfonyl)-amino]-ethoxy}-N-[4-(phenylpyrrolidin-1-yl-methyl)-cyclohexyl]-acetamide
(607) 2-{2-[methyl-(2,4,6-trichlorobenzenesulfonyl)-amino]-ethoxy}-N-[4-(morpholin-4-ylphenylmethyl)-cyclohexyl]-acetamide
(608) N-[4-(dimethylaminophenylmethyl)-cyclohexyl]-2-[1-(2,4,6-trichlorobenzenesulfonyl)-piperidin-3-yloxy]-acetamide
(609) N-[4-(dimethylaminophenylmethyl)-cyclohexyl]-2-[1-(2,4,6-trichlorobenzenesulfonyl)-pyrrolidin-3-yloxy]-acetamide
(610) N-[4-(morpholin-4-ylphenylmethyl)-cyclohexyl]-2-[1-(2,4,6-trichlorobenzenesulfonyl)-pyrrolidin-3-yloxy]-acetamide
(611) N-[4-(dimethylaminophenylmethyl)-cyclohexyl]-2-[1-(2,4,6-trichlorobenzenesulfonyl)-pyrrolidin-2-ylmethoxy]-acetamide
(612) N-[4-(dimethylaminophenylmethyl)-cyclohexyl]-2-[1-(2,4,6-trichlorobenzenesulfonyl)-pyrrolidin-2-ylmethoxy]-acetamide
(613) N-[4-(dimethylaminophenylmethyl)-cyclohexyl]-2-[1-(2,4,6-trichlorobenzenesulfonyl)-pyrrolidin-2-ylmethoxy]-acetamide
(614) N-[4-(dimethylaminophenylmethyl)-cyclohexylmethyl]-2-{2-[(2,4,6-trichlorobenzenesulfonyl)-methylamino]-ethoxy}-acetamide
(615) N-[3-(dimethylaminophenylmethyl)-cyclopentyl]-2-{2-[(2,4,6-trichlorobenzenesulfonyl)-methylamino]-ethoxy}-acetamide
(616) N-[4-(1-dimethylamino-2-phenylethyl)-cyclohexyl]-2-{2-[methyl-(2,4,6-trichlorobenzenesulfonyl)-amino]-ethoxy}-acetamide
(617) 2-{2-[(4-methoxy-2,3,6-trimethylbenzenesulfonyl)-methylamino]-ethoxy}-N-[4-(phenylpiperidin-1-yl-methyl)-cyclohexyl]-acetamide (618) 2-{2-[(4-methoxy-2,3,6-trimethylbenzenesulfonyl)-methylamino]-ethoxy}-N-[4-(phenylpyrrolidin-1-yl-methyl)-cyclohexyl]-acetamide
(619) 2-{2-[(4-methoxy-2,3,6-trimethylbenzenesulfonyl)-methylamino]-ethoxy}-N-[4-(morpholin-4-yl-phenylmethyl)-cyclohexyl]-acetamide
(620) N-[4-(dimethylaminophenylmethyl)-cyclohexyl]-3-{[methyl-(2,4,6-trichlorobenzenesulfonyl)-amino]-methoxy}-propionamide
(621) N-[4-(dimethylaminophenylmethyl)-cyclohexylmethyl]-2-[1-(2,4,6-trichlorobenzenesulfonyl)-piperidin-3-yloxy]-acetamide
(622) N-[4-(dimethylaminophenylmethyl)-cyclohexylmethyl]-2-[1-(2,4,6-trichlorobenzenesulfonyl)-pyrrolidin-2-ylmethoxy]-acetamide
(623) N-[4-(dimethylaminophenylmethyl)-cyclohexylmethyl]-2-{2-[(4-methoxy-2,3,6-trimethylbenzenesulfonyl)-methylamino]-ethoxy}-acetamide
(624) N-[4-(dimethylaminophenylmethyl)-cyclohexylmethyl]-3-{[methyl-(2,4,6-trichlorobenzenesulfonyl)-amino]-methoxy}-propionamide
(625) N-(4-(phenyl(pyrrolidin-1-yl)methyl)cyclohexyl)-2-(2-(2,4,6-trichloro-N-methylphenylsulfonamido)ethoxy)acetamide
(626) N-((4-(phenyl(pyrrolidin-1-yl)methyl)cyclohexyl)methyl)-2-(2-(2,4,6-trichloro-N-methylphenylsulfonamido)ethoxy)acetamide
(627) 2-(2-(2,4-dichloro-N-methylphenylsulfonamido)ethoxy)-N-(4-(phenyl(pyrrolidin-1-yl)methyl)cyclohexyl)acetamide
(628) 2-(2-(4-methoxy-N,2,6-trimethylphenylsulfonamido)ethoxy)-N-(4-(phenyl(pyrrolidin-1-yl)methyl)cyclohexyl)acetamide
(629) 2-(1-(4-methoxy-2,6-dimethylphenylsulfonyl)pyrrolidin-3-yloxy)-N-(4-(phenyl(pyrrolidin-1-yl)methyl)cyclohexyl)acetamide
(630) 2-(2-(2,6-dichloro-N-methyl-4-(trifluoromethyl)phenylsulfonamido)ethoxy)-N-(4-(phenyl(pyrrolidin-1-yl)methyl)cyclohexyl)acetamide
(631) N-(4-(phenyl(pyrrolidin-1-yl)methyl)cyclohexyl)-2-(1-(2,4,6-trichlorophenylsulfonyl)piperidin-3-yloxy)acetamide
(632) 2-((1-(4-methoxy-2,6-dimethylphenylsulfonyl)pyrrolidin-2-yl)methoxy)-N-(4-(phenyl(pyrrolidin-1-yl)methyl)cyclohexyl)acetamide
(633) N-(4-(phenyl(pyrrolidin-1-yl)methyl)cyclohexyl)-2-((1-(2,4,6-trichlorophenylsulfonyl)piperidin-3-yl)methoxy)acetamide
(634) 2-(2-(2,6-dichloro-N-methylphenylsulfonamido)ethoxy)-N-(4-(phenyl(pyrrolidin-1-yl)methyl)cyclohexyl)acetamide
(635) N-(4-(phenyl(pyrrolidin-1-yl)methyl)cyclohexyl)-2-(1-(2,4,6-trichlorophenylsulfonyl)pyrrolidin-3-yloxy)acetamide
(636) N-(4-(1-morpholino-3-phenylpropyl)cyclohexyl)-2-(2-(2,4,6-trichloro-N-methylphenylsulfonamido)ethoxy)acetamide
(637) N-(4-(3-phenyl-1-(piperidin-1-yl)propyl)cyclohexyl)-2-(2-(2,4,6-trichloro-N-methylphenylsulfonamido)ethoxy)acetamide
(638) N-(4-(morpholino(phenyl)methyl)cyclohexyl)-2-(2-(2,4,6-trichloro-N-methylphenylsulfonamido)ethoxy)acetamide
(639) N-((4-(morpholino(phenyl)methyl)cyclohexyl)methyl)-2-(2-(2,4,6-trichloro-N-methylphenylsulfonamido)ethoxy)acetamide
(640) N-((4-(3-phenyl-1-(pyrrolidin-1-yl)propyl)cyclohexyl)methyl)-2-(2-(2,4,6-trichloro-N-methylphenylsulfonamido)ethoxy)acetamide
(641) 2-(2-(2,4-dichloro-N-methylphenylsulfonamido)ethoxy)-N-((4-(phenyl(pyrrolidin-1-yl)methyl)cyclohexyl)methyl)acetamide
(642) 2-(2-(4-methoxy-N,2,6-trimethylphenylsulfonamido)ethoxy)-N-((4-(phenyl(pyrrolidin-1-yl)methyl)cyclohexyl)methyl)acetamide
(643) 2-(2-(2,6-dichloro-N-methylphenylsulfonamido)ethoxy)-N-((4-(phenyl(pyrrolidin-1-yl)methyl)cyclohexyl)methyl)acetamide
(644) N-((4-(phenyl(pyrrolidin-1-yl)methyl)cyclohexyl)methyl)-2-(1-(2,4,6-trichlorophenylsulfonyl)pyrrolidin-3-yloxy)acetamide
(645) 2-(1-(4-methoxy-2,6-dimethylphenylsulfonyl)pyrrolidin-3-yloxy)-N-((4-(phenyl(pyrrolidin-1-yl)methyl)cyclohexyl)methyl)acetamide
(646) 2-(2-(2,6-dichloro-N-methyl-4-(trifluoromethyl)phenylsulfonamido)ethoxy)-N-((4-(phenyl(pyrrolidin-1-yl)methyl)cyclohexyl)methyl)acetamide
(647) 2-(1-(4-methoxy-2,6-dimethylphenylsulfonyl)piperidin-3-yloxy)-N-(4-(phenyl(pyrrolidin-1-yl)methyl)cyclohexyl)acetamide
(648) 2-(1-(4-methoxy-2,6-dimethylphenylsulfonyl)piperidin-3-yloxy)-N-((4-(phenyl(pyrrolidin-1-yl)methyl)cyclohexyl)methyl)acetamide
(649) 2-((1-(4-methoxy-2,6-dimethylphenylsulfonyl)pyrrolidin-2-yl)methoxy)-N-((4-(phenyl(pyrrolidin-1-yl)methyl)cyclohexyl)methyl)acetamide
(650) N-(4-(phenyl(pyrrolidin-1-yl)methyl)cyclohexyl)-2-((1-(2,4,6-trichlorophenylsulfonyl)pyrrolidin-2-yl)methoxy)acetamide
(651) N-((4-(phenyl(pyrrolidin-1-yl)methyl)cyclohexyl)methyl)-2-((1-(2,4,6-trichlorophenylsulfonyl)pyrrolidin-2-yl)methoxy)acetamide
(652) 2-((1-(4-methoxy-2,6-dimethylphenylsulfonyl)piperidin-2-yl)methoxy)-N-(4-(phenyl(pyrrolidin-1-yl)methyl)cyclohexyl)acetamide
(653) N-(4-(phenyl(pyrrolidin-1-yl)methyl)cyclohexyl)-2-((1-(2,4,6-trichlorophenylsulfonyl)piperidin-2-yl)methoxy)acetamide
(654) 2-(1-(4-methoxy-2,6-dimethylphenylsulfonyl)piperidin-3-yl)methoxy)-N-(4-(phenyl(pyrrolidin-1-yl)methyl)cyclohexyl)acetamide
(655) 2-((1-(4-methoxy-2,6-dimethylphenylsulfonyl)piperidin-3-yl)methoxy)-N-((4-(phenyl(pyrrolidin-1-yl)methyl)cyclohexyl)methyl)acetamide
(656) N-((4-(phenyl(pyrrolidin-1-yl)methyl)cyclohexyl)methyl)-2-(1-(2,4,6-trichlorophenylsulfonyl)piperidin-3-yloxy)acetamide
(657) 2-((1-(4-methoxy-2,6-dimethylphenylsulfonyl)piperidin-2-yl)methoxy)-N-((4-(phenyl(pyrrolidin-1-yl)methyl)cyclohexyl)methyl)acetamide
(658) N-((4-(phenyl(pyrrolidin-1-yl)methyl)cyclohexyl)methyl)-2-((1-(2,4,6-trichlorophenylsulfonyl)piperidin-2-yl)methoxy)acetamide
(659) N-((4-(phenyl(pyrrolidin-1-yl)methyl)cyclohexyl)methyl)-2-((1-(2,4,6-trichlorophenylsulfonyl)piperidin-3-yl)methoxy)acetamide
(660) 2-(2-(2,4-dichloro-N-methylphenylsulfonamido)ethoxy)-N-(4-(1-morpholino-3-phenylpropyl)cyclohexyl)acetamide
(661) 2-(2-(2,4-dichloro-N-methylphenylsulfonamido)ethoxy)-N-(4-(3-phenyl-1-(piperidin-1-yl)propyl)cyclohexyl)acetamide (662) 2-(2-(4-methoxy-N,2,6-trimethylphenylsulfonamido)ethoxy)-N-(4-(1-morpholino-3-phenylpropyl)cyclohexyl)acetamide
(663) 2-(2-(4-methoxy-N,2,6-trimethylphenylsulfonamido)ethoxy)-N-(4-(3-phenyl-1-(piperidin-1-yl)propyl)cyclohexyl)acetamide
(664) 2-(2-(2,6-dichloro-N-methylphenylsulfonamido)ethoxy)-N-(4-(1-morpholino-3-phenylpropyl)cyclohexyl)acetamide
(665) 2-(2-(2,6-dichloro-N-methylphenylsulfonamido)ethoxy)-N-(4-(3-phenyl-1-(piperidin-1-yl)propyl)cyclohexyl)acetamide
(666) N-(4-(1-morpholino-3-phenylpropyl)cyclohexyl)-2-(1-(2,4,6-trichlorophenylsulfonyl)pyrrolidin-3-yloxy)acetamide
(667) N-(4-(3-phenyl-1-(piperidin-1-yl)propyl)cyclohexyl)-2-(1-(2,4,6-trichlorophenylsulfonyl)pyrrolidin-3-yloxy)acetamide
(668) 2-(1-(4-methoxy-2,6-dimethylphenylsulfonyl)pyrrolidin-3-yloxy)-N-(4-(1-morpholino-3-phenylpropyl)cyclohexyl)acetamide
(669) 2-(1-(4-methoxy-2,6-dimethylphenylsulfonyl)pyrrolidin-3-yloxy)-N-(4-(3-phenyl-1-(piperidin-1-yl)propyl)cyclohexyl)acetamide
(670) 2-(2-(2,6-dichloro-N-methyl-4-(trifluoromethyl)phenylsulfonamido)ethoxy)-N-(4-(1-morpholino-3-phenylpropyl)cyclohexyl)acetamide
(671) 2-(2-(2,6-dichloro-N-methyl-4-(trifluoromethyl)phenylsulfonamido)ethoxy)-N-(4-(3-phenyl-1-(piperidin-1-yl)propyl)cyclohexyl)acetamide
(672) N-(4-(1-morpholin-3-phenylpropyl)cyclohexyl)-2-(1-(2,4,6-trichlorophenylsulfonyl)piperidin-3-yloxy)acetamide
(673) N-(4-(3-phenyl-1-(piperidin-1-yl)propyl)cyclohexyl)-2-(1-(2,4,6-trichlorophenylsulfonyl)piperidin-3-yloxy)acetamide
(674) 2-(1-(4-methoxy-2,6-dimethylphenylsulfonyl)piperidin-3-yloxy)-N-(4-(1-morpholino-3-phenylpropyl)cyclohexyl)acetamide
(675) 2-(1-(4-methoxy-2,6-dimethylphenylsulfonyl)piperidin-3-yloxy)-N-(4-(3-phenyl-1-(piperidin-1-yl)propyl)cyclohexyl)acetamide
(676) 2-((1-(4-methoxy-2,6-dimethylphenylsulfonyl)pyrrolidin-2-yl)methoxy)-N-(4-(1-morpholino-3-phenylpropyl)cyclohexyl)acetamide
(677) 2-((1-(4-methoxy-2,6-dimethylphenylsulfonyl)pyrrolidin-2-yl)methoxy)-N-(4-(3-phenyl-1-(piperidin-1-yl)propyl)cyclohexyl)acetamide
(678) 2-((1-(4-methoxy-2,6-dimethylphenylsulfonyl)piperidin-3-yl)methoxy)-N-(4-(1-morpholino-3-phenylpropyl)cyclohexyl)acetamide
(679) N-(4-(3-phenyl-1-(piperidin-1-yl)propyl)cyclohexyl)-2-((1-(2,4,6-trichlorophenylsulfonyl)piperidin-3-yl)methoxy)acetamide
(680) 2-(2-(2,4-dichloro-N-methylphenylsulfonamido)ethoxy)-N-(4-(morpholino(phenyl)methyl)cyclohexyl)acetamide
(681) 2-(2-(4-methoxy-N,2,6-trimethylphenylsulfonamido)ethoxy)-N-(4-(morpholino(phenyl)methyl)cyclohexyl)acetamide
(682) 2-(2-(4-methoxy-N,2,6-trimethylphenylsulfonamido)ethoxy)-N-(4-((4-methylpiperazin-1-yl)(phenyl)methyl)cyclohexyl)acetamide
(683) 2-(2-(2,6-dichloro-N-methylphenylsulfonamido)ethoxy)-N-(4-(morpholino(phenyl)methyl)cyclohexyl)acetamide
(684) 2-(2-(2,6-dichloro-N-methylphenylsulfonamido)ethoxy)-N-(4-((4-methylpiperazin-1-yl)(phenyl)methyl)cyclohexyl)acetamide
(685) N-(4-(morpholin(phenyl)methyl)cyclohexyl)-2-(1-(2,4,6-trichlorophenylsulfonyl)pyrrolidin-3-yloxy)acetamide
(686) N-(4-((4-methylpiperazin-1-yl)(phenyl)methyl)cyclohexyl)-2-(1-(2,4,6-trichlorophenylsulfonyl)pyrrolidin-3-yloxy)acetamide
(687) 2-(1-(4-methoxy-2,6-dimethylphenylsulfonyl)pyrrolidin-3-yloxy)-N-(4-(morpholino(phenyl)methyl)cyclohexyl)acetamide
(688) 2-(1-(4-methoxy-2,6-dimethylphenylsulfonyl)pyrrolidin-3-yloxy)-N-(4-((4-methylpiperazin-1-yl)(phenyl)methyl)cyclohexyl)acetamide
(689) 2-(2-(2,6-dichloro-N-methyl-4-(trifluoromethyl)phenylsulfonamido)ethoxy)-N-(4-(morpholino(phenyl)methyl)cyclohexyl)acetamide
(690) 2-(2-(2,6-dichloro-N-methyl-4-(trifluoromethyl)phenylsulfonamido)ethoxy)-N-(4-((4-methylpiperazin-1-yl)(phenyl)methyl)cyclohexyl)acetamide
(691) N-(4-(morpholino(phenyl)methyl)cyclohexyl)-2-(1-(2,4,6-trichlorophenylsulfonyl)piperidin-3-yloxy)acetamide
(692) N-(4-((4-methylpiperazin-1-yl)(phenyl)methyl)cyclohexyl)-2-(1-(2,4,6-trichlorophenylsulfonyl)piperidin-3-yloxy)acetamide
(693) 2-(1-(4-methoxy-2,6-dimethylphenylsulfonyl)piperidin-3-yloxy)-N-(4-(morpholino(phenyl)methyl)cyclohexyl)acetamide
(694) 2-((1-(4-methoxy-2,6-dimethylphenylsulfonyl)pyrrolidin-2-yl)methoxy)-N-(4-(morpholino(phenyl)methyl)cyclohexyl)acetamide
(695) 2-((1-(4-methoxy-2,6-dimethylphenylsulfonyl)pyrrolidin-2-yl)methoxy)-N-(4-((4-methylpiperazin-1-yl)(phenyl)methyl)cyclohexyl)acetamide
(696) N-(4-(1-morpholino-3-phenylpropyl)cyclohexyl)-2-((1-(2,4,6-trichlorophenylsulfonyl)pyrrolidin-2-yl)methoxy)acetamide
(697) N-(4-(3-phenyl-1-(piperidin-1-yl)propyl)cyclohexyl)-2-((1-(2,4,6-trichlorophenylsulfonyl)pyrrolidin-2-yl)methoxy)acetamide
(698) N-(4-(morpholino(phenyl)methyl)cyclohexyl)-2-((1-(2,4,6-trichlorophenylsulfonyl)pyrrolidin-2-yl)methoxy)acetamide
(699) 2-((1-(4-methoxy-2,6-dimethylphenylsulfonyl)piperidin-2-yl)methoxy)-N-(4-(morpholino(phenyl)methyl)cyclohexyl)acetamide
(700) N-(4-(morpholino(phenyl)methyl)cyclohexyl)-2-((1-(2,4,6-trichlorophenylsulfonyl)piperidin-2-yl)methoxy)acetamide
(701) 2-((1-(4-methoxy-2,6-dimethylphenylsulfonyl)piperidin-3-yl)methoxy)-N-(4-(morpholino(phenyl)methyl)cyclohexyl)acetamide
(702) 2-((1-(4-methoxy-2,6-dimethylphenylsulfonyl)piperidin-3-yl)methoxy)-N-(4-((4-methylpiperazin-1-yl)(phenyl)methyl)cyclohexyl)acetamide
(703) N-(4-(morpholino(phenyl)methyl)cyclohexyl)-2-((1-(2,4,6-trichlorophenylsulfonyl)piperidin-3-yl)methoxy)acetamide
(704) 2-(2-(2,4-dichloro-N-methylphenylsulfonamido)ethoxy)-N-(4-((4-methylpiperazin-1-yl)(phenyl)methyl)cyclohexyl)acetamide
(705) 2-(2-(2,4-dichloro-N-methylphenylsulfonamido)ethoxy)-N-((4-(morpholino(phenyl)methyl)cyclohexyl)methyl)acetamide (706) 2-(2-(2,6-dichloro-N-methylphenylsulfonamido)ethoxy)-N-((4-(morpholino(phenyl)methyl)cyclohexyl)methyl)acetamide
(707) N-((4-(morpholino(phenyl)methyl)cyclohexyl)methyl)-2-(1-(2,4,6-trichlorophenylsulfonyl)piperidin-3-yloxy)acetamide
(708) 2-(1-(4-methoxy-2,6-dimethylphenylsulfonyl)piperidin-3-yloxy)-N-(4-((4-methylpiperazin-1-yl)(phenyl)methyl)cyclohexyl)acetamide
(709) 2-((1-(4-methoxy-2,6-dimethylphenylsulfonyl)pyrrolidin-2-yl)methoxy)-N-((4-(morpholino(phenyl)methyl)cyclohexyl)methyl)acetamide
(710) N-((4-(morpholino(phenyl)methyl)cyclohexyl)methyl)-2-((1-(2,4,6-trichlorophenylsulfonyl)pyrrolidin-2-yl)methoxy)acetamide
(711) 2-((1-(4-methoxy-2,6-dimethylphenylsulfonyl)piperidin-2-yl)methoxy)-N-((4-(morpholino(phenyl)methyl)cyclohexyl)methyl)acetamide
(712) N-((4-(morpholino(phenyl)methyl)cyclohexyl)methyl)-2-((1-(2,4,6-trichlorophenylsulfonyl)piperidin-2-yl)methoxy)acetamide
(713) N-((4-(morpholino(phenyl)methyl)cyclohexyl)methyl)-2-((1-(2,4,6-trichlorophenylsulfonyl)piperidin-3-yl)methoxy)acetamide
(714) N-(4-((4-methylpiperazin-1-yl)(phenyl)methyl)cyclohexyl)-2-(2-(2,4,6-trichloro-N-methylphenylsulfonamido)ethoxy)acetamide
(715) N-((4-(1-morpholino-3-phenylpropyl)cyclohexyl)methyl)-2-(2-(2,4,6-trichloro-N-methylphenylsulfonamido)ethoxy)acetamide
(716) 2-(2-(2,4-dichloro-N-methylphenylsulfonamido)ethoxy)-N-((4-(1-morpholino-3-phenylpropyl)cyclohexyl)methyl)acetamide
(717) 2-(2-(2,4-dichloro-N-methylphenylsulfonamido)ethoxy)-N-((4-(3-phenyl-1-(pyrrolidin-1-yl)propyl)cyclohexyl)methyl)acetamide
(718) 2-(2-(4-methoxy-N,2,6-trimethylphenylsulfonamido)ethoxy)-N-((4-(morpholino(phenyl)methyl)cyclohexyl)methyl)acetamide
(719) 2-(2-(4-methoxy-N,2,6-trimethylphenylsulfonamido)ethoxy)-N-((4-(1-morpholino-3-phenylpropyl)cyclohexyl)methyl)acetamide
(720) 2-(2-(4-methoxy-N,2,6-trimethylphenylsulfonamido)ethoxy)-N-((4-(3-phenyl-1-(pyrrolidin-1-yl)propyl)cyclohexyl)methyl)acetamide
(721) 2-(2-(2,6-dichloro-N-methylphenylsulfonamido)ethoxy)-N-((4-(1-morpholino-3-phenylpropyl)cyclohexyl)methyl)acetamide
(722) 2-(2-(2,6-dichloro-N-methylphenylsulfonamido)ethoxy)-N-((4-(3-phenyl-1-(pyrrolidin-1-yl)propyl)cyclohexyl)methyl)acetamide
(723) N-((4-(3-phenyl-1-(pyrrolidin-1-yl)propyl)cyclohexyl)methyl)-2-(1-(2,4,6-trichlorophenylsulfonyl)pyrrolidin-3-yloxy)acetamide
(724) 2-(1-(4-methoxy-2,6-dimethylphenylsulfonyl)pyrrolidin-3-yloxy)-N-((4-(morpholino(phenyl)methyl)cyclohexyl)methyl)acetamide
(725) 2-(1-(4-methoxy-2,6-dimethylphenylsulfonyl)pyrrolidin-3-yloxy)-N-((4-(1-morpholino-3-phenylpropyl)cyclohexyl)methyl)acetamide
(726) 2-(1-(4-methoxy-2,6-dimethylphenylsulfonyl)pyrrolidin-3-yloxy)-N-((4-(3-phenyl-1-(pyrrolidin-1-yl)propyl)cyclohexyl)methyl)acetamide
(727) 2-(2-(2,6-dichloro-N-methyl-4-(trifluoromethyl)phenylsulfonamido)ethoxy)-N-((4-(morpholino(phenyl)methyl)cyclohexyl)methyl)acetamide
(728) 2-(2-(2,6-dichloro-N-methyl-4-(trifluoromethyl)phenylsulfonamido)ethoxy)-N-((4-(1-morpholino-3-phenylpropyl)cyclohexyl)methyl)acetamide
(729) N-((4-(3-phenyl-1-(pyrrolidin-1-yl)propyl)cyclohexyl)methyl)-2-(1-(2,4,6-trichlorophenylsulfonyl)piperidin-3-yloxy)acetamide
(730) 2-(1-(4-methoxy-2,6-dimethylphenylsulfonyl)piperidin-3-yloxy)-N-((4-(morpholino(phenyl)methyl)cyclohexyl)methyl)acetamide
(731) 2-(1-(4-methoxy-2,6-dimethylphenylsulfonyl)piperidin-3-yloxy)-N-((4-(3-phenyl-1-(pyrrolidin-1-yl)propyl)cyclohexyl)methyl)acetamide
(732) N-(4-((4-methylpiperazin-1-yl)(phenyl)methyl)cyclohexyl)-2-((1-(2,4,6-trichlorophenylsulfonyl)pyrrolidin-2-yl)methoxy)acetamide
(733) 2-((1-(4-methoxy-2,6-dimethylphenylsulfonyl)piperidin-2-yl)methoxy)-N-(4-(1-morpholino-3-phenylpropyl)cyclohexyl)acetamide
(734) 2-((1-(4-methoxy-2,6-dimethylphenylsulfonyl)piperidin-2-yl)methoxy)-N-(4-(3-phenyl-1-(piperidin-1-yl)propyl)cyclohexyl)acetamide
(735) 2-((1-(4-methoxy-2,6-dimethylphenylsulfonyl)piperidin-2-yl)methoxy)-N-((4-((4-methylpiperazin-1-yl)(phenyl)methyl)cyclohexyl)acetamide
(736) 2-((1-(4-methoxy-2,6-dimethylphenylsulfonyl)piperidin-2-yl)methoxy)-N-((4-(3-phenyl-1-(pyrrolidin-1-yl)propyl)cyclohexyl)methyl)acetamide
(737) N-(4-(1-morpholino-3-phenylpropyl)cyclohexyl)-2-((1-(2,4,6-trichlorophenylsulfonyl)piperidin-2-yl)methoxy)acetamide
(738) N-(4-(3-phenyl-1-(piperidin-1-yl)propyl)cyclohexyl)-2-((1-(2,4,6-trichlorophenylsulfonyl)piperidin-2-yl)methoxy)acetamide
(739) N-(4-((4-methylpiperazin-1-yl)(phenyl)methyl)cyclohexyl)-2-((1-(2,4,6-trichlorophenylsulfonyl)piperidin-2-yl)methoxy)acetamide
(740) 2-((1-(4-methoxy-2,6-dimethylphenylsulfonyl)piperidin-3-yl)methoxy)-N-(4-(3-phenyl-1-(piperidin-1-yl)propyl)cyclohexyl)acetamide
(741) N-(4-(1-morpholino-3-phenylpropyl)cyclohexyl)-2-((1-(2,4,6-trichlorophenylsulfonyl)piperidin-3-yl)methoxy)acetamide
(742) N-(4-((4-methylpiperazin-1-yl)(phenyl)methyl)cyclohexyl)-2-((1-(2,4,6-trichlorophenylsulfonyl)piperidin-3-yl)methoxy)acetamide
(743) N-((4-(morpholino(phenyl)methyl)cyclohexyl)methyl)-2-(1-(2,4,6-trichlorophenylsulfonyl)pyrrolidin-3-yloxy)acetamide
(744) 2-((1-(4-methoxy-2,6-dimethylphenylsulfonyl)piperidin-3-yl)methoxy)-N-((4-(morpholino(phenyl)methyl)cyclohexyl)methyl)acetamide
(745) N-((4-(1-morpholino-3-phenylpropyl)cyclohexyl)methyl)-2-(1-(2,4,6-trichlorophenylsulfonyl)pyrrolidin-3-yloxy)acetamide
(746) 2-(2-(2,6-dichloro-N-methyl-4-(trifluoromethyl)phenylsulfonamido)ethoxy)-N-((4-(3-phenyl-1-(pyrrolidin-1-yl)propyl)cyclohexyl)methyl)acetamide
(747) N-((4-(1-morpholino-3-phenylpropyl)cyclohexyl)methyl)-2-(1-(2,4,6-trichlorophenylsulfonyl)piperidin-3-yloxy)acetamide
(748) 2-(1-(4-methoxy-2,6-dimethylphenylsulfonyl)piperidin-3-yloxy)-N-((4-(1-morpholino-3-phenylpropyl)cyclohexyl)methyl)acetamide
(749) 2-((1-(4-methoxy-2,6-dimethylphenylsulfonyl)pyrrolidin-2-yl)methoxy)-N-((4-(1-morpholino-3-phenylpropyl)cyclohexyl)methyl)acetamide (750) 2-((1-(4-methoxy-2,6-dimethylphenylsulfonyl)pyrrolidin-2-yl)methoxy)-N-((4-(3-phenyl-1-(pyrrolidin-1-yl)propyl)cyclohexyl)methyl)acetamide
(751) N-((4-(1-morpholino-3-phenylpropyl)cyclohexyl)methyl)-2-((1-(2,4,6-trichlorophenylsulfonyl)pyrrolidin-2-yl)methoxy)acetamide
(752) N-((4-(3-phenyl-1-(pyrrolidin-1-yl)propyl)cyclohexyl)methyl)-2-((1-(2,4,6-trichlorophenylsulfonyl)pyrrolidin-2-yl)methoxy)acetamide
(753) 2-((1-(4-methoxy-2,6-dimethylphenylsulfonyl)piperidin-2-yl)methoxy)-N-((4-(1-morpholino-3-phenylpropyl)cyclohexyl)methyl)acetamide
(754) N-((4-(1-morpholino-3-phenylpropyl)cyclohexyl)methyl)-2-((1-(2,4,6-trichlorophenylsulfonyl)piperidin-2-yl)methoxy)acetamide
(755) N-((4-(3-phenyl-1-(pyrrolidin-1-yl)propyl)cyclohexyl)methyl)-2-((1-(2,4,6-trichlorophenylsulfonyl)piperidin-2-yl)methoxy)acetamide
(756) 2-((1-(4-methoxy-2,6-dimethylphenylsulfonyl)piperidin-3-yl)methoxy)-N-((4-(1-morpholino-3-phenylpropyl)cyclohexyl)methyl)acetamide
(757) 2-((1-(4-methoxy-2,6-dimethylphenylsulfonyl)piperidin-3-yl)methoxy)-N-((4-(3-phenyl-1-(pyrrolidin-1-yl)propyl)cyclohexyl)methyl)acetamide
(758) N-((4-(1-morpholino-3-phenylpropyl)cyclohexyl)methyl)-2-((1-(2,4,6-trichlorophenylsulfonyl)piperidin-3-yl)methoxy)acetamide
(759) N-((4-(3-phenyl-1-(pyrrolidin-1-yl)propyl)cyclohexyl)methyl)-2-((1-(2,4,6-trichlorophenylsulfonyl)piperidin-3-yl)methoxy)acetamide
(760) 3-(3,5-dichloro-phenyl)-[1,2,4]oxadiazole-5-carboxylic acid {[4-(dimethylamino-phenyl-methyl)-cyclohexylcarbamoyl]-methyl}-amide
(761) 3-(3,5-dichloro-phenyl)-[1,2,4]oxadiazole-5-carboxylic acid {2-[4-(dimethylamino-phenyl-methyl)-cyclohexylcarbamoyl]-ethyl}-amide
(762) 3-(2,4-dichloro-6-methyl-phenyl)-[1,2,4]oxadiazole-5-carboxylic acid {[4-(dimethylamino-phenyl-methyl)-cyclohexylcarbamoyl]-methyl}-amide
(763) 3-(2-methoxy-phenyl)-[1,2,4]oxadiazole-5-carboxylic acid {[4-(dimethylamino-phenyl-methyl)-cyclohexylcarbamoyl]-methyl}-amide
(764) 3-thiophen-2-yl-[1,2,4]oxadiazole-5-carboxylic acid {[4-(dimethylamino-phenyl-methyl)-cyclohexylcarbamoyl]-methyl}-amide
(765) 3-(4-trifluoromethyl-phenyl)-[1,2,4]oxadiazole-5-carboxylic acid {[4-(dimethylamino-phenyl-methyl)-cyclohexylcarbamoyl]-methyl}-amide
(766) 3-(4-tert-butyl-phenyl)-[1,2,4]oxadiazole-5-carboxylic acid {[4-(dimethylamino-phenyl-methyl)-cyclohexylcarbamoyl]-methyl}-amide
(767) 3-(5-fluoro-2-methyl-phenyl)-[1,2,4]oxadiazole-5-carboxylic acid {[4-(dimethylamino-phenyl-methyl)-cyclohexylcarbamoyl]-methyl}-amide
(768) 3-benzo[1,3]dioxol-5-yl-[1,2,4]oxadiazole-5-carboxylic acid {2-[4-(dimethylamino-phenyl-methyl)-cyclohexylcarbamoyl]-ethyl}-amide
(769) 3-benzenesulfonylmethyl-[1,2,4]oxadiazole-5-carboxylic acid {[4-(dimethylamino-phenyl-methyl)-cyclohexylcarbamoyl]-methyl}-amide
(770) 3-(2,6-dichloro-phenyl)-[1,2,4]oxadiazole-5-carboxylic acid {[4-(dimethylamino-phenyl-methyl)-cyclohexylcarbamoyl]-methyl}-amide
(771) 3-pyridin-2-yl-[1,2,4]oxadiazole-5-carboxylic acid {2-[4-(dimethylamino-phenyl-methyl)-cyclohexylcarbamoyl]-ethyl}-amide
(772) 3-(2,4,6-trimethyl-phenyl)-[1,2,4]oxadiazole-5-carboxylic acid {[4-(dimethylamino-phenyl-methyl)-cyclohexylcarbamoyl]-methyl}-amide
(773) 3-(2,4-dichloro-phenyl)-[1,2,4]oxadiazole-5-carboxylic acid {2-[4-(dimethylamino-phenyl-methyl)-cyclohexylcarbamoyl]-ethyl}-amide
(774) 3-(3,4-dimethoxy-phenyl)-[1,2,4]oxadiazole-5-carboxylic acid {2-[4-(dimethylamino-phenyl-methyl)-cyclohexylcarbamoyl]-ethyl}-amide
(775) 3-(3,4-dimethoxy-phenyl)-[1,2,4]oxadiazole-5-carboxylic acid {[4-(dimethylamino-phenyl-methyl)-cyclohexylcarbamoyl]-methyl}-amide
(776) 3-thiophen-2-yl-[1,2,4]oxadiazole-5-carboxylic acid {2-[4-(dimethylamino-phenyl-methyl)-cyclohexylcarbamoyl]-ethyl}-amide
(777) 3-(4-trifluoromethyl-phenyl)-[1,2,4]oxadiazole-5-carboxylic acid {[4-(dimethylamino-thiophen-2-yl-methyl)-cyclohexylcarbamoyl]-methyl}-amide
(778) 3-(4-trifluoromethyl-phenyl)-[1,2,4]oxadiazole-5-carboxylic acid [({4-[dimethylamino-(3-fluoro-phenyl)-methyl]-cyclohexylmethyl}-carbamoyl)-methyl]-amide
(779) 3-(4-tert-butyl-phenyl)-[1,2,4]oxadiazole-5-carboxylic acid {[4-(dimethylamino-thiophen-2-yl-methyl)-cyclohexylcarbamoyl]-methyl}-amide
(780) 3-thiophen-2-yl-[1,2,4]oxadiazole-5-carboxylic acid [2-({4-[dimethylamino-(3-fluoro-phenyl)-methyl]-cyclohexylmethyl}-carbamoyl)-ethyl]-amide
(781) 3-benzenesulfonylmethyl-[1,2,4]oxadiazole-5-carboxylic acid [({4-[dimethylamino-(3-fluoro-phenyl)-methyl]-cyclohexylmethyl}-carbamoyl)-methyl]-amide
(782) 3-(2-methoxy-phenyl)-[1,2,4]oxadiazole-5-carboxylic acid {[4-(1-dimethylamino-3-phenyl-propyl)-cyclohexylcarbamoyl]-methyl}-amide
(783) 3-benzo[1,3]dioxol-5-yl-[1,2,4]oxadiazole-5-carboxylic acid {[4-(1-dimethylamino-3-phenyl-propyl)-cyclohexylcarbamoyl]-methyl}-amide
(784) 3-thiophen-2-yl-[1,2,4]oxadiazole-5-carboxylic acid {[4-(1-dimethylamino-3-phenyl-propyl)-cyclohexylcarbamoyl]-methyl}-amide
(785) 3-(4-trifluoromethyl-phenyl)-[1,2,4]oxadiazole-5-carboxylic acid {[4-(1-dimethylamino-3-phenyl-propyl)-cyclohexylcarbamoyl]-methyl}-amide
(786) 3-(4-tert-butyl-phenyl)-[1,2,4]oxadiazole-5-carboxylic acid {[4-(1-dimethylamino-3-phenyl-propyl)-cyclohexylcarbamoyl]-methyl}-amide
(787) 3-(2-methoxy-phenyl)-[1,2,4]oxadiazole-5-carboxylic acid [({4-[dimethylamino-(3-fluoro-phenyl)-methyl]-cyclohexylmethyl}-carbamoyl)-methyl]-amide
(788) 3-(2,4-dichloro-phenyl)-[1,2,4]oxadiazole-5-carboxylic acid {2-[4-(1-dimethylamino-3-phenyl-propyl)-cyclohexylcarbamoyl]-ethyl}-amide
(789) 3-(3,4-dimethoxy-phenyl)-[1,2,4]oxadiazole-5-carboxylic acid {2-[4-(1-dimethylamino-3-phenyl-propyl)-cyclohexylcarbamoyl]-ethyl}-amide
(790) 3-(3,5-dichloro-phenyl)-[1,2,4]oxadiazole-5-carboxylic acid {[4-(1-dimethylamino-3-phenyl-propyl)-cyclohexylcarbamoyl]-methyl}-amide
(791) 3-pyridin-2-yl-[1,2,4]oxadiazole-5-carboxylic acid {[4-(1-dimethylamino-3-phenyl-propyl)-cyclohexylcarbamoyl]-methyl}-amide
(792) 3-benzo[1,3]dioxol-5-yl-[1,2,4]oxadiazole-5-carboxylic acid {2-[4-(1-dimethylamino-3-phenyl-propyl)-cyclohexylcarbamoyl]-ethyl}-amide
(793) 3-(2,6-dichloro-phenyl)-[1,2,4]oxadiazole-5-carboxylic acid {[4-(1-dimethylamino-3-phenyl-propyl)-cyclohexylcarbamoyl]-methyl}-amide (794) 3-(3,4-dimethoxy-phenyl)-[1,2,4]oxadiazole-5-carboxylic acid {[4-(1-dimethylamino-3-phenyl-propyl)-cyclohexylcarbamoyl]-methyl}-amide
(795) 3-(2,4-dichloro-phenyl)-[1,2,4]oxadiazole-5-carboxylic acid {[4-(1-dimethylamino-3-phenyl-propyl)-cyclohexylcarbamoyl]-methyl}-amide
(796) 3-(5-fluoro-2-methyl-phenyl)-[1,2,4]oxadiazole-5-carboxylic acid {[4-(1-dimethylamino-3-phenyl-propyl)-cyclohexylcarbamoyl]-methyl}-amide
(797) 3-thiophen-2-yl-[1,2,4]oxadiazole-5-carboxylic acid {2-[4-(1-dimethylamino-3-phenyl-propyl)-cyclohexylcarbamoyl]-ethyl}-amide
(798) 4-methoxy-N,2,6-trimethyl-N-(2-(2-(4-((4-methylpiperazin-1-yl)(phenyl)methyl)piperidin-1-yl)-2-oxoethoxy)ethyl)benzenesulfonamide
(799) N-(2-(2-(4-((3-fluorophenyl)(4-methylpiperazin-1-yl)methyl)piperidin-1-yl)-2-oxoethoxy)ethyl)-4-methoxy-N,2,6-trimethylbenzenesulfonamide
(800) 1-(4-((3-fluorophenyl)(4-methylpiperazin-1-yl)methyl)piperidin-1-yl)-2-((1-(4-methoxy-2,6-dimethylphenylsulfonyl)piperidin-2-yl)methoxy)ethanone
(801) 4-methoxy-N,2,6-trimethyl-N-(2-(2-(4-(1-(4-methylpiperazin-1-yl)-3-phenylpropyl)piperidin-1-yl)-2-oxoethoxy)ethyl)benzenesulfonamide
(802) 2-((1-(4-methoxy-2,6-dimethylphenylsulfonyl)piperidin-2-yl)methoxy)-1-(4-(1-(4-methylpiperazin-1-yl)-2-phenylethyl)piperidin-1-yl)ethanone
(803) 4-methoxy-N,2,6-trimethyl-N-(2-(2-(4-(1-(4-methylpiperazin-1-yl)-2-phenylethyl)piperidin-1-yl)-2-oxoethoxy)ethyl)benzenesulfonamide
(804) N-(2-(2-(4-((4-fluorophenyl)(4-methylpiperazin-1-yl)methyl)piperidin-1-yl)-2-oxoethoxy)ethyl)-4-methoxy-N,2,6-trimethylbenzenesulfonamide
(805) 1-(4-((4-fluorophenyl)(4-methylpiperazin-1-yl)methyl)piperidin-1-yl)-2-((1-(4-methoxy-2,6-dimethylphenylsulfonyl)piperidin-2-yl)methoxy)ethanone
(806) 2-((1-(4-methoxy-2,6-dimethylphenylsulfonyl)piperidin-2-yl)methoxy)-1-(4-(1-(4-methylpiperazin-1-yl)-3-phenylpropyl)piperidin-1-yl)ethanone
(807) 2-((1-(4-methoxy-2,6-dimethylphenylsulfonyl)piperidin-2-yl)methoxy)-1-(4-((4-methylpiperazin-1-yl)(phenyl)methyl)piperidin-1-yl)ethanone
(808) 2-((1-(3,4-dichlorophenylsulfonyl)-1,2,3,4-tetrahydroquinolin-2-yl)methoxy)-1-(4-((4-fluorophenyl)(4-methylpiperazin-1-yl)methyl)piperidin-1-yl)ethanone
(809) 2-((1-(3,4-dichlorophenylsulfonyl)-1,2,3,4-tetrahydroquinolin-2-yl)methoxy)-1-(4-((3-fluorophenyl)(4-methylpiperazin-1-yl)methyl)piperidin-1-yl)ethanone
(810) 2-((1-(3,4-dichlorophenylsulfonyl)-1,2,3,4-tetrahydroquinolin-2-yl)methoxy)-1-(4-((4-methylpiperazin-1-yl)(phenyl)methyl)piperidin-1-yl)ethanone
(811) 2-((1-(3,4-dichlorophenylsulfonyl)-1,2,3,4-tetrahydroquinolin-2-yl)methoxy)-1-(4-(1-(4-methylpiperazin-1-yl)-3-phenylpropyl)piperidin-1-yl)ethanone, and
(812) 2-((1-(3,4-dichlorophenylsulfonyl)-1,2,3,4-tetrahydroquinolin-2-yl)methoxy)-1-(4-(1-(4-methylpiperazin-1-yl)-2-phenylethyl)piperidin-1-yl)ethanone.

The invention also includes a process for the preparation of a substituted amide derivative according to the invention.

In order to prepare the compounds of formula I, amines of formula II are reacted with acids of formula K with the addition of a coupling reagent. This can be carried out, for example, by the following methods:

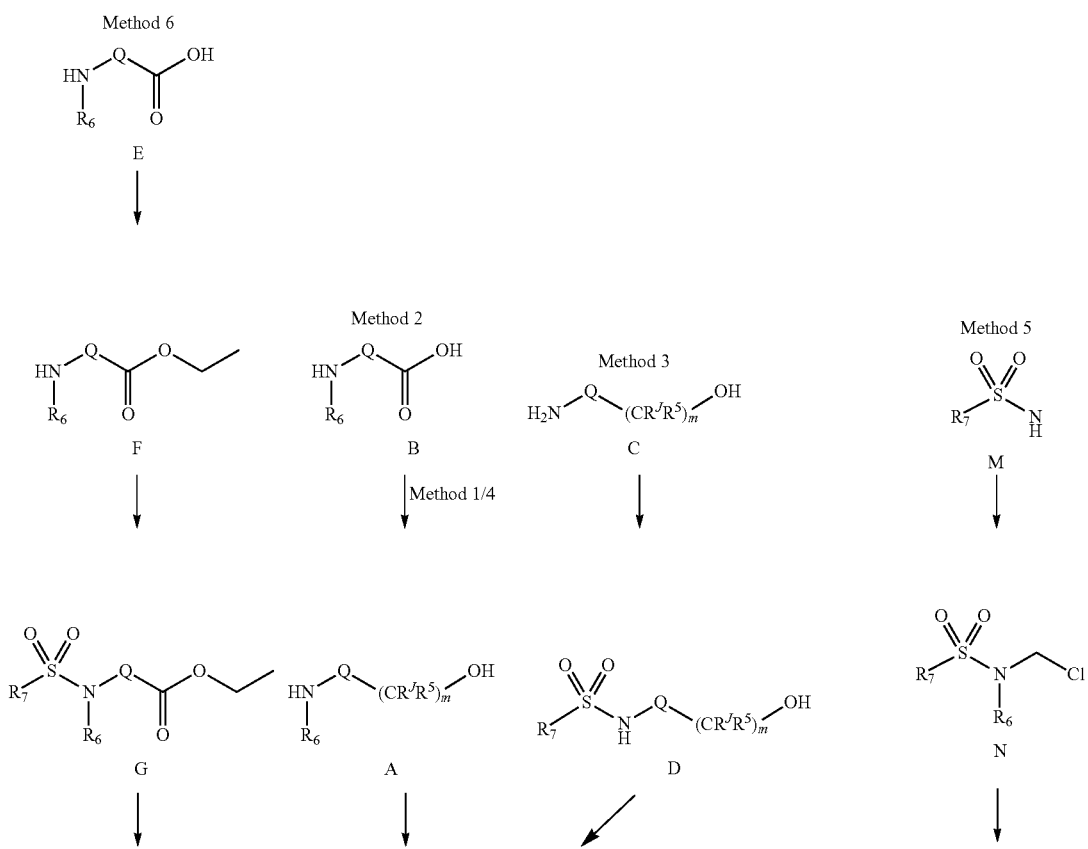

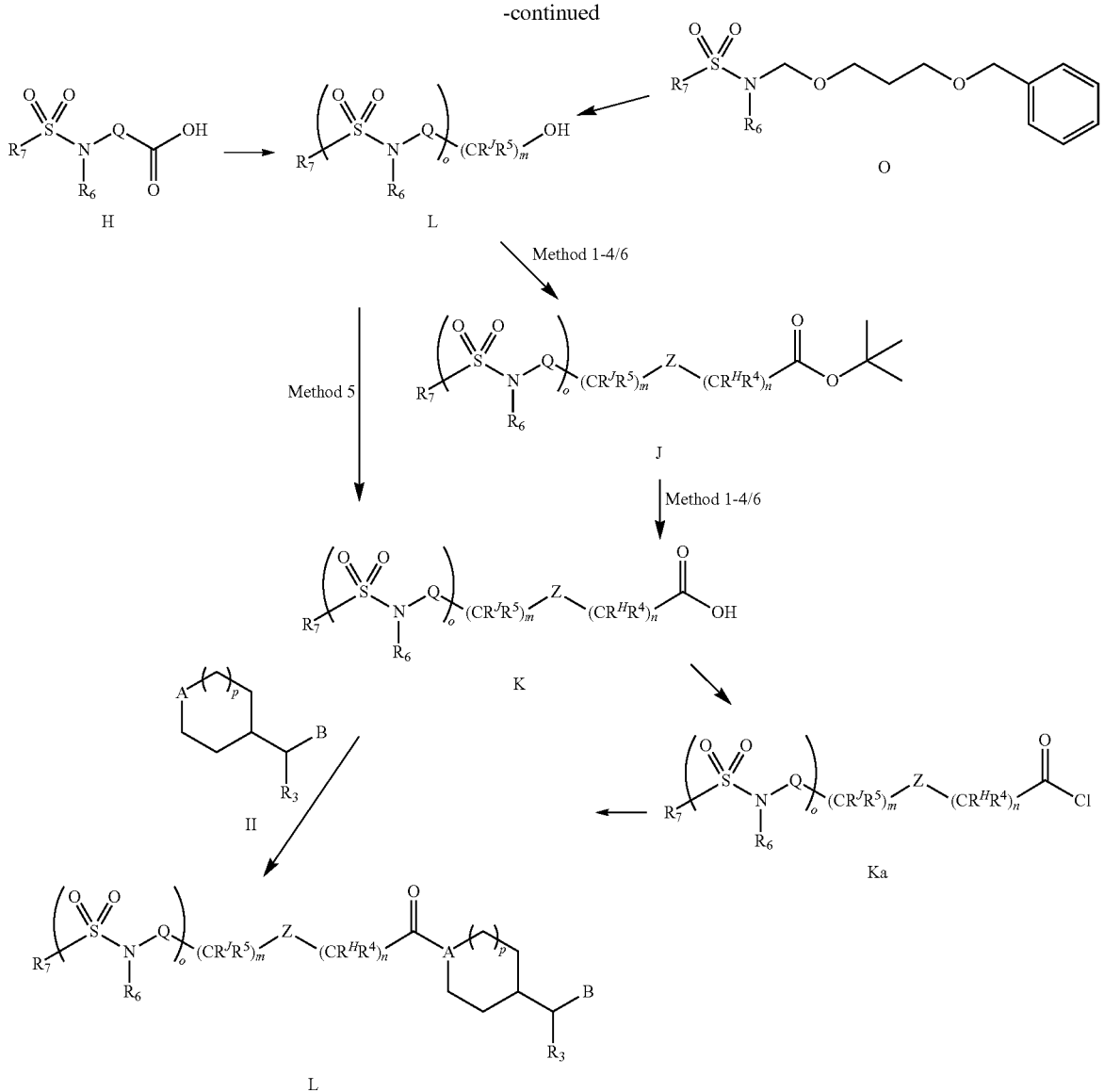

In Methods 1 and 4 shown, the racemic (R and S configuration) or enantiomerically pure (R or S configuration) amino alcohols A are reacted in a sulfonylation with sulfonyl chlorides, bromides or pentafluorophenolate $R_3SO_2X$ (X=Cl, Br, OPFP), optionally in the presence of an organic or inorganic base, for example potassium carbonate, sodium bicarbonate, diisopropylethylamine, triethylamine, pyridine, diethylamine or DBU, preferably in an organic solvent, for example acetonitrile, methylene chloride or tetrahydrofuran, to give the sulfonylated amino alcohols L.

In Method 2, the racemic (R and S configuration) or enantiomerically pure (R or S configuration) amino acids B are converted by a reduction into an amino alcohol A (if this is not commercially available) using metal hydrides as reducing agents, such as, for example, $LiAlH_4$, $BH_3 \times DMS$ or $NaBH_4$, in an organic solvent, such as THF or diethyl ether. The amino alcohols A are reacted further in a sulfonylation with sulfonyl chlorides, bromides or pentafluorophenolate $R_3SO_2X$ (X=Cl, Br, OPFP), optionally in the presence of an organic or inorganic base, for example potassium carbonate, sodium bicarbonate, diisopropylethylamine, triethylamine, pyridine, diethylamine or DBU, preferably in an organic solvent, for example acetonitrile, methylene chloride or tetrahydrofuran, to give the sulfonylated amino alcohols L.

In Method 3, the amino alcohols C are reacted in a sulfonylation with sulfonyl chlorides, bromides or pentafluorophenolate $R_1SO_2X$ (X=Cl, Br, OPFP), optionally in the presence of an organic or inorganic base, for example potassium carbonate, sodium bicarbonate, diisopropylethylamine, triethylamine, pyridine, diethylamine or DBU, preferably in an organic solvent, for example acetonitrile, methylene chloride or tetrahydrofuran, to give the sulfonylated amino alcohols D. The sulfonylated amino alcohols D are then reacted in an alkylation reaction with alkyl halides (RX, X=I, Br, Cl) or mesylates or alternative alkylating reagents, optionally in the presence of an organic or inorganic base, for example sodium hydride, potassium carbonate, caesium carbonate, DBU or DIPEA, preferably in an organic solvent, for example dimethylformamide, acetone, THF, acetonitrile, dioxane or these solvents as mixtures, to give the sulfonylated amino alcohols L.

In Method 5, the N-methyl-sulfonamides M are reacted in the presence of paraformaldehyde or formaldehyde and chlorotrimethylsilane, thionyl chloride or hydrogen chloride, optionally in the presence of sulfuric acid, optionally in an organic solvent, for example chloroform, benzene or tetrahydrofuran, to give the sulfonamides N. The sulfonamides N are then reacted in an alkylation reaction with an alcohol using tetrabutylammonium chloride or bromide or tetrabutylammonium hydrogen sulfate, in a phase transfer reaction using an organic solvent, such as toluene, benzene, methylene chloride or xylene, or also mixtures of these solvents, and an inorganic base, such as potassium hydroxide, sodium hydroxide, sodium carbonate, sodium bicarbonate or potassium carbonate, or in the presence of an organic or inorganic base, conventional inorganic bases are metal alcoholates, such as sodium methanolate, sodium ethanolate or potassium tert-butylate, lithium or sodium bases, such as lithium diisopropylamide, butyllithium, tert-butyllithium or sodium methylate, or metal hydrides, such as potassium hydride, lithium hydride or sodium hydride, conventional organic bases are diisopropylethylamine or triethylamine, in an organic solvent, such as methylene chloride, toluene, THF or diethyl ether, to give the products of the general structure O. The benzyl alcohols O are reacted in the presence of palladium hydroxide on charcoal, palladium on charcoal or alternative suitable known catalysts, in the presence of hydrogen or ammonium formate, optionally in the presence of formic acid or acetic acid, in an organic solvent, such as methanol, ethyl acetate or tetrahydrofuran, to give the alcohols L, which give, using pyridinium dichromate, pyridinium chlorochromate or combinations of potassium permanganate and sodium hydroxide solution, sodium periodate and ruthenium(III) chloride, chromium(VI) oxide and sulfuric acid or 2,2,6,6-tetramethylpiperidin-1-yloxy radical and [bis(acetoxy)iodo]benzene, in organic solvents, such as acetone, DMF, acetonitrile, water or these solvents as mixtures, or under other generally known oxidation conditions, the acid stages of the general formula K.

In Method 6, the racemic (R and S configuration) or enantiomerically pure (R or S configuration) amino acids E are esterified using dehydrating reagents, for example inorganic acids, such as $H_2SO_4$ or phosphorus oxides, or organic reagents, such as thionyl chloride, in organic solvents, such as THF, diethyl ether, methanol, ethanol or methylene chloride, to give the amino esters F, and these are then reacted in a sulfonylation with sulfonyl chlorides, bromides or pentafluorophenolates $R_3SO_2X$ (X=Cl, Br, OPFP), optionally in the presence of an organic or inorganic base, for example potassium carbonate, sodium bicarbonate, diisopropylethylamine, triethylamine, pyridine, diethylamine or DBU, preferably in an organic solvent, for example acetonitrile, methylene chloride or tetrahydrofuran, to give the sulfonylated amino esters G. In Method 6, the sulfonylated amino esters G give, in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium bicarbonate, potassium carbonate, in an organic solvent, such as methanol, dioxane, methylene chloride, THF, diethyl ether or these solvents as mixtures, the sulfonylated amino acids H. The amino acids H are converted by a reduction into a sulfonylated amino alcohol L using metal hydrides as reducing agents, such as, for example, $LiAlH_4$, $BH_3 \times DMS$ or $NaBH_4$, in an organic solvent, such as THF or diethyl ether.

In Methods 1 to 4 and 6, the sulfonylated amino alcohols L are reacted in an alkylation reaction with halogenated ester derivatives using tetrabutylammonium chloride or bromide or tetrabutylammonium hydrogen sulfate, in a phase transfer reaction using an organic solvent, such as toluene, benzene, methylene chloride or xylene, or also mixtures of these solvents, and an inorganic base, such as potassium hydroxide, sodium hydroxide, sodium carbonate, sodium bicarbonate or potassium carbonate, or in the presence of an organic or inorganic base, conventional inorganic bases are metal alcoholates, such as sodium methanolate, sodium ethanolate or potassium tert-butylate, lithium or sodium bases, such as lithium diisopropylamide, butyllithium, tert-butyllithium or sodium methylate, or metal hydrides, such as potassium hydride, lithium hydride or sodium hydride, conventional organic bases are diisopropylethylamine or triethylamine, in an organic solvent, such as methylene chloride, toluene, THF or diethyl ether, to give the products of the general structure J, which give, in an ester cleavage using organic acids, such as trifluoroacetic acid or aqueous inorganic acids, such as hydrochloric acid, or using aqueous inorganic bases, such as lithium hydroxide, potassium hydroxide, sodium hydroxide, sodium carbonate, sodium bicarbonate or potassium carbonate, in organic solvents, such as methanol, dioxane, methylene chloride, THF, diethyl ether or these solvents as mixtures, the acid stages of the general formula K.

In Methods 1-6, the carboxylic acids K are reacted in an amide formation using primary or secondary amines of the general formula II in the presence of dehydrating agents, such as sodium sulfate or magnesium sulfate, phosphorus oxide or reagents such as, for example, CDI, DCC (optionally bonded to a polymer), TBTU, EDCI, PyBOP or PFPTFA, also in the presence of HOAt or HOBt and an organic base, for example DIPEA or pyridine, in an organic solvent, such as THF, methylene chloride, diethyl ether, dioxane, DMF or acetonitrile, to give the products of the general formula I.

In a further process, acid chlorides or optionally bromides of the general formula Ka are reacted with the amines of the general formula II in polar or nonpolar aprotic solvents, in the presence of organic or inorganic auxiliary bases, preferably tertiary amines, such as triethylamine, diisopropylethylamine or DMAP, to give the products of the general formula I. Pyridine, for example, is furthermore also suitable as a base and as a solvent. Preferably, acid chlorides are reacted with amines at −30° to +40° C. in methylene chloride or chloroform in the presence of triethylamine or pyridine and optionally catalytic amounts of DMAP.

The amine units of the general formula II used can be prepared, for example, by the following processes. Amine units wherein A in the unit of the general formula II represents $CHNH_2$ or $(CH_2)_nNH_2$ can be prepared by the process called Process A in the following.

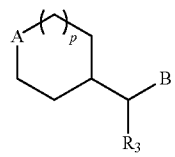

II

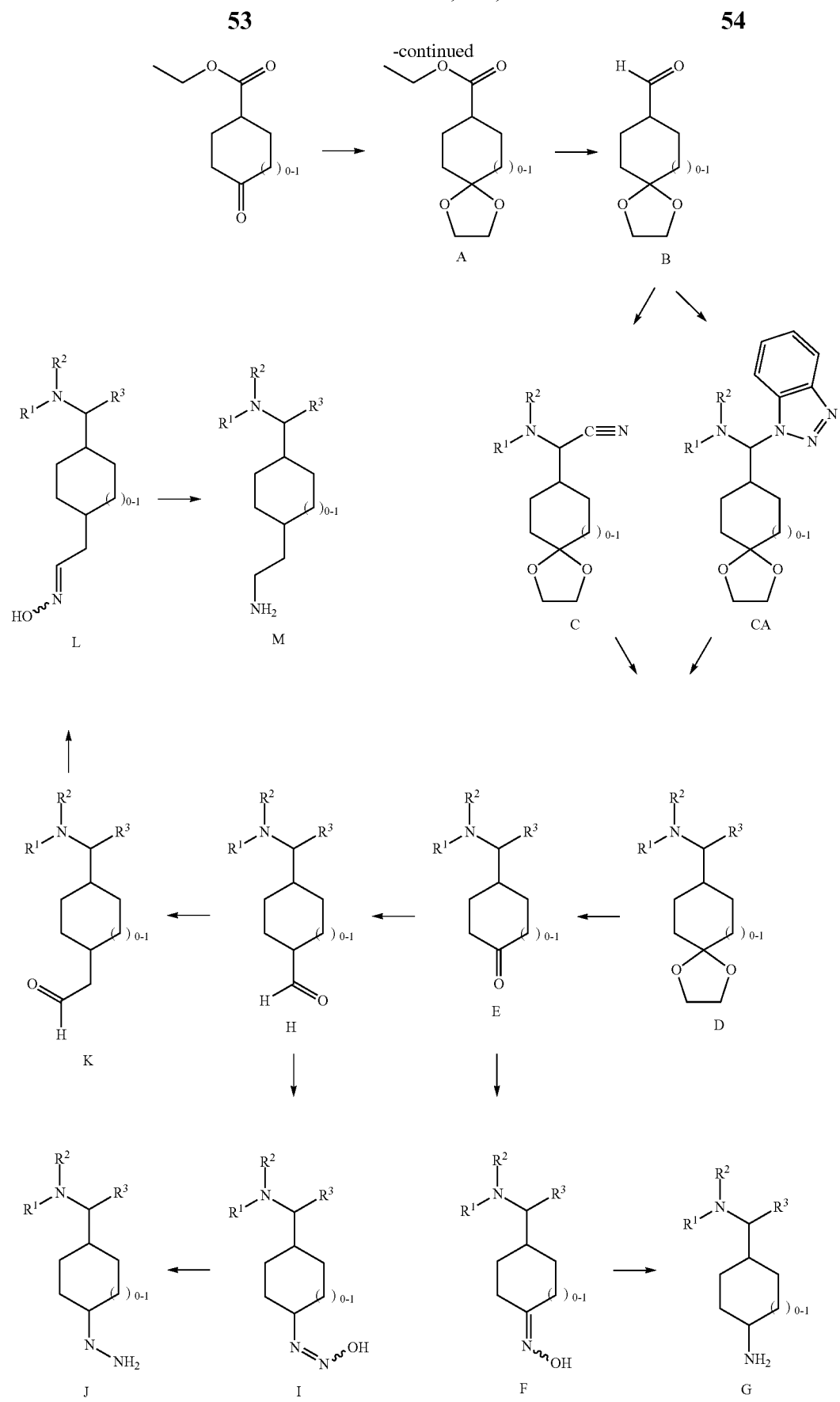

In this process, ethyl 4-oxocyclohexanecarboxylate or cyclopentanone-3-carboxylic acid ethyl ester is reacted in an acetal formation reaction with a diol derivative in an organic solvent, such as benzene, toluene or xylene, methylene chloride, cyclohexane or ethanol, if appropriate with the addition of catalytic amounts of p-toluenesulfonic acid, camphorsulfonic acid, pyridinium tosylate or acetic acid, possibly also in the presence of a dehydrating reagent, such as sulfuric acid, sodium sulfate or magnesium sulfate, a molecular sieve or phosphorus oxides, at a temperature of from RT to the reflux temperature of the particular organic solvent, to give the acetal A.

Prior esterification of the cyclopentanone-3-carboxylic acid to give the cyclopentanone-3-carboxylic acid ethyl ester can be carried out by reaction of the cyclopentanone-3-carboxylic acid with ethanol using sulfuric acid or hydrochloric acid, or by reaction of the cyclopentanone-3-carboxylic acid with iodoethane using sodium ethanolate or caesium carbonate in DMF.

The acetal A can be reduced in a reduction reaction with a reducing agent, for example diisobutylaluminium hydride, sodium aluminium hydride or borane-THF complex, in diethyl ether, methylene chloride, THF, hexane, toluene or a mixture of the solvent mentioned, at a temperature of from −95° C. to −20° C. to give the aldehyde B.

The aldehyde B can be converted into the nitrile C by addition of an amine and a source of cyanide. The reaction can be carried out in one or two stages. In the two-stage variant, a nitrile alcohol is first formed and isolated. The nitrile alcohol can be formed by reaction of the aldehyde B with HCN, KCN or NaCN. Suitable solvents are water, methanol, ethanol, THF, piperidine, diethyl ether or a mixture of these solvents. If NaCN and KCN are used, the cyanide required can typically be liberated by addition of, for example, sodium hydrogen sulfite, sulfuric acid, acetic acid or hydrochloric acid. Trimethylsilyl cyanide, for example, is likewise suitable as a source of nitrile. In this case the cyanide can be liberated, for example, by boron trifluoride etherate, InF$_3$ or HCl. Typical solvents here are water or toluene.

(Cyano-C)diethylaluminium, for example, is suitable as a further source of cyanide. THF, toluene or a mixture of the two solvents can be used as the solvent. The reaction temperature can be between −78° C. and +25° C. for all the variants. Alcohols, such as methanol or ethanol, are particularly suitable as the solvent for the reaction of the nitrile alcohol with the amine. The reaction temperature can be between 0° C. and +25° C. In the one-stage variant, the nitrile alcohol primarily formed is formed in situ and reacted with the amine. In one variant of the reaction procedure, the aldehyde B is reacted in an aminal formation reaction with an amine and 1H-benzotriazole to give the benzotriazole aminal CA. The benzotriazole aminal can be present in equilibrium both in the 1H and in the 2H form.

Suitable solvents are benzene, toluene, ethanol, diethyl ether or THF. The use of a Dean-Stark water separator, a molecular sieve or other dehydrating means may be necessary. The reaction time can be between 1 and 20 h at a reaction temperature of from +20° C. to +110° C. Both the nitrile C and the benzotriazole aminal CA can be reacted with metal organyls, such as magnesium, zinc or lithium organyls, in organic solvents, for example diethyl ether, dioxane or tetrahydrofuran, to give amino acetals D.

The amine ketones E are obtained in an acetal cleavage reaction under acidic conditions. Suitable acids are both inorganic Broenstedt or Lewis acids, such as hydrochloric acid, sulfuric acid, ammonium chloride or hydrogen sulfate, or AlI$_3$, and organic acids, such as e.g. p-toluenesulfonic acid, acetic acid, oxalic acid, trifluoromethanesulfonic acid, formic acid, trifluoroacetic acid or citric acid. The reaction can be carried out in various solvents, such as, for example, toluene, THF, chloroform, MC, xylene, acetonitrile, water, dioxane, acetone, diethyl ether or ethyl acetate, at temperatures of from −10° C. to room temperature.

The aldehyde H is obtained from the amine ketone E in a Wittig reaction using phosphorylidene and a strong base, for example potassium tert-butylate, n-butyllithium, s-butyllithium, phenyllithium, lithium diisopropylamide or lithium hexamethyldisilazide, in organic solvents, such as THF, diethyl ether, cyclohexane, toluene or a mixture of the solvents, at a temperature of from −78° C. to +30° C., after acidic working up of the reaction mixture.

To synthesize the aldehyde K, the Wittig reaction is repeated under the same conditions with the aldehyde H as the starting compound. For synthesis of units in which A represents (CH$_2$)$_n$NH$_2$ where n is >1, the step is repeated n times. The ketone E is reacted in an oxime formation reaction with hydroxylamine hydrochloride, sulfate or acetate in an organic solvent, for example ethanol, methanol, 2-propanol, 2-methyl-propan-2-ol or acetonitrile, with the addition of an organic base, such as, for example, pyridine, sodium acetate, triethylamine, 4-dimethylaminopyridine or potassium t-butylate, or an aqueous solution of an inorganic base, such as sodium bicarbonate, sodium carbonate, potassium carbonate, sodium hydroxide or potassium hydroxide, or the basic ion exchanger Amberlyst, to give the oximes F.

The aldehydes H and K can likewise be converted into the oximes I and L respectively under the same conditions. The amines G can be obtained by a reduction reaction of the oximes F with a reducing agent, such as, for example, LiAlH$_4$, sodium, zinc, borane dimethylsulfide, sodium borohydride/nickel(II) chloride hexahydrate, in ethanol, methanol, glacial acetic acid, THF, diethyl ether or dioxane, or by catalytic hydrogenation with palladium or platinum oxide as a heterogeneous catalyst, with the addition of HCl in an alcohol, such as methanol or ethanol. The amines J and M can be prepared from the oximes I and L respectively under the same conditions.

Amine units corresponding to formula II wherein A denotes NH used can be prepared by the following process:

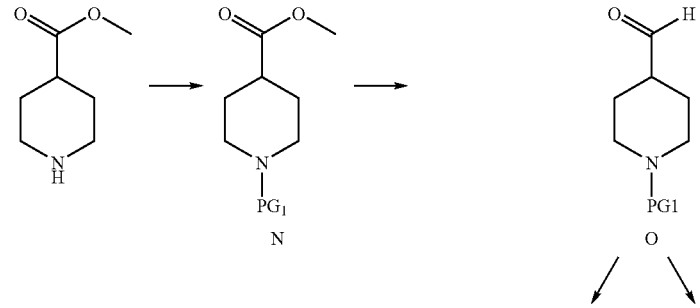

-continued

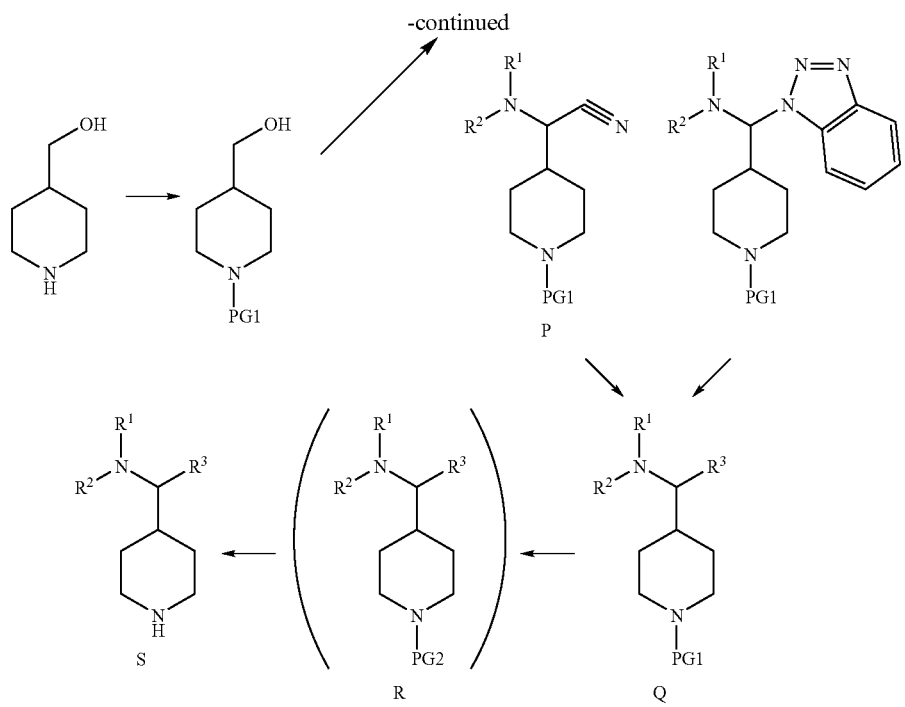

Isonipecotic acid methyl ester or piperidin-4-ylmethanol is subjected to an alkylation reaction. p-Methoxybenzyl halides are suitable in particular as the alkylating reagent. The reaction can be carried out by reaction of p-methoxybenzyl chloride or bromide in THF, benzene, toluene, dimethylformamide, acetonitrile, methylene chloride, ethanol or acetone using a base, such as, for example, triethylamine, diisopropylethylamine, potassium carbonate or sodium carbonate, at a temperature of from +20° C. to +80° C. in 1-72 h.

As an alternative, a BOC can also be introduced as a protective group by reaction with di-tert-butyl dicarbonate in an organic solvent, such as THF, methylene chloride, methanol, dioxane, DMF or diethyl ether, if appropriate using an inorganic base, such as sodium carbonate, sodium bicarbonate or sodium hydroxide, or an organic base, such as triethylamine, diisopropylethylamine or n-butyllithium, at a temperature of between −78° C. and room temperature.

The synthesis steps for reducing the ester N to the aldehyde O, reaction of the aldehyde O to give the aminonitrile P and reaction with a metal organyl to give the protected amine Q are carried out analogously to the synthesis steps such as have been described for the compounds A →B →C →D.

The protected piperidin-4-ylmethanol can be reacted using reagents such as PCC, periodinane, IBX, TPAP, NMO, $MnO_2$ or oxalyl chloride, optionally also in the presence of a molecular sieve or a base, such as triethylamine, in an organic solvent, such as methylene chloride, DMSO, methanol, ethanol, diethyl ether, THF, DMF or DME, at a temperature of from −78° C. up to the reflux temperature of the particular organic solvent, to give the aldehyde O.

An alternative route for the conversion of the compounds Q into the compound R is carried out analogously to the synthesis steps such as have been described for the compounds B →CA →D.

The debenzylation of the compounds Q to give the piperidine derivative S can be carried out directly with cerium ammonium nitrate in acetonitrile at room temperature in the course of 0.5-2 h, or indirectly by reaction of the compound Q with chloroformic acid benzyl ester in methylene chloride at room temperature, to give the compounds of the general formula R.

Various methods are known for deprotection of the compounds R, e.g. if benzyl carbamate protective groups are used, such as, for example, catalytic hydrogenation with Pd or $Pd(OH)_2$ as the catalyst in solvents, such as alcohols, preferably methanol or ethanol, THF, dioxane, ethyl acetate, DMF or mixtures of the solvents mentioned. Auxiliary reagents, such as, for example, acetic acid, acetyl chloride, HCl, ammonium acetate, ammonium formate, water, potassium carbonate, potassium hydroxide, cyclohexene or 1,4-cyclohexadiene, can optionally be added. Deprotection with the aid of trimethylsilyl iodide in organic solvents, such as chloroform, methylene chloride or acetonitrile, is likewise known. Methylsulfonic acid can furthermore be used with the addition of anisole in chloroform or methylene chloride, or also HCl gas in chloroform or methylene chloride, or HBr in glacial acetic acid.

BOC protective groups can be split off by reaction with HCl in organic solvents, such as dioxane, methanol, ethanol, acetonitrile or ethyl acetate, or by reaction with trifluoroacetic acid or methanesulfonic acid in methylene chloride or THF at a temperature of from 0° C. to 110° C. over a reaction time of 0.5-20 h.

The diastereomers optionally obtained during the syntheses of the end products can be separated by methods known to the person skilled in the art for separation of diastereomers, e.g. by chromatography, in particular over silica gel, normal phase or reverse phase. RP-HPLC (mobile phase acetonitrile/water or methanol/water) is particularly suitable for separation of the diastereomers.

It has been found that the substances according to the invention not only bind to the μ opioid receptor, but also inhibit the reuptake of serotonin and noradrenaline. Noradrenaline and serotonin reuptake inhibitors have an antidepressant and anxiolytic action, but are also suitable for treatment of pain—(Analgesics—from Chemistry and Pharmacology to Clinical Application, Wiley 2002, p. 265-284).

The substances according to the invention are suitable as pharmaceutically active compounds in medicaments. The invention therefore also provides pharmaceutical compositions containing at least one substituted amide derivative according to the invention and optionally suitable additives and/or auxiliary substances and/or optionally further active compounds.

The pharmaceutical compositions according to the invention optionally contain, in addition to at least one substituted amide derivative according to the invention, suitable additives and/or auxiliary substances, that is to say also carrier materials, fillers, solvents, diluents, dyestuffs and/or binders, and can be administered as liquid medicament forms in the form of injection solutions, drops or juices or as semi-solid medicament forms in the form of granules, tablets, pellets, patches, capsules, plasters or aerosols. The choice of auxiliary substances etc. and the amounts thereof to be employed depend on whether the medicament is to be administered orally, perorally, parenterally, intravenously, intraperitoneally, intradermally, intramuscularly, intranasally, buccally, rectally or locally, for example to the skin, the mucous membranes or into the eyes.

Formulations in the form of tablets, coated tablets, capsules, granules, drops, juices and syrups are suitable for oral administration, and solutions, suspensions, easily reconstitutable dry formulations and sprays are suitable for parenteral, topical and inhalatory administration. Substituted amide derivatives according to the invention in a depot, in dissolved form or in a plaster, optionally with the addition of agents which promote penetration through the skin, are suitable formulations for percutaneous administration. Formulation forms which can be used orally or percutaneously can release the substituted amide derivatives according to the invention in a delayed manner. In principle, other further active compounds known to the person skilled in the art can be added to the medicaments according to the invention.

The amount of active compound to be administered to patients varies as a function of the weight of the patient, the mode of administration, the indication and the severity of the disease. 0.005 to 20 mg/kg, preferably 0.05 to 5 mg/kg of at least one amide derivative according to the invention are conventionally administered.

The pharmaceutical composition can contain a substituted amide derivative according to the invention as the pure diastereomer and/or enantiomer, as a racemate or as a non-equimolar or equimolar mixture of the diastereomers and/or enantiomers.

The invention also includes the use of a substituted amide derivative according to the invention for the treatment of pain, in particular acute, visceral, chronic or neuropathic pain and inflammation pain. The invention also provides the use of a substituted amide derivative according to the invention for treatment of depression or for anxiolysis. The invention also includes the use of a substituted amide derivative according to the invention for treatment of diseases of the respiratory tract.

The substituted amide compounds corresponding to formula I are also suitable for treating urinary incontinence, diarrhea, pruritus, alcohol and drug abuse, lack of drive, migraine, diabetes, diseases of the respiratory tract, inflammatory intestinal diseases, neurological diseases, inflammations of the skin, rheumatic diseases, septic shock, reperfusion syndrome and obesity and as an angiogenesis inhibitor.

The invention therefore also provides the use of a substituted amide compound corresponding to formula I for treatment of urinary incontinence, diarrhea, pruritus, alcohol and drug abuse, lack of drive, migraine, diabetes, inflammatory intestinal diseases, neurological diseases, inflammations of the skin, rheumatic diseases, septic shock, reperfusion syndrome and obesity and as an angiogenesis inhibitor.

EXAMPLES

The following examples are intended to illustrate the invention, but do not limit the invention. The yields of the compounds prepared were not optimized. All the temperatures are uncorrected.

The term "RT" denotes room temperature, "conc." concentrated, "d" days, "min" minutes, "h" hours, "M" is a concentration stated in mol/l, "MeOH" methanol, "THF" tetrahydrofuran, "aq." aqueous, "sat." saturated, "soln." solution, "EtOAc" ethyl acetate, "NaHCO$_3$ soln." sodium bicarbonate soln., "MC" methylene chloride, "CHCl$_3$" chloroform, "DMF" N,N-dimethylformamide, "Et$_2$O" diethyl ether, "Et$_3$N" triethylamine, "i. vac." in vacuo, "Na$_2$SO$_4$" sodium sulfate, "NH$_4$Cl soln." sat. aq. ammonium chloride soln.

The chemicals and solvents employed were obtained commercially from the conventional suppliers (Acros, Avocado, Aldrich, Bachem, Fluka, Lancaster, Maybridge, Merck, Sigma, TCI etc.) or synthesized by conventional methods known to persons skilled in the art. Silica gel 60 (0.040-0.063 mm) from E. Merck, Darmstadt was used as the stationary phase for the column chromatography.

ABBREVIATIONS

TBTU=O-(Benzotriazol-1-yl)-N,N,N',N'-tetramethyluronium tetrafluoroborate
CDI=1,1'-Carbonyldiimidazole
DCC=Dicyclohexylcarbodiimide
EDCI=1-Ethyl-3-(3-dimethylaminopropyl)carbodiimide
HOAt=1-Hydroxy-7-azabenzotriazole
DIPEA=N,N-Diisopropylamine
HOBt=1-Hydroxybenzotriazole
EDCI=N-(3-Dimethylaminopropyl)-N'-ethylcarbodiimide hydrochloride
PyBOP=Benzotriazol-1-yl-oxy-tris-pyrrolidino-phosphonium hexafluorophosphate
PFPTFA=Pentafluorophenyltrifluoroacetyl
OPFP=O-Pentafluorophenyl
DBU=1,8-Diazabicyclo[5.4.0]undec-7-ene
AcOH=Acetic acid
DIBAL-H=Diisobutylaluminium hydride
EtOH=Ethanol
HBt=1H-Benzotriazole
KtOBu=Potassium tert-butylate
LAH=Lithium aluminium hydride
PG=Protective group
TEA=Triethylamine
TFA=Trifluoroacetic acid
p-TosOH=p-Toluenesulfonic acid Thin layer chromatography investigations were carried out with HPTLC precoated plates, silica gel 60 F 254 from E. Merck, Darmstadt.

The mixing ratios of solvents, mobile phases or for chromatography investigations are always stated in volume/volume.

Preparation of the Amine Units

| Designation | Name |
|---|---|
| AM1 | 4-(Dimethylamino-thiophen-2-yl-methyl)-cyclohexylamine |
| AM2 | 4-[Dimethylamino-(4-fluorophenyl)-methyl]-cyclohexylamine |
| AM3 | 2-[4-(Dimethylamino-thiophen-2-yl-methyl)-cyclohexyl]-ethylamine |
| AM4 | 2-{4-[Dimethylamino-(3-fluorophenyl)-methyl]-cyclohexyl}-ethylamine |
| AM5 | 2-{4-[(4-Chlorophenyl)-dimethylamino-methyl]-cyclohexyl}-ethylamine |
| AM6 | [(4-Aminomethyl-cyclohexyl)-thiophen-2-yl-methyl]-dimethylamine |
| AM7 | [(4-Aminomethyl-cyclohexyl)-(4-fluorophenyl)-methyl]-dimethylamine |
| AM8 | [1-(4-Aminomethyl-cyclohexyl)-3-phenyl-propyl]-dimethylamine |
| AM9 | [(4-Aminomethyl-cyclohexyl)-phenyl-methyl]-dimethylamine |
| AM10 | [(4-Aminomethyl-cyclohexyl)-(3-fluorophenyl)-methyl]-dimethylamine |
| AM11 | 4-[Dimethylamino-(3-fluorophenyl)-methyl]-cyclohexylamine |
| AM12 | [(4-Aminomethyl-cyclohexyl)-(4-chlorophenyl)-methyl]-dimethylamine |
| AM13 | 4-(Dimethylamino-phenyl-methyl)-cyclohexylamine |
| AM14 | 4-(1-Dimethylamino-3-phenyl-propyl)-cyclohexylamine |
| AM15 | 2-[4-(Dimethylamino-phenyl-methyl)-cyclohexyl]-ethylamine |
| AM16 | 4-(Morpholin-4-yl-phenyl-methyl)-cyclohexylamine |

-continued

| Designation | Name |
|---|---|
| AM17 | 4-(Phenyl-pyrrolidin-1-yl-methyl)-cyclohexylamine |
| AM18 | 4-(Phenyl-piperidin-1-yl-methyl)-cyclohexylamine |
| AM19 | 4-(1-Dimethylamino-2-phenyl-ethyl)-cyclohexylamine |
| AM20 | 3-(Dimethylamino-phenyl-methyl)-cyclopentylamine |
| AM21 | 4-[(Benzyl-methylamino)-phenyl-methyl]-cyclohexylamine |
| AM22 | C-[4-(Morpholin-4-yl-phenyl-methyl)-cyclohexyl]-methylamine |
| AM23 | C-[4-(1-Morpholin-4-yl-3-phenyl-propyl)-cyclohexyl]-methylamine |
| AM24 | C-[4-(3-Phenyl-1-pyrrolidin-1-yl-propyl)-cyclohexyl]-methylamine |
| AM25 | C-[4-(Phenyl-pyrrolidin-1-yl-methyl)-cyclohexyl]-methylamine |
| AM26 | 4-(3-Phenyl-1-piperidin-1-yl-propyl)-cyclohexylamine |
| AM27 | 4-(1-Morpholin-4-yl-3-phenyl-propyl)-cyclohexylamine |
| AM28 | 4-[(4-Methyl-piperazin-1-yl)-phenyl-methyl]-cyclohexylamine |
| AM29 | 4-(Phenyl-piperidin-4-yl-methyl)-morpholine |
| AM30 | 4-(2-Phenyl-1-piperidin-4-yl-ethyl)-morpholine |
| AM31 | N,N-Dimethyl(phenyl)(piperidin-4-yl)methanamine |
| AM32 | 2-(4-Aminocyclohexyl)-2-phenylacetonitrile |
| AM33 | 1-Methyl-4-(phenyl(piperidin-4-yl)methyl)piperazine |
| AM34 | 1-((4-Fluorophenyl)(piperidin-4-yl)methyl)-4-methylpiperazine |
| AM35 | 1-((3-Fluorophenyl)(piperidin-4-yl)methyl)-4-methylpiperazine |
| AM36 | 1-Methyl-4-(2-phenyl-1-(piperidin-4-yl)ethyl)piperazine |
| AM37 | 1-Methyl-4-(3-phenyl-1-(piperidin-4-yl)propyl)piperazine |

Synthesis of the Amine Units

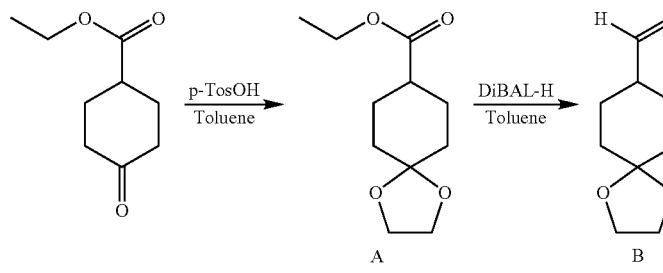

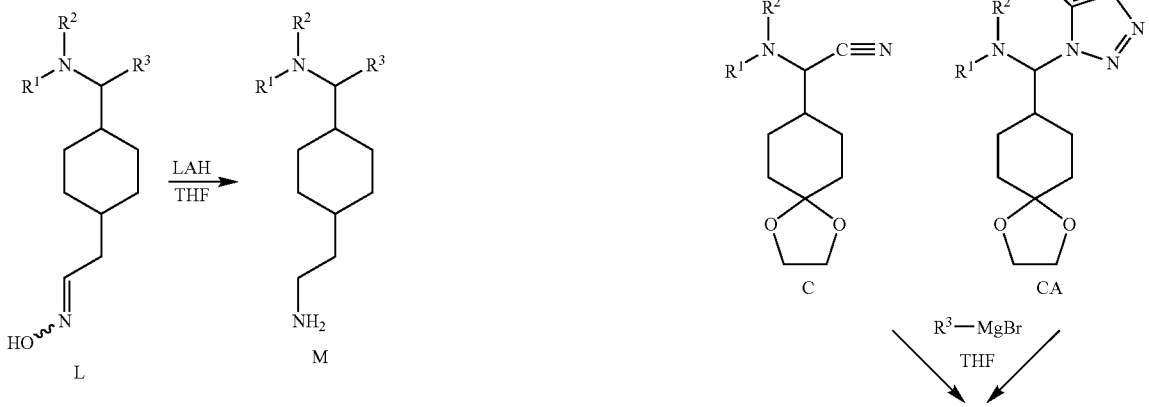

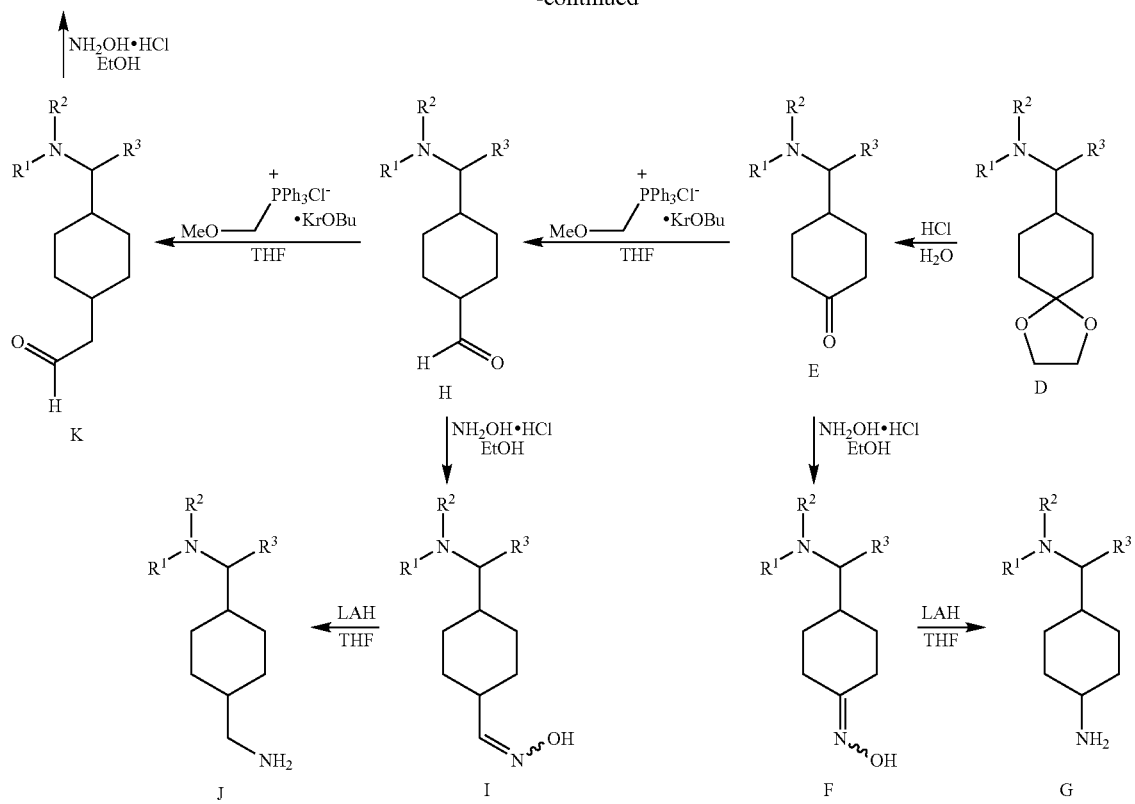

a) Synthesis of the Cyclohexanones Used

The ketones were obtained in a multi-stage synthesis from the commercially obtainable 4-oxo-cyclohexanecarboxylic acid ethyl ester. The yields of the compounds prepared are not optimized. All the temperatures are uncorrected.

1,4-Dioxa-spiro[4.5]decane-8-carboxylic Acid Ethyl Ester

4-Oxo-cyclohexanecarboxylic acid ethyl ester (52.8 g, 0.31 mol, Merck, order no. 814249, ethylene glycol (67.4 g, 1.08 mol) and p-toluenesulfonic acid (0.7 g) in toluene (160 ml) were stirred at RT for 20 h, the reaction solution was poured into diethyl ether (300 ml) and the mixture was washed with water, sodium bicarbonate solution and sodium chloride solution. The solution was dried ($Na_2SO_4$) and concentrated i. vac. and the colourless liquid which remained was processed further without purification.

Yield: 66.5 g (100%)

$^1$H-NMR ($CDCl_3$): 1.24 (t, 3 H); 1.53 (m, 2 H); 1.76 (m, 4 H); 1.92 (m, 2 H); 2.31 (m, 1 H); 3.91 (s, 4 H); 4.11 (q, 2 H).

$^{13}$C-NMR ($CDCl_3$): 14.28 (q); 26.32 (t); 33.76 (t); 41.59 (d); 60.14 (t); 64.21 (t); 107.90 (d); 174.77 (s).

1,4-Dioxa-spiro[4.5]decane-8-carbaldehyde

Diisobutylaluminium hydride (1.5 M solution in toluene, 102 ml, 153 mmol) was added dropwise to a solution of 1,4-dioxa-spiro[4.5]decane-8-carboxylic acid ethyl ester (32.13 g, 150 mmol) in absol. toluene (160 ml) at −70 to −65° C. under argon and the mixture was stirred for 30 min. The mixture was then quenched at −70 to −60° C. by addition of methanol (80 ml). The reaction solution was warmed to RT, saturated sodium chloride solution (100 ml) was added and the reaction solution was filtered out with suction over kieselguhr. The kieselguhr was washed twice with ethyl acetate and the aqueous solution was separated off and extracted twice with ethyl acetate. The combined organic extracts were washed with saturated sodium chloride solution, dried over sodium sulfate and concentrated i. vac. Yield: 24.01 g (94%), yellow oil $^1$H-NMR ($CDCl_3$): 1.54 (m, 2 H); 1.74 (m, 4 H); 1.91 (m, 2 H); 2.21 (m, 1 H); 3.91 (s, 4 H); 9.60 (s, 1 H).

$^{13}$C-NMR ($CDCl_3$): 23.35 (t); 33.37 (t); 48.18 (d); 64.30 (t); 107.89 (d); 203.51 (s).

Dimethylamino-(1,4-dioxa-spiro[4.5]dec-8-yl)-acetonitrile 40 percent strength aqueous dimethylamine solution (85 ml, 0.67 mol), 1,4-dioxa-spiro[4.5]decane-8-carbaldehyde (240 g, 0.141 mol) and potassium cyanide (22.05 g, 0.338 mol) were added to a mixture of 4 N hydrochloric acid (37 ml) and methanol (22 ml), while cooling with ice. The mixture was stirred at room temperature for 4 d and then, after addition of water (80 ml), extracted with diethyl ether (4×100 ml). The organic phase was dried over sodium sulfate and concentrated i. vac. and the product was obtained as a white solid. Yield: 25.2 g (81%), melting point: 48-51° C.

$^1$H-NMR ($CDCl_3$): 1.23-2.03 (m, 9 H); 2.28 (s, 6 H); 3.16 (d, 1 H); 3.93 (m, 4 H).

$^{13}$C-NMR ($CDCl_3$): 26.67 (t); 27.93 (t); 33.87 (t); 36.94 (d); 41.90 (q); 64.30 (t); 64.36 (t); 108.33 (d); 115.94 (s).

[(1,4-Dioxa-spiro[4.5]dec-8-yl)-phenyl-methyl]-dimethyl-amine ($R^3$=phenyl)

A solution of the aminonitrile (23.56 g, 105 mmol) in absol. THF (100 ml) was added dropwise to a 25 percent strength solution of phenylmagnesium chloride (144 ml, 262.5 mmol) in THF under argon and while cooling with ice and the mixture was stirred at RT for 20 h. For working up of the reaction mixture, saturated ammonium chloride solution (100 ml) and water (100 ml) were added, while cooling with ice, and the mixture was extracted with diethyl ether (3×100 ml). The organic phase was washed with water and saturated sodium chloride solution, dried ($Na_2SO_4$) and concentrated.

Yield: 28.9 g (100%).

$^{13}$C-NMR ($CDCl_3$): 27.05; 28.13; 34.48; 34.57; 36.94 ($C_8$); 41.64 ($N(CH_3)_2$); 64.15; 74.33 (CH); 109.02 ($C_5$); 126.70 ($C_{arom}$); 127.49 ($C_{arom}$); 129.12 ($C_{arom}$); 136.57 ($C_{arom}$).

[(1,4-Dioxa-spiro[4.5]dec-8-yl)-4-fluorophenyl-methyl]-dimethylamine ($R^3$=4-fluorophenyl)

A solution of the aminonitrile (19.89 g, 88 mmol) in absol. THF (160 ml) was added dropwise to a 1 M solution of 4-fluorophenylmagnesium bromide in THF (220 ml, 220 mmol) under argon and while cooling with ice and the mixture was stirred at RT for 20 h. For working up of the reaction mixture, saturated ammonium chloride solution (100 ml) and water (100 ml) were added, while cooling with ice, and the mixture was extracted with diethyl ether (3×100 ml). The organic phase was washed with water and saturated sodium chloride solution, dried ($Na_2SO_4$) and concentrated.

Yield: 31 g (>100%)

$^{13}$C-NMR ($CDCl_3$): 26.68 (t); 28.11 (t); 34.43 (t); 34.55 (t); 37.37 (d); 41.68 (q); 64.12 (t); 73.65 (d); 108.88 (d); 114.23 (d); 114.44 (d); 130.27; 130.35; 132.43; 160.36 (s); 162.78 (s).

[(1,4-Dioxa-spiro[4.5]dec-8-yl)-3-fluorophenyl-methyl]-dimethylamine ($R^3$=3-fluorophenyl)

A solution of the aminonitrile (23.45 g, 104 mmol) in absol. THF (100 ml) was added dropwise to a 1 M solution of 3-fluorophenylmagnesium bromide in THF (208 ml, 208 mmol) under argon and while cooling with ice and the mixture was stirred at RT for 20 h. For working up of the reaction mixture, saturated ammonium chloride solution (100 ml) and water (100 ml) were added, while cooling with ice, and the mixture was extracted with diethyl ether (3×100 ml). The organic phase was washed with water and saturated sodium chloride solution, dried and concentrated.

Yield: 30.33 g (99%).

$^1$H-NMR ($CDCl_3$): 1.12 (m, 1 H); 1.26 (m, 1 H); 1.46-1.81 (m, 7 H); 2.10 (s, 6 H); 3.10 (d, 1 H); 3.90 (m, 4 H); 6.85 (m, 3 H); 7.27 (m, 1 H).

$^{13}$C-NMR ($CDCl_3$): 26.80 (t); 28.08 (t); 34.48 (t); 34.45 (t); 34.59 (t); 37.26 (d); 41.71 (q); 64.19 (t); 74.04 (t); 108.91 (d); 113.51 (d); 113.71 (d); 115.52 (d); 115.72 (d); 124.83 (d); 128.82 (d); 128.90 (d); 139.66 (s); 161.15 (s); 163.58 (s).

[(4-Chlorophenyl)-(1,4-dioxa-spiro[4.5]dec-8-yl)-methyl]-dimethylamine ($R^3$=4-chlorophenyl)

A Solution of the Aminonitrile (22.43 g, 100 mmol) in Absol. Ether (100 ml) was added dropwise to a 1 M solution of 4-chlorophenylmagnesium bromide in ether (200 ml, 200 mmol) under argon and while cooling with ice and the mixture was stirred at RT for 20 h. For working up of the reaction mixture, saturated ammonium chloride solution (100 ml) and water (100 ml) were added, while cooling with ice, and the mixture was extracted with diethyl ether (3×100 ml). The organic phase was washed with water and saturated sodium chloride solution, dried and concentrated.

Yield: 30.9 g (100%)

$^{13}$C-NMR ($CDCl_3$): 26.65 (t); 28.11 (t); 34.46 (t); 34.60 (t); 37.28 (d); 41.76 (q); 64.17 (t); 73.80 (d); 108.88 (s); 127.72 (d); 129.53 (d); 132.39 (d); 135.33 (d).

[(1,4-Dioxa-spiro[4.5]dec-8-yl)-thiophen-2-yl-methyl]-dimethylamine ($R^3$=2-thienyl)

A solution of the aminonitrile (2.24 g, 10 mmol) in absol. THF (10 ml) was added dropwise to a 1 M solution of thiophen-2-yl-magnesium bromide in THF (20 ml, 20 mmol) under argon and while cooling with ice and the mixture was stirred at RT for 20 h. For working up of the reaction mixture, saturated ammonium chloride solution (10 ml) and water (10 ml) were added, while cooling with ice, and the mixture was extracted with diethyl ether (3×10 ml). The organic phase was washed with water and saturated sodium chloride solution, dried and concentrated.

Yield: 2.8 g (100%)

$^{13}$C-NMR ($CDCl_3$): 27.72 (t); 27.88 (t); 34.27 (t); 39.28 (d); 41.10 (q); 64.11 (t); 68.89 (d); 108.88 (s); 123.55 (d); 125.88 (d); 127.53 (d); 139.50 (s).

[1-(1,4-Dioxa-spiro[4.5]dec-8-yl)-3-phenyl-propyl]-dimethylamine ($R^3$=phenethyl)

A solution of the aminonitrile (21.93 g, 97 mmol) in absol. THF (180 ml) was added dropwise to a 1 M solution of phenylethylmagnesium chloride in THF (242 ml, 242 mmol) under argon and while cooling with ice and the mixture was stirred at RT for 20 h. For working up of the reaction mixture, saturated ammonium chloride solution (100 ml) and water (100 ml) were added, while cooling with ice, and the mixture was extracted with diethyl ether (3×100 ml). The organic phase was washed with water and saturated sodium chloride solution, dried and concentrated.

Yield: 34 g.

$^{13}$C-NMR ($CDCl_3$): 27.43 (t); 28.95 (t); 29.42 (t); 34.82 (t); 35.40 (t); 38.76 (d); 41.16 (q); 64.17 (t); 67.41 (d); 108.86 (s); 125.41 (d); 127.66 (d); 128.11 (d); 142.69 (s).

4-(Dimethylamino-phenyl-methyl)-cyclohexanone ($R^3$=phenyl)

The ketal (28.9 g, 0.105 mol) was dissolved in water (44 ml), conc. hydrochloric acid (64 ml) was added and the mixture was stirred at RT for 20 h. The reaction mixture was extracted by shaking with diethyl ether (2×100 ml), the aqueous phase was rendered alkaline with 5 N NaOH, while cooling with ice, the mixture was extracted with methylene chloride (3×100 ml) and the extract was dried and concentrated. The ketone was isolated as a colourless oil.

Yield: 18.2 g (75%)

$^1$H-NMR ($CDCl_3$): 1.20 (1 H, m); 1.33 (1 H, m); 1.74 (1 H, m); 2.17 (6 H, s, $N(CH_3)_2$); 2.70 (6 H, m); 3.10 (1 H, d, $C_8$—H); 7.07 (2 H, m, $C_{arom}$—H); 7.23 (3 H, m, $C_{arom}$—H).

$^{13}$C-NMR ($CDCl_3$): 29.13; 30.56; 36.90 ($C_4$); 40.61; 40.82; 41.89 ($N(CH_3)_2$); 73.79 (CH); 127.05 ($C_{arom}$); 127.67 ($C_{arom}$); 129.00 ($C_{arom}$); 136.13 ($C_{arom}$); 211.79 (C=O).

4-[Dimethylamino-(4-fluorophenyl)-methyl]-cyclohexanone ($R^3$=4-fluorophenyl)

The crude product of the ketal (26 g, 88 mmol) was dissolved in water (40 ml), conc. hydrochloric acid (59 ml) was added and the mixture was stirred at RT for 20 h. The reaction mixture was extracted with diethyl ether (2×100 ml), the aqueous phase was rendered alkaline with 5 N NaOH, while cooling with ice, the mixture was extracted with methylene chloride (3×100 ml) and the extract was dried and concentrated. Yield: 21.36 g (98%)

$^{13}$C-NMR (CDCl$_3$): 28.90 (t); 30.48 (t); 37.00 (t); 40.49 (t); 40.72 (t); 41.79 (q); 72.98 (d); 114.42 (d); 114.62 (d); 130.20 (d); 130.28 (d); 131.88 (s); 160.50 (s); 162.93 (s); 211.44 (s).

4-[Dimethylamino-(3-fluorophenyl)-methyl]-cyclohexanone ($R^3$=3-fluorophenyl)

The ketal (30.3 g, 103 mmol) was dissolved in water (44 ml), conc. hydrochloric acid (64 ml) was added and the mixture was stirred at RT for 20 h. The reaction mixture was extracted by shaking with diethyl ether (2×100 ml), the aqueous phase was rendered alkaline with 5 N NaOH, while cooling with ice, the mixture was extracted with methylene chloride (3×100 ml) and the extract was dried and concentrated. The ketone was isolated as a colourless solid. Yield: 22.4 g (87%)

Melting point: 72-75° C.

$^{13}$C-NMR (CDCl$_3$): 28.97 (t); 30.44 (t); 36.90 (t); 40.52 (t); 40.75 (t); 41.82 (q); 73.37 (d); 113.84; 114.06; 115.42; 115.62; 124.71; 129.03; 129.11; 139.00; 139.06; 161.16; 163.60; 211.40 (s).

4-[(4-Chlorophenyl)-dimethylamino-methyl]-cyclohexanone ($R^3$=4-chlorophenyl)

The ketal (30.98 g, 100 mmol) was dissolved in water (44 ml), conc. hydrochloric acid (64 ml) was added and the mixture was stirred at RT for 20 h. The reaction mixture was extracted by shaking with diethyl ether (2×100 ml), the aqueous phase was rendered alkaline with 5 N NaOH, while cooling with ice, the mixture was extracted with methylene chloride (3×100 ml) and the extract was dried and concentrated. The ketone was isolated as an oil.

Yield: 21.9 g (82%)

$^{13}$C-NMR (CDCl$_3$): 28.88 (t); 30.45 (t); 36.89 (t); 40.49 (t); 40.74 (t); 41.83 (q); 73.12 (d); 127.87 (d); 130.16 (d); 132.75 (d); 13470 (s); 211.35 (s).

4-(Dimethylamino-thiophen-2-yl-methyl)-cyclohexanone ($R^3$=2-thienyl)

The ketal (2.80 g, 10 mmol) was dissolved in water (4.4 ml), conc. hydrochloric acid (6.4 ml) was added and the mixture was stirred at RT for 20 h. The reaction mixture was extracted by shaking with diethyl ether (2×10 ml), the aqueous phase was rendered alkaline with 5 N NaOH, while cooling with ice, the mixture was extracted with methylene chloride (3×10 ml) and the extract was dried and concentrated. The ketone was isolated as an oil. Yield: 1.79 g (75%)

$^{13}$C-NMR (CDCl$_3$): 30.02 (t); 30.18 (t); 38.84 (t); 40.29 (t); 39.28 (d); 41.17 (q); 68.24 (d); 123.88 (d); 126.01 (d); 126.34 (d); 138.77 (d); 211.49 (s).

4-(1-Dimethylamino-3-phenyl-propyl)-cyclohexanone ($R^3$=phenethyl)

The crude product of the ketal (29.6 g, 97 mmol) was dissolved in water (44 ml), conc. hydrochloric acid (64 ml) was added and the mixture was stirred at RT for 20 h. The reaction mixture was extracted by shaking with diethyl ether (2×100 ml), the aqueous phase was rendered alkaline with 5 N NaOH, while cooling with ice, the mixture was extracted with methylene chloride (3×100 ml) and the extract was dried and concentrated. The ketone was isolated as a colorless oil.

Yield: 16.9 g (58%)

$^{13}$C-NMR (CDCl$_3$): 29.40 (t); 30.02 (t); 30.97 (t); 35.34 (t); 38.71 (t); 40.79 (t); 41.01 (t); 41.23 (q); 66.65 (d); 125.66 (d); 128.12 (d); 128.19 (d); 142.27 (s); 211.70 (s).

Synthesis of the Amino-, Aminomethyl- and Aminoethylcyclohexyls

The corresponding amines can now be obtained from the cyclohexanone derivatives by simple transformation.

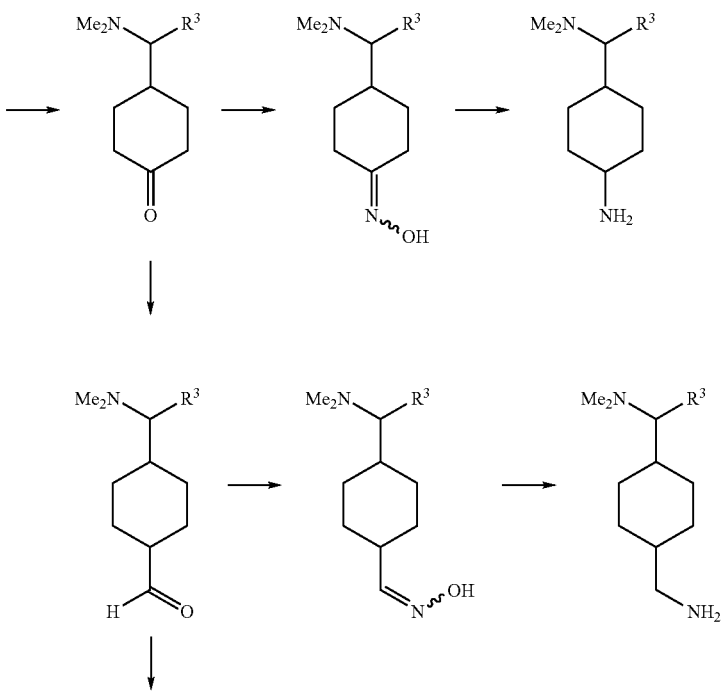

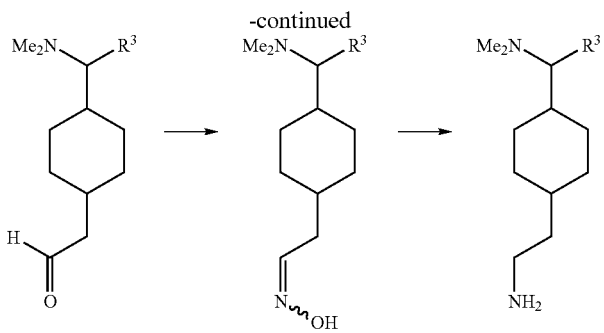

-continued

Synthesis of the Aminocyclohexanes

The aminocyclohexanes were prepared by two-stage reactions from the correspondingly substituted cyclohexanones with hydroxylamine hydrochloride and subsequent cleavage with lithium aluminium hydride.

4-(Dimethylamino-phenyl-methyl)-cyclohexanone oxime ($R^3$=phenyl)

The ketone (9.25 g, 40 mmol) and hydroxylamine hydrochloride (4.17 g, 60 mmol) were dissolved in absol. ethanol (150 ml), the basic ion exchanger Amberlyst A21 (28 g) was added and the mixture was stirred at RT overnight. The ion exchanger was filtered out and washed with ethanol (2×50 ml). The solution was concentrated and the residue was adjusted to pH 11 with 5 N NaOH. The aqueous phase was extracted with ethyl acetate (3×50 ml) and the organic phase was dried over sodium sulfate and concentrated i. vac.

Yield: 9.54 g (97%)

Melting point: 110-115° C., (colourless crystals)

$^{13}$C-NMR (CDCl$_3$): 23.53; 23.70; 27.87; 29.04; 29.48; 30.70; 31.26; 31.40; 37.89 (C$_4$); 42.02 (N(CH$_3$)$_2$); 74.36 (CH); 126.87 (C$_{arom}$); 127.56 (C$_{arom}$); 129.09 (C$_{arom}$); 136.57 (C$_{arom}$); 160.12 (C=N—O).

AM 13: 4-(Dimethylamino-phenyl-methyl)-cyclohexylamine ($R^3$=phenyl)

LiAlH$_4$ (2.92 g, 77 mmol) was added to absolute THF (400 ml) under argon, the mixture was heated to 60° C. and the oxime (9.5 g, 38.5 mmol), dissolved in THF (90 ml), was added dropwise. After stirring at 60° C. for 4 hours, water (100 ml) was added dropwise, while cooling with an ice-bath (10° C.), and the solution was filtered out with suction over kieselguhr. The residue on the filter was washed with THF. The THF was removed i. vac. and the residue was adjusted to pH 11 with 5 N NaOH and extracted with ethyl acetate (4×40 ml). The organic phase was dried over sodium sulfate and evaporated and the residue was purified over a silica gel column (30 g) with MeCN/MeOH/0.5 M NH$_4$Cl (9:1:1). The individual fractions were dissolved in water and methylene chloride, the solution was rendered alkaline with ammonia and the aqueous phase was extracted with CH$_2$Cl$_2$ (twice). Total yield: 6.33 g (71%), oil $^{13}$C-NMR (CDCl$_3$): 24.22; 24.80; 28.24; 29.96; 32.39; 32.45; 36.03; 36.58; 36.79; 37.93 (C$_4$); 41.33; 41.89 (N(CH$_3$)$_2$); 47.42; 50.85; 71.95; 75.22 (CH); 126.52 (C$_{arom}$); 127.29 (C$_{arom}$); 127.33 (C$_{arom}$); 129.04 (C$_{arom}$); 129.11 (C$_{arom}$); 136.22 (C$_{arom}$); 137.03 (C$_{arom}$).

4-[Dimethylamino-(4-fluorophenyl)-methyl]-cyclohexanone oxime ($R^3$=4-fluorophenyl)

The ketone (10.68 g, 43 mmol) and hydroxylamine hydrochloride (4.52 g, 65 mmol) were dissolved in absol. ethanol (160 ml), the basic ion exchanger Amberlyst A21 (30 g) was added and the mixture was stirred at RT overnight. The ion exchanger was filtered out and washed with ethanol (2×50 ml). The solution was concentrated, the residue was adjusted to pH 11 with 5 N NaOH, the aqueous phase was extracted with ethyl acetate (3×50 ml) and the organic phase was dried over sodium sulfate and concentrated i. vac. Yield: 10.49 g (93%)

$^{13}$C-NMR (CDCl$_3$): 23.76; 23.66; 27.69; 28.87; 29.50; 30.73; 31.22; 31.38; 38.06 (C$_4$); 42.01 (N(CH$_3$)$_2$); 73.66 (CH); 114.36 (C$_{arom}$); 114.57 (C$_{arom}$); 130.32 (C$_{arom}$); 130.40 (C$_{arom}$); 132.40 (C$_{arom}$); 160.03 (C=N—O); 160.49 (C$_{arom}$); 162.93 (C$_{arom}$).

AM 2: 4-[Dimethylamino-(4-fluorophenyl)-methyl]-cyclohexylamine ($R^3$=4-fluorophenyl)

LiAlH$_4$ (3.04 g, 82 mmol) was added to absolute THF (435 ml) under argon, the mixture was heated to 60° C. and the oxime (10.49 g, 40 mmol), dissolved in THF (90 ml), was added dropwise. After stirring at 60° C. for 4 hours, water (100 ml) was added dropwise, while cooling with an ice-bath (10° C.), and the mixture was filtered out with suction over kieselguhr. The residue on the filter was washed with THF. The THF was removed i. vac. and the residue was adjusted to pH 11 with 5 N NaOH and extracted with ethyl acetate (4×50 ml). The organic phase was dried over sodium sulfate and evaporated and the residue was purified by flash chromatography with MeCN/MeOH/0.5 M NH$_4$Cl (9:1:1). The individual fractions were dissolved in water and methylene chloride, the solution was rendered alkaline with ammonia and the aqueous phase was extracted twice with CH$_2$Cl$_2$.

Yield: 6.95 g (70%), oil $^{13}$C-NMR (CDCl$_3$): 24.01; 24.76; 27.99; 29.92; 32.32; 36.26; 36.51; 36.73; 38.07; 41.26 (C$_4$); 41.85 (N(CH$_3$)$_2$); 47.31; 50.81; 71.25; 74.44 (CH); 114.01 (C$_{arom}$); 114.08 (C$_{arom}$); 130.20 (C$_{arom}$); 130.27 (C$_{arom}$); 132.02 (C$_{arom}$); 132.85 (C$_{arom}$); 160.22 (C$_{arom}$); 162.64 (C$_{arom}$).

4-[Dimethylamino-(3-fluorophenyl)-methyl]-cyclohexanone oxime ($R^3$=3-fluorophenyl)

The ketone (10 g, 40 mmol) and hydroxylamine hydrochloride (4.17 g, 60 mmol) were dissolved in absol. ethanol (150 ml), the basic ion exchanger Amberlyst A21 (28 g) was added and the mixture was stirred at RT overnight. The ion exchanger was filtered out and washed with ethanol (2×50 ml). The solution was concentrated, the residue was adjusted to pH 11 with 5 N NaOH, the aqueous phase was extracted with ethyl acetate (3×50 ml) and the organic phase was dried over sodium sulfate and concentrated i. vac. Yield: 10.05 g (95%)

$^{13}$C-NMR (CDCl$_3$): 23.48; 23.66; 27.69; 28.87; 29.39; 30.61; 31.18; 31.33; 37.91 (C$_4$); 41.99 (N(CH$_3$)$_2$); 74.00 (CH); 113.70 (C$_{arom}$); 113.90 (C$_{arom}$); 115.51 (C$_{arom}$); 124.80 (C$_{arom}$); 128.90 (C$_{arom}$); 128.98 (C$_{arom}$); 139.48 (C$_{arom}$); 139.54 (C$_{arom}$); 159.89 (C=N—O); 161.13 (C$_{arom}$); 163.57 (C$_{arom}$).

AM 11: 4-[Dimethylamino-(3-fluorophenyl)-methyl]-cyclohexylamine 21 (R$^3$=3-fluorophenyl)

LiAlH$_4$ (2.83 g, 75 mmol) was added to absolute THF (400 ml) under argon, the mixture was heated to 60° C. and the oxime (9.86 g, 37.3 mmol), dissolved in THF (90 ml), was added dropwise. After stirring at 60° C. for 4 hours, water (100 ml) was added dropwise, while cooling with an ice-bath (10° C.), and the mixture was filtered out with suction over kieselguhr. The residue on the filter was washed with THF. The THF was removed i. vac. and the residue was adjusted to pH 11 with 5 N NaOH and extracted with ethyl acetate (4×40 ml). The organic phase was dried over sodium sulfate and evaporated and the residue was purified over a silica gel column (300 g) with MeCN/MeOH/0.5 M NH$_4$Cl (9:1:1).

The individual fractions were dissolved in water and methylene chloride, the solution was rendered alkaline with ammonia and the aqueous phase was extracted twice with CH$_2$Cl$_2$.

Yield: 6.81 g (73%), oil $^{13}$C-NMR (CDCl$_3$): 24.08; 24.69; 28.05; 29.84; 32.33; 32.37; 36.10; 36.48; 36.69; 37.95; 41.27 (C$_4$); 41.85 (N(CH$_3$)$_2$); 47.32; 50.81; 71.63; 74.81 (CH); 113.29 (C$_{arom}$); 115.43 (C$_{arom}$); 124.74 (C$_{arom}$); 128.58 (C$_{arom}$); 139.19 (C$_{arom}$); 139.99 (C$_{arom}$); 160.97 (C$_{arom}$); 163.41 (C$_{arom}$).

4-(Dimethylamino-thiophen-2-yl-methyl)-cyclohexanone oxime (R$^3$=2-thiophene)

The ketone (9.49 g, 40 mmol) and hydroxylamine hydrochloride (4.17 g, 60 mmol) were dissolved in absol. ethanol (150 ml), the basic ion exchanger Amberlyst A21 (28 g) was added and the mixture was stirred at RT overnight. The ion exchanger was filtered out and washed with ethanol (2×50 ml). The solution was concentrated and the residue was adjusted to pH 11 with 5 N NaOH. The aqueous phase was extracted with ethyl acetate (3×50 ml) and the organic phase was dried over sodium sulfate and concentrated i. vac. Yield: 9.21 g (91%), melting point: 118-121° C., yellow crystals

AM 1: 4-(Dimethylamino-thiophen-2-yl-methyl)-cyclohexylamine (R$^3$=2-thiophene)

LiAlH$_4$ (2.73 g, 72 mmol) was added to absolute THF (300 ml) under argon, the mixture was heated to 60° C. and the oxime (9.08 g, 35.9 mmol), dissolved in THF (80 ml), was added dropwise. After stirring at 60° C. for 4 hours, water (80 ml) was added dropwise, while cooling with an ice-bath (10° C.), and the solution was filtered out with suction over kieselguhr. The residue on the filter was washed with THF. The THF was removed i. vac. and the residue was adjusted to pH 11 with 5 N NaOH and extracted with ethyl acetate (3×50 ml). The organic phase was dried over sodium sulfate and evaporated and the residue was purified over a silica gel column (300 g) with MeCN/MeOH/0.5 M NH$_4$Cl (8:2:1). The individual fractions were dissolved in water and methylene chloride, the solution was rendered alkaline with ammonia and the aqueous phase was extracted twice with CH$_2$Cl$_2$. Total yield: 5.66 g (66%), oil $^{13}$C-NMR (CDCl$_3$): 24.81; 24.96; 29.26; 29.76; 32.18; 32.22; 36.46; 36.58; 38.10; 39.99; 40.86; 41.20 (N(CH$_3$)$_2$); 47.66; 50.80; 64.27; 69.82; 123.43; 125.71; 125.75; 125.95; 126.07; 139.34; 139.79.

4-(1-Dimethylamino-3-phenyl-propyl)-cyclohexanone oxime (R$^3$=phenethyl)

The ketone (10.2 g, 40 mmol) and hydroxylamine hydrochloride (4.17 g, 60 mmol) were dissolved in absol. ethanol (150 ml), the basic ion exchanger Amberlyst A21 (28 g) was added and the mixture was stirred at RT overnight. The ion exchanger was filtered out and washed with ethanol (2×50 ml), the solution was concentrated and the residue was adjusted to pH 11 with 5 N NaOH. The aqueous phase was extracted with ethyl acetate (3×50 ml) and the organic phase was dried over sodium sulfate and concentrated i. vac. Yield: 10.8 g (100%), oil $^{13}$C-NMR (CDCl$_3$): 23.80; 23.96; 28.80; 29.27; 30.00; 31.21; 31.49; 31.58; 35.89 (C$_4$); 39.29; 41.26 (N(CH$_3$)$_2$); 67.24 (CH); 125.58 (C$_{arom}$); 128.13 (C$_{arom}$); 142.40 (C$_{arom}$); 159.99; 160.04 (C=N—O).

AM 14: 4-(1-Dimethylamino-3-phenyl-propyl)-cyclohexylamine (R$^3$=phenethyl)

LiAlH$_4$ (3.04 g, 82 mmol) was added to absolute THF (435 ml) under argon, the mixture was heated to 60° C. and the oxime (11.14 g, 40 mmol), dissolved in THF (90 ml), was added dropwise. After stirring at 60° C. for 4 hours, water (100 ml) was added dropwise, while cooling with an ice-bath (10° C.), and the mixture was filtered with suction over kieselguhr. The residue on the filter was washed with THF. The THF was removed i. vac. and the residue was adjusted to pH 11 with 5 N NaOH and extracted with ethyl acetate (4×50 ml). The organic phase was dried over sodium sulfate and evaporated and the residue was purified over a silica gel column (300 g) with MeCN/MeOH/0.5 M NH$_4$Cl (9:1:1) and (9:4:1).

The individual fractions were dissolved in water and methylene chloride, the solution was rendered alkaline with ammonia and the aqueous phase was extracted twice with CH$_2$Cl$_2$.

Yield: 5.02 g (50%), oil $^{13}$C-NMR (CDCl$_3$): 24.70; 25.36; 29.22; 29.35; 30.42; 32.98; 35.46; 35.72; 36.95; 37.07; 38.89 (C$_4$); 39.32; 41.04; 41.26 (N(CH$_3$)$_2$); 46.98; 50.85; 66.01; 68.05 (CH); 125.49 (C$_{arom}$); 128.11 (C$_{arom}$); 128.14 (C$_{arom}$); 142.75 (C$_{arom}$).

Synthesis of the Aminomethylcyclohexanes

The aminomethylcyclohexanes were prepared by three-stage reactions from the correspondingly substituted cyclohexanones via the stage of the cyclohexylaldehydes by reaction with hydroxylamine hydrochloride and subsequent cleavage with lithium aluminium hydride.

4-(Dimethylamino-phenyl-methyl)-cyclohexane-carbaldehyde (R$^3$=phenyl)

(Methoxymethyl)triphenylphosphonium chloride (31.5 g, 0.092 mol) was suspended in absol. THF (150 ml) under argon, potassium tert-butylate (10.38 g, 0.092 mol), dissolved in absol. THF (100 ml), was added dropwise at 0° C. and the mixture was then subsequently stirred at 0° C. for 15 min (solution became deep orange in colour).

The ketone (14.2 g, 0.061 mol), dissolved in absol. THF (100 ml), was then added dropwise to the above solution at RT and the mixture was stirred at RT overnight. While cooling with ice-water, the mixture was hydrolyzed dropwise with water (50 ml) and 6 N HCl (150 ml). After stirring at RT for 1 h, the mixture was extracted with ether (10×50 ml), the aqueous phase was brought to pH 11 with 5 N NaOH and extracted by shaking with ethyl acetate (3×50 ml) and the extract was dried over $Na_2SO_4$ and concentrated i. vac. The crude product was purified over a silica gel column (300 g) with ethyl acetate/cyclohexane (1:1). Yield: 12.2 g (82%)

$^{13}$C-NMR (CDCl$_3$): 24.01; 24.22; 25.90; 26.06; 26.40; 27.33; 28.21; 29.92; 37.00; 38.19 (C$_4$); 41.51; 41.98; (N(CH$_3$)$_2$); 47.45; 50.60; 73.37; 75.24 (CH); 126.72 (C$_{arom}$); 126.76 (C$_{arom}$); 127.48 (C$_{arom}$); 129.13 (C$_{arom}$); 136.14 (C$_{arom}$); 136.79 (C$_{arom}$); 204.22; 205.05 (CHO).

4-(Dimethylamino-phenyl-methyl)-cyclohexane-carbaldehyde oxime (R$^3$=phenyl)

The carbaldehyde (7.36 g, 30 mmol) and hydroxylamine hydrochloride (3.12 g, 45 mmol) were dissolved in absol. ethanol (100 ml), the basic ion exchanger Amberlyst A21 (21 g) was added and the mixture was stirred at RT overnight. The ion exchanger was filtered out and washed with ethanol (2×50 ml). The solution was concentrated and the residue was adjusted to pH 11 with 5 N NaOH. The aqueous phase was extracted with ethyl acetate (3×50 ml) and the organic phase was dried over sodium sulfate and concentrated i. vac. Yield: 7.81 g (100%)

$^{13}$C-NMR (CDCl$_3$): 25.83; 26.34; 27.10; 27.55; 28.25; 29.41; 30.12; 30.32; 34.20; 36.45; 36.74; 37.00; 38.19 (C$_4$); 41.37; 41.03; (N(CH$_3$)$_2$); 72.28; 75.59 (CH); 126.77 (C$_{arom}$); 127.50 (C$_{arom}$); 129.22 (C$_{arom}$); 136.14 (C$_{arom}$); 136.94 (C$_{arom}$); 137.05 (C$_{arom}$); 154.84; 155.55; 156.35.

AM 9: [(4-Aminomethyl-cyclohexyl)-phenyl-methyl]-dimethylamine (R$^3$=phenyl)

LiAlH$_4$ (2.27 g, 60 mmol) was added to absolute THF (300 ml) under argon, the mixture was heated to 60° C. and the oxime (7.81 g, 30 mmol), dissolved in THF (60 ml), was added dropwise. After stirring at 60° C. for 4 hours, water (70 ml) was added dropwise, while cooling with an ice-bath (10° C.), and the reaction solution was filtered with suction over kieselguhr. The residue on the filter was washed with THF. The combined organic phases were concentrated i. vac. and the residue was adjusted to pH 11 with 5 N NaOH and extracted with ethyl acetate (4×40 ml). The organic phase was dried over sodium sulfate and concentrated. Yield: 6.4 g (87%), oil $^{13}$C-NMR (CDCl$_3$): 25.53; 26.03; 26.64; 26.68; 29.06; 30.37; 30.51; 30.67; 30.74; 36.01; 38.83; 38.93; (C$_4$); 41.50; 41.94; (N(CH$_3$)$_2$); 72.28; 75.59 (CH); 126.77 (C$_{arom}$); 127.50 (C$_{arom}$); 129.22 (C$_{arom}$); 136.14 (C$_{arom}$); 136.94 (C$_{arom}$); 137.05 (C$_{arom}$); 154.84; 155.55; 156.35.

4-[Dimethylamino-(4-fluorophenyl)-methyl]-cyclohexane-carbaldehyde (R$^3$=4-fluorophenyl)

(Methoxymethyl)triphenylphosphonium chloride (25.7 g, 75 mmol) was suspended in absol. THF (100 ml) under argon, potassium tert-butylate (8.42 g, 75 mmol), dissolved in absol. THF (70 ml), was added dropwise at 0° C. and the mixture was then subsequently stirred at 0° C. for 15 min. The ketone (12.44 g, 50 mmol), dissolved in absol. THF (75 ml), was then added dropwise to the above solution at RT and the mixture was stirred at RT overnight. While cooling with ice-water, the mixture was hydrolyzed dropwise with water (38 ml) and 6 N HCl (112 ml). After stirring at RT for 1 h, the mixture was extracted with ether (10×50 ml), the aqueous phase was brought to pH 11 with 5 N NaOH and extracted by shaking with ethyl acetate (3×50 ml) and the extract was dried over Na$_2$SO$_4$ and concentrated i. vac. The crude product was purified by flash chromatography with ethyl acetate/cyclohexane (1:1). Yield: 9.13 g (70%).

$^{13}$C-NMR (CDCl$_3$, both diastereomers): δ=23.97; 24.21; 25.85; 26.02; 26.17; 27.35; 28.00; 29.90; 37.26; 38.34; 41.50; 41.95; 47.36; 50.55; 72.75; 75.84; 114.25; 114.45; 130.33; 130.40; 132.61; 160.41; 162.83; 204.10; 204.93.

4-[Dimethylamino-(4-fluorophenyl)-methyl]-cyclohexanecarbaldehyde oxime (R$^3$=4-fluorophenyl)

The aldehyde (6.50 g, 25 mmol) and hydroxylamine hydrochloride (2.6 g, 37.5 mmol) were dissolved in absol. ethanol (80 ml), the basic ion exchanger Amberlyst A21 (16.5 g) was added and the mixture was stirred at RT overnight. The ion exchanger was filtered out and washed with ethanol (2×50 ml). The solution was concentrated and the residue was adjusted to pH 11 with 5 N NaOH. The aqueous phase was extracted with ethyl acetate (3×50 ml) and the organic phase was dried over sodium sulfate and concentrated i. vac.

Yield: 6.9 g (99%)

AM 7: [(4-Aminomethyl-cyclohexyl)-(4-fluorophenyl)-methyl]-dimethylamine (R$^3$=4-fluorophenyl)

LiAlH$_4$ (1.9 g, 50 mmol) was added to absolute THF (360 ml) under argon, the mixture was heated to 60° C. and the oxime (6.9 g, 25 mmol), dissolved in THF (60 ml), was added dropwise. After stirring at 60° C. for 4 hours, water (93 ml) was added dropwise, while cooling with an ice-bath (10° C.), and the reaction solution was filtered with suction over kieselguhr. The residue on the filter was washed with THF. The combined organic phases were concentrated i. vac. and the residue was adjusted to pH 11 with 5 N NaOH and extracted three times with ethyl acetate (100 ml each time). The organic phase was dried over sodium sulfate and concentrated. Yield: 5.4 g (82%), oil $^{13}$C-NMR (CDCl$_3$): 25.25; 25.93; 26.60; 28.75; 30.30; 30.40; 30.67; 36.20; 38.78; 38.93 (C$_4$); 41.24; 41.43 (N(CH$_3$)$_2$); 48.71; 70.62; 74.69 (CH); 113.97 (C$_{arom}$); 114.04 (C$_{arom}$); 130.24 (C$_{arom}$); 130.31 (C$_{arom}$); 132.94 (C$_{arom}$); 160.19; 162.62 (C$_{arom}$).

4-[Dimethylamino-(3-fluorophenyl)-methyl]-cyclohexane-carbaldehyde (R$^3$=3-fluorophenyl)

(Methoxymethyl)Triphenylphosphonium Chloride (15.42 g, 45 mmol) was suspended in absol. THF (50 ml) under argon, potassium tert-butylate (5.05 g, 45 mmol), dissolved in absol. THF (50 ml), was added dropwise at 0° C. and the mixture was then subsequently stirred at 0° C. for 15 min. The ketone (7.48 g, 0.30 mmol), dissolved in absol. THF (50 ml), was then added dropwise to the above solution at RT and the mixture was stirred at RT overnight. While cooling with ice-water, the mixture was hydrolyzed dropwise with water (25 ml) and 6 N HCl (75 ml). After stirring at RT for 1 h, the mixture was extracted with ether (10×50 ml), the aqueous phase was brought to pH 11 with 5 N NaOH and extracted with ethyl acetate (3×50 ml) and the extract was dried over Na$_2$SO$_4$ and concentrated i. vac. The crude product was purified by flash chromatography with ethyl acetate/cyclohexane (1:1). Yield: 6.55 g (83%). Melting point: 40-43° C.

$^1$H-NMR (DMSO, 600 MHz, selected signals): δ=1.99 (s, 3 H); 2.01 (s, 3 H); 3.10 (d, 1 H, J=9.06 Hz); 3.18 (d, 1 H, J=9.82 Hz); 9.54 (s, 1 H); 9.56 (s, 1 H).

$^{13}$C-NMR (CDCl$_3$): 23.93; 24.12; 25.79; 25.95; 26.19; 27.19; 27.99; 29.77; 37.05; 38.16; 41.45; 41.91; 47.30; 50.49; 71.50; 74.78; 113.50; 115.37; 124.78; 128.24; 130.59; 131.24; 131.67; 139.14; 139.76; 160.06; 163.50; 204.01; 204.85.

4-[Dimethylamino-(3-fluorophenyl)-methyl]-cyclohexane-carbaldehyde oxime (R$^3$=3-fluorophenyl)

The carbaldehyde (6.32 g, 24 mmol) and hydroxylamine hydrochloride (2.5 g, 36 mmol) were dissolved in absol. ethanol (90 ml), the basic ion exchanger Amberlyst A21 (17 g) was added and the mixture was stirred at RT for 3.5 h. The ion exchanger was filtered out and washed with ethanol (2×50 ml). The solution was concentrated and the residue was adjusted to pH 11 with 5 N NaOH. The aqueous phase was extracted with ethyl acetate (3×50 ml) and the organic phase was dried over sodium sulfate and concentrated in vacuo.

Yield: 6.68 g (100%)

$^{13}$C-NMR (CDCl$_3$): 25.59; 26.21; 27.38; 28.02; 28.36; 29.27; 29.45; 30.00; 34.14; 35.58; 36.56; 38.19 (C$_4$); 41.33; 41.99; (N(CH$_3$)$_2$); 72.02; 75.05; 75.19 (CH); 113.55 (C$_{arom}$); 115.62 (C$_{arom}$); 124.88 (C$_{arom}$); 128.78 (C$_{arom}$); 128.86 (C$_{arom}$); 139.84 (C$_{arom}$); 139.90 (C$_{arom}$); 154.38; 155.13; 161.10 (C$_{arom}$); 163.54 (C$_{arom}$).

AM 10: [(4-Aminomethyl-cyclohexyl)-(3-fluorophenyl)-methyl]-dimethylamine (R$^3$=3-fluorophenyl)

LiAlH$_4$ (1.82 g, 48 mmol) was added to absolute THF (300 ml) under argon, the mixture was heated to 60° C. and the oxime (6.68 g, 24 mmol), dissolved in THF (60 ml), was added dropwise to this. After stirring at 60° C. for 4 hours, water (70 ml) was added dropwise, while cooling with an ice-bath (10° C.), and the reaction solution was filtered over kieselguhr. The residue on the filter was washed with THF, the organic phases were combined, the THF was removed i. vac. and the residue was adjusted to pH 11 with 5 N NaOH and extracted with ethyl acetate (4×40 ml). The organic phase was dried over sodium sulfate and concentrated.

Yield: 5.7 g (90%), oil $^{13}$C-NMR (CDCl$_3$): 25.38; 25.93; 26.44; 28.89; 30.36; 30.45; 30.65; 36.10; 38.87; (C$_4$); 41.33; 41.49; 41.93 (N(CH$_3$)$_2$); 71.05; 75.11 (CH); 113.94 (C$_{arom}$); 115.53 (C$_{arom}$); 124.86 (C$_{arom}$); 128.59 (C$_{arom}$); 128.67 (C$_{arom}$); 140.14 (C$_{arom}$); 141.21 (C$_{arom}$); 161.03 (C$_{arom}$); 163.46 (C$_{arom}$).

4-[(4-Chloro-phenyl)-dimethylamino-methyl]-cyclohexanecarbaldehyde (R$^3$=4-chlorophenyl)

(Methoxymethyl)triphenylphosphonium chloride (68.55 g, 200 mmol) was suspended in absol. THF (200 ml) under argon, potassium tert-butylate (22.44 g, 200 mmol), dissolved in absol. THF (300 ml), was added dropwise at 0° C. and the mixture was then subsequently stirred at 0° C. for 15 min. The ketone (38 g, 143 mmol), dissolved in absol. THF (200 ml) was then added dropwise to the above solution at RT and the mixture was stirred at RT overnight. While cooling with ice-water, the mixture was hydrolyzed dropwise with water (150 ml) and 6 N HCl (450 ml). After stirring at RT for 1 h, the mixture was extracted with ether (10×100 ml), the aqueous phase was brought to pH 11 with 5 N NaOH and extracted by shaking with ethyl acetate (3×100 ml) and the extract was dried over Na$_2$SO$_4$ and concentrated i. vac. The crude product was purified over two silica gel columns (400 g) with ethyl acetate/cyclohexane (1:1).

Yield: 32.17 g (80%).

$^1$H-NMR (DMSO, 600 MHz, selected signals): δ=1.97 (s, 3 H); 1.99 (s, 3 H); 3.07 (d, 1 H, J=9.07 Hz); 3.14 (d, 1 H, J=9.82 Hz); 9.53 (s, 1 H); 9.55 (s, 1 H).

$^{13}$C-NMR (CDCl$_3$): δ=23.92; 24.16; 25.80; 25.97; 26.13; 27.25; 27.90; 29.81; 37.08; 38.19; 41.47; 41.96; 47.29; 50.48; 72.81; 74.54; 127.65; 130.28; 132.40; 134.78; 135.43; 203.98; 204.82.

4-[(4-Chlorophenyl)-dimethylamino-methyl]-cyclohexanecarbaldehyde oxime (R$^3$=4-chlorophenyl)

The carbaldehyde (7.55 g, 27 mmol) and hydroxylamine hydrochloride (2.81 g, 40 mmol) were dissolved in absol. ethanol (100 ml), the basic ion exchanger Amberlyst A21 (19 g) was added and the mixture was stirred at RT for 3.5 h. The ion exchanger was filtered out and washed with ethanol (2×50 ml). The solution was concentrated and the residue was adjusted to pH 11 with 5 N NaOH. The aqueous phase was extracted with ethyl acetate (3×50 ml) and the organic phase was dried over sodium sulfate and concentrated in vacuo.

Yield: 7.57 g (96%)

AM 12: [(4-Aminomethyl-cyclohexyl)-(4-chlorophenyl)-methyl]-dimethylamine (R$^3$=4-chlorophenyl)

LiAlH$_4$ (1.89 g, 50 mmol) was added to absolute THF (300 ml) under argon, the mixture was heated to 60° C. and the oxime (7.5 g, 25 mmol), dissolved in THF (60 ml), was added dropwise to this. After stirring at 60° C. for 4 hours, water (70 ml) was added dropwise, while cooling with an ice-bath (10° C.), and the reaction solution was filtered over kieselguhr. The residue on the filter was washed with THF, the organic phases were combined, the THF was removed i. vac. and the residue was adjusted to pH 11 with 5 N NaOH and extracted with ethyl acetate (4×40 ml). The organic phase was dried over sodium sulfate and concentrated.

Yield: 6.3 g (90%), oil $^{13}$C-NMR (CDCl$_3$): 25.22; 25.87; 26.58; 28.70; 30.36; 30.53; 30.59; 36.02; 38.76 (C$_4$); 41.29; 41.39; 41.91 (N(CH$_3$)$_2$); 45.64; 48.72; 70.72; 74.77 (CH); 127.46 (C$_{arom}$); 127.52 (C$_{arom}$); 130.27 (C$_{arom}$); 132.11 (C$_{arom}$); 132.15 (C$_{arom}$); 134.80 (C$_{arom}$); 135.72 (C$_{arom}$).

4-(Dimethylamino-thiophen-2-yl-methyl)-cyclohexanecarbaldehyde (R$^3$=2-thienyl)

(Methoxymethyl)triphenylphosphonium chloride (20.56 g, 60 mmol) was suspended in absol. THF (70 ml) under argon, potassium tert-butylate (6.73 g, 60 mmol), dissolved in absol. THF (70 ml), was added dropwise at 0° C. and the mixture was then subsequently stirred at 0° C. for 15 min. The ketone (9.4 g, 40 mmol), dissolved in absol. THF (70 ml), was then added dropwise to the above solution at RT and the mixture was stirred at RT overnight. While cooling with ice-water, the mixture was hydrolyzed dropwise with water (60 ml) and 6 N HCl (180 ml). After stirring at RT for 1 h, the mixture was extracted with ether (5×50 ml) the aqueous phase was brought to pH 11 with 5 N NaOH and extracted by shaking with ethyl acetate (3×50 ml), and the extract was dried over Na$_2$SO$_4$ and concentrated i. vac. The crude product was purified by flash chromatography with ethyl acetate/cyclohexane (1:1). Yield: 7.66 g (77%).

$^1$H-NMR (DMSO, 600 MHz, selected signals): δ=2.03 (s, 3 H); 2.05 (s, 3 H); 3.44 (d, 1 H, J=9.82 Hz); 3.52 (d, 1 H, J=10.58 Hz); 9.54 (s, 1 H); 9.58 (s, 1 H).

$^{13}$C-NMR (CDCl$_3$): δ=23.74; 23.83; 25.80; 25.84; 26.98; 27.09; 29.15; 29.68; 39.13; 40.20; 40.98; 41.29 (N(CH$_3$)$_2$); 47.48; 50.49; 67.81; 69.79; 123.61; 123.70; 125.89; 126.20; 126.24; 139.14; 139.48; 204.07; 204.82.

4-(Dimethylamino-thiophen-2-yl-methyl)-cyclohexanecarbaldehyde oxime (R$^3$=2-thiophene)

The carbaldehyde (7.54 g, 30 mmol) and hydroxylamine hydrochloride (3.12 g, 45 mmol) were dissolved in absol. ethanol (100 ml), the basic ion exchanger Amberlyst A21 (21 g) was added and the mixture was stirred at RT overnight. The ion exchanger was filtered out and washed with ethanol (2×50 ml). The solution was concentrated and the residue was adjusted to pH 11 with 5 N NaOH. The aqueous phase was extracted with ethyl acetate (3×50 ml) and the organic phase was dried over sodium sulfate and concentrated in vacuo.

Yield: 7.99 g (100%)

AM 6: [(4-Aminomethyl-cyclohexyl)-thiophen-2-yl-methyl]-dimethylamine (R$^3$=2-thiophene)

LiAlH$_4$ (2.27 g, 60 mmol) was Added to Absolute THF (300 ml) Under Argon, the mixture was heated to 60° C. and the oxime (7.99 g, 30 mmol), dissolved in THF (60 ml), was added dropwise to this. After stirring at 60° C. for 4 hours, water (70 ml) was added dropwise, while cooling with an ice-bath (10° C.), and the reaction solution was filtered over kieselguhr. The residue on the filter was washed with THF, the organic phases were combined, the THF was removed i. vac. and the residue was adjusted to pH 11 with 5 N NaOH and extracted with ethyl acetate (3×50 ml). The organic phase was dried over sodium sulfate and concentrated.

Yield: 6.72 g (89%), oil $^{13}$C-NMR (CDCl$_3$): 25.93; 26.11; 26.24; 26.30; 29.97. 30.34; 30.42; 38.03; 40.65; 40.82; 41.18; 41.34 (N(CH$_3$)$_2$); 46.19; 48.67; 65.58; 70.06; 123.61; 125.88; 126.23; 140.08.

4-(1-Dimethylamino-3-phenyl-propyl)-cyclohexanecarbaldehyde (R$^3$=phenethyl)

(Methoxymethyl)triphenylphosphonium chloride (20.56 g, 60 mmol) was suspended in absol. THF (85 ml) under argon, potassium tert-butylate (6.73 g, 60 mmol), dissolved in absol. THF (70 ml), was added dropwise at 0° C. and the mixture was then subsequently stirred at 0° C. for 15 min. The ketone (10.2 g, 40 mmol), dissolved in absol. THF (60 ml), was then added dropwise to the above solution at RT and the mixture was stirred at RT overnight. While cooling with ice-water, the mixture was hydrolyzed dropwise with water (35 ml) and 6 N HCl (90 ml). After stirring at RT for 1 h, the mixture was extracted with ether (10×50 ml), the aqueous phase was brought to pH 11 with 5 N NaOH and extracted with ethyl acetate (3×50 ml) and the extract was dried over Na$_2$SO$_4$ and concentrated i. vac. The crude product was purified by flash chromatography with ethyl acetate/cyclohexane (1:1).

Yield: 6.73 g (63%).

$^1$H-NMR (DMSO, 600 MHz, selected signals): δ=2.18 (s, 3 H); 2.20 (s, 3 H); 9.54 (s, 1 H); 9.61 (s, 1 H).

$^{13}$C-NMR (CDCl$_3$): δ=24.35; 24.49; 26.00; 26.09; 26.85; 27.79; 29.07; 29.13; 35.27; 39.02; 40.98; 41.19; 46.99; 50.33; 66.85; 67.85; 70.54; 71.42; 125.40; 125.44; 128.02; 128.13; 131.15; 131.17; 142.45; 204.10; 205.01.

4-(1-Dimethylamino-3-phenyl-propyl)-cyclohexanecarbaldehyde oxime (R$^3$=phenethyl)

The aldehyde (6.55 g, 24 mmol) and hydroxylamine hydrochloride (2.5 g, 36 mmol) were dissolved in absol. ethanol (90 ml), the basic ion exchanger Amberlyst A21 (15.6 g) was added and the mixture was stirred at RT overnight. The ion exchanger was filtered out and washed twice with ethanol (50 ml each time). The solution was concentrated and the residue was adjusted to pH 11 with 5 N NaOH. The aqueous phase was extracted three times with ethyl acetate (50 ml each time) and the organic phase was dried over sodium sulfate and concentrated in vacuo.

Yield: 6.90 g (100%)

AM 8: [1-(4-Aminomethyl-cyclohexyl)-3-phenyl-propyl]-dimethylamine (R$^3$=phenethyl)

LiAlH$_4$ (1.82 g, 48 mmol) was added to absolute THF (360 ml) under argon, the mixture was heated to 60° C. and the oxime (6.90 g, 24 mmol), dissolved in THF (60 ml), was added dropwise to this. After stirring at 60° C. for 4 hours, water (90 ml) was added dropwise, while cooling with an ice-bath (10° C.), and the reaction solution was filtered over kieselguhr. The residue on the filter was washed with THF, the organic phases were combined, the THF was removed i. vac. and the residue was adjusted to pH 11 with 5 N NaOH and extracted with ethyl acetate (4×40 ml). The organic phase was dried over sodium sulfate and concentrated.

Yield: 5.6 g (85%), oil $^{13}$C-NMR (CDCl$_3$): 25.93; 26.58; 27.09; 29.21; 29.90; 30.32; 30.73; 30.77; 35.38; 35.66; 38.73; (C$_4$); 40.06; 40.90; 41.19 (N(CH$_3$)$_2$); 48.78; 65.15; 68.22 (CH); 125.36; 127.99; 128.05; 142.69.

Synthesis of the Aminoethylcyclohexanes

The aminoethylcyclohexanes were prepared by three-stage reactions from the correspondingly substituted cyclohexylaldehydes by chain lengthening (Wittig) and reaction with hydroxylamine hydrochloride and subsequent cleavage with lithium aluminium hydride.

[4-(Dimethylamino-phenyl-methyl)-cyclohexyl]-acetaldehyde (R$^3$=phenyl)

(Methoxymethyl)triphenylphosphonium chloride (38.39 g, 0.112 mol) was suspended in absol. THF (150 ml) under argon, potassium tert-butylate (12.56 g, 0.112 mmol), dissolved in absol. THF (120 ml), was added dropwise at 0° C. and the mixture was then subsequently stirred at 0° C. for 15 min (the solution became deep orange in colour).

The aldehyde (18.4 g, 0.075 mmol), dissolved in absol. THF (120 ml), was then added dropwise at RT and the mixture was stirred at RT overnight. While cooling with ice-water, the mixture was hydrolyzed dropwise with water (50 ml) and 6 N HCl (150 ml). After stirring at RT for 1 h, the mixture was extracted with ether (10×100 ml). The aqueous phase was brought to pH 11 with 5 N NaOH and extracted by shaking with ethyl acetate (3×80 ml) and the extract was dried over Na$_2$SO$_4$ and concentrated in vacuo. The crude product was purified by flash chromatography with ethyl acetate/cyclohexane (1:1). Yield: 16.31 g (84%), oil $^{13}$C-NMR (CDCl$_3$): 25.30; 25.92; 29.04; 29.19; 29.74; 30.86; 32.99; 33.02; 35.98; 38.31 (C$_4$); 41.42; 42.06; (N(CH$_3$)$_2$); 48.04; 51.24; 71.82; 75.47 (CH); 126.64 (C$_{arom}$);

126.68 (C$_{arom}$); 127.39 (C$_{arom}$); 127.46 (C$_{arom}$); 129.15 (C$_{arom}$); 136.20 (C$_{arom}$); 137.11 (C$_{arom}$); 202.27; 202.37 (CHO).

[4-(Dimethylamino-phenyl-methyl)-cyclohexyl]-acetaldehyde oxime (R$^3$=phenyl)

The carbaldehyde (11.04 g, 42.5 mmol) and hydroxylamine hydrochloride (4.44 g, 64 mmol) were dissolved in absol. ethanol (150 ml), the basic ion exchanger Amberlyst A21 (30 g) was added and the mixture was stirred at RT for 4 h. The ion exchanger was filtered out and washed with ethanol (2×50 ml). The solution was concentrated, the residue was adjusted to pH 11 with 5 N NaOH, the aqueous phase was extracted with ethyl acetate (3×50 ml) and the organic phase was dried over sodium sulfate and concentrated i. vac. Yield: 11.66 g (100%)

$^{13}$C-NMR (CDCl$_3$): 25.41; 25.57; 28.87; 29.11; 30.92; 30.97; 32.33; 32.99; 33.67; 35.99; 36.10; 38.59 (C$_4$); 41.31; 41.40; 42.11; 42.14 (N(CH$_3$)$_2$); 71.74; 75.63 (CH); 126.71 (C$_{arom}$); 127.46 (C$_{arom}$); 129.26 (C$_{arom}$); 137.26 (C$_{arom}$); 150.95; 151.37; 151.56 (C=N—O).

AM 15: 2-[4-Dimethylamino-phenyl-methyl)-cyclohexyl]-ethylamine (R$^3$=phenyl)

LiAlH$_4$ (3.22 g, 85 mmol) was added to absolute THF (400 ml) under argon, the mixture was heated to 60° C. and the oxime (11.66 g, 42.5 mmol), dissolved in THF (80 ml), was added dropwise. After stirring at 60° C. for 4 hours, water (100 ml) was added dropwise, while cooling with an ice-bath (10° C.), the reaction solution was filtered with suction over kieselguhr and the kieselguhr was washed with THF. The combined THF solutions were concentrated i. vac. and the residue was adjusted to pH 11 with 5 N NaOH and extracted with ethyl acetate (4×50 ml). The organic phase was dried over sodium sulfate and evaporated to dryness.

Yield: 9.15 g (83%), oil $^{13}$C-NMR (CDCl$_3$): 25.58; 26.08; 29.16; 29.21; 30.39; 31.10; 32.49; 33.16; 33.33; 35.54; 36.22; 38.80 (C$_4$); 40.32; 41.36; 41.50; 42.11; (N(CH$_3$)$_2$); 71.77; 75.66 (CH); 126.52 (C$_{arom}$); 127.31 (C$_{arom}$); 127.38 (C$_{arom}$); 129.18 (C$_{arom}$); 139.39 (C$_{arom}$); 137.41 (C$_{arom}$).

{4-[Dimethylamino-(3-fluorophenyl)-methyl]-cyclohexyl}-acetaldehyde (R$^3$=3-fluorophenyl)

(Methoxymethyl)triphenylphosphonium chloride (26.73 g, 78 mmol) was suspended in absol. THF (90 ml) under argon, potassium tert-butylate (8.75 g, 78 mmol), dissolved in absol. THF (90 ml), was added dropwise at 0° C. and the mixture was then subsequently stirred at 0° C. for 15 min. The aldehyde (13.69 g, 52 mmol), dissolved in absol. THF (90 ml), was then added dropwise at RT and the mixture was stirred at RT overnight. While cooling with ice-water, the mixture was hydrolyzed dropwise with water (50 ml) and 6 N HCl (150 ml). After stirring at RT for 1 h, the mixture was extracted ten times with ether (50 ml each time). The aqueous phase was brought to pH 11 with 5 N NaOH and extracted by shaking three times with ethyl acetate (100 ml each time), and the extract was dried over Na$_2$SO$_4$ and concentrated i. vac. The crude product was purified by flash chromatography with ethyl acetate/cyclohexane (1:1). Yield: 12.61 g (87%).

$^{13}$C-NMR (CDCl$_3$): δ=25.19; 25.83; 28.90; 29.06; 29.14; 29.68; 30.77; 32.92; 32.98; 33.10; 36.05; 38.36; 41.39; 42.04; 48.02; 51.20; 71.48; 75.07; 113.43; 113.49; 113.64; 113.69; 115.55; 115.76; 124.89; 128.70; 128.78; 128.88; 139.24; 140.08; 140.14; 161.09; 163.52; 202.19; 202.27.

{4-[Dimethylamino-(3-fluorophenyl)-methyl]-cyclohexyl}-acetaldehyde oxime (R$^3$=3-fluorophenyl)

The carbaldehyde (7.18 g, 25.8 mmol) and hydroxylamine hydrochloride (2.71 g, 39 mmol) were dissolved in absol. ethanol (90 ml), the basic ion exchanger Amberlyst A21 (20 g) was added and the mixture was stirred at RT for 20 h. The ion exchanger was filtered out and washed with ethanol (2×50 ml). The solution was concentrated, the residue was adjusted to pH 11 with 5 N NaOH, the aqueous phase was extracted with ethyl acetate (3×50 ml) and the organic phase was dried over sodium sulfate and concentrated i. vac. Yield: 7.54 g (100%)

AM 4: 2-{4-[Dimethylamino-(3-fluorophenyl)-methyl]-cyclohexyl}-ethylamine (R$^3$=3-fluorophenyl)

LiAlH$_4$ (1.97 g, 52 mmol) was added to absolute THF (300 ml) under argon, the mixture was heated to 60° C. and the oxime (7.54 g, 25.8 mmol), dissolved in THF (70 ml), was added dropwise. After stirring at 60° C. for 4 hours, water (100 ml) was added dropwise, while cooling with an ice-bath (10° C.), the reaction solution was filtered with suction over kieselguhr and the kieselguhr was washed with THF. The combined THF solutions were concentrated i. vac. and the residue was adjusted to pH 11 with 5 N NaOH and extracted with ethyl acetate (3×50 ml). The organic phase was dried over sodium sulfate and concentrated i. vac. Yield: 6.3 g (88%), oil $^{13}$C-NMR (CDCl$_3$): 25.28; 25.84; 28.87; 28.98; 30.28; 32.30; 32.93; 33.13; 35.38; 36.16; 37.81; 38.69 (C$_4$); 39.69; 41.20; 41.37; 41.94 (N(CH$_3$)$_2$); 71.29; 75.11 (CH); 113.14; 113.18; 113.38; 115.41; 115.62; 124.73; 128.44; 128.53; 139.25; 140.27; 140.33; 160.91; 163.34.

{4-[(4-Chlorophenyl)-dimethylamino-methyl]-cyclohexyl}-acetaldehyde (R$^3$=4-chlorophenyl)

(Methoxymethyl)triphenylphosphonium chloride (25.02 g, 73 mmol) was suspended in absol. THF (90 ml) under argon, potassium tert-butylate (8.19 g, 73 mmol), dissolved in absol. THF (90 ml), was added dropwise at 0° C. and the mixture was then subsequently stirred at 0° C. for 15 min. The aldehyde (13.86 g, 49 mmol), dissolved in absol. THF (90 ml), was then added dropwise at RT and the mixture was stirred at RT overnight. While cooling with ice-water, the mixture was hydrolyzed dropwise with water (50 ml) and 6 N HCl (150 ml). After stirring at RT for 1 h, the mixture was extracted ten times with ether (50 ml each time). The aqueous phase was brought to pH 11 with 5 N NaOH and extracted by shaking three times with ethyl acetate (100 ml each time) and the extract was dried over Na$_2$SO$_4$ and concentrated i. vac. The crude product was purified by flash chromatography with ethyl acetate/cyclohexane (1:1). Yield: 12.07 g (84%).

$^{13}$C-NMR (CDCl$_3$): δ=25.06; 25.82; 28.74; 29.00; 29.13; 29.60; 30.77; 32.87; 32.94; 33.07; 36.06; 38.32; 41.38; 42.05; 47.95; 51.17; 71.23; 74.80; 127.58; 127.66; 130.31; 132.28; 132.34; 134.81; 135.77; 202.12; 202.20.

{4-[Dimethylamino-(4-chlorophenyl)-methyl]-cyclohexyl}-acetaldehyde oxime (R$^3$=4-chlorophenyl)

The carbaldehyde (6.72 g, 22.8 mmol) and hydroxylamine hydrochloride (2.36 g, 34 mmol) were dissolved in absol.

ethanol (90 ml), the basic ion exchanger Amberlyst A21 (16 g) was added and the mixture was stirred at RT for 20 h. The ion exchanger was filtered out and washed with ethanol (2×50 ml). The solution was concentrated, the residue was adjusted to pH 11 with 5 N NaOH, the aqueous phase was extracted with ethyl acetate (3×50 ml) and the organic phase was dried over sodium sulfate and concentrated i. vac. Yield: 7.04 g (100%)

AM 5: 2-{4-[Dimethylamino-(4-chlorophenyl)-methyl]-cyclohexyl}-ethylamine ($R^3$=4-chlorophenyl)

LiAlH$_4$ (1.73 g, 45.6 mmol) was added to absolute THF (300 ml) under argon, the mixture was heated to 60° C. and the oxime (7.04 g, 22.8 mmol), dissolved in THF (60 ml), was added dropwise. After stirring at 60° C. for 4 hours, water (100 ml) was added dropwise, while cooling with an ice-bath (10° C.), the reaction solution was filtered with suction over kieselguhr and the kieselguhr was washed with THF. The combined THF solutions were concentrated i. vac. and the residue was adjusted to pH 11 with 5 N NaOH and extracted with ethyl acetate (3×50 ml). The organic phase was dried over sodium sulfate and concentrated i. vac. Yield: 5.76 g (86%), oil $^{13}$C-NMR (CDCl$_3$): 25.67; 26.35; 29.23; 29.44; 30.74; 31.39; 33.41; 33.61; 35.86; 36.71; 38.20; 39.18; 40.17; 40.67; 41.72; 41.81; 42.50 (N(CH$_3$)$_2$); 71.59; 75.37; 127.86; 127.95; 130.70; 132.52; 135.38; 136.45.

{4-[Dimethylamino-thiophen-2-yl-methyl]-cyclohexyl}-acetaldehyde ($R^3$=2-thienyl)

(Methoxymethyl)triphenylphosphonium chloride (28.79 g, 84 mmol) was suspended in absol. THF (100 ml) under argon, potassium tert-butylate (9.42 g, 84 mmol), dissolved in absol. THF (100 ml), was added dropwise at 0° C. and the mixture was then subsequently stirred at 0° C. for 15 min. The aldehyde (14.08 g, 56 mmol), dissolved in absol. THF (100 ml), was then added dropwise at RT and the mixture was stirred at RT overnight. While cooling with ice-water, the mixture was hydrolyzed dropwise with water (50 ml) and 6 N HCl (150 ml). After stirring at RT for 1 h, the mixture was extracted ten times with ether (50 ml each time). The aqueous phase was brought to pH 11 with 5 N NaOH and extracted by shaking three times with ethyl acetate (100 ml each time) and the extract was dried over Na$_2$SO$_4$ and concentrated i. vac. The crude product was purified by flash chromatography with ethyl acetate/cyclohexane (1:2). Yield: 11.48 g (77%).

$^{13}$C-NMR (CDCl$_3$): δ=25.80; 25.88; 28.73; 29.95; 30.49; 32.23; 32.76; 37.89; 40.21; 40.88; 41.23; 48.36; 51.09; 66.02; 69.97; 123.19; 123.72; 125.95; 126.31; 139.42; 139.91; 202.61.

[4-(Dimethylamino-thiophen-2-yl-methyl)-cyclohexyl]-acetaldehyde oxime ($R^3$=2-thiophene)

The carbaldehyde (6.3 g, 23.7 mmol) and hydroxylamine hydrochloride (2.5 g, 36 mmol) were dissolved in absol. ethanol (90 ml), the basic ion exchanger Amberlyst A21 (20 g) was added and the mixture was stirred at RT for 20 h. The ion exchanger was filtered out and washed with ethanol (2×50 ml). The solution was concentrated, the residue was adjusted to pH 11 with 5 N NaOH, the aqueous phase was extracted with ethyl acetate (3×50 ml) and the organic phase was dried over sodium sulfate and concentrated i. vac. Yield: 6.64 g (100%)

AM 3: 2-[4-(Dimethylamino-thiophen-2-yl-methyl)-cyclohexyl]-ethylamine ($R^3$=2-thiophene)

LiAlH$_4$ (1.78 g, 47 mmol) was added to absolute THF (250 ml) under argon, the mixture was heated to 60° C. and the oxime (6.64 g, 23.7 mmol), dissolved in THF (60 ml), was added dropwise. After stirring at 60° C. for 4 hours, water (100 ml) was added dropwise, while cooling with an ice-bath (10° C.), the reaction solution was filtered with suction over kieselguhr and the kieselguhr was washed with THF. The combined THF solutions were concentrated i. vac. and the residue was adjusted to pH 11 with 5 N NaOH and extracted with ethyl acetate (3×50 ml). The organic phase was dried over sodium sulfate and concentrated i. vac. Yield: 5.62 g (89%), oil $^{13}$C-NMR (CDCl$_3$): 25.97; 26.13; 28.72; 28.79; 30.15; 30.23; 30.74; 32.61; 32.90; 35.32; 38.22; 39.70; 40.09; 40.69; 40.84; 41.26 (N(CH$_3$)$_2$); 70.14; 123.56; 123.60; 125.86; 126.21; 126.23; 139.70; 140.24.

Amine Units A16-A18, A22-A27

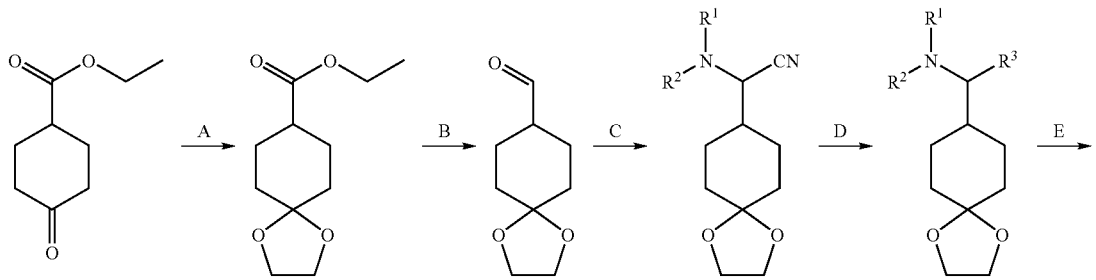

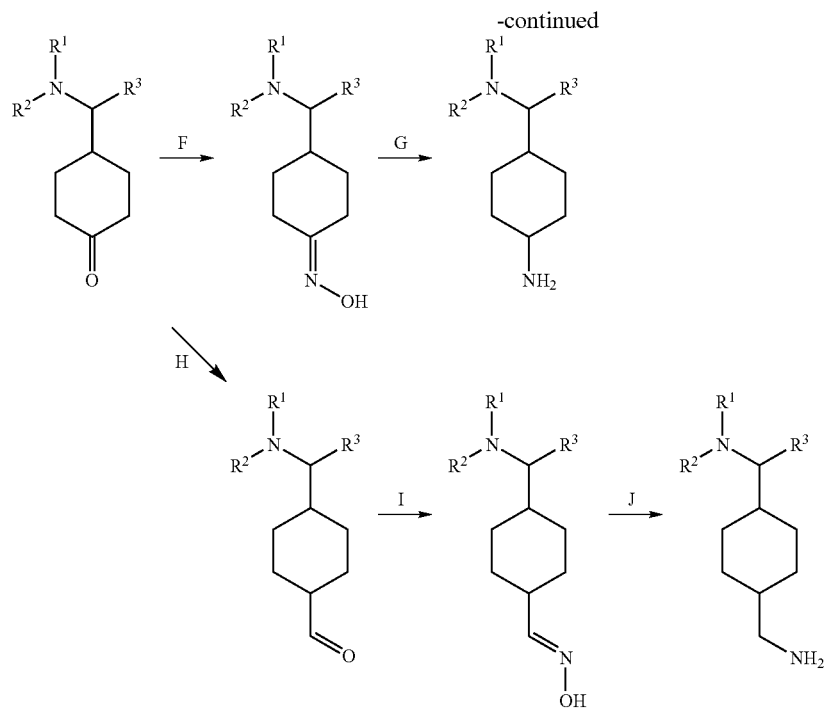

Stage A

Ethylene glycol (1.08 mol) and p-toluenesulfonic acid (0.7 g) were added to a solution of 4-oxo-cyclohexanecarboxylic acid ethyl ester (0.31 mol) in toluene (160 ml) and the mixture was stirred at 25° C. for 20 h. Ethyl acetate (300 ml) was then added. The organic phase separated off was washed with water, aqueous saturated $NaHCO_3$ solution and NaCl solution. After drying of the organic phase over $Na_2SO_4$ and filtration, the solvent was removed in vacuo. The product was employed in the next stage without further purification.

Stage B

Diisobutylammonium hydride (153 mmol, 1.5 M in toluene) was added dropwise to a solution of 1,4-dioxa-spiro[4,5]decane-8-carboxylic acid ethyl ester (150 mmol) in absolute toluene (160 ml) under argon at −70° C. and the mixture was stirred for 1 h. Methanol (80 ml) was then added slowly at −70° C. and the reaction solution was allowed to warm to RT. After the addition of aqueous saturated NaCl solution (100 ml), the reaction mixture was filtered over silica and washed with ethyl acetate. The aqueous phase separated off was extracted twice with ethyl acetate.

The combined organic phases were washed with aqueous saturated NaCl solution, dried over $Na_2SO_4$ and then filtered. The solvent was removed in vacuo and the product was employed in the next stage without further purification.

Stage C

KCN (0.17 mol) and the corresponding amine (0.17 mol) were added to a solution of 1,4-dioxa-spiro[4,5]decane-8-carboxaldehyde (0.141 mol) in a mixture of ethanol (141 ml) and water (70 ml) and the mixture was stirred at 25° C. for 72 h. After addition of ethyl acetate (700 ml), the organic phase was separated off and washed successively with water (4×150 ml) and aqueous $FeSO_4$ solution (4×150 ml). The organic phase separated, dried over $Na_2SO_4$ and then filtered. The solvent was removed in vacuo and the product was employed in the next stage without further purification.

Stage D

The Grignard solution (2.5 equivalents) in THF was added dropwise to a solution of the aminonitrile (105 mmol) in THF (100 ml) under argon at 0° C. and the mixture was then stirred at 25° C. for a further 20 h. After addition of an aqueous saturated $NH_4Cl$ solution (200 ml), the reaction mixture was extracted with ethyl acetate (3×100 ml). The combined organic phases were then washed with water and with aqueous saturated NaCl solution. The organic phase separated off was dried over $Na_2SO_4$ and filtered. The solvent was removed in vacuo and the product was purified via column chromatography (2-5% methanol/methylene chloride).

Stage E

Conc. HCl and water (1.1, 88 ml) were slowly added to the Grignard adduct (105 mmol) at 0° C. and the mixture was stirred at 25° C. for 20 h. The reaction solution was then extracted with ethyl acetate (2×100 ml). After addition of 5 N sodium hydroxide solution, to establish a basic pH, the mixture was extracted with methylene chloride (3×100 ml). The combined organic phases were dried over $Na_2SO_4$ and filtered. The solvent was removed in vacuo and the product was used in the next stage without further purification.

Stage F and I

Amberlyst A21 (40 g) was added to a solution of the ketone (40 mmol) in absolute ethanol (200 ml) and the mixture was stirred at 25° C. for 20 h. After filtration and washing with ethanol (2×200 ml), the solvent was removed in vacuo. The product was employed in the next stage without further purification.

Stage G and J

The oxime (38.5 mmol) in THF (90 ml) was added dropwise to a reaction mixture of lithium aluminium hydride (77 mmol) in absolute THF (400 ml) at 60° C. and the mixture was stirred at 60° C. for 4 h. Water (100 ml) was then slowly added at 10° C. and the reaction mixture was filtered over silica. The residue on the filter was washed with ethyl acetate and the solvent of the combined organic phases was removed in vacuo. The product was purified via column chromatography (5-10% methanol/methylene chloride).

Stage H

A solution of potassium tert-butylate (0.1 mol) in THF (100 ml) was added dropwise to a suspension of (methoxytriphenyl)phosphonium chloride (0.1 mol) in absolute THF (150 ml) under argon at 0° C. and the mixture was stirred for 15 min. The ketone (0.06 mol) in absolute THF was then added dropwise at 25° C. and the mixture was stirred for 16 h. After addition of 6 N HCl at 0-5° C. and stirring for 1 h, the mixture was extracted with ethyl acetate (10×50 ml). The aqueous phase was adjusted to pH 11 with 5 N sodium hydroxide solution and extracted with ethyl acetate (3×100 ml). The combined organic phases were dried over $Na_2SO_4$ and filtered. The solvent was removed in vacuo and the product was used in the next stage without further purification.

Synthesis of Amine Unit AM28

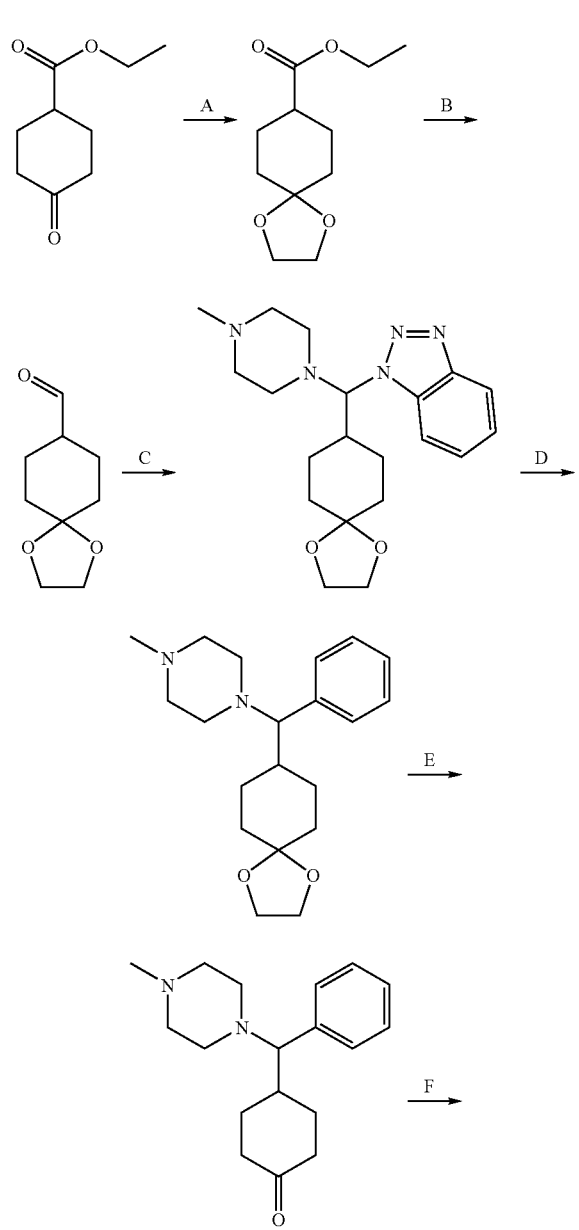

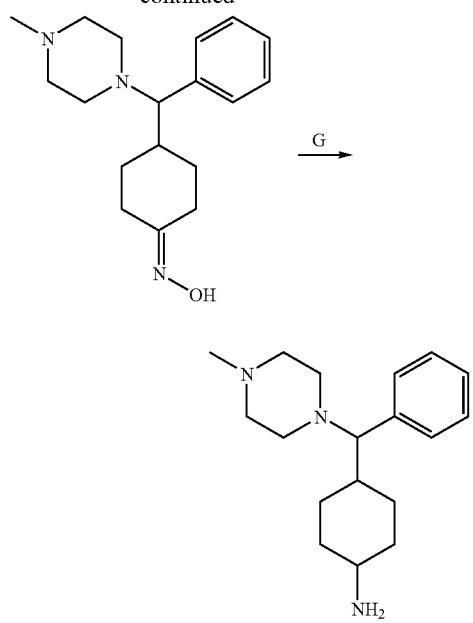

Stages A, B, E, F and G are analogous to the amine unit syntheses Examples AM16-AM18 and AM22-AM27.

Stage C

The aldehyde (23.4 mmol), N-methylpiperazine (23.4 mmol) and 1H-benzotriazole (23.4 mmol) were heated under reflux in benzene (60 ml) for 16 h and the water of reaction formed was removed via a water separator. The benzene was removed in vacuo and the residue was employed directly in the next stage.

Stage D

A solution of the benzotriazole adduct (23.5 mmol) in THF was added dropwise to a solution of phenylmagnesium chloride (47.1 mmol) in THF and the mixture was stirred at 25° C. for 16 h. The reaction solution was cooled to 0° C., aqueous saturated $NH_4Cl$ solution was added and the mixture was then extracted with ethyl acetate (2×300 ml). The organic phase was washed with water and aqueous saturated NaCl solution. After drying of the organic phase over $Na_2SO_4$ and filtration, the solvent was removed in vacuo. The product was purified via column chromatography (2-5% methanol/methylene chloride).

Amine Units AM29 and AM30

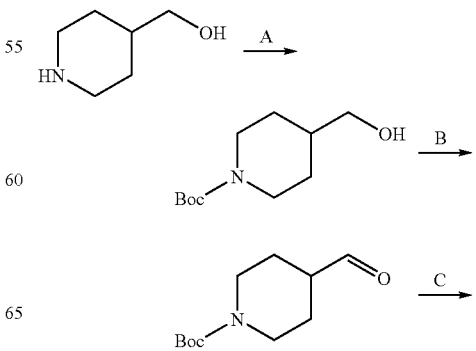

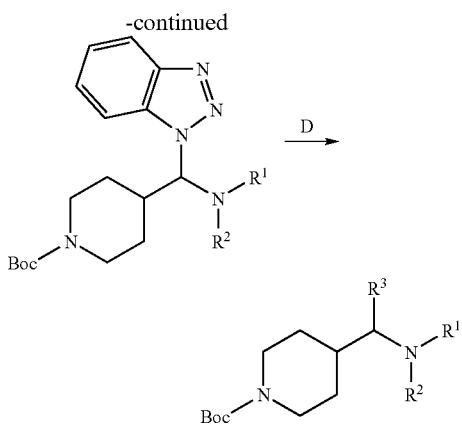

Stage A

Triethylamine (1.5 equivalents) and Boc anhydride (1.2 equivalents) were added to a solution of 4-hydroxymethylpiperidine in $CH_2Cl_2$ under an inert gas atmosphere at 0° C. and the mixture was stirred at 25° C. for 1 h. After addition of $CH_2Cl_2$, the organic phase was separated off and washed with water and aqueous saturated NaCl solution. After drying of the organic phase over $Na_2SO_4$ and filtration, the solvent was removed in vacuo. The product was purified via column chromatography (30% ethyl acetate/hexane).

Stage B

DMSO (2.2 equivalents) was added to solution of oxalyl chloride (1.1 equivalents) in dry $CH_2Cl_2$ under an inert gas atmosphere at –78° C. and the mixture was stirred for 1 h. A solution of N-Boc-4-piperidinemethanol (1 equivalent) in dry $CH_2Cl_2$ was added dropwise to the reaction mixture at –70° C. and the mixture was stirred for 2 h. After addition of triethylamine (2.5 equivalents), the reaction solution was allowed to warm to RT and aqueous saturated $NH_4Cl$ solution and $CH_2Cl_2$ were added. The organic phase separated off was washed with water and aqueous saturated NaCl solution. After drying of the organic phase over $Na_2SO_4$ and filtration, the solvent was removed in vacuo. The product was used in the next stage without further purification.

Stage C

The aldehyde (23.4 mmol), morpholine (23.4 mmol) and 1H-benzotriazole (23.4 mmol) were heated under reflux in benzene (60 ml) for 16 h and the water of reaction formed was removed via a water separator. The benzene was removed in vacuo and the residue was employed directly in the next stage.

Stage D

A solution of the benzotriazole adduct (23.5 mmol) in THF was added dropwise to a solution of the Grignard reagent (47.1 mmol) in THF and the mixture was stirred at 25° C. for 16 h. The reaction solution was cooled to 0° C., aqueous saturated $NH_4Cl$ solution was added and the mixture was then extracted with ethyl acetate (2×300 ml). The organic phase was washed with water and aqueous saturated NaCl solution. After drying of the organic phase over $Na_2SO_4$ and filtration, the solvent was removed in vacuo. The product was purified via column chromatography (2-5% methanol/methylene chloride).

Amine Unit AM31

Preparation of Methyl 1-(4-methoxybenzyl)piperidine-4-carboxylate

4-Methoxybenzyl chloride (1.10 g, 6.98 mmol) was added dropwise to a solution of isonipecotic acid methyl ester (1.00 g, 6.98 mmol) and triethylamine (1.40 g, 14 mmol) in THF (30 ml) and the mixture was stirred at 60° C. for 72 h. 5% strength sodium bicarbonate solution (50 ml) was then added to the reaction mixture and the mixture was extracted with ethyl acetate (3×50 ml). The combined organic phases were dried with sodium sulfate and concentrated i. vac. The residue was purified by flash chromatography with cyclohexane/ethyl acetate (2:1).

Yield: 1.23 g (67%) of methyl 1-(4-methoxybenzyl)piperidine-4-carboxylate $^1$H-NMR (DMSO-$d_6$): 1.53 (dq, 2H); 1.77 (dd, 2H); 1.93 (dt, 2H); 2.28 (tt, 1H); 2.71 (td, 2H); 3.35 (s, 2H); 3.58 (s, 3H); 3.72 (s, 3H); 6.86 (d, 2H); 7.17 (d, 2H).

Preparation of 1-(4-methoxybenzyl)piperidine-4-carbaldehyde

A 1.5 M solution of diisobutylaluminium hydride in toluene (3.12 ml, 4.68 mmol) was added dropwise to a solution of methyl 1-(4-methoxybenzyl)piperidine-4-carboxylate (1.23 g, 4.68 mmol) in toluene (30 ml) under argon at –78° C. in the course of 30 min and the mixture was then stirred at this temperature for 30 min. Thereafter, methanol (15 ml) was added dropwise such that the internal temperature remained at –78° C., before the mixture was then slowly warmed to room temperature. Saturated sodium chloride solution (20 ml) was added to the reaction mixture and the suspension was filtered through sea sand. The organic phase was dried with sodium sulfate and concentrated i. vac. The residue was purified by flash chromatography with cyclohexane/ethyl acetate (1:3).

Yield: 750 mg (69%) of 1-(4-methoxybenzyl)piperidine-4-carbaldehyde $^1$H-NMR (DMSO-$d_6$): 1.47 (dtd, 2H); 1.78 (m, 2H); 2.00 (dt, 2H); 2.27 (m, 1H); 2.66 (td, 2H); 3.36 (s, 2H); 3.73 (s, 3H); 6.86 (d, 2H); 7.18 (d, 2H); 9.57 (s, 1H).

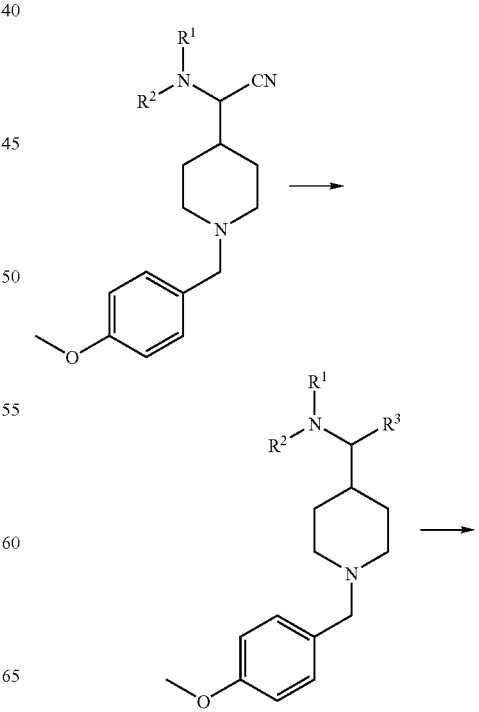

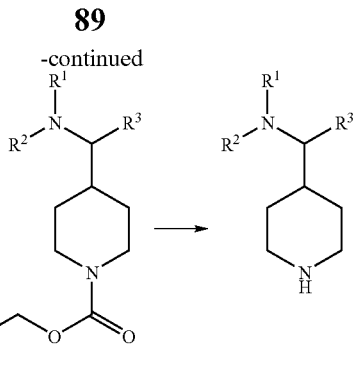

Preparation of 2-(dimethylamino)-2-(1-(4-methoxybenzyl)piperidin-4-yl)acetonitrile ($R^1$, $R^2$=methyl)

40% strength aqueous dimethylamine solution (2.66 ml, 21 mmol), 1-(4-methoxybenzyl)piperidine-4-carbaldehyde (750 mg, 3.2 mmol) and potassium cyanide (688 mg, 10.6 mmol) were added to a mixture of 4 N hydrochloric acid (1.2 ml) and methanol (5 ml), while cooling with ice. The reaction mixture was stirred at room temperature for 5 d, water (50 ml) was then added and the mixture was extracted with ethyl acetate (3×50 ml). The combined organic phases were dried with sodium sulfate and concentrated i. vac.

Yield: 875 mg (95%) of 2-(dimethylamino)-2-(1-(4-methoxybenzyl)piperidin-4-yl)acetonitrile $^1$H-NMR (DMSO-$d_6$): 1.22-1.29 (m, 2H); 1.57 (ddt, 1H); 1.76-1.97 (m, 4H); 2.18 (s, 6H); 2.73-2.88 (m, 3H); 3.36 (s, 3H); 3.73 (s, 2H); 6.85 (d, 2H); 7.16 (d, 2H).

Preparation of (1-(4-methoxybenzyl)piperidin-4-yl)-N,N-dimethyl(phenyl)methanamine ($R^1$, $R^2$=methyl, $R^3$=phenyl)

A 2 M phenylmagnesium chloride solution in THF (3.75 ml, 7.5 mmol) was added dropwise to an ice-cooled solution of 2-(dimethylamino)-2-(1-(4-methoxybenzyl)-piperidin-4-yl)acetonitrile (875 mg, 3.0 mmol) in THF (20 ml) and the reaction mixture was then warmed slowly to room temperature and stirred for 16 h. Thereafter, saturated ammonium chloride solution (50 ml) was added to the reaction solution, the mixture was extracted with ethyl acetate (3×50 ml), the combined organic phases were dried with sodium sulfate and concentrated I. vac. and the residue was purified by flash chromatography with chloroform/methanol/triethylamine (9:1:0.1).

Yield: 832 mg (82%) of 1-(1-(4-methoxybenzyl)piperidin-4-yl)-N,N-dimethyl-1-phenylmethanamine $^1$H-NMR (DMSO-$d_6$): 0.84-1.18 (m, 3H); 1.74-1.89 (m, 4H); 1.99 (s, 6H); 2.68 (d, 1H); 2.80 (d, 1H); 3.07 (d, 1H, J=8.9 Hz); 3.32 (s, 2H); 3.71 (s, 3H); 6.84 (d, 2H); 7.15 (q, 4H); 7.21-7.33 (m, 3H).

Preparation of Benzyl 4-((dimethylamino)(phenyl)methyl)piperidine-1-carboxylate ($R^1$, $R^2$=methyl, $R^3$=phenyl)

Chloroformic acid benzyl ester (1.50 g, 1.25 ml, 8.86 mmol) was added to a solution of 1-(1-(4-methoxybenzyl)piperidin-4-yl)-N,N-dimethyl-1-phenylmethanamine (3.00 g, 8.86 mmol) in MC (50 ml) and the mixture was stirred at room temperature for 30 min. Sodium bicarbonate solution (40 ml) was then added to the reaction mixture, the phases were separated and the aqueous phase was extracted with MC (2×30 ml). The combined organic phases were dried with sodium sulfate and concentrated i. vac. and the residue was purified by flash chromatography with chloroform/methanol/triethylamine (100:5:1).

Yield: 2.32 g (74%), benzyl 4-((dimethylamino)(phenyl)methyl)piperidine-1-carboxylate $^1$H-NMR (DMSO-$d_6$): 0.82 (ddd, 2H); 0.97 (ddd, 2H); 1.27 (d, 1H); 2.00 (s, 6H); 2.69-2.84 (m, 2H); 3.11 (d, 1H); 3.89 (d, 1H); 4.03 (d, 1H); 5.03 (s, 2H); 7.14 (m, 2H); 7.20-7.35 (m, 8H).

Preparation of N,N-dimethyl-1-phenyl-1-(piperidin-4-yl)methanamine ($R^1$, $R^2$=methyl, $R^3$=phenyl)

33% strength hydrogen bromide in glacial acetic acid (20 ml) was added to a solution of benzyl 4-((dimethylamino)(phenyl)methyl)piperidine-1-carboxylate (2.32 g, 6.58 mmol) in acetic acid (20 ml) and the mixture was stirred at room temperature for 1.5 h. By addition of diethyl ether, a solid precipitated out. The supernatant solution was decanted, and diethyl ether was repeatedly added to the residue and in each case decanted again. The residue was dried i. vac. and dissolved in methanol (20 ml), the strongly basic ion exchanger Dowex 1×2-200 was added to the solution and the mixture was stirred at room temperature for 1 h. The mixture was then filtered, the residue on the filter was washed with methanol and the filtrate was concentrated i. vac.

Yield: 1.09 g (76%) of N,N-dimethyl-1-phenyl-1-(piperidin-4-yl)methanamine $^1$H-NMR (DMSO-$d_6$): 1.06 (ddd, 1H); 1.23 (td, 2H); 1.72 (br s, 1H); 1.99 (s, 6H); 2.20 (dd, 1H); 2.66 (dt, 1H); 2.77 (dt, 1H); 3.03 (d, 1H); 3.10 (d, 1H); 3.17 (d, 1H); 7.15 (d, 2H); 7.25 (m, 1H); 7.34 (m, 2H).

Amine units AM 19 and 21 were prepared by the same process using dimethylamine and, respectively, N-methyl (phenyl)methanamine in the preparation of the amino-(1,4-dioxa-spiro[4.5]dec-8-yl)-acetonitrile intermediate.

Preparation of Amine Unit AM20, 3-(dimethylaminophenylmethyl)-cyclopentylamine, by an Analogous Process Starting from 3-oxocyclopentanecarboxylic Acid Ethyl Ester

Preparation of 3-oxocyclopentanecarboxylic Acid Ethyl Ester

A solution of cyclopentanone-3-carboxylic acid (5.00 g, 39 mmol), caesium carbonate (12.82 g, 39 mmol) and ethyl iodide (9.12 g, 4.75 ml, 58.5 mmol) in DMF (50 ml) was stirred at RT for 18 h. The mixture was then concentrated i. vac., the residue was taken up in toluene, the mixture was concentrated again and 2 N hydrochloric acid and EtOAc were then added. The aq. phase was extracted with EtOAc (3×30 ml) and the combined organic phases were washed with aq. sodium thiosulfate soln. The organic phase was dried with $Na_2SO_4$ and concentrated i. vac.

Yield: 4.34 g (71%)

Synthesis of the Amine Units AM33-AM37

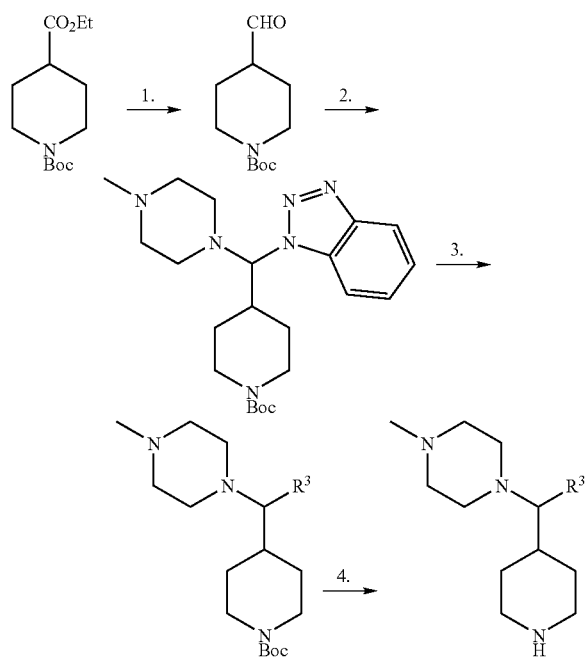

Stage 1. Diisobutylaluminium hydride (15.3 mmol, 1.5 M solution in toluene) was added dropwise to a solution of piperidine-1,4-dicarboxylic acid 1-tert-butyl ester 4-ethyl ester (15 mmol) in dry toluene (20 ml) under an argon atmosphere at −70° C. and the mixture was stirred at this temperature for 2 h. When the reaction was complete (TLC control), methanol (20 ml) was added at −70° C. and the reaction mixture was warmed to RT. A saturated sodium chloride solution (30 ml) was added and the mixture was filtered over silica gel. Rinsing was carried out with ethyl acetate and the aqueous solution was separated off and extracted once more with ethyl acetate. The combined organic phases were washed with saturated sodium chloride solution and then dried over sodium sulfate and concentrated. The crude product was employed further without further purification.

Stage 2. tert-Butyl 4-formylpiperidine-1-carboxylate (15 mmol), N-methylpiperazine (15 mmol) and benzotriazole (15 mmol) were heated under reflux in benzene (60 ml) using a Dean-Stark water separator. The solvent was then stripped off under reduced pressure. The crude product obtained was used further without further purification.

Stage 3. tert-Butyl 4-((1H-benzo[d][1,2,3]triazol-1-yl)(4-methylpiperazin-1-yl)methyl)piperidine-1-carboxylate (12 mmol) in THF was added dropwise to a solution of the corresponding Grignard reagent in THF (60 mmol) at 0° C. The reaction mixture was warmed to 25° C. and stirred at this temperature for 16 h (TLC control). It was then cooled to 0° C., saturated ammonium chloride solution was added and the mixture was extracted with ethyl acetate. The organic phase was washed successively with water and saturated sodium chloride solution and dried over sodium sulfate. The solvent was removed and the crude product obtained was purified by column chromatography (silica gel, MC/methanol, 98:2→95:5)

Stage 4. TFA (20% in MC, 5 ml/mmol) was added to the Boc-protected compound at 0° C. and the mixture was then stirred at room temperature for 3 h (TLC control). The solvent was removed completely and the crude product (TFA salt) was used further without further purification.

The following amine units were prepared:

| Name | | $R^3$ |
|---|---|---|
| AM33 | 1-methyl-4-(phenyl(piperidin-4-yl)methyl)piperazine | phenyl |
| AM34 | 1-((4-Fluorophenyl)(piperidin-4-yl)methyl)-4-methylpiperazine | 4-fluorophenyl |
| AM35 | 1-((3-Fluorophenyl)(piperidin-4-yl)methyl)-4-methylpiperazine | 3-fluorophenyl |
| AM36 | 1-Methyl-4-(2-phenyl-1-(piperidin-4-yl)ethyl)piperazine | benzyl |
| AM37 | 1-Methyl-4-(3-phenyl-1-(piperidin-4-yl)propyl)piperazine | phenethyl | b) Preparation of the Acid Units

| Designation | Synthesis method | Ester cleavage variant | Name |
|---|---|---|---|
| AC1 | 1 | A | {2-[Methyl-(2,4,6-trimethyl-benzenesulfonyl)-amino]-ethoxy}-acetic acid |
| AC2 | 1 | A | {2-[Methyl-(3-trifluoromethyl-benzenesulfonyl)-amino]-ethoxy}-acetic acid |
| AC3 | 1 | B | {2-[Benzyl-(4-methoxy-2,6-dimethyl-benzenesulfonyl)-amino]-ethoxy}-acetic acid |
| AC4 | 1 | B | {2-[Benzyl-(4-methoxy-2,3,6-trimethyl-benzenesulfonyl)-amino]-ethoxy}-acetic acid |
| AC5 | 3 | C | {2-[Ethyl-(4-methoxy-2,3,6-trimethyl-benzenesulfonyl)-amino]-ethoxy}-acetic acid |

-continued

| Designation | Synthesis method | Ester cleavage variant | Name |
|---|---|---|---|
| AC6 | 1 | B | [2-(Benzenesulfonyl-benzyl-amino)-ethoxy]-acetic acid |
| AC7 | 1 | C | {2-[Methyl-(2,4,6-trichloro-benzenesulfonyl)-amino]-ethoxy}-acetic acid |
| AC8 | 1 | A | {2-[(3,4-Dimethoxy-benzenesulfonyl)-methyl-amino]-ethoxy}-acetic acid |
| AC9 | 1 | A | {2-[(4-Methoxy-benzenesulfonyl)-methyl-amino]-ethoxy}-acetic acid |
| AC10 | 1 | C | {2-[(2,6-Dichloro-benzenesulfonyl)-methyl-amino]-ethoxy}-acetic acid |
| AC11 | 4 | — | {2-[(4-Methoxy-2,3,6-trimethyl-benzenesulfonyl)-methyl-amino]-ethoxy}-acetic acid |
| AC12 | 1 | A | [2-(Methyl-pentafluorobenzenesulfonyl-amino)-ethoxy]-acetic acid |
| AC13 | 1 | A | {2-[(4-fluoro-benzenesulfonyl)-methyl-amino]-ethoxy}-acetic acid |
| AC14 | 1 | C | {2-[(2,4-Dichloro-benzenesulfonyl)-methyl-amino]-ethoxy}-acetic acid |
| AC15 | 1 | A | {2-[(4-Methoxy-2,6-dimethyl-benzenesulfonyl)-methyl-amino]-ethoxy}-acetic acid |
| AC16 | 1 | C | {2-[(4-Chloro-benzenesulfonyl)-methyl-amino]-ethoxy}-acetic acid |
| AC17 | 1 | A | {2-[Methyl-(toluene-4-sulfonyl)-amino]-ethoxy}-acetic acid |
| AC18 | 1 | A | {2-[Methyl-(4-trifluoromethoxy-benzenesulfonyl)-amino]-ethoxy}-acetic acid |
| AC19 | 1 | A | [2-(Benzenesulfonyl-methyl-amino)-ethoxy]-acetic acid |
| AC20 | 6 | — | {2-[Cyclopropyl-(2,4,6-trichloro-benzenesulfonyl)-amino]-ethoxy}-acetic acid |
| AC21 | 1 | C | {2-[(2,6-Dichloro-4-trifluoromethyl-benzenesulfonyl)-methyl-amino]-ethoxy}-acetic acid |
| AC22 | 2 | B | [1-(2,4-Dimethoxy-benzenesulfonyl)-piperidin-2-ylmethoxy]-acetic acid |
| AC23 | 2 | B | [1-(3,4-Dimethoxy-benzenesulfonyl)-piperidin-2-ylmethoxy]-acetic acid |
| AC24 | 2 | B | [1-(4-Methoxy-benzenesulfonyl)-piperidin-2-ylmethoxy]-acetic acid |
| AC25 | 2 | B | [1-(3,4-Dichloro-benzenesulfonyl)-piperidin-2-ylmethoxy]-acetic acid |
| AC26 | 2 | B | [1-(2,3-Dichloro-benzenesulfonyl)-piperidin-2-ylmethoxy]-acetic acid |
| AC27 | 2 | B | [1-(4-Chloro-benzenesulfonyl)-piperidin-2-ylmethoxy]-acetic acid |
| AC28 | 2 | B | [1-(4-Methoxy-2,6-dimethyl-benzenesulfonyl)-piperidin-2-ylmethoxy]-acetic acid |
| AC29 | 2 | C | [1-(2,4,6-Trichloro-benzenesulfonyl)-piperidin-2-ylmethoxy]-acetic acid |
| AC30 | 1 | C | {2-[1-(4-Methoxy-benzenesulfonyl)-piperidin-2-yl]-ethoxy}-acetic acid |
| AC31 | 1 | C | (1-Benzenesulfonyl-piperidin-3-ylmethoxy)-acetic acid |
| AC32 | 1 | C | [1-(2,4,6-Trichloro-benzenesulfonyl)-piperidin-3-ylmethoxy]-acetic acid |
| AC33 | 1 | C | [1-(4-Methoxy-2,6-dimethyl-benzenesulfonyl)-piperidin-3-ylmethoxy]-acetic acid |
| AC34 | 3 | B | {2-[(3,4-Dichloro-benzenesulfonyl)-methyl-amino]-cyclohexyloxy}-acetic acid |
| AC35 | 2 | B | [2-(4-Methoxy-benzenesulfonyl)-1,2,3,4-tetrahydro-isoquinolin-3-ylmethoxy]-acetic acid |
| AC36 | 2 | B | [1-(4-Methoxy-benzenesulfonyl)-pyrrolidin-2-ylmethoxy]-acetic acid |
| AC37 | 2 | B | [1-(3,4-Dichloro-benzenesulfonyl)-pyrrolidin-2-ylmethoxy]-acetic acid |
| AC38 | 2 | B | [1-(2,4,6-Trichloro-benzenesulfonyl)-pyrrolidin-2-ylmethoxy]-acetic acid |
| AC39 | 2 | B | [1-(4-Methoxy-2,6-dimethyl-benzenesulfonyl)-pyrrolidin-2-ylmethoxy]-acetic acid |

-continued

| Designation | Synthesis method | Ester cleavage variant | Name |
|---|---|---|---|
| AC40 | 1 | C | {2-[4-(4-Methoxy-2,3,6-trimethyl-benzenesulfonyl)-piperazin-1-yl]-ethoxy}-acetic acid |
| AC41 | 1 | C | [2-(4-Benzenesulfonyl-piperazin-1-yl)-ethoxy]-acetic acid |
| AC42 | 1 | C | {2-[1-(4-Methoxy-2,3,6-trimethyl-benzenesulfonyl)-piperidin-4-yl]-ethoxy}-acetic acid |
| AC43 | 1 | C | [2-(1-Benzenesulfonyl-piperidin-4-yl)-ethoxy]-acetic acid |
| AC44 | 1 | C | [1-(4-Methoxy-2,3,6-trimethyl-benzenesulfonyl)-piperidin-3-yloxy]-acetic acid |
| AC45 | 1 | C | (1-Benzenesulfonyl-piperidin-3-yloxy)-acetic acid |
| AC46 | 1 | C | [1-(2,4,6-Trichloro-benzenesulfonyl)-piperidin-3-yloxy]-acetic acid |
| AC47 | 1 | C | [1-(4-Methoxy-2,6-dimethyl-benzene-sulfonyl)-piperidin-3-yloxy]-acetic acid |
| AC48 | 1 | C | [1-(4-Methoxy-2,3,6-trimethyl-benzenesulfonyl)-piperidin-4-yloxy]-acetic acid |
| AC49 | 1 | C | (1-Benzenesulfonyl-piperidin-4-yloxy)-acetic acid |
| AC50 | 1 | C | {2-[(3,4-Dichloro-benzenesulfonyl)-methyl-amino]-phenoxy}-acetic acid |
| AC51 | 2 | C | {2-[(3,4-Dichloro-benzenesulfonyl)-methyl-amino]-4,5,6,7-tetrahydro-benzo[b]thiophen-3-ylmethoxy}-acetic acid |
| AC52 | 1 | B | [1-(4-Methoxy-2,3,6-trimethyl-benzenesulfonyl)-pyrrolidin-3-yloxy]-acetic acid |
| AC53 | 1 | B | [1-(4-Methoxy-2,6-dimethyl-benzenesulfonyl)-pyrrolidin-3-yloxy]-acetic acid |
| AC54 | 1 | B | [1-(2,4,6-Trimethyl-benzenesulfonyl)-pyrrolidin-3-yloxy]-acetic acid |
| AC55 | 1 | B | [1-(3-Trifluoromethyl-benzenesulfonyl)-pyrrolidin-3-yloxy]-acetic acid |
| AC56 | 1 | B | [1-(Toluene-4-sulfonyl)-pyrrolidin-3-yloxy]-acetic acid |
| AC57 | 1 | B | [1-(3,4-Dimethoxy-benzenesulfonyl)-pyrrolidin-3-yloxy]-acetic acid |
| AC58 | 1 | C | [1-(2,4-Dichloro-benzenesulfonyl)-pyrrolidin-3-yloxy]-acetic acid |
| AC59 | 1 | B | [1-(4-Chloro-benzenesulfonyl)-pyrrolidin-3-yloxy]-acetic acid |
| AC60 | 1 | B | (1-Benzenesulfonyl-pyrrolidin-3-yloxy)-acetic acid |
| AC61 | 1 | C | [1-(2,4,6-Trichloro-benzenesulfonyl)-pyrrolidin-3-yloxy]-acetic acid |
| AC62 | 1 | B | [1-(4-Fluoro-benzenesulfonyl)-pyrrolidin-3-yloxy]-acetic acid |
| AC63 | 5 | — | 3-((2,4,6-Trichloro-N-methylphenyl-sulfonamido)methoxy)propionic acid |
| AC64 | * | * | 2-(Benzyloxy)acetic acid |
| AC65 | * | * | 2-(4-Chlorophenoxy)acetic acid |
| AC66 | * | * | 2-Phenoxypropionic acid |
| AC67 | * | * | 2-Acetoxy-2-phenylacetic acid |
| AC68 | * | * | 2-Methoxy-2-oxoacetic acid |
| AC69 | * | * | 2-Ethoxy-2-oxoacetic acid |
| AC70 | 7 | — | 2-(3-(3,5-Dichlorophenyl)-1,2,4-oxadiazole-5-carboxamido)acetic acid |
| AC71 | 7 | — | 3-(3-(3,5-Dichlorophenyl)-1,2,4-oxadiazole-5-carboxamido)propionic acid |
| AC72 | 7 | — | 2-(3-(2,4-Dichloro-6-methylphenyl)-1,2,4-oxadiazole-5-carboxamido)acetic acid |
| AC73 | 7 | — | 2-(3-(2-Methoxyphenyl)-1,2,4-oxadiazole-5-carboxamido)acetic acid |
| AC74 | 7 | — | 2-(3-(Thiophen-2-yl)-1,2,4-oxadiazole-5-carboxamido)acetic acid |

-continued

| Designation | Synthesis method | Ester cleavage variant | Name |
|---|---|---|---|
| AC75 | 7 | — | 2-(3-(4-(Trifluoromethyl)phenyl)-1,2,4-oxadiazole-5-carboxamido)acetic acid |
| AC76 | 7 | — | 2-(3-(4-tert-Butylphenyl)-1,2,4-oxadiazole-5-carboxamido)acetic acid |
| AC77 | 7 | — | 2-(3-(5-Fluoro-2-methylphenyl)-1,2,4-oxadiazole-5-carboxamido)acetic acid |
| AC78 | 7 | — | 3-(3-(Benzo[d][1,3]dioxol-5-yl)-1,2,4-oxadiazole-5-carboxamido)propionic acid |
| AC79 | 7 | — | 2-(3-(Phenylsulfonylmethyl)-1,2,4-oxadiazole-5-carboxamido)acetic acid |
| AC80 | 7 | — | 2-(3-(2,6-Dichlorophenyl)-1,2,4-oxadiazole-5-carboxamido)acetic acid |
| AC81 | 7 | — | 3-(3-(Pyridin-2-yl)-1,2,4-oxadiazole-5-carboxamido)propionic acid |
| AC82 | 7 | — | 2-(3-Mesityl-1,2,4-oxadiazole-5-carboxamido)acetic acid |
| AC83 | 7 | — | 3-(3-(2,4-Dichlorophenyl)-1,2,4-oxadiazole-5-carboxamido)propionic acid |
| AC84 | 7 | — | 3-(3-(3,4-Dimethoxyphenyl)-1,2,4-oxadiazole-5-carboxamido)propionic acid |
| AC85 | 7 | — | 2-(3-(3,4-Dimethoxyphenyl)-1,2,4-oxadiazole-5-carboxamido)acetic acid |
| AC86 | 7 | — | 3-(3-(Thiophen-2-yl)-1,2,4-oxadiazole-5-carboxamido)propionic acid |
| AC87 | 7 | — | 2-(3-(Benzo[d][1,3]dioxol-5-yl)-1,2,4-oxadiazole-5-carboxamido)acetic acid |
| AC88 | 7 | — | 2-(3-(Pyridin-2-yl)-1,2,4-oxadiazole-5-carboxamido)acetic acid |
| AC89 | 7 | — | 2-(3-(2,4-Dichlorophenyl)-1,2,4-oxadiazole-5-carboxamido)acetic acid |
| AC90 | 8 | — | 2-((1-(3,4-Dichlorophenylsulfonyl)-1,2,3,4-tetrahydroquinolin-2-yl)methoxy)acetic acid |

\* commercially obtainable acid chloride units

Method 1

General Preparation of Sulfonylated Acid Units Starting from Amino Alcohols

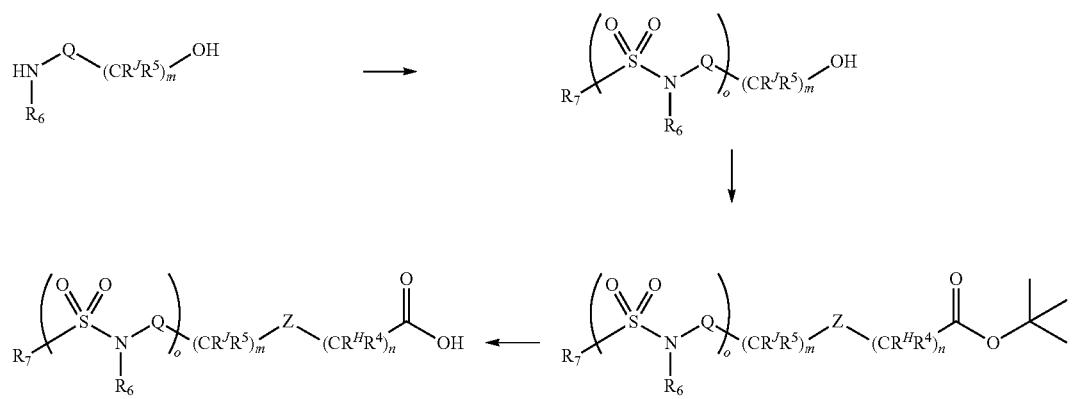

1. $Et_3N$ (80 mmol) was added to a solution of the amino alcohol (35 mmol) in $CH_2Cl_2$ (200 ml) and the mixture was cooled to 0° C. using an ice-bath. The sulfonyl chloride (32 mmol) was then added and the mixture was stirred at RT for 3 h. After addition of 0.5 M HCl (100 ml), the organic phase was separated off, washed with water, dried over $Na_2SO_4$ and filtered and the solvent was removed in vacuo. The crude product was used in the next stage without further purification.

2. $n\text{-}Bu_4NCl$ (10 mmol) was added to a solution of the product from stage 1 (30 mmol) in toluene (125 ml), the mixture was cooled to 0° C. and first aqueous 35% strength NaOH (150 ml) and then bromoacetic acid tert-butyl ester (45 mmol) in toluene (25 ml) were added dropwise. The reaction mixture was stirred for 3 h and then washed neutral with water and dried with $Na_2SO_4$ and the organic solvent was removed in vacuo. The crude product was used in the next stage without further purification or was purified by column chromatography.

Method 2

General Preparation of Sulfonylated Acid Units Starting from Amino Acids

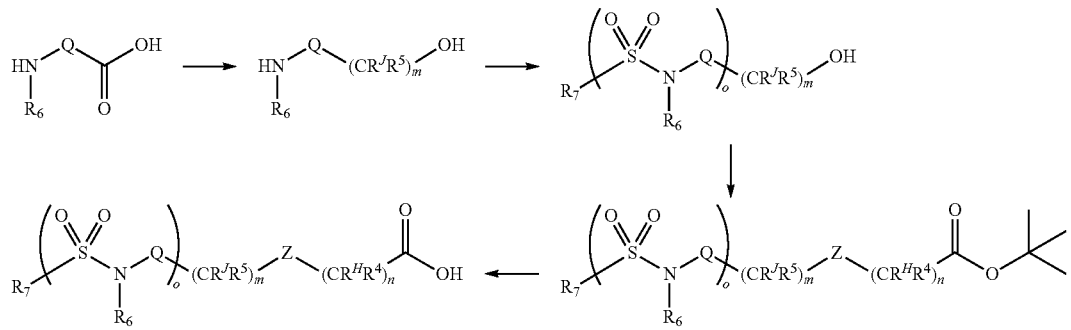

1. LiAlH$_4$ (100 ml, 1.0 M in diethyl ether) was added successively to a suspension of the amino acid (100 mmol) in THF (150 ml) under an inert gas atmosphere, while stirring and at a temperature of between −10° C. and RT. The reaction mixture was stirred for 16 h, during which it warmed up to RT. It was then cooled again to 0° C. and ethyl acetate (20 ml), water (8 ml), 15% strength aqueous NaOH (8 ml) and water (20 ml) were added, while stirring. After filtration, the residue was washed with diethyl ether. The solvent of the combined organic phases was removed in vacuo and the product was employed in the next stage without further purification.

2. Et$_3$N (125 mmol) was added to a solution of the amino alcohol (100 mmol) in CH$_2$Cl$_2$ (200 ml) and the mixture was cooled to 0° C. using an ice-bath. The particular sulfonyl chloride (50 mmol) was then added undiluted or as a solution in CH$_2$Cl$_2$ (100 ml) and the mixture was stirred at RT for 3 h. After addition of 0.5 M hydrochloric acid (100 ml), the organic phase was separated off, washed with water, dried over Na$_2$SO$_4$ and filtered and the solvent was removed in vacuo. The crude product was used in the next stage without further purification or was purified by column chromatography.

3. n-Bu$_4$NCl (10 mmol) was added to a solution of the product from stage 2 (31 mmol) in toluene (200 ml), the mixture was cooled to 0° C. and first aqueous 35% strength NaOH (200 ml) and then bromoacetic acid tert-butyl ester (46 mmol) were added dropwise. The reaction mixture was stirred for 3 h and then washed neutral with water and dried with Na$_2$SO$_4$ and the organic solvent was removed in vacuo. The crude product was used in the next stage without further purification or was purified by column chromatography.

Method 3

General Preparation of Sulfonylated Acid Units Starting from Amino Alcohols

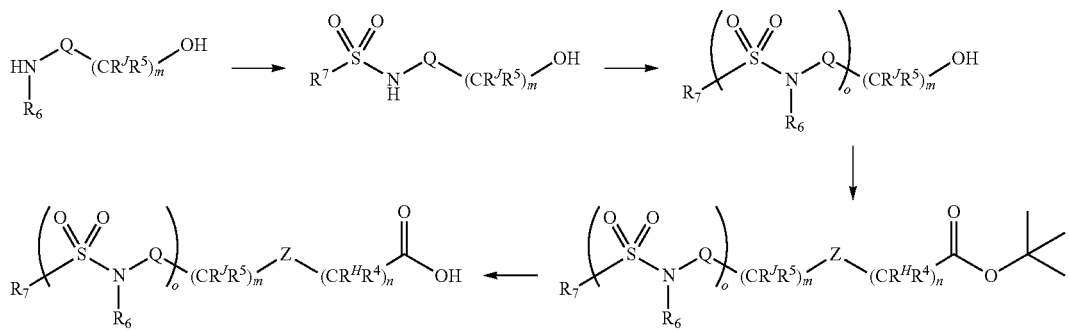

1. Et$_3$N (80 mmol) was added to a solution of the amino alcohol (35 mmol) in CH$_2$Cl$_2$ (200 ml) and the mixture was cooled to 0° C. using an ice-bath. The sulfonyl chloride (32 mmol) was then added and the mixture was stirred at RT for 3 h. After addition of 0.5 M HCl (100 ml), the organic phase was separated off, washed with water, dried over Na$_2$SO$_4$ and filtered and the solvent was removed in vacuo. The crude product was used without further purification.

2. Solid K$_2$CO$_3$ (50 mmol) was added to a solution of the product from stage 1 (26 mmol) and alkyl halide (50 mmol) in acetone (200 ml) and the reaction mixture was stirred at 40° C. overnight. After filtration and removal of the solvent, the product was obtained and was either used without further purification or purified via chromatography.

3. n-Bu$_4$NCl (10 mmol) was added to a solution of the product from stage 2 (30 mmol) in toluene (125 ml), the mixture was cooled to 0° C. and first aqueous 35% strength NaOH (150 ml) and then bromoacetic acid tert-butyl ester (45 mmol) in toluene (25 ml) were added dropwise. The reaction mixture was stirred for 3 h and then washed neutral with water and dried with Na$_2$SO$_4$ and the organic solvent was removed in vacuo. The crude product was used in the next stage without further purification or was purified by column chromatography.

Variant A

The educt (20 mmol) was dissolved in 4 N hydrochloric acid in dioxane (80 mmol) and the solution was stirred at RT overnight. The solvent was largely distilled off and the crude product was purified by recrystallization or chromatography.

Variant B

The educt (30 mmol) was dissolved in $CH_2Cl_2$ (200 ml), with TFA (30 ml), and the solution was stirred at RT for 2 h. The solvent was largely distilled off and the crude product was purified by recrystallization or chromatography.

Variant C

The educt (30 mmol) was dissolved in THF (100 ml) and MeOH (100 ml), 6 N NaOH (150 ml) was added and the reaction mixture was stirred at RT for 1 h. The solvent was largely distilled off and 6 N HCl (155 ml) was added at 0° C. After extraction with $CH_2Cl_2$, drying over $Na_2SO_4$, filtering off of the drying agent and distilling off of the solvent, the crude product was obtained, which was purified via column chromatography.

Method 4

Synthesis instructions for the preparation of {2-[(4-methoxy-2,3,6-trimethylbenzenesulfonyl)-methylamino]-ethoxy}-acetic acid AC11

N-(2-Hydroxyethyl)-4-methoxy-2,3,6,N-tetramethyl-benzenesulfonamide (Intermediate A)

A soln. of 4-methoxy-2,3,6-trimethylbenzenesulfonyl chloride (2.29 g, 9.19 mmol) in THF (30 ml) was added dropwise to a soln. of 2-methylaminoethanol (0.89 g, 0.95 ml, 11.8 mmol) and $Et_3N$ (5 ml) in THF (15 ml) at 0° C. The mixture was subsequently stirred at RT for 5 h and then concentrated i. vac., the residue was taken up in $NaHCO_3$ soln. and the mixture was extracted with EtOAc (3×30 ml). The combined organic phases were dried with $Na_2SO_4$ and concentrated i. vac.

Yield: 2.38 g (90%)

{2-[(4-Methoxy-2,3,6-trimethylbenzenesulfonyl)-methylamino]-ethoxy}-acetic Acid Tert-Butyl Ester (Intermediate B)

35% strength aq. sodium hydroxide solution (40 ml) was added to a solution of N-(2-hydroxyethyl)-4-methoxy-2,3,6-N-tetramethylbenzenesulfonamide (2.34 g, 8.2 mmol) and tetra-n-butylammonium hydrogen sulfate (611 mg, 1.8 mmol) in toluene (40 ml) at 0° C. A soln. of bromoacetic acid tert-butyl ester (2.40 g, 1.82 ml, 12.3 mmol) in toluene (35 ml) was then added dropwise to the intensively stirred two-phase system. The mixture was subsequently stirred at RT for 2 h, the aqueous phase was then separated off and the organic phase was washed neutral with water (3×40 ml). The organic phase was dried with $Na_2SO_4$ and concentrated i. vac. and the residue was purified by flash chromatography with EtOAc/cyclohexane (1:3).

Yield: 2.50 g (76%)

{2-[(4-Methoxy-2,3,6-trimethylbenzenesulfonyl)-methylamino]-ethoxy}-acetic Acid (AC11)

First triethylsilane (1.12 g, 1.54 ml, 9.6 mmol) and then trifluoroacetic acid (5 ml) were added to a solution of {2-[(4-methoxy-2,3,6-trimethylbenzenesulfonyl)-methylamino]-ethoxy}-acetic acid tert-butyl ester (2.48 g, 6.18 mmol) in MC (50 ml) and the mixture was stirred at RT for 5 h. The mixture was then concentrated i. vac., and the residue was taken up repeatedly in toluene and the mixture in each case concentrated again. The crude product was dissolved in EtOAc and the solution was extracted with 5% strength $NaHCO_3$ soln. (3×50 ml). The combined aqueous phases were adjusted to pH 1 with conc. hydrochloric acid and extracted again with EtOAc (3×50 ml). The combined EtOAc phases were dried with $Na_2SO_4$ and concentrated i. vac. Yield: 2.41 g (>99%)

The preparation of acid units AC52 and AC67 proceeded analogously to Method C.

Method 5

Synthesis Instructions for the Preparation of 3-((2,4,6-trichloro-N-methylphenylsulfonamido)methoxy)propionic Acid (AC63)

2,4,6-Trichloro-N-methylbenzenesulfonamide (Intermediate D)

40% strength aq. methylamine soln. (36.0 g, 464 mmol) was added dropwise to a soln. of 2,4,6-trichorobenzenesulfonic acid chloride (10.0 g, 35.7 mmol) in 1,4-dioxane (60 ml) and the mixture was stirred at RT for 30 min. Water (500 ml) was then added, with vigorous stirring, whereupon a white precipitate formed, which was filtered out and dried over potassium hydroxide in a desiccator.

Yield: 8.45 g (86%)

2,4,6-Trichloro-N-chloromethyl-N-methylbenzene-sulfonamide (Intermediate E)

A soln. of 2,4,6-trichloro-N-methylbenzenesulfonamide (8.45 g, 30.8 mmol) and paraformaldehyde (1.61 g, 53.7 mmol) in chlorotrimethylsilane (80 ml) was stirred at 100° C. in a Teflon pressure vessel for 72 h. After cooling to RT, the product crystallized out spontaneously. The mixture was left to stand at 5-10° C. for 3 d and the white crystals were filtered out and washed with MC (50 ml). Yield: 7.22 g (73%)

N-(3-Benzyloxypropoxymethyl)-2,4,6-trichloro-N-methylbenzenesulfonamide (Intermediate F)

A soln. of 3-benzyloxy-1-propanol (4.08 g, 3.90 ml, 24.5 mmol) and tetra-n-butylammonium hydrogen sulfate (1.78 g, 5.25 mmol) in toluene (100 ml) was cooled in an ice-bath and 35% strength sodium hydroxide solution (49.0 g, 140 ml, 1.22 mol) was added. A soln. of 2,4,6-trichloro-N-chloromethyl-N-methylbenzenesulfonamide (7.10 g, 22 mmol) in MC (60 ml) was then slowly added dropwise. The mixture was then stirred at RT for 15-20 h. Thereafter, the phases were separated and the organic phase was washed neutral with water (6×50 ml) and saturated sodium chloride solution (2×40 ml), dried with $Na_2SO_4$ and concentrated i. vac. The crude product was purified by means of flash chromatography with cyclohexane/EtOAc (9:1).

Yield: 2.60 g (26%)

2,4,6-Trichloro-N-(3-hydroxypropoxymethyl)-N-methylbenzenesulfonamide (Intermediate G)

10% palladium on charcoal (350 mg) was added to a soln. of N-(3-benzyloxypropoxymethyl)-2,4,6-trichloro-N-methylbenzenesulfonamide (2.60 g, 5.7 mmol) in THF (100 ml) under argon and hydrogenation was carried out at RT under 3 bar. The reaction soln. was then filtered through Celite, the residue on the filter was washed with THF (50 ml) and the filtrate was concentrated i. vac. The crude product (1.63 g) was purified by means of flash chromatography with cyclohexane/EtOAc (1:1).
Yield: 1.05 g (51%)

3-((2,4,6-Trichloro-N-methylphenylsulfonamido)methoxy)propionic Acid (AC63)

2,4,6-Trichloro-N-(3-hydroxypropoxymethyl)-N-methylbenzenesulfonamide (363 mg, 1 mmol), 2,2,6,6-tetramethylpiperidin-1-yloxy radical (38 mg, 0.245 mmol) and [bis(acetoxy)iodo]benzene (705 mg, 2.19 mmol) were dissolved in acetonitrile/water (1:1; 8 ml) and the solution was stirred at RT for 30 min. The reaction soln. was then cooled with ice, and 2 N hydrochloric acid (4 ml) and EtOAc (40 ml) were added. The phases were separated and the organic phase was washed with water (3×20 ml) and saturated sodium chloride solution (2×20 ml), dried with $Na_2SO_4$ and concentrated i. vac. The compound was taken up in 1 N sodium carbonate soln. (30 ml) and the mixture was extracted with EtOAc (3×20 ml). The aqueous phase was then adjusted to pH 3 with 2 N hydrochloric acid and extracted with EtOAc (3×20 ml). The combined organic phases were washed with water (3×20 ml) and saturated sodium chloride solution (2×20 ml), dried with $Na_2SO_4$ and concentrated i. vac. Yield: 310 mg (82%)

Method 6

Synthesis Instructions for the Preparation of {2-[cyclopropyl-(2,4,6-trichlorobenzenesulfonyl)-amino]-ethoxy}-acetic Acid (AC20)

Cyclopropylaminoacetic Acid Ethyl Ester (Intermediate I)

Bromoacetic acid ethyl ester (14.2 g, 9.37 ml, 84.8 mmol) was added dropwise to a soln. of cyclopropylamine (19.4 g; 23.5 ml, 0.34 mol) in EtOH (100 ml), while cooling with ice. The reaction mixture was stirred at RT for 18 h and then concentrated i. vac. Water was added to the residue and the mixture was extracted with $CHCl_3$ (5×100 ml). The combined organic phases were washed with half-saturated sodium chloride soln., dried with $Na_2SO_4$ and concentrated i. vac. The crude product was distilled at approx. 85° C. under 24 mbar.
Yield: 12.03 g (99%)

[Cyclopropyl-(2,4,6-trichlorobenzenesulfonyl)-amino]-acetic Acid Ethyl Ester (Intermediate J)

The synthesis was carried out analogously to N-(2-hydroxyethyl)-4-methoxy-2,3,6,N-tetramethylbenzenesulfonamide, but without addition of $Et_3N$.
Yield: 2.97 g (38%)

[Cyclopropyl-(2,4,6-trichlorobenzenesulfonyl)-amino]-acetic Acid (Intermediate K)

A soln. of lithium hydroxide (298 mg, 12.5 mmol) in water (15 ml) was added to a soln. of [cyclopropyl-(2,4,6-trichlorobenzenesulfonyl)-amino]-acetic acid ethyl ester (2.91 g, 7.5 mmol) in THF (25 ml) and the mixture was stirred at RT for approx. 18 h. The mixture was concentrated i. vac. and water was added to the residue. The alkaline residue was extracted with MC (2×50 ml). The aqueous phase was adjusted to pH 1-2 with conc. hydrochloric acid and extracted with EtOAc (3×30 ml). These combined organic phases were dried with $Na_2SO_4$ and concentrated i. vac. Toluene was repeatedly added to the residue and the mixture concentrated i. vac. Yield: 1.77 g (65%)

2,4,6-Trichloro-N-cyclopropyl-N-(2-hydroxyethyl)-benzenesulfonamide (Intermediate L)

A 2 M soln. of borane-dimethylsulfide complex in THF (4.96 ml, 9.92 mmol) was added to a soln. of [cyclopropyl-(2,4,6-trichlorobenzenesulfonyl)-amino]-acetic acid (1.77 g, 4.96 mmol) in anhydrous THF (30 ml) and the mixture was stirred for 1 h, while cooling with ice. The reaction mixture was stirred at RT for approx. 18 h, MeOH (2 ml) was then cautiously added and the mixture was concentrated i. vac. MeOH was repeatedly added to the residue and the mixture concentrated i. vac. 5% strength $NaHCO_3$ soln. was added to the crude product, the mixture was extracted with EtOAc and the organic phase was dried with $Na_2SO_4$ and concentrated i. vac. Yield: 1.02 g (60%)

{2-[Cyclopropyl-(2,4,6-trichlorobenzenesulfonyl)-amino]-ethoxy}-acetic Acid Tert-Butyl Ester (Intermediate M)

The synthesis was carried out analogously to the synthesis path described for {2-[(4-methoxy-2,3,6-trimethylbenzenesulfonyl)-methylamino]-ethoxy}-acetic acid tert-butyl ester, but tetra-n-butylammonium hydrogen sulfate was replaced by tetra-n-butylammonium chloride. Yield: 956 mg (71%)

{2-[Cyclopropyl-(2,4,6-trichlorobenzenesulfonyl)-amino]-ethoxy}-acetic Acid (AC20)

The synthesis was carried out analogously to the synthesis path described for {2-[(4-methoxy-2,3,6-trimethylbenzenesulfonyl)-methylamino]-ethoxy}-acetic acid.
Yield: 697 mg (84%)

Method 8

Synthesis of 2-((1-(3,4-dichlorophenylsulfonyl)-1,2,3,4-tetrahydroquinolin-2-yl)methoxy)-acetic Acid (AC90)

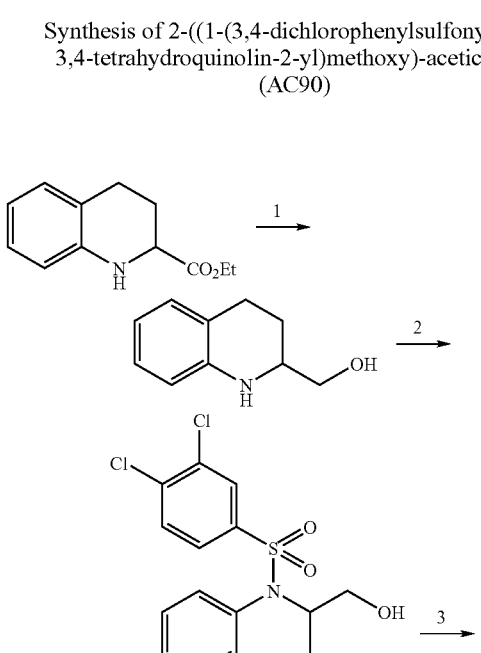

-continued

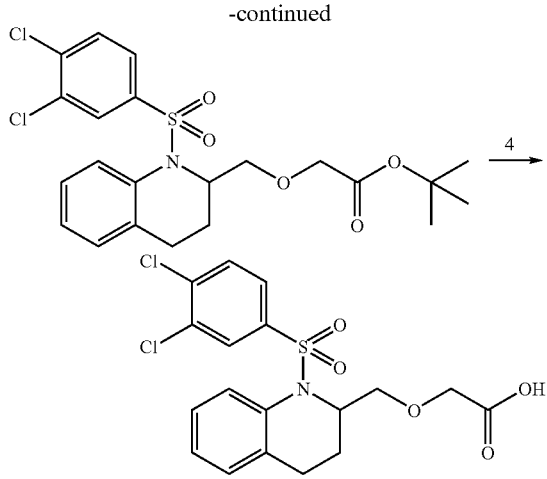

Stage 1. 1,2,3,4-Tetrahydroquinoline-2-carboxylic acid ethyl ester (4.75 g, 25 mmol) in THF (5 ml/mol) was added dropwise to a suspension of LAH (2 eq.) in THF (50 ml) at 0° C. The reaction mixture was stirred at RT for 1 h and then heated under reflux for 4 h. After addition of aqueous saturated $Na_2SO_4$ solution, the mixture was filtered and the organic solvent was removed in vacuo. The product was purified by column chromatography (silica gel, 3:7 ethyl acetate/hexane).

Yield: 50%

Stage 2. Pyridine (5 eq.), DMAP (0.5 eq.) and 3,4-dichlorobenzenesulfonyl chloride (1.2 eq.), dissolved in MC (2.6 ml/mmol sulfonic acid chloride), were added to a suspension, cooled to 0° C., of the alcohol (1 eq.) in MC (5 ml/mmol). After stirring at 0° C. for 5 h, MC was added and the mixture was washed with aqueous copper sulfate solution, water and saturated NaCl solution. After drying over $Na_2SO_4$ and filtration, the solvent was removed in vacuo. The product was purified by column chromatography (silica gel, MC/methanol, 95:5).

Stage 3. A solution of the sulfonamide (1 eq.) dissolved in THF (6.3 ml/mmol) was added dropwise to a suspension, cooled to 0° C., of NaH (2 eq.) in THF (10 ml/mmol), while stirring. After stirring for 45 min at this temperature, a solution of tert-butyl bromoacetate (1.5 eq.) in THF (2 ml/mmol) was added. The reaction mixture was heated at 50° C. for 20 h. It was then cooled to 0° C., ice was added and the mixture was extracted with ethyl acetate. The organic phase was washed with aqueous saturated NaCl solution and dried over $Na_2SO_4$. After filtration, the solvent was removed in vacuo. The product was purified by column chromatography (silica gel, hexane/ethyl acetate, 9:1).

Stage 4. The corresponding tert-butyl methoxyacetate was stirred in a solution of TFA (0.7 ml/mmol) and MC (4.7 ml/mmol) at RT for 2 h. When the reaction had ended, the solvent was removed on a rotary evaporator, the residue was taken up in toluene and the mixture was concentrated again.

Preparation of the Compounds of the General Formula I

Parallel Synthesis Method A

Acid solution (0.05 M in $CH_2Cl_2$, 2 ml) was added to 105 µmol of CDI solution (0.105 M in $CH_2Cl_2$, 1 ml) and the mixture was shaken at RT for 1 h. 100 µmol of the amine solution (0.1 M in $CH_2Cl_2$) were then added at RT and the mixture was shaken at RT for a further 12 h. 3 ml of water were then added to the reaction mixture, the mixture was shaken for 15 min and the organic phase was separated off. After removal of the solvent in vacuo, the crude products were analyzed by means of LC-MS and purified via HPLC.

Parallel Synthesis Method B

The acid chloride derivative (300 µmol, 1 ml, 0.3 M in pyridine) was added, while stirring, to a solution of the amine (100 µmol, 1 ml, 0.1 M in pyridine) and triethylamine solution (100 µmol, 1 ml, 0.1 M in pyridine), to which DMAP (1 mg/10 ml of solution) had been added. The reaction solution was stirred at RT for 24 h. $CH_2Cl_2$ (3 ml) and 9.5% strength aqueous $NaHCO_3$ solution (1 ml) were then added at RT. The solution was extracted for 30 min and filtered and the vessel was rinsed out with MC (1 ml).

The phases were separated. $CH_2Cl_2$ (2 ml) was added to the aqueous phase and the mixture was extracted. After centrifugation, the organic phase was separated off and combined with the first fraction. The aqueous phase was extracted analogously a second time with $CH_2Cl_2$. The combined organic phases were then dried over an $MgSO_4$ cartridge and the solvent was removed in a vacuum centrifuge. The crude products were analyzed by means of LC-MS and purified via HPLC.

The following example compounds were synthesized by Method B; the remaining compounds prepared by automated synthesis were prepared by Method A, unless stated otherwise.

2, 50, 79, 108, 121, 122, 134, 153, 181, 236, 237, 238, 245, 270, 315, 316, 353, 360, 421, 455, 482, 495, 505, 516, 529, 545, 564, 577, 579, 582

The example compounds are defined in the following Table 1 by the amine and acid units employed. The units were linked to one another as described above via the amine function and the acid function, water being split off.

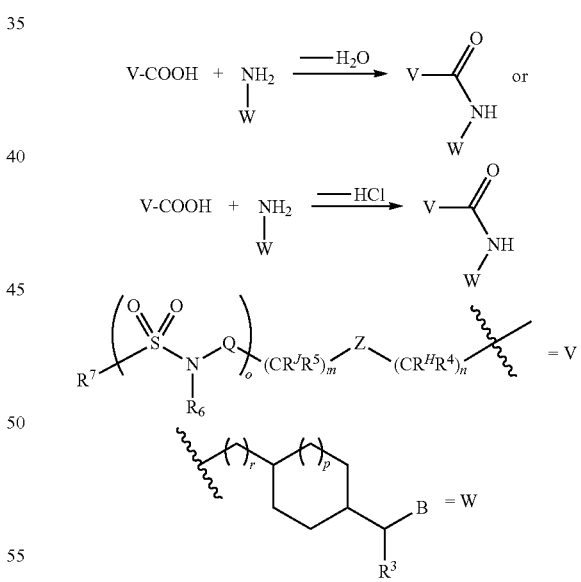

In all cases, the conversion was detected by HPLC-MS (ESI). The molecular peak found in each case is stated in the table. The compounds have a purity of >80%, the main product being the compound according to the invention in all cases.

By linking the units stated in the table via the amine and acid functions mentioned, the compounds according to the invention were obtained.

Binding data of the compounds on the µ opioid receptor and data on the inhibition of reuptake of serotonin (5-HT) are given in Table 1. The data were measured in the assay mentioned below. The data for the μ receptor were measured at a test concentration of 1 μM, and those for the serotonin reuptake at 10 μM. The values are stated in % inhibition.

TABLE 1

Examples and molecular pharmacology data

| Example | Acid | Amine | Mass | μ | 5-HT |
|---|---|---|---|---|---|
| 1 | AC48 | AM1 | 591.28 | 100 | 94 |
| 2 | AC66 | AM6 | 400.22 | 99 | 69 |
| 3 | AC30 | AM13 | 571.31 | 99 | 92 |
| 4 | AC17 | AM6 | 521.24 | 99 | 92 |
| 5 | AC42 | AM1 | 619.31 | 99 | 87 |
| 6 | AC30 | AM1 | 577.26 | 99 | 91 |
| 7 | AC35 | AM6 | 625.26 | 99 | 92 |
| 8 | AC14 | AM6 | 575.14 | 98 | 81 |
| 9 | AC14 | AM3 | 589.16 | 98 | 91 |
| 10 | AC13 | AM1 | 511.20 | 98 | 76 |
| 11 | AC55 | AM1 | 573.19 | 98 | 86 |
| 12 | AC54 | AM1 | 547.25 | 98 | 79 |
| 13 | AC10 | AM9 | 569.19 | 98 | 84 |
| 14 | AC7 | AM9 | 603.15 | 98 | 99 |
| 15 | AC6 | AM9 | 577.30 | 98 | 99 |
| 16 | AC5 | AM6 | 593.30 | 98 | 98 |
| 17 | AC26 | AM9 | 609.22 | 98 | 93 |
| 18 | AC37 | AM9 | 595.20 | 98 | 95 |
| 19 | AC35 | AM9 | 619.31 | 98 | 92 |
| 20 | AC40 | AM13 | 614.35 | 97 | 96 |
| 21 | AC58 | AM3 | 601.16 | 97 | 94 |
| 22 | AC57 | AM9 | 573.29 | 97 | 87 |
| 23 | AC57 | AM6 | 579.24 | 97 | 82 |
| 24 | AC26 | AM13 | 595.20 | 97 | 67 |
| 25 | AC55 | AM6 | 587.21 | 97 | 82 |
| 26 | AC54 | AM9 | 555.31 | 97 | 83 |
| 27 | AC54 | AM6 | 561.27 | 97 | 84 |
| 28 | AC62 | AM1 | 523.20 | 97 | 76 |
| 29 | AC44 | AM9 | 599.34 | 97 | 93 |
| 30 | AC24 | AM3 | 591.28 | 97 | 98 |
| 31 | AC34 | AM6 | 629.19 | 97 | 88 |
| 32 | AC2 | AM3 | 589.23 | 97 | 97 |
| 33 | AC14 | AM13 | 555.17 | 49 | 73 |
| 34 | AC7 | AM13 | 589.13 | 96 | 79 |
| 35 | AC11 | AM6 | 579.28 | 96 | 84 |
| 36 | AC60 | AM6 | 519.22 | 96 | 102 |
| 37 | AC16 | AM3 | 555.20 | 96 | 90 |
| 38 | AC35 | AM13 | 605.29 | 96 | 61 |
| 39 | AC34 | AM13 | 609.22 | 96 | 91 |
| 40 | AC11 | AM9 | 573.32 | 96 | 84 |
| 41 | AC10 | AM4 | 601.19 | 96 | 79 |
| 42 | AC45 | AM1 | 519.22 | 96 | 91 |
| 43 | AC52 | AM1 | 577.26 | 96 | 90 |
| 44 | AC52 | AM9 | 585.32 | 96 | 94 |
| 45 | AC24 | AM6 | 577.26 | 96 | 91 |
| 46 | AC30 | AM3 | 605.30 | 96 | 96 |
| 47 | AC35 | AM1 | 611.25 | 96 | 98 |
| 48 | AC35 | AM3 | 639.28 | 96 | 101 |
| 49 | AC22 | AM6 | 607.27 | 96 | 86 |
| 50 | AC66 | AM9 | 394.26 | 95 | 65 |
| 51 | AC6 | AM13 | 563.28 | 95 | 88 |
| 52 | AC11 | AM3 | 593.30 | 95 | 91 |
| 53 | AC18 | AM9 | 585.25 | 95 | 92 |
| 54 | AC59 | AM6 | 553.18 | 95 | 84 |
| 55 | AC16 | AM6 | 541.18 | 95 | 92 |
| 56 | AC13 | AM6 | 525.21 | 95 | 100 |
| 57 | AC1 | AM6 | 549.27 | 95 | 101 |
| 58 | AC52 | AM6 | 591.28 | 95 | 94 |
| 59 | AC5 | AM1 | 579.28 | 95 | 92 |
| 60 | AC44 | AM6 | 605.30 | 95 | 92 |
| 61 | AC40 | AM9 | 628.37 | 95 | 95 |
| 62 | AC30 | AM11 | 589.30 | 95 | 96 |
| 63 | AC1 | AM13 | 529.30 | 94 | 79 |
| 64 | AC54 | AM13 | 541.30 | 94 | 83 |
| 65 | AC18 | AM3 | 605.22 | 96 | 95 |
| 66 | AC59 | AM3 | 567.20 | 93 | 85 |
| 67 | AC58 | AM9 | 581.19 | 96 | 87 |
| 68 | AC56 | AM6 | 533.24 | 93 | 82 |
| 69 | AC15 | AM6 | 565.26 | 96 | 86 |
| 70 | AC14 | AM10 | 587.18 | 91 | 86 |
| 71 | AC54 | AM3 | 575.29 | 94 | 79 |
| 72 | AC10 | AM10 | 587.18 | 92 | 84 |
| 73 | AC9 | AM1 | 523.22 | 90 | 77 |
| 74 | AC52 | AM3 | 605.30 | 90 | 98 |
| 75 | AC42 | AM3 | 647.34 | 92 | 96 |
| 76 | AC40 | AM11 | 632.34 | 93 | 96 |
| 77 | AC36 | AM3 | 577.26 | 96 | 98 |
| 78 | AC34 | AM9 | 623.24 | 95 | 86 |
| 79 | AC66 | AM10 | 412.25 | 93 | 64 |
| 80 | AC11 | AM13 | 559.31 | 93 | 84 |
| 81 | AC59 | AM9 | 547.23 | 91 | 91 |
| 82 | AC17 | AM3 | 535.25 | 95 | 85 |
| 83 | AC16 | AM1 | 527.17 | 94 | 89 |
| 84 | AC15 | AM3 | 579.28 | 95 | 92 |
| 85 | AC13 | AM3 | 539.23 | 92 | 98 |
| 86 | AC53 | AM6 | 577.26 | 95 | 96 |
| 87 | AC26 | AM10 | 627.21 | 93 | 94 |
| 88 | AC24 | AM9 | 571.31 | 94 | 95 |
| 89 | AC30 | AM9 | 585.32 | 93 | 92 |
| 90 | AC30 | AM6 | 591.28 | 95 | 94 |
| 91 | AC2 | AM9 | 569.25 | 91 | 93 |
| 92 | AC2 | AM6 | 575.21 | 94 | 86 |
| 93 | AC18 | AM6 | 591.20 | 95 | 93 |
| 94 | AC57 | AM3 | 593.26 | 93 | 88 |
| 95 | AC27 | AM13 | 561.24 | 91 | 84 |
| 96 | AC55 | AM3 | 601.23 | 92 | 81 |
| 97 | AC62 | AM6 | 537.21 | 92 | 91 |
| 98 | AC53 | AM1 | 563.25 | 91 | 92 |
| 99 | AC41 | AM3 | 576.28 | 92 | 95 |
| 100 | AC45 | AM3 | 547.25 | 94 | 97 |
| 101 | AC31 | AM6 | 547.25 | 92 | 94 |
| 102 | AC6 | AM6 | 583.25 | 94 | 92 |
| 103 | AC5 | AM3 | 607.31 | 94 | 95 |
| 104 | AC48 | AM6 | 605.30 | 90 | 93 |
| 105 | AC36 | AM6 | 563.25 | 93 | 95 |
| 106 | AC22 | AM9 | 601.32 | 92 | 85 |
| 107 | AC22 | AM3 | 621.29 | 92 | 90 |
| 108 | AC66 | AM10 | 412.25 | 91 | 63 |
| 109 | AC45 | AM13 | 513.27 | 89 | 87 |
| 110 | AC16 | AM9 | 535.23 | 87 | 94 |
| 111 | AC15 | AM1 | 551.25 | 92 | 85 |
| 112 | AC13 | AM9 | 519.26 | 85 | 85 |
| 113 | AC55 | AM9 | 581.25 | 90 | 88 |
| 114 | AC45 | AM9 | 527.28 | 85 | 96 |
| 115 | AC31 | AM3 | 561.27 | 91 | 97 |
| 116 | AC6 | AM3 | 597.27 | 91 | 97 |
| 117 | AC5 | AM10 | 605.33 | 92 | 94 |
| 118 | AC42 | AM11 | 631.35 | 90 | 92 |
| 119 | AC37 | AM10 | 613.19 | 90 | 96 |
| 120 | AC23 | AM3 | 621.29 | 92 | 91 |
| 121 | AC66 | AM11 | 398.24 | 90 | |
| 122 | AC66 | AM10 | 412.25 | 90 | 57 |
| 123 | AC56 | AM13 | 513.27 | 27 | |
| 124 | AC43 | AM13 | 541.30 | 87 | 89 |
| 125 | AC56 | AM9 | 527.28 | 91 | 91 |
| 126 | AC14 | AM4 | 601.19 | 92 | 86 |
| 127 | AC8 | AM6 | 567.24 | 87 | 79 |
| 128 | AC9 | AM3 | 551.25 | 91 | 83 |
| 129 | AC31 | AM9 | 541.30 | 89 | 95 |
| 130 | AC44 | AM3 | 619.31 | 94 | 95 |
| 131 | AC42 | AM6 | 633.33 | 86 | 91 |
| 132 | AC34 | AM11 | 627.21 | 91 | 83 |
| 133 | AC23 | AM6 | 607.27 | 89 | 88 |
| 134 | AC64 | AM15 | 408.28 | 89 | 67 |
| 135 | AC43 | AM13 | 555.17 | 89 | 83 |
| 136 | AC12 | AM13 | 577.20 | 89 | 83 |
| 137 | AC15 | AM9 | 559.31 | 89 | 89 |
| 138 | AC62 | AM3 | 551.23 | 87 | 98 |
| 139 | AC55 | AM11 | 585.23 | 83 | 79 |
| 140 | AC54 | AM11 | 559.29 | 83 | 72 |
| 141 | AC54 | AM10 | 573.30 | 88 | 80 |
| 142 | AC9 | AM6 | 537.23 | 89 | 70 |
| 143 | AC48 | AM9 | 599.34 | 89 | 93 |
| 144 | AC44 | AM1 | 591.28 | 89 | 87 |
| 145 | AC44 | AM10 | 617.33 | 87 | 91 |
| 146 | AC42 | AM9 | 627.37 | 88 | 95 |

TABLE 1-continued

Examples and molecular pharmacology data

| Example | Acid | Amine | Mass | μ | 5-HT |
|---|---|---|---|---|---|
| 147 | AC26 | AM4 | 641.23 | 90 | 96 |
| 148 | AC3 | AM9 | 635.34 | 90 | 95 |
| 149 | AC3 | AM3 | 655.31 | 91 | 91 |
| 150 | AC23 | AM9 | 601.32 | 86 | 94 |
| 151 | AC22 | AM10 | 619.31 | 90 | 87 |
| 152 | AC2 | AM1 | 561.19 | 89 | 87 |
| 153 | AC66 | AM11 | 398.24 | 88 | 27 |
| 154 | AC24 | AM13 | 557.29 | 83 | 90 |
| 155 | AC57 | AM1 | 565.23 | 88 | 87 |
| 156 | AC56 | AM1 | 519.22 | 80 | 87 |
| 157 | AC17 | AM9 | 515.28 | 87 | 88 |
| 158 | AC16 | AM10 | 553.22 | 87 | 91 |
| 159 | AC11 | AM11 | 577.30 | 85 | 72 |
| 160 | AC11 | AM10 | 591.31 | 88 | 80 |
| 161 | AC6 | AM1 | 569.24 | 86 | 94 |
| 162 | AC36 | AM1 | 549.23 | 86 | 81 |
| 163 | AC35 | AM10 | 637.30 | 87 | 96 |
| 164 | AC34 | AM10 | 641.23 | 86 | 90 |
| 165 | AC53 | AM13 | 557.29 | 87 | 20 |
| 166 | AC10 | AM13 | 603.17 | 87 | 91 |
| 167 | AC56 | AM11 | 531.26 | 82 | 86 |
| 168 | AC17 | AM1 | 507.22 | 83 | 85 |
| 169 | AC8 | AM9 | 561.29 | 85 | 94 |
| 170 | AC55 | AM10 | 599.24 | 83 | 89 |
| 171 | AC10 | AM11 | 573.16 | 84 | 78 |
| 172 | AC62 | AM11 | 535.23 | 78 | 79 |
| 173 | AC53 | AM9 | 571.31 | 87 | 95 |
| 174 | AC7 | AM4 | 635.16 | 90 | 97 |
| 175 | AC6 | AM11 | 581.27 | 85 | 97 |
| 176 | AC5 | AM11 | 591.31 | 87 | 90 |
| 177 | AC48 | AM3 | 619.31 | 88 | 93 |
| 178 | AC42 | AM2 | 631.35 | 81 | 94 |
| 179 | AC24 | AM10 | 589.30 | 85 | 92 |
| 180 | AC24 | AM4 | 603.31 | 90 | 93 |
| 181 | AC66 | AM13 | 380.25 | 86 | 46 |
| 182 | AC36 | AM13 | 543.28 | 82 | 85 |
| 183 | AC11 | AM4 | 605.33 | 83 | 93 |
| 184 | AC57 | AM10 | 591.28 | 91 | 88 |
| 185 | AC56 | AM10 | 545.27 | 78 | 102 |
| 186 | AC16 | AM4 | 567.23 | 87 | 88 |
| 187 | AC22 | AM13 | 587.30 | 79 | 81 |
| 188 | AC7 | AM10 | 621.14 | 87 | 98 |
| 189 | AC52 | AM11 | 589.30 | 84 | 96 |
| 190 | AC35 | AM4 | 651.31 | 83 | 79 |
| 191 | AC23 | AM4 | 633.32 | 85 | 89 |
| 192 | AC2 | AM4 | 601.26 | 88 | 94 |
| 193 | AC4 | AM13 | 635.34 | 85 | 92 |
| 194 | AC60 | AM1 | 505.21 | 83 | 86 |
| 195 | AC60 | AM9 | 513.27 | 83 | 101 |
| 196 | AC16 | AM11 | 539.20 | 81 | 92 |
| 197 | AC15 | AM4 | 591.31 | 85 | 85 |
| 198 | AC23 | AM13 | 587.30 | 78 | 88 |
| 199 | AC53 | AM3 | 591.28 | 87 | 96 |
| 200 | AC40 | AM4 | 660.37 | 80 | 95 |
| 201 | AC4 | AM9 | 649.35 | 88 | 89 |
| 202 | AC37 | AM4 | 627.21 | 85 | 98 |
| 203 | AC30 | AM10 | 603.31 | 83 | 93 |
| 204 | AC59 | AM11 | 551.20 | 81 | 86 |
| 205 | AC13 | AM11 | 523.23 | 76 | 84 |
| 206 | AC8 | AM1 | 553.23 | 78 | 84 |
| 207 | AC10 | AM12 | 603.15 | 77 | 72 |
| 208 | AC7 | AM11 | 607.12 | 79 | 93 |
| 209 | AC5 | AM4 | 619.35 | 85 | 94 |
| 210 | AC26 | AM11 | 613.19 | 85 | 91 |
| 211 | AC37 | AM11 | 599.18 | 83 | 90 |
| 212 | AC30 | AM2 | 589.30 | 80 | 92 |
| 213 | AC30 | AM4 | 617.33 | 87 | 98 |
| 214 | AC34 | AM3 | 643.21 | 85 | 83 |
| 215 | AC18 | AM4 | 617.25 | 85 | 90 |
| 216 | AC56 | AM4 | 559.29 | 72 | 87 |
| 217 | AC14 | AM4 | 573.16 | 89 | 85 |
| 218 | AC13 | AM4 | 551.26 | 82 | 101 |
| 219 | AC62 | AM9 | 531.26 | 82 | 96 |
| 220 | AC31 | AM10 | 559.29 | 73 | 95 |
| 221 | AC44 | AM4 | 631.35 | 82 | 95 |
| 222 | AC40 | AM2 | 632.34 | 77 | 92 |
| 223 | AC40 | AM10 | 646.36 | 77 | 96 |
| 224 | AC36 | AM4 | 589.30 | 85 | 97 |
| 225 | AC58 | AM10 | 599.18 | 83 | 85 |
| 226 | AC17 | AM11 | 519.26 | 74 | 91 |
| 227 | AC17 | AM10 | 533.27 | 77 | 86 |
| 228 | AC15 | AM11 | 563.28 | 76 | 85 |
| 229 | AC13 | AM10 | 537.25 | 79 | 89 |
| 230 | AC49 | AM3 | 547.25 | 82 | 94 |
| 231 | AC5 | AM9 | 587.34 | 82 | 83 |
| 232 | AC48 | AM4 | 631.35 | 78 | 98 |
| 233 | AC26 | AM7 | 627.21 | 75 | 91 |
| 234 | AC35 | AM2 | 623.28 | 76 | 95 |
| 235 | AC1 | AM1 | 535.25 | 76 | 86 |
| 236 | AC66 | AM7 | 412.25 | 81 | 63 |
| 237 | AC66 | AM12 | 428.22 | 81 | 52 |
| 238 | AC66 | AM12 | 428.22 | 81 | 38 |
| 239 | AC15 | AM13 | 545.29 | 38 | 78 |
| 240 | AC17 | AM4 | 547.29 | 74 | 87 |
| 241 | AC13 | AM5 | 567.23 | 67 | 102 |
| 242 | AC9 | AM9 | 531.28 | 77 | 77 |
| 243 | AC24 | AM1 | 563.25 | 79 | 73 |
| 244 | AC34 | AM33 | 655.24 | 81 | 88 |
| 245 | AC64 | AM13 | 380.25 | 80 | 59 |
| 246 | AC18 | AM11 | 589.22 | 76 | 91 |
| 247 | AC59 | AM4 | 579.23 | 75 | 89 |
| 248 | AC15 | AM10 | 577.30 | 81 | 90 |
| 249 | AC14 | AM7 | 587.18 | 70 | 95 |
| 250 | AC9 | AM11 | 535.25 | 70 | 84 |
| 251 | AC53 | AM11 | 575.28 | 77 | 98 |
| 252 | AC52 | AM10 | 603.31 | 82 | 93 |
| 253 | AC52 | AM4 | 617.33 | 76 | 96 |
| 254 | AC4 | AM3 | 669.33 | 83 | 94 |
| 255 | AC24 | AM11 | 575.28 | 72 | 91 |
| 256 | AC34 | AM2 | 627.21 | 73 | 84 |
| 257 | AC49 | AM13 | 513.27 | 74 | 86 |
| 258 | AC59 | AM10 | 565.22 | 80 | 84 |
| 259 | AC58 | AM4 | 613.19 | 83 | 90 |
| 260 | AC57 | AM12 | 607.25 | 76 | 88 |
| 261 | AC23 | AM1 | 593.26 | 72 | 85 |
| 262 | AC57 | AM4 | 605.29 | 82 | 90 |
| 263 | AC13 | AM12 | 553.22 | 72 | 102 |
| 264 | AC54 | AM4 | 587.32 | 77 | 82 |
| 265 | AC53 | AM10 | 589.30 | 79 | 95 |
| 266 | AC31 | AM11 | 545.27 | 74 | 97 |
| 267 | AC37 | AM7 | 613.19 | 73 | 94 |
| 268 | AC36 | AM11 | 561.27 | 70 | 92 |
| 269 | AC34 | AM12 | 657.20 | 74 | 87 |
| 270 | AC66 | AM15 | 408.28 | 77 | 73 |
| 271 | AC60 | AM11 | 517.24 | 72 | 93 |
| 272 | AC56 | AM3 | 547.25 | 73 | 88 |
| 273 | AC17 | AM12 | 549.24 | 68 | 91 |
| 274 | AC10 | AM5 | 617.16 | 68 | 81 |
| 275 | AC62 | AM10 | 549.25 | 71 | 80 |
| 276 | AC49 | AM6 | 533.24 | 78 | 93 |
| 277 | AC45 | AM11 | 531.26 | 68 | 93 |
| 278 | AC6 | AM4 | 609.30 | 77 | 98 |
| 279 | AC44 | AM11 | 603.31 | 77 | 85 |
| 280 | AC22 | AM12 | 635.28 | 73 | 78 |
| 281 | AC22 | AM4 | 633.32 | 77 | 89 |
| 282 | AC18 | AM1 | 577.19 | 74 | 52 |
| 283 | AC58 | AM11 | 585.16 | 74 | 91 |
| 284 | AC16 | AM12 | 569.19 | 70 | 87 |
| 285 | AC10 | AM33 | 601.19 | 69 | 89 |
| 286 | AC48 | AM11 | 603.31 | 76 | 92 |
| 287 | AC48 | AM10 | 617.33 | 71 | 96 |
| 288 | AC35 | AM7 | 637.30 | 65 | 94 |
| 289 | AC2 | AM5 | 617.23 | 67 | 94 |
| 290 | AC58 | AM2 | 585.16 | 67 | 89 |
| 291 | AC14 | AM5 | 617.16 | 65 | 81 |
| 292 | AC9 | AM4 | 563.28 | 74 | 83 |
| 293 | AC8 | AM4 | 593.29 | 75 | 95 |
| 294 | AC31 | AM12 | 575.26 | 63 | 88 |
| 295 | AC31 | AM4 | 573.30 | 71 | 99 |
| 296 | AC6 | AM10 | 595.29 | 64 | 96 |
| 297 | AC2 | AM11 | 573.23 | 74 | 86 |
| 298 | AC11 | AM12 | 607.28 | 64 | 79 |

TABLE 1-continued

Examples and molecular pharmacology data

| Example | Acid | Amine | Mass | μ | 5-HT |
|---|---|---|---|---|---|
| 299 | AC60 | AM12 | 547.23 | 63 | 103 |
| 300 | AC49 | AM9 | 527.28 | 66 | 94 |
| 301 | AC45 | AM12 | 561.24 | 69 | 92 |
| 302 | AC2 | AM10 | 587.24 | 75 | 92 |
| 303 | AC18 | AM10 | 603.24 | 66 | 83 |
| 304 | AC56 | AM12 | 561.24 | 64 | 88 |
| 305 | AC56 | AM5 | 575.26 | 63 | 88 |
| 306 | AC17 | AM5 | 563.26 | 60 | 91 |
| 307 | AC53 | AM4 | 603.31 | 73 | 97 |
| 308 | AC41 | AM10 | 574.30 | 60 | 93 |
| 309 | AC45 | AM10 | 545.27 | 69 | 94 |
| 310 | AC5 | AM12 | 621.30 | 61 | 83 |
| 311 | AC24 | AM5 | 619.28 | 67 | 95 |
| 312 | AC30 | AM12 | 619.28 | 61 | 89 |
| 313 | AC36 | AM10 | 575.28 | 71 | 93 |
| 314 | AC2 | AM12 | 603.21 | 64 | 93 |
| 315 | AC66 | AM3 | 414.23 | 72 | 61 |
| 316 | AC65 | AM13 | 400.19 | 72 | 59 |
| 317 | AC11 | AM5 | 621.30 | 62 | 88 |
| 318 | AC7 | AM12 | 637.11 | 65 | 91 |
| 319 | AC42 | AM10 | 645.36 | 71 | 87 |
| 320 | AC40 | AM5 | 676.34 | 65 | 98 |
| 321 | AC24 | AM12 | 605.27 | 70 | 86 |
| 322 | AC22 | AM11 | 605.29 | 70 | 78 |
| 323 | AC57 | AM11 | 577.26 | 67 | 91 |
| 324 | AC9 | AM12 | 565.24 | 62 | 83 |
| 325 | AC41 | AM4 | 588.31 | 68 | 96 |
| 326 | AC45 | AM4 | 559.29 | 67 | 97 |
| 327 | AC5 | AM7 | 605.33 | 67 | 90 |
| 328 | AC26 | AM2 | 613.19 | 59 | 88 |
| 329 | AC23 | AM10 | 619.31 | 66 | 91 |
| 330 | AC55 | AM2 | 585.23 | 54 | 90 |
| 331 | AC55 | AM12 | 615.21 | 61 | 84 |
| 332 | AC54 | AM2 | 559.29 | 58 | 88 |
| 333 | AC43 | AM10 | 573.30 | 65 | 84 |
| 334 | AC10 | AM7 | 587.18 | 66 | 83 |
| 335 | AC49 | AM11 | 531.26 | 58 | 93 |
| 336 | AC6 | AM2 | 581.27 | 59 | 96 |
| 337 | AC26 | AM33 | 641.23 | 64 | 96 |
| 338 | AC57 | AM5 | 621.26 | 69 | 86 |
| 339 | AC8 | AM5 | 609.26 | 63 | 78 |
| 340 | AC9 | AM10 | 549.27 | 69 | 81 |
| 341 | AC41 | AM1 | 548.25 | 64 | 85 |
| 342 | AC6 | AM7 | 595.29 | 57 | 94 |
| 343 | AC6 | AM12 | 611.26 | 62 | 94 |
| 344 | AC37 | AM2 | 599.18 | 64 | 97 |
| 345 | AC24 | AM7 | 589.30 | 64 | 92 |
| 346 | AC36 | AM5 | 605.27 | 63 | 95 |
| 347 | AC16 | AM5 | 583.20 | 63 | 93 |
| 348 | AC15 | AM12 | 593.27 | 61 | 83 |
| 349 | AC24 | AM33 | 603.31 | 66 | 94 |
| 350 | AC30 | AM7 | 603.31 | 61 | 92 |
| 351 | AC36 | AM12 | 591.25 | 63 | 97 |
| 352 | AC23 | AM11 | 605.29 | 65 | 91 |
| 353 | AC64 | AM11 | 398.24 | 67 | 60 |
| 354 | AC11 | AM33 | 605.33 | 61 | 90 |
| 355 | AC60 | AM10 | 531.26 | 66 | 102 |
| 356 | AC14 | AM2 | 573.16 | 55 | 84 |
| 357 | AC13 | AM2 | 523.23 | 57 | 86 |
| 358 | AC3 | AM4 | 667.35 | 71 | 92 |
| 359 | AC34 | AM7 | 641.23 | 60 | 90 |
| 360 | AC67 | AM12 | 456.22 | 66 | 15 |
| 361 | AC18 | AM2 | 589.22 | 59 | 87 |
| 362 | AC17 | AM7 | 533.27 | 54 | 105 |
| 363 | AC10 | AM2 | 573.16 | 59 | 73 |
| 364 | AC41 | AM11 | 560.28 | 58 | 95 |
| 365 | AC52 | AM2 | 589.30 | 49 | 90 |
| 366 | AC40 | AM7 | 646.36 | 55 | 96 |
| 367 | AC23 | AM12 | 635.28 | 60 | 89 |
| 368 | AC2 | AM33 | 601.26 | 61 | 95 |
| 369 | AC51 | AM13 | 677.19 | 66 | 66 |
| 370 | AC59 | AM2 | 551.20 | 59 | 83 |
| 371 | AC56 | AM2 | 531.26 | 57 | 85 |
| 372 | AC3 | AM11 | 639.31 | 59 | 89 |
| 373 | AC35 | AM8 | 647.34 | 62 | 85 |
| 374 | AC35 | AM5 | 667.28 | 59 | 90 |
| 375 | AC60 | AM5 | 561.24 | 53 | 88 |
| 376 | AC60 | AM4 | 545.27 | 62 | 88 |
| 377 | AC16 | AM33 | 567.23 | 59 | 88 |
| 378 | AC15 | AM5 | 607.28 | 58 | 83 |
| 379 | AC8 | AM12 | 595.25 | 45 | 81 |
| 380 | AC11 | AM2 | 577.30 | 55 | 81 |
| 381 | AC62 | AM2 | 535.23 | 54 | 79 |
| 382 | AC7 | AM2 | 607.12 | 60 | 96 |
| 383 | AC30 | AM5 | 633.30 | 59 | 94 |
| 384 | AC59 | AM12 | 581.19 | 55 | 87 |
| 385 | AC1 | AM3 | 563.29 | 59 | 93 |
| 386 | AC7 | AM33 | 635.16 | 63 | 98 |
| 387 | AC40 | AM33 | 660.37 | 53 | 95 |
| 388 | AC3 | AM10 | 653.33 | 65 | 91 |
| 389 | AC35 | AM33 | 651.31 | 58 | 93 |
| 390 | AC2 | AM7 | 587.24 | 55 | 90 |
| 391 | AC58 | AM7 | 599.18 | 56 | 85 |
| 392 | AC15 | AM33 | 591.31 | 57 | 89 |
| 393 | AC54 | AM12 | 589.27 | 55 | 70 |
| 394 | AC62 | AM12 | 565.22 | 56 | 93 |
| 395 | AC45 | AM5 | 575.26 | 54 | 96 |
| 396 | AC5 | AM2 | 591.31 | 60 | 90 |
| 397 | AC42 | AM4 | 659.38 | 67 | 93 |
| 398 | AC30 | AM33 | 617.33 | 59 | 97 |
| 399 | AC16 | AM7 | 553.22 | 52 | 89 |
| 400 | AC13 | AM7 | 537.25 | 55 | 103 |
| 401 | AC8 | AM11 | 565.26 | 49 | 99 |
| 402 | AC55 | AM7 | 599.24 | 53 | 77 |
| 403 | AC53 | AM12 | 605.27 | 52 | 93 |
| 404 | AC7 | AM7 | 621.14 | 53 | 96 |
| 405 | AC22 | AM7 | 619.31 | 52 | 89 |
| 406 | AC16 | AM2 | 539.20 | 51 | 93 |
| 407 | AC62 | AM4 | 563.26 | 54 | 95 |
| 408 | AC49 | AM2 | 531.26 | 48 | 93 |
| 409 | AC36 | AM33 | 589.30 | 54 | 97 |
| 410 | AC34 | AM5 | 671.21 | 50 | 78 |
| 411 | AC18 | AM12 | 619.21 | 60 | 91 |
| 412 | AC52 | AM5 | 633.30 | 50 | 95 |
| 413 | AC5 | AM33 | 619.35 | 55 | 96 |
| 414 | AC4 | AM10 | 667.35 | 64 | 67 |
| 415 | AC37 | AM8 | 623.24 | 55 | 88 |
| 416 | AC1 | AM5 | 591.29 | 53 | 103 |
| 417 | AC1 | AM33 | 575.32 | 60 | 91 |
| 418 | AC44 | AM7 | 617.33 | 51 | 98 |
| 419 | AC4 | AM11 | 653.33 | 53 | 76 |
| 420 | AC22 | AM8 | 629.35 | 53 | 74 |
| 421 | AC69 | AM8 | 374.26 | 57 | 26 |
| 422 | AC15 | AM2 | 563.28 | 43 | 81 |
| 423 | AC45 | AM2 | 531.26 | 47 | 95 |
| 424 | AC31 | AM7 | 559.29 | 39 | 96 |
| 425 | AC31 | AM5 | 589.27 | 48 | 97 |
| 426 | AC6 | AM5 | 625.27 | 48 | 95 |
| 427 | AC52 | AM7 | 603.31 | 50 | 94 |
| 428 | AC52 | AM12 | 619.28 | 49 | 88 |
| 429 | AC40 | AM12 | 662.33 | 54 | 95 |
| 430 | AC57 | AM33 | 605.29 | 56 | 92 |
| 431 | AC55 | AM5 | 629.23 | 45 | 93 |
| 432 | AC54 | AM7 | 573.30 | 56 | 82 |
| 433 | AC41 | AM7 | 574.30 | 46 | 95 |
| 434 | AC5 | AM5 | 635.32 | 46 | 82 |
| 435 | AC44 | AM2 | 603.31 | 48 | 91 |
| 436 | AC4 | AM4 | 681.36 | 57 | 88 |
| 437 | AC26 | AM8 | 637.25 | 56 | 86 |
| 438 | AC2 | AM2 | 573.23 | 51 | 84 |
| 439 | AC18 | AM7 | 603.24 | 50 | 94 |
| 440 | AC62 | AM5 | 579.23 | 47 | 95 |
| 441 | AC53 | AM2 | 575.28 | 49 | 99 |
| 442 | AC7 | AM5 | 651.13 | 54 | 91 |
| 443 | AC49 | AM5 | 575.26 | 45 | 96 |
| 444 | AC49 | AM4 | 559.29 | 56 | 96 |
| 445 | AC16 | AM8 | 563.26 | 44 | 87 |
| 446 | AC18 | AM33 | 617.25 | 51 | 90 |
| 447 | AC56 | AM7 | 545.27 | 44 | 95 |
| 448 | AC17 | AM2 | 519.26 | 41 | 94 |
| 449 | AC44 | AM12 | 633.30 | 46 | 73 |
| 450 | AC24 | AM2 | 575.28 | 50 | 90 |

TABLE 1-continued

Examples and molecular pharmacology data

| Example | Acid | Amine | Mass | μ | 5-HT |
|---|---|---|---|---|---|
| 451 | AC34 | AM8 | 651.27 | 48 | 84 |
| 452 | AC17 | AM8 | 543.31 | 46 | 88 |
| 453 | AC11 | AM8 | 601.35 | 46 | 89 |
| 454 | AC48 | AM2 | 603.31 | 48 | 95 |
| 455 | AC66 | AM33 | 426.27 | 51 | 74 |
| 456 | AC58 | AM33 | 613.19 | 50 | 88 |
| 457 | AC17 | AM33 | 547.29 | 47 | 90 |
| 458 | AC15 | AM7 | 577.30 | 48 | 85 |
| 459 | AC14 | AM12 | 603.15 | 36 | 68 |
| 460 | AC9 | AM5 | 579.25 | 52 | 86 |
| 461 | AC36 | AM2 | 561.27 | 43 | 94 |
| 462 | AC23 | AM33 | 633.32 | 51 | 90 |
| 463 | AC60 | AM2 | 517.24 | 38 | 97 |
| 464 | AC59 | AM33 | 579.23 | 46 | 88 |
| 465 | AC12 | AM3 | 611.19 | 48 | 72 |
| 466 | AC55 | AM33 | 613.26 | 30 | 89 |
| 467 | AC52 | AM33 | 617.33 | 40 | 95 |
| 468 | AC44 | AM33 | 631.35 | 53 | 95 |
| 469 | AC24 | AM8 | 599.34 | 50 | 87 |
| 470 | AC43 | AM33 | 587.32 | 35 | 82 |
| 471 | AC49 | AM12 | 561.24 | 35 | 94 |
| 472 | AC48 | AM5 | 647.32 | 44 | 95 |
| 473 | AC3 | AM12 | 669.30 | 34 | 64 |
| 474 | AC22 | AM5 | 649.30 | 46 | 88 |
| 475 | AC54 | AM8 | 583.34 | 48 | 87 |
| 476 | AC10 | AM8 | 597.22 | 47 | 80 |
| 477 | AC49 | AM10 | 545.27 | 51 | 95 |
| 478 | AC31 | AM2 | 545.27 | 40 | 97 |
| 479 | AC31 | AM33 | 573.30 | 42 | 97 |
| 480 | AC48 | AM33 | 631.35 | 38 | 98 |
| 481 | AC42 | AM7 | 645.36 | 38 | 88 |
| 482 | AC64 | AM5 | 442.24 | 47 | 55 |
| 483 | AC3 | AM13 | 621.32 | 38 | 65 |
| 484 | AC8 | AM33 | 593.29 | 35 | 96 |
| 485 | AC44 | AM5 | 647.32 | 46 | 92 |
| 486 | AC22 | AM8 | 629.35 | 36 | 73 |
| 487 | AC13 | AM33 | 551.26 | 37 | 101 |
| 488 | AC45 | AM7 | 545.27 | 40 | 94 |
| 489 | AC6 | AM33 | 609.30 | 35 | 97 |
| 490 | AC1 | AM2 | 547.29 | 42 | 86 |
| 491 | AC56 | AM33 | 559.29 | 34 | 90 |
| 492 | AC53 | AM5 | 619.28 | 44 | 97 |
| 493 | AC41 | AM33 | 588.31 | 34 | 96 |
| 494 | AC3 | AM7 | 653.33 | 42 | 89 |
| 495 | AC66 | AM8 | 422.29 | 44 | 48 |
| 496 | AC58 | AM8 | 609.22 | 41 | 89 |
| 497 | AC57 | AM7 | 591.28 | 37 | 86 |
| 498 | AC48 | AM12 | 633.30 | 36 | 88 |
| 499 | AC42 | AM12 | 661.33 | 37 | 75 |
| 500 | AC22 | AM33 | 633.32 | 43 | 90 |
| 501 | AC54 | AM33 | 587.32 | 45 | 77 |
| 502 | AC41 | AM2 | 560.28 | 33 | 97 |
| 503 | AC52 | AM8 | 613.35 | 37 | 90 |
| 504 | AC3 | AM2 | 639.31 | 43 | 89 |
| 505 | AC65 | AM11 | 418.18 | 42 | 59 |
| 506 | AC54 | AM5 | 603.29 | 42 | 86 |
| 507 | AC43 | AM9 | 555.31 | 32 | 75 |
| 508 | AC9 | AM7 | 549.27 | 31 | 80 |
| 509 | AC53 | AM33 | 603.31 | 43 | 97 |
| 510 | AC42 | AM33 | 659.38 | 33 | 99 |
| 511 | AC36 | AM7 | 575.28 | 39 | 98 |
| 512 | AC57 | AM2 | 577.26 | 42 | 86 |
| 513 | AC14 | AM8 | 597.22 | 38 | 89 |
| 514 | AC8 | AM7 | 579.28 | 27 | 70 |
| 515 | AC7 | AM8 | 631.18 | 42 | 97 |
| 516 | AC66 | AM2 | 398.24 | 40 | |
| 517 | AC59 | AM7 | 565.22 | 40 | 86 |
| 518 | AC62 | AM33 | 563.26 | 35 | 102 |
| 519 | AC9 | AM33 | 563.28 | 39 | 88 |
| 520 | AC45 | AM33 | 559.29 | 31 | 97 |
| 521 | AC42 | AM8 | 655.40 | 39 | 89 |
| 522 | AC62 | AM7 | 549.25 | 35 | 98 |
| 523 | AC4 | AM2 | 653.33 | 34 | 81 |
| 524 | AC22 | AM2 | 605.29 | 33 | 86 |
| 525 | AC15 | AM8 | 587.34 | 31 | 84 |
| 526 | AC41 | AM8 | 584.34 | 32 | 90 |
| 527 | AC48 | AM7 | 617.33 | 38 | 96 |
| 528 | AC40 | AM8 | 656.40 | 34 | 94 |
| 529 | AC64 | AM2 | 398.24 | 37 | 59 |
| 530 | AC60 | AM33 | 545.27 | 26 | 89 |
| 531 | AC43 | AM5 | 603.29 | 23 | 98 |
| 532 | AC60 | AM7 | 531.26 | 35 | 99 |
| 533 | AC6 | AM8 | 605.33 | 28 | 93 |
| 534 | AC23 | AM7 | 619.31 | 24 | 88 |
| 535 | AC30 | AM8 | 613.35 | 34 | 85 |
| 536 | AC5 | AM8 | 615.37 | 43 | 84 |
| 537 | AC23 | AM7 | 619.31 | 35 | 92 |
| 538 | AC56 | AM8 | 555.31 | 25 | 91 |
| 539 | AC13 | AM8 | 547.29 | 32 | 102 |
| 540 | AC23 | AM5 | 649.30 | 23 | 81 |
| 541 | AC53 | AM7 | 589.30 | 34 | 95 |
| 542 | AC3 | AM8 | 663.37 | 33 | 87 |
| 543 | AC43 | AM4 | 587.32 | 29 | 76 |
| 544 | AC31 | AM8 | 569.33 | 24 | 92 |
| 545 | AC66 | AM14 | 408.28 | 30 | 52 |
| 546 | AC48 | AM8 | 627.37 | 33 | 91 |
| 547 | AC3 | AM33 | 667.35 | 30 | 90 |
| 548 | AC8 | AM2 | 565.26 | 26 | 99 |
| 549 | AC9 | AM2 | 535.25 | 29 | 81 |
| 550 | AC9 | AM8 | 559.31 | 20 | 74 |
| 551 | AC44 | AM8 | 627.37 | 35 | 85 |
| 552 | AC55 | AM8 | 609.28 | 23 | 90 |
| 553 | AC49 | AM33 | 559.29 | 26 | 94 |
| 554 | AC4 | AM33 | 681.36 | 28 | 92 |
| 555 | AC23 | AM2 | 605.29 | 23 | 86 |
| 556 | AC2 | AM8 | 597.28 | 27 | 86 |
| 557 | AC59 | AM8 | 575.26 | 26 | 88 |
| 558 | AC45 | AM8 | 555.31 | 29 | 92 |
| 559 | AC23 | AM8 | 629.35 | 14 | 84 |
| 560 | AC4 | AM12 | 683.32 | 22 | 47 |
| 561 | AC42 | AM5 | 675.35 | 26 | 79 |
| 562 | AC4 | AM8 | 677.39 | 23 | 96 |
| 563 | AC4 | AM7 | 667.35 | 25 | 90 |
| 564 | AC65 | AM14 | 428.22 | 24 | 47 |
| 565 | AC53 | AM8 | 599.34 | 20 | 94 |
| 566 | AC57 | AM8 | 601.32 | 19 | 87 |
| 567 | AC18 | AM8 | 613.28 | 23 | 93 |
| 568 | AC49 | AM7 | 545.27 | 11 | 97 |
| 569 | AC3 | AM5 | 683.32 | 10 | 52 |
| 570 | AC23 | AM8 | 629.35 | 16 | 87 |
| 571 | AC8 | AM8 | 589.32 | 14 | 88 |
| 572 | AC36 | AM8 | 585.32 | 29 | 93 |
| 573 | AC60 | AM8 | 541.30 | 23 | 100 |
| 574 | AC62 | AM8 | 559.29 | 18 | 94 |
| 575 | AC18 | AM5 | 633.23 | 11 | 77 |
| 576 | AC4 | AM5 | 697.33 | 15 | 73 |
| 577 | AC66 | AM14 | 408.28 | 14 | 16 |
| 578 | AC49 | AM8 | 555.31 | 12 | 94 |
| 579 | AC68 | AM15 | 346.23 | 11 | 59 |
| 580 | AC10 | AM8 | 597.22 | 13 | 77 |
| 581 | AC23 | AM4 | 633.32 | 9 | 70 |
| 582 | AC64 | AM14 | 408.28 | 9 | 75 |
| 583 | AC43 | AM7 | 573.30 | 7 | 77 |
| 584 | AC43 | AM12 | 589.27 | 7 | 64 |
| 585 | AC13 | AM13 | 505.24 | 41 | |
| 586 | AC14 | AM33 | 601.19 | 3 | 73 |
| 587 | AC1 | AM4 | 575.32 | −5 | 86 |
| 588 | AC19 | AM13 | 487.25 | 29 | |
| 589 | AC16 | AM13 | 521.21 | 25 | |
| 590 | AC9 | AM13 | 517.26 | 75 | |
| 591 | AC62 | AM13 | 517.24 | 93 | |
| 592 | AC8 | AM13 | 547.27 | 83 | |
| 593 | AC2 | AM13 | 555.24 | 91 | |
| 594 | AC18 | AM13 | 571.23 | 94 | |
| 595 | AC60 | AM13 | 499.25 | 51 | |
| 596 | AC58 | AM13 | 567.17 | 84 | |

Synthesis of Individual Substances

The analytical studies were carried out by mass spectroscopy and/or NMR.

Unless indicated otherwise, the compounds are isomer mixtures in the ratio of approx. 1:1.

In analogous syntheses, there may be slight variations with respect to the solvents, the equivalents of the reagents/educts, the reaction times etc.

Example 597

N-[4-(Dimethylaminophenylmethyl)-cyclohexyl]-2-{2-[(4-methoxy-2,3,6-trimethylbenzenesulfonyl)-methylamino]-ethoxy}-acetamide N,N'-Carbonyldiimidazole (195 mg, 1.2 mmol) was added to a soln. of {2-[(4-methoxy-2,3,6-trimethylbenzenesulfonyl)-methylamino]-ethoxy}-acetic acid (Intermediate C) (346 mg, 1 mmol) in THF (5 ml) and the mixture was stirred at RT for 1 h. A soln. of 4-(dimethylaminophenylmethyl)-cyclohexylamine (Intermediate VII) (256 mg, 1.1 mmol) in THF (5 ml) was then added and the reaction mixture was stirred at RT for 3 d. Thereafter, the soln. was concentrated i. vac., the residue was taken up in NaHCO$_3$ soln. and the mixture was extracted with MC (3×30 ml). The combined organic phases were dried with Na$_2$SO$_4$ and concentrated i. vac. Further purification was carried out by means of flash chromatography with CHCl$_3$/MeOH (95:5).

Yield: 329 mg (59%)

$^1$H-NMR (DMSO-d$_6$): 1.10-1.90 (m, 11H); 1.96 and 2.00 (3s, 6H); 2.10 (s, 3H); 2.42 and 2.44 (2 s, 3H); 2.60 (s, 3H); 2.63 and 2.65 (2 s, 3H); 3.04 (br d, 1H); 3.45 (br s, 1H); 3.56 (s, 2H); 3.78 and 3.82 (2 s, 2H); 3.84 (s, 3H); 6.85 (s, 1H); 7.05-7.48 (m, 6H).

The Following Examples were Prepared from the Corresponding Carboxylic Acids and Amines by an Analogous Process:

(The intermediates {2-[(2,4,6-trichlorobenzenesulfonyl)-methylamino]-ethoxy}-acetic acid, 2-(1-(2,4,6-trichlorobenzenesulfonyl)-pyrrolidin-3-yloxy)-acetic acid and 2-[1-(2,4,6-trichlorobenzenesulfonyl)-piperidin-3-yloxy]-acetic acid were prepared analogously to {2-[(4-methoxy-2,3,6-trimethylbenzenesulfonyl)-methylamino]-ethoxy}-acetic acid (Intermediate C).

Example 598

N-[4-(Dimethylaminophenylmethyl)-cyclohexyl]-2-{2-[methyl-(2,4,6-trichlorobenzenesulfonyl)-amino]-ethoxy}-acetamide ( )

Yield: 135 mg (44%)

$^1$H-NMR (DMSO-d$_6$): 0.68-1.08 (m, 1H); 1.08-1.33 (m, 2H); 1.35 (s, 3H); 1.40-1.72 (m, 2H); 1.75-1.92 (m, 1H); 1.96 and 1.99 (2 s, 6H), 2.00-2.12 (m, 1H); 2.87 and 2.88 (2 s, 3H); 3.40-3.54 (m, 2H); 3.55-3.64 (m, 2H); 3.76-3.80 (m, 1H); 3.81 and 3.84 (2 s, 2H); 7.07-7.20 (m, 2H); 7.20-7.40 (m, 4H); 7.91 and 7.93 (2 s, 2H).

Example 599

N-{4-[(Benzylmethylamino)-phenylmethyl]-cyclohexyl}-2-{2-[methyl-(2,4,6-trichlorobenzenesulfonyl)-amino]-ethoxy}-acetamide ( )

Yield: 275 mg (51%)

$^1$H-NMR (DMSO-d$_6$): 0.68-1.12 (m, 1H); 1.20-1.84 (m, 4H); 1.87 and 1.93 (2 s, 4H); 2.00-2.40 (m, 2H); 2.86 and 2.87 (2 s, 3H); 3.16-3.32 (m, 2H); 3.36-3.64 (m, 5H); 3.82 and 3.86 (2 s, 2H); 7.15-7.40 (m, 11H); 7.86 and 7.90 (2 s, 2H). 3H was not to be identified $^{13}$C-NMR (DMSO-d$_6$): 24.8; 25.2; 26.3; 28.3; 29.0; 29.4; 31.8; 32.0; 34.1; 34.2; 36.2; 36.6; 36.7; 45.0; 47.8; 49.0; 49.2; 57.8; 58.0; 67.4; 67.5; 69.6; 72.4; 126.6; 126.7; 127.7; 128.0; 128.1; 128.2; 129.0; 131.2; 131.3; 134.1; 135.2; 136.0; 136.3; 137.2; 139.8; 167.6.

Example 600

2-{2-[Cyclopropyl-(2,4,6-trichlorobenzenesulfonyl)-amino]-ethoxy}-N-[4-(dimethylaminophenylmethyl)-cyclohexyl]-acetamide ( )

Yield: 317 mg (51%)

$^1$H-NMR (DMSO-d$_6$): 0.29-0.39 (m, 2H); 0.59-0.69 (m, 2H); 0.70-2.10 (m, 9H); 1.94 (s, 3H, 1.99 (s, 3H); 2.60 (m, 1H); 3.04 (d, 0.5H); 3.32-3.55 (m, 1.5H); 3.55-3.70 (m, 4H); 3.72-3.85 (m, 1H); 3.90 (s, 1H); 3.87 (s, 1H); 7.00-7.45 (m, 6H); 7.93 (s, 1H); 7.96 (s, 1H).

Example 601

2-{2-[Methyl-(2,4,6-trichlorobenzenesulfonyl)-amino]-ethoxy}-N-[4-(phenylpiperidin-1-yl-methyl)-cyclohexyl]-acetamide ( )

Yield: 206 mg (33%)

$^1$H-NMR (DMSO-d$_6$): 0.71-2.25 (m, 21H); 2.87-3.86 (m, 10H); 7.07-7.37 (m, 5H); 7.91 (d, 1.2H); 7.91 (d, 0.7H).

This is a cis/trans isomer mixture in the ratio of approx. 2:1.

Example 602

2-{2-[Cyclopropyl-(2,4,6-trichlorobenzenesulfonyl)-amino]-ethoxy}-N-[4-(phenylpiperidin-1-ylmethyl)-cyclohexyl]-acetamide ( )

Yield: 358 mg (58%)

$^1$H-NMR (DMSO-d$_6$): 0.32-0.39 (m, 2H); 0.60-0.68 (m, 2H); 0.70-2.35 (m, 15H); 2.55-2.68 (m, 2H); 3.10 (d, 0.5H); 3.37 (d, 0.5H); 3.50 (m, 1H); 3.60-3.65 (m, 6H); 3.75 (m, 1H); 3.88 (s, 1H); 3.91)s, 1H); 7.03-7.35 (m, 6H); 7.91 (s, 1H); 7.933 (s, 1H).

Example 603

2-{2-[Cyclopropyl-(2,4,6-trichlorobenzenesulfonyl)-amino]-ethoxy}-N-[4-(phenylpyrrolidin-1-ylmethyl)-cyclohexyl]-acetamide ( )

Yield: 152 mg (23%)

$^1$H-NMR (DMSO-d$_6$): 0.29-0.32 (m, 2H); 0.59-0.65 (m, 2H); 0.65-1.90 (m, 14H); 2.10-2.45 (m, 4H); 3.15-3.30 (m, 2H); 3.55-3.73 (m, 4H); 3.86 (m, 2H); 7.15-7.35 (m, 6H); 7.92 (s, 2H).

$^{13}$C-NMR (DMSO-d$_6$): 6.2; 22.6; 25.7; 28.0; 29.4; 31.8; 32.1; 47.6; 48.8; 50.9; 54.8; 67.0; 69.7; 72.9; 127.5; 128.9; 131.4; 134.6; 135.7; 137.6; 167.6.

This is probably only one of the two possible cis/trans isomers.

Example 604

N-{4-[(Benzylmethylamino)-phenylmethyl]-cyclohexyl}-2-{2-[cyclopropyl-(2,4,6-trichlorobenzenesulfonyl)-amino]-ethoxy}-acetamide Yield: 287 mg (56%)
$^1$H-NMR (DMSO-$d_6$): 0.30-0.36 (m, 2H); 0.59-0.68 (m, 2H); 0.69-2.00 (m, 9H); 1.84 (s, 1.5H); 1.93 (s, 1.5H); 2.52-2.68 (m, 1H); 3.15-3.45 (m, 4H); 3.50-3.75 (m, 4H); 3.89 (s, 1H); 3.92 (s, 1H); 7.10-7.41 (11H); 7.84 (s, 1H); 7.91 (s, 1H).

Example 605

2-{2-[Cyclopropyl-(2,4,6-trichlorobenzenesulfonyl)-amino]-ethoxy}-N-[4-(morpholin-4-yl-phenylmethyl)-cyclohexyl]-acetamide ( )

Yield: 85 mg (38%)
$^1$H-NMR (DMSO-$d_6$): 0.30-0.38 (m, 2H); 0.57-0.68 (m, 2H); 0.70-2.30 (m, 9H); 2.52-2.65 (m, 1H); 3.12 (d, 0.5H); 3.35 (d, 0.5H); 3.37-3.58 (m, 6H); 3.58-3.72 (m, 6H); 3.75-3.90 (m, 1H); 3.88 (s, 1H); 3.91 (s, 1H); 7.02-7.40 (m, 5H); 7.91 (s, 1H); 7.94 (s, 1H).

Example 606

2-{2-[Methyl-(2,4,6-trichlorobenzenesulfonyl)-amino]-ethoxy}-N-[4-(phenylpyrrolidin-1-yl-methyl)-cyclohexyl]-acetamide Yield: 354 mg (57%)
$^1$H-NMR (DMSO-$d_6$): 0.60-2.31 (m, 18H); 2.85 (2 s, 3H); 3.10-3.79 (m, 8H); 7.02-37 (m, 5H); 7.90 (d, 1H); 7.92 (d, 1H).

Example 607

2-{2-[Methyl-(2,4,6-trichlorobenzenesulfonyl)-amino]-ethoxy}-N-[4-(morpholin-4-ylphenylmethyl)-cyclohexyl]-acetamide Yield: 360 mg (57%)
$^1$H-NMR (DMSO-$d_6$): 0.75-2.35 (m, 9H); 2.89 (2 s, 3H); 3.35-3.65 (m, 12H); 3.83 (s, 2H); 3.85 (s, 2H); 7.05-7.35 (m, 6H); 7.89 (d, 1H); 7.90 (d, 1H).

Example 608

N-[4-(Dimethylaminophenylmethyl)-cyclohexyl]-2-[1-(2,4,6-trichlorobenzenesulfonyl)-piperidin-3-yloxy]-acetamide Yield: 467 mg (60%)
$^1$H-NMR (DMSO-$d_6$): 0.72-2.08 (18H); 3.02-3.85 (11H); 7.10-7.32 (m, 6H); 7.89 (d, 1H); 7.89 (d, 1H).

Example 609

N-[4-(Dimethylaminophenylmethyl)-cyclohexyl]-2-[1-(2,4,6-trichlorobenzenesulfonyl)-pyrrolidin-3-yloxy]-acetamide Yield: 490 mg (79%) 1H-NMR (DMSO-$d_6$): 0.70-2.10 (m, 11H); 2.00 (s, 6H); 3.03 (d, 0.5H); 3.33-3.57 (m, 5H); 3.72-3.85 (m, 2.5H); 4.16 (m, 1H); 7.08-7.38 (m, 6H); 7.88 (3 s, 2H).

Example 610

N-[4-(Morpholin-4-ylphenylmethyl)-cyclohexyl]-2-[1-(2,4,6-trichlorobenzenesulfonyl)-pyrrolidin-3-yloxy]-acetamide Yield: 280 mg (42%)
$^1$H-NMR (DMSO-$d_6$): 0.70-2.30 (m, 15H); 3.12 (d, 0.5H); 3.36-3.58 (m, 9.5H); 3.75-3.85 (m, 2H); 4.16 (m, 1H); 7.08-7.35 (m, 6H); 7.87 (3 s, 2H).

Examples 611, 612, 613

N-[4-(Dimethylaminophenylmethyl)-cyclohexyl]-2-[1-(2,4,6-trichlorobenzenesulfonyl)-pyrrolidin-2-ylmethoxy]-acetamide Yield: 620 mg (52%)
The isomer mixture obtained in this way was separated by medium pressure chromatography with EtOAc/cyclohexane (4:1).
nonpolar product
130 mg (21%)
$^1$H-NMR (DMSO-$d_6$): 0.90-1.92 (m, 12H); 1.94 and 1.96 (2 s, 6H); 2.00-2.12 (m, 1H); 3.30-3.48 (m, 5H); 3.76-3.84 (m, 1H); 3.77 (s, 2H); 4.16-4.26 (m, 1H); 7.06-7.12 (m, 2H); 7.20-7.36 (m, 4H); 7.92 (s, 2H).
$^{13}$C-NMR (DMSO-$d_6$): 23.8; 24.8; 24.9; 28.2; 40.6; 45.0; 45.4; 48.0; 59.8; 52.2; 59.3; 69.9; 71.9; 72.1; 126.7; 127.5; 129.1; 131.4; 135.6; 137.5; 167.5.
polar product 120 mg (19%)
$^1$H-NMR (DMSO-$d_6$): 0.70-1.98 (m, 12H); 1.99 (2 s, 6H); 2.01-2.10 (m, 1H); 3.03 (d, 1H, J=9.8 Hz); 3.35-3.47 (m, 4H); 3.72 (s, 2H); 3.75-3.81 (m, 1H); 4.12-4.20 (m, 1H); 7.12-7.16 (m, 2H); 7.22-7.36 (m, 4H); 7.88 (s, 2H).
$^{13}$C-NMR (DMSO-$d_6$): 23.7; 28.1; 28.2; 29.4; 31.8; 32.0; 36.8; 41.2; 47.8; 48.3; 59.2; 69.9; 72.0; 73.8; 126.6; 127.5; 129.0; 131.4; 133.9; 135.5; 136.4; 137.4; 167.5. 140 mg (22%) of mixed fractions were furthermore also isolated.

Example 614

N-[4-(Dimethylaminophenylmethyl)-cyclohexylmethyl]-2-{2-[(2,4,6-trichlorobenzenesulfonyl)-methylamino]-ethoxy}-acetamide Yield: 349 mg (48%)
$^1$H-NMR (DMSO-$d_6$): 0.60-1.96 (m, 7H); 1.99 (s, 8H); 2.04 (m, 1H); 2.88 (s, 3H); 2.93 (t, 2H); 2.96-3.14 (m, 1H); 3.47 (t, 2H); 3.60 (t, 2H); 3.83 (s, 2H); 7.13 (t, 2H); 7.20-7.27 (m, 1H); 7.29 (t, 2H); 7.47 (t, 1H); 7.88 (s, 2H).

Example 615

N-[3-(Dimethylaminophenylmethyl)-cyclopentyl]-2-{2-[(2,4,6-trichlorobenzenesulfonyl)-methylamino]-ethoxy}-acetamide Yield: 450 mg (52%)
$^1$H-NMR (DMSO-$d_6$): 1.15-2.00 (m, 8H); 1.99 and 2.00 (2 s, 6H); 2.84, 2.86 and 2.89 (3 s, 3H); 3.18 (m, 1H); 3.40-3.65

(m, 4H); 3.76; 3.80, 3.84 and 3.86 (4 s, 2H), 7.10-7.48 (m, 6H); 7.87, 7.88, 7.89 and 7.90 (4 d, 2H).

Example 616

N-[4-(1-Dimethylamino-2-phenylethyl)-cyclohexyl]-2-{2-[methyl-(2,4,6-trichlorobenzenesulfonyl)-amino]-ethoxy}-acetamide Yield: 173 mg (34%)
$^1$H-NMR (DMSO-$d_6$): 0.92-1.06 (m, 2H); 1.12-1.25 (m, 2H); 1.27-1.58 (m, 5H); 1.60-1.80 (m, 2H); 1.86-1.95 (m, 1H); 2.17 (d, 6H); 2.53-2.71 (m, 1H); 2.73-2.81 (m, 1H); 2.87 (2s, 3H); 3.45-3.53 (m, 2H); 3.56-3.62 (m, 2H); 3.83 (d, 2H); 7.06-7.33 (m, 5H); 7.86 (s, 1H); 7.89 (s, 1H).

Example 617

2-{2-[(4-Methoxy-2,3,6-trimethylbenzenesulfonyl)-methylamino]-ethoxy}-N-[4-(phenylpiperidin-1-yl-methyl)-cyclohexyl]-acetamide Yield: 323 mg (59%)
$^1$H-NMR (DMSO-$d_6$): 0.90-2.10 (m, 16H); 2.09 (s, 3H); 2.25 (s, 2H); 2.42 (s, 3H); 2.59 (s, 3H); (s, 3H); 2.65 (s, 3H); 3.09 (br s, 1H); 3.49 (br s, 1H); 3.56 (s, 2H); 3.78 (s, 2H); 3.84 (s, 3H); 6.85 (s, 1H); 7.00-7.50 (m, 6H).

Example 618

2-{2-[(4-Methoxy-2,3,6-trimethylbenzenesulfonyl)-methylamino]-ethoxy}-N-[4-(phenylpyrrolidin-1-yl-methyl)-cyclohexyl]-acetamide Yield: 323 mg (55%)
$^1$H-NMR (DMSO-$d_6$): 0.85-2.05 (m, 15H); 2.09 and 2.10 (2 s, 3H); 2.23-2.40 (m, 4H); 2.41 and 2.42 (2 s, 3H); 2.58 and 2.60 (2 s, 3H); 2.61 (s, 3H); 3.08 (d, 0.5H); 3.20-3.30 (m, 1.5H); 3.48 (t, 1H); 3.53 (t, 1H); 3.74 and 3.76 (2 s, 2H); 3.84 (s, 3H); 6.85 and 6.86 (2 s, 1H); 7.03-7.45 (m, 6H).

Example 619

2-{2-[(4-Methoxy-2,3,6-trimethylbenzenesulfonyl)-methylamino]-ethoxy}-N-[4-(morpholin-4-yl-phenylmethyl)-cyclohexyl]-acetamide Yield: 117 mg (32%)
$^1$H-NMR (DMSO-$d_6$): 0.70-2.05 (m, 11H); 2.09 (s, 3H); 2.12-2.38 (m, 4H); 2.42 and 2.44 (2 s, 3H); 2.59 (s, 3H); 2.63 and 2.64 (2 s, 3H); 3.10 (d, 0.7H); 3.30-3.38 (m, 1.3H); 3.40-3.65 (m, 6H); 3.79 and 3.82 (2 s, 2H); 3.84 (s, 3H); 6.85 (s, 1H); 7.05 (d, 1H); 7.10-7.45 (m, 5H).

Example 620

N-[4-(Dimethylaminophenylmethyl)-cyclohexyl]-3-{[methyl-(2,4,6-trichlorobenzenesulfonyl)-amino]-methoxy}-propionamide Yield: 380 mg (64%)
$^1$H-NMR (DMSO-$d_6$): 0.69-2.11 (m, 10H); 1.99 (s, 6H); 2.28 (t, 1H); 2.33 (t, 1H); 2.79 (s, 3H); 3.03 (d, 0.5H); 3.58-3.63 (m, 2H); 3.70-3.79 (m, 0.5H); 4.77 (s, 2H); 7.12-7.36 (m, 5H); 7.63 (d, 0.5H); 7.70 (d, 0.5H); 7.89 (s, 1H); 7.90 (s, 1H).

Example 621

N-[4-(Dimethylaminophenylmethyl)-cyclohexylmethyl]-2-[1-(2,4,6-trichlorobenzenesulfonyl)-piperidin-3-yloxy]-acetamide Yield: 464 mg (73%)
$^1$H-NMR (DMSO-$d_6$): 0.60-1.90 (m, 16H); 2.00 (s, 6H); 2.93 (t, 1H); 3.01 (br t, 1H); 3.12-3.26 (m, 2H); 3.43-3.56 (m, 2H); 3.842 and 3.847 (2 s, 2H); 7.15 (t, 2H); 7.25 (d, 1H); 7.31 (t, 2H); 7.43-7.50 (m, 1H); 7.859 and 7.861 (2 s, 2H).

Example 622

N-[4-(Dimethylaminophenylmethyl)-cyclohexylmethyl]-2-[1-(2,4,6-trichlorobenzenesulfonyl)-pyrrolidin-2-ylmethoxy]-acetamide Yield: 330 mg (74%)
$^1$H-NMR (DMSO-$d_6$): 0.58-1.93 (m, 14H); 1.98 (s, 6H); 2.91 (t, 1H); 3.00 (d, 1H); 3.35-3.48 (m, 4H); 3.74 (s, 2H); 4.10-4.19 (m, 1H); 7.13 (t, 2H, J=6.5 Hz); 7.18-7.36 (m, 3H); 7.38-7.49 (m, 1H); 7.87 (s, 2H).

Example 623

N-[4-(Dimethylaminophenylmethyl)-cyclohexylmethyl]-2-{2-[(4-methoxy-2,3,6-trimethylbenzenesulfonyl)-methylamino]-ethoxy}-acetamide Yield: 451 mg (78%)
$^1$H-NMR (DMSO-$d_6$): 1.10-2.10 (10H, m); 1.98 (s, 6H); 2.08 (s, 3H); 2.40 (s, 3H); 2.55 (s, 3H); 2.62 (s, 3H); 2.90-3.05 (m, 3H); 3.27-3.39 (m, 2H); 3.55 (t, 2H); 3.80 (s, 2H); 3.84 (s, 3H); 6.80 (s, 1H); 7.10-7.30 (m, 5H); 7.50-7.60 (m, 1H).

Example 624

N-[4-(Dimethylaminophenylmethyl)-cyclohexylmethyl]-3-{[methyl-(2,4,6-trichlorobenzenesulfonyl)-amino]-methoxy}-propionamide Yield: 84 mg (26%)
$^1$H-NMR (CDCl$_3$): 0.76-1.89 (m, 10H); 2.08 (s, 2H); 2.10 (s, 4H) 2.45 (t, 2H); 2.87 (s, 3H); 3.00 (d, 1.4H); 3.08 (t, 1H); 3.33 (d, 0.6H); 3.80 (t, 2H); 4.83 (s, 2H); 5.86-5.92 (m, 1H); 7.08-7.32 (m, 5H); 7.470 (s, 1H); 7.472 (s, 1H).

The following biological data were recorded for the individually synthesized compounds. The assays are described below. The numerical values are stated in % inhibition.

TABLE 2

| Molecular pharmacology data for selected individual compounds | | |
|---|---|---|
| Example | µ receptor | 5-HT reuptake |
| 597 | 87 | n.d. |
| 598 | 91 | 75 |
| 599 | 91 | 33 |
| 600 | 95 | 60 |
| 601 | 45 | 75 |
| 602 | 55 | 51 |
| 603 | 45 | 74 |
| 606 | 46 | 85 |

TABLE 2-continued

Molecular pharmacology data for selected individual compounds

| Example | µ receptor | 5-HT reuptake |
|---|---|---|
| 608 | 89 | 81 |
| 609 | 94 | 86 |
| 611 | 93 | 84 |
| 612 | 88 | 84 |
| 613 | 90 | 62 |
| 614 | 96 | 90 |
| 615 | 89 | 81 |
| 616 | 64 | n.d. |
| 617 | 29 | |
| 618 | 43 | |
| 619 | −11 | |
| 620 | 92 | |
| 621 | 90 | |
| 622 | 96 | |
| 623 | 93 | |
| 624 | 98 | |

The example compounds are defined in the following Table 3 by the amine and acid units employed. The units were linked to one another as described above via the amine function and the acid function, water being split off.

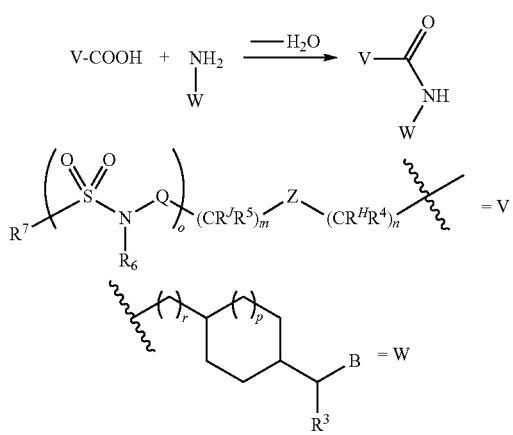

Parallel Synthesis Method C and Preparation of the Examples in Table 3

Examples 625-759 and 798 to 812

A solution of EDCI (1.5 equivalents), HOBT (1 equivalent) and DIPEA (2 equivalents) in MC (3 ml/mmol) was added to the acid unit (50 mg, 1 equivalent) and the amine unit (50-70 mg, 1.2 equivalents) and the mixture was stirred at RT for 16 h. After removal of the solvent in vacuo, the crude products were purified via column chromatography and analyzed by means of LC-MS.

In all cases, the conversion was detected by HPLC-MS (ESI). The molecular peak found in each case is stated in the table. The compounds have a purity of >90%, the main product being the compound according to the invention in all cases. By linking the units via the amine and acid functions mentioned, the compounds according to the invention were obtained. The name of the compound according to the invention can be generated from the structural formula obtained in this way via commercial software, such as, for example, Chemdraw Ultra 9.0, Cambridgesoft and is therefore part of the disclosure.

The following Table 3 shows further example compounds which were prepared by automated synthesis. The table is to be read in the same way as Table 1.

TABLE 3

Further examples

| Example | Amine | Acid | Mass | µ |
|---|---|---|---|---|
| 625 | AM17 | AC7 | 615.15 | 72 |
| 626 | AM25 | AC7 | 629.16 | 71 |
| 627 | AM17 | AC14 | 581.19 | 69 |
| 628 | AM17 | AC15 | 571.31 | 36 |
| 629 | AM17 | AC53 | 583.31 | 37 |
| 630 | AM17 | AC21 | 649.18 | 72 |
| 631 | AM17 | AC46 | 641.16 | 88 |
| 632 | AM17 | AC39 | 597.32 | 68 |
| 633 | AM17 | AC46 | 655.18 | 91 |
| 634 | AM17 | AC10 | 581.19 | 68 |
| 635 | AM17 | AC61 | 627.15 | 78 |
| 636 | AM27 | AC7 | 659.18 | 8 |
| 637 | AM26 | AC7 | 657.20 | 35 |
| 638 | AM16 | AC7 | 631.14 | 2 |
| 639 | AM22 | AC7 | 645.16 | 3 |
| 640 | AM24 | AC7 | 657.20 | 27 |
| 641 | AM25 | AC14 | 595.20 | 66 |
| 642 | AM25 | AC15 | 585.32 | 54 |
| 643 | AM25 | AC10 | 595.20 | 76 |
| 644 | AM25 | AC61 | 641.16 | 59 |
| 645 | AM25 | AC53 | 597.32 | 38 |
| 646 | AM25 | AC21 | 663.19 | 49 |
| 647 | AM17 | AC47 | 597.32 | 49 |
| 648 | AM25 | AC47 | 611.34 | 95 |
| 649 | AM25 | AC39 | 611.34 | 67 |
| 650 | AM17 | AC38 | 641.16 | 92 |
| 651 | AM25 | AC38 | 655.18 | 83 |
| 652 | AM17 | AC28 | 611.34 | 70 |
| 653 | AM17 | AC29 | 655.18 | 94 |
| 654 | AM17 | AC33 | 611.34 | 53 |
| 655 | AM25 | AC33 | 625.35 | 38 |
| 656 | AM25 | AC46 | 655.18 | 89 |
| 657 | AM25 | AC28 | 625.35 | 84 |
| 658 | AM25 | AC29 | 669.20 | 88 |
| 659 | AM25 | AC32 | 669.20 | 79 |
| 660 | AM27 | AC14 | 625.21 | 4 |
| 661 | AM26 | AC14 | 623.24 | 21 |
| 662 | AM27 | AC15 | 615.33 | 3 |
| 663 | AM26 | AC15 | 613.35 | 26 |
| 664 | AM27 | AC10 | 625.21 | 5 |
| 665 | AM26 | AC10 | 623.24 | 18 |
| 666 | AM27 | AC61 | 671.18 | 6 |
| 667 | AM26 | AC61 | 669.20 | 32 |
| 668 | AM27 | AC53 | 627.33 | 10 |
| 669 | AM26 | AC53 | 625.35 | 20 |
| 670 | AM27 | AC21 | 693.20 | 7 |
| 671 | AM26 | AC21 | 691.22 | 9 |
| 672 | AM27 | AC46 | 685.19 | 16 |
| 673 | AM26 | AC46 | 683.21 | 71 |
| 674 | AM27 | AC47 | 641.35 | 7 |
| 675 | AM26 | AC47 | 639.37 | 37 |
| 676 | AM27 | AC39 | 641.35 | 10 |
| 677 | AM26 | AC39 | 639.37 | 60 |
| 678 | AM27 | AC33 | 655.37 | 6 |
| 679 | AM26 | AC32 | 697.23 | 51 |
| 680 | AM16 | AC14 | 597.18 | 4 |
| 681 | AM16 | AC15 | 587.30 | 10 |
| 682 | AM28 | AC15 | 600.33 | 36 |
| 683 | AM16 | AC10 | 597.18 | 5 |
| 684 | AM28 | AC10 | 610.21 | 29 |
| 685 | AM16 | AC61 | 643.14 | 3 |
| 686 | AM28 | AC61 | 656.18 | 30 |
| 687 | AM16 | AC53 | 599.30 | 6 |
| 688 | AM28 | AC53 | 612.33 | 20 |
| 689 | AM16 | AC21 | 665.17 | 6 |
| 690 | AM28 | AC21 | 678.20 | 26 |
| 691 | AM16 | AC46 | 657.16 | 58 |
| 692 | AM28 | AC46 | 670.19 | 65 |
| 693 | AM16 | AC47 | 613.32 | 9 |
| 694 | AM16 | AC39 | 613.32 | 10 |
| 695 | AM28 | AC39 | 626.35 | 27 |

TABLE 3-continued

Further examples

| Example | Amine | Acid | Mass | μ |
|---|---|---|---|---|
| 696 | AM27 | AC38 | 685.19 | 21 |
| 697 | AM26 | AC38 | 683.21 | 76 |
| 698 | AM16 | AC38 | 657.16 | 40 |
| 699 | AM16 | AC28 | 627.33 | 15 |
| 700 | AM16 | AC29 | 671.18 | 27 |
| 701 | AM16 | AC33 | 627.33 | 2 |
| 702 | AM28 | AC33 | 640.37 | 19 |
| 703 | AM16 | AC32 | 671.18 | 19 |
| 704 | AM28 | AC14 | 610.21 | 27 |
| 705 | AM22 | AC14 | 611.20 | 8 |
| 706 | AM22 | AC10 | 611.20 | 7 |
| 707 | AM22 | AC46 | 671.18 | 28 |
| 708 | AM28 | AC47 | 626.35 | 29 |
| 709 | AM22 | AC39 | 627.33 | 8 |
| 710 | AM22 | AC38 | 671.18 | 24 |
| 711 | AM22 | AC28 | 641.35 | 33 |
| 712 | AM22 | AC29 | 685.19 | 40 |
| 713 | AM22 | AC32 | 665.25 | 14 |
| 714 | AM28 | AC7 | 644.18 | 52 |
| 715 | AM23 | AC7 | 673.19 | 10 |
| 716 | AM23 | AC14 | 639.23 | 13 |
| 717 | AM24 | AC14 | 623.24 | 22 |
| 718 | AM22 | AC15 | 601.32 | 4 |
| 719 | AM23 | AC15 | 629.35 | 6 |
| 720 | AM24 | AC15 | 613.35 | 26 |
| 721 | AM23 | AC10 | 639.23 | 7 |
| 722 | AM24 | AC10 | 623.24 | 32 |
| 723 | AM24 | AC61 | 669.20 | 35 |
| 724 | AM22 | AC53 | 613.32 | 8 |
| 725 | AM23 | AC53 | 641.35 | 10 |
| 726 | AM24 | AC53 | 625.35 | 23 |
| 727 | AM22 | AC21 | 679.19 | 10 |
| 728 | AM23 | AC21 | 707.22 | 12 |
| 729 | AM24 | AC46 | 683.21 | 79 |
| 730 | AM22 | AC47 | 627.33 | 11 |
| 731 | AM24 | AC47 | 639.37 | 49 |
| 732 | AM28 | AC38 | 670.19 | 61 |
| 733 | AM27 | AC28 | 655.37 | 21 |
| 734 | AM26 | AC28 | 653.39 | 80 |
| 735 | AM28 | AC28 | 640.37 | 56 |
| 736 | AM24 | AC28 | 653.39 | 34 |
| 737 | AM27 | AC29 | 699.21 | 22 |
| 738 | AM26 | AC29 | 697.23 | 77 |
| 739 | AM28 | AC29 | 684.21 | 62 |
| 740 | AM26 | AC33 | 653.39 | 15 |
| 741 | AM27 | AC32 | 699.21 | 16 |
| 742 | AM28 | AC32 | 684.21 | 29 |
| 743 | AM22 | AC61 | 657.16 | 8 |
| 744 | AM22 | AC33 | 641.35 | 13 |
| 745 | AM23 | AC61 | 685.19 | 8 |
| 746 | AM24 | AC21 | 691.22 | 8 |
| 747 | AM23 | AC46 | 699.21 | 23 |
| 748 | AM23 | AC47 | 655.37 | 20 |
| 749 | AM23 | AC39 | 655.37 | 12 |
| 750 | AM24 | AC39 | 639.37 | 52 |
| 751 | AM23 | AC38 | 699.21 | 32 |
| 752 | AM24 | AC38 | 683.21 | 82 |
| 753 | AM23 | AC28 | 669.38 | 17 |
| 754 | AM23 | AC29 | 713.22 | 2 |
| 755 | AM24 | AC29 | 697.23 | 62 |
| 756 | AM23 | AC33 | 669.38 | 5 |
| 757 | AM24 | AC33 | 653.39 | 32 |
| 758 | AM23 | AC32 | 713.22 | 25 |
| 759 | AM24 | AC32 | 697.23 | 87 |
| 798 | AM33 | AC15 | 586.32 | 19 |
| 799 | AM35 | AC15 | 604.31 | 16 |
| 800 | AM35 | AC28 | 644.34 | 7 |
| 801 | AM37 | AC15 | 614.35 | 21 |
| 802 | AM36 | AC28 | 640.37 | 27 |
| 803 | AM36 | AC15 | 600.33 | 13 |
| 804 | AM34 | AC15 | 604.31 | 9 |
| 805 | AM34 | AC28 | 644.34 | 4 |
| 806 | AM37 | AC28 | 654.38 | 12 |
| 807 | AM33 | AC28 | 626.35 | 11 |
| 808 | AM34 | AC90 | 702.22 | 12 |
| 809 | AM35 | AC90 | 702.22 | 6 |
| 810 | AM33 | AC90 | 684.23 | 19 |
| 811 | AM37 | AC90 | 712.26 | 20 |
| 812 | AM36 | AC90 | 698.25 | 37 |

Method 7

General Synthesis Equation, Acid Units AC 70-89

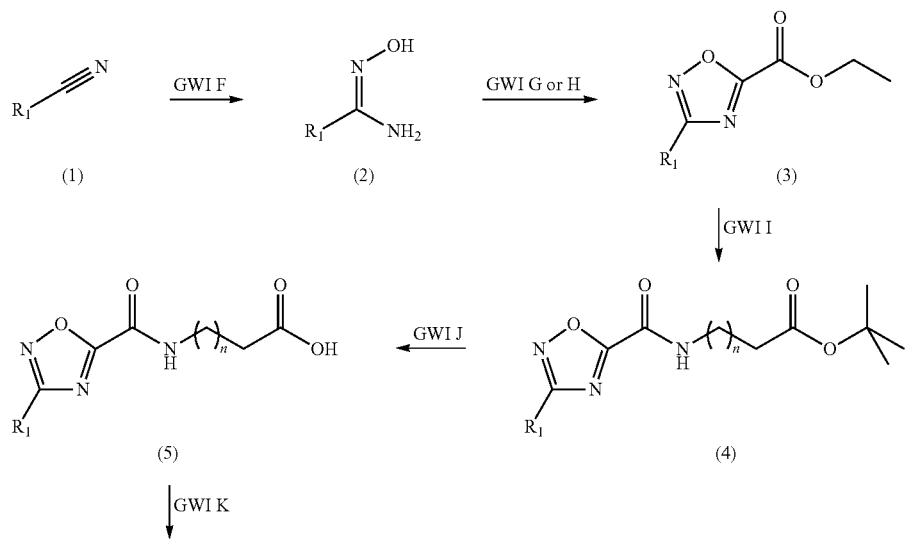

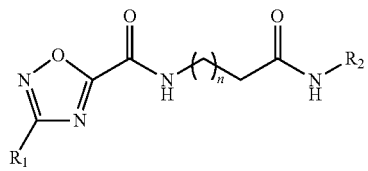

(6)

General Synthesis Processes

In Method GWI F, the nitrites (1) are reacted using hydroxylamine hydrochloride in the presence of an organic or inorganic base, for example sodium carbonate, potassium carbonate, sodium bicarbonate, sodium hydroxide, potassium hydroxide, sodium ethanolate, diisopropylethylamine, triethylamine, pyridine, diethylamine or DBU, and a solvent, for example methanol, ethanol, dioxane, methanol/water, ethanol/water, dioxane/water, THF, diethyl ether, methylene chloride or DMF, in a temperature range between RT and the reflux temperature to give the corresponding amide oximes (2).

Amide oximes (2) can furthermore be prepared by known methods, as described e.g. by F. Eloy & R. Lenaers in Chemical Reviews 1962, page 155-183.

In Method GWI G & H, the amide oximes (2) are reacted using oxalic acid monoester chlorides in an organic solvent, for example THF, diethyl ether, acetonitrile, methylene chloride, dioxane or DMF, optionally in the presence of an organic base, for example pyridine, imidazole, triethylamine or diisopropylethylamine, to give the oxadiazole esters (3).

In Method GWI I, oxadiazole esters (3) are reacted with amino acid esters directly or their salts in the presence of an organic base, for example triethylamine, diisopropylethylamine, pyridine, DBU or imidazole, in an organic solvent, for example acetonitrile, methanol, ethanol, dioxane, methylene chloride, THF, diethyl or DMF, to give the amides (4).

In Method GWI J, tert-butyl esters (4) are reacted in an ester cleavage reaction of organic acids, such as trifluoroacetic acid, methanesulfonic acid, HCl/MeOH or HCl/dioxane, or aqueous inorganic acids, such as hydrochloric acid or sulfuric acid, in organic solvents, such as methanol, dioxane, methylene chloride, THF or diethyl ether, also in the presence of water, to give the free acids (5).

Corresponding acids can furthermore give the acid stages of the general formula (5) in an ester cleavage using organic acids, such as trifluoroacetic acid, or aqueous inorganic acids, such as hydrochloric acid, or using aqueous inorganic bases, such as lithium hydroxide, potassium hydroxide, sodium hydroxide, sodium carbonate, sodium bicarbonate or potassium carbonate, in organic solvents, such as methanol, dioxane, methylene chloride, THF, diethyl ether or these solvents as mixtures.

In Method GWI K, the carboxylic acids (5) are reacted in an amide formation using primary or secondary amines in the presence of dehydrating agents, such as sodium sulfate or magnesium sulfate, phosphorus oxide or reagents such as, for example, CDI, DCC (optionally bonded to a polymer), TBTU, EDCI, PyBOP or PFPTFA, also in the presence of HOAt or HOBt and an organic base, for example DIPEA or pyridine, in an organic solvent, such as THF, methylene chloride, diethyl ether, dioxane, DMF or acetonitrile, to give the final products of the general formula (6).

General Working Instructions (GWI F to GWI J):

GWI F (Amide Oxime Preparation):

A solution of hydroxylamine hydrochloride (5 eq.) in water (approx. 0.3 ml/mmol of hydroxylamine hydrochloride) is added to a solution of the corresponding nitrile (1, 1 eq.) in methanol (approx. 3 ml/mmol of nitrile). Solid sodium carbonate (5 eq.) is cautiously added to the reaction mixture and the mixture is then heated under reflux until the conversion is complete according to TLC (approx. 4 hours).

For working up, diethyl ether and water are added to the reaction mixture until 2 phases form. The undissolved solid is filtered out. The organic phase is separated off and the aqueous extracted 3× with MC. The combined organic phases are dried over magnesium sulfate, filtered and concentrated. The crude product is employed further without further purification.

GWI G (Oxadiazole Preparation):

A solution of ethyl chloro(oxo)acetate (1.1 eq.) in tetrahydrofuran (approx. 0.4 ml/mmol of ethyl chloro(oxo)acetate) is slowly added dropwise to a solution of the corresponding amide oxime (2, 1 eq.) in tetrahydrofuran (approx. 2 ml/mmol of amide oxide). The reaction mixture is then heated under reflux until the conversion is complete according to TLC (approx. 2.5 hours).

For working up, the solid which has precipitated out is filtered out and the reaction mixture is concentrated. After recrystallization of the mother liquor from ethanol, the desired oxadiazole is obtained.

GWI H (Oxadiazole Preparation):

A solution of ethyl chloro(oxo)acetate (2.4 eq.) in methylene chloride (approx. 0.2 ml/mmol of ethyl chloro(oxo)acetate) is slowly added dropwise to a solution of the corresponding amide oxime (2, 1 eq.) in methylene chloride (approx. 1.3 ml/mmol of amide oxide) and pyridine (2.5 eq.). The reaction mixture is stirred at room temperature for approx. 24 h.

After concentration of the reaction mixture and purification of the residue by column chromatography (SiO₂, diethyl ether/hexane), the desired oxadiazole is obtained.

GWI I (Amidation):

The corresponding amine (1.5 eq.) and ethanol (approx. 15.0 ml/mmol of oxadiazole ester) are added to the corresponding oxadiazole ester (3, 1 eq.). The reaction mixture is stirred at room temperature for approx. 12 h.

After concentration of the reaction mixture and recrystallization of the residue from ethanol, the desired amide is obtained. Should a recrystallization not be possible, the crude product was purified by column chromatography (SiO₂, diethyl ether/hexane).

GWI I (Ester Cleavage):

Trifluoroacetic acid (20 eq.) is added dropwise to a solution of the corresponding tert-butyl ester (4, 1 eq.) in methylene chloride (approx. 1.5 ml/mmol of tert-butyl ester) and the reaction mixture is stirred at room temperature until the conversion is complete according to TLC. For working up, the reaction mixture is concentrated on a rotary evaporator. The crude product is employed further without further purification.

Parallel Synthesis Method K
GWI K (Amidation):

For the amidation, stock solutions of the corresponding acid (0.1 M in methylene chloride), of the amine (0.1 M in methylene chloride) and of carbonyldiimidazole (0.105 M in methylene chloride) are prepared. A mixture of 1 ml of the corresponding acid stock solution and 1 ml of the carbonyldiimidazole stock solution is shaken at room temperature for 30 minutes, before 1 ml of the corresponding amine stock solution is added. The mixture is shaken at room temperature for 16 h.

For working up, the reaction mixture is washed with 3 ml of water and 3 ml of saturated sodium chloride solution and finally concentrated.

The compounds synthesized by Method K are summarized in Table 4:

TABLE 4

Example compounds synthesized by method K

| Example | Name | Mass |
|---|---|---|
| 760 | 3-(3,5-Dichloro-phenyl)-[1,2,4]oxadiazole-5-carboxylic acid {[4-(dimethylamino-phenyl-methyl)-cyclohexylcarbamoyl]-methyl}-amide | 529.16 |
| 761 | 3-(3,5-Dichloro-phenyl)-[1,2,4]oxadiazole-5-carboxylic acid {2-[4-(dimethylamino-phenyl-methyl)-cyclohexylcarbamoyl]-ethyl}-amide | 543.18 |
| 762 | 3-(2,4-Dichloro-6-methyl-phenyl)-[1,2,4]oxadiazole-5-carboxylic acid {[4-(dimethylamino-phenyl-methyl)-cyclohexylcarbamoyl]-methyl}-amide | 543.18 |
| 763 | 3-(2-Methoxy-phenyl)-[1,2,4]oxadiazole-5-carboxylic acid {[4-(dimethylamino-phenyl-methyl)-cyclohexylcarbamoyl]-methyl}-amide | 491.25 |
| 764 | 3-Thiophen-2-yl-[1,2,4]oxadiazole-5-carboxylic acid {[4-(dimethylamino-phenyl-methyl)-cyclohexylcarbamoyl]-methyl}-amide | 467.20 |
| 765 | 3-(4-Trifluoromethyl-phenyl)-[1,2,4]oxadiazole-5-carboxylic acid {[4-(dimethylamino-phenyl-methyl)-cyclohexylcarbamoyl]-methyl}-amide | 529.23 |
| 766 | 3-(4-tert-Butyl-phenyl)-[1,2,4]oxadiazole-5-carboxylic acid {[4-(dimethylamino-phenyl-methyl)-cyclohexylcarbamoyl]-methyl}-amide | 517.31 |
| 767 | 3-(5-Fluoro-2-methyl-phenyl)-[1,2,4]oxadiazole-5-carboxylic acid {[4-(dimethylamino-phenyl-methyl)-cyclohexylcarbamoyl]-methyl}-amide | 493.25 |
| 768 | 3-Benzo[1,3]dioxol-5-yl-[1,2,4]oxadiazole-5-carboxylic acid {2-[4-(dimethylamino-phenyl-methyl)-cyclohexylcarbamoyl]-ethyl}-amide | 519.25 |
| 769 | 3-Benzenesulfonylmethyl-[1,2,4]oxadiazole-5-carboxylic acid {[4-(dimethylamino-phenyl-methyl)-cyclohexylcarbamoyl]-methyl}-amide | 539.22 |
| 770 | 3-(2,6-Dichloro-phenyl)-[1,2,4]oxadiazole-5-carboxylic acid {[4-(dimethylamino-phenyl-methyl)-cyclohexylcarbamoyl]-methyl}-amide | 529.16 |
| 771 | 3-Pyridin-2-yl-[1,2,4]oxadiazole-5-carboxylic acid {2-[4-(dimethylamino-phenyl-methyl)-cyclohexylcarbamoyl]-ethyl}-amide | 476.25 |
| 772 | 3-(2,4,6-Trimethyl-phenyl)-[1,2,4]oxadiazole-5-carboxylic acid {[4-(dimethylamino-phenyl-methyl)-cyclohexylcarbamoyl]-methyl}-amide | 503.29 |
| 773 | 3-(2,4-Dichloro-phenyl)-[1,2,4]oxadiazole-5-carboxylic acid {2-[4-(dimethylamino-phenyl-methyl)-cyclohexylcarbamoyl]-ethyl}-amide | 543.18 |
| 774 | 3-(3,4-Dimethoxy-phenyl)-[1,2,4]oxadiazole-5-carboxylic acid {2-[4-(dimethylamino-phenyl-methyl)-cyclohexylcarbamoyl]-ethyl}-amide | 535.28 |
| 775 | 3-(3,4-Dimethoxy-phenyl)-[1,2,4]oxadiazole-5-carboxylic acid {[4-(dimethylamino-phenyl-methyl)-cyclohexylcarbamoyl]-methyl}-amide | 521.26 |
| 776 | 3-Thiophen-2-yl-[1,2,4]oxadiazole-5-carboxylic acid {2-[4-(dimethylamino-phenyl-methyl)-cyclohexylcarbamoyl]-ethyl}-amide | 481.21 |
| 777 | 3-(4-Trifluoromethyl-phenyl)-[1,2,4]oxadiazole-5-carboxylic acid {[4-(dimethylamino-thiophen-2-yl-methyl)-cyclohexylcarbamoyl]-methyl}-amide | 535.19 |
| 778 | 3-(4-Trifluoromethyl-phenyl)-[1,2,4]oxadiazole-5-carboxylic acid [({4-[dimethylamino-(3-fluoro-phenyl)-methyl]-cyclohexylmethyl}-carbamoyl)-methyl]-amide | 561.24 |
| 779 | 3-(4-tert-Butyl-phenyl)-[1,2,4]oxadiazole-5-carboxylic acid {[4-(dimethylamino-thiophen-2-yl-methyl)-cyclohexylcarbamoyl]-methyl}-amide | 523.26 |
| 780 | 3-Thiophen-2-yl-[1,2,4]oxadiazole-5-carboxylic acid [2-({4-[dimethylamino-(3-fluoro-phenyl)-methyl]-cyclohexylmethyl}-carbamoyl)-ethyl]-amide | 513.22 |
| 781 | 3-Benzenesulfonylmethyl-[1,2,4]oxadiazole-5-carboxylic acid [({4-[dimethylamino-(3-fluoro-phenyl)-methyl]-cyclohexylmethyl}-carbamoyl)-methyl]-amide | 571.23 |
| 782 | 3-(2-Methoxy-phenyl)-[1,2,4]oxadiazole-5-carboxylic acid {[4-(1-dimethylamino-3-phenyl-propyl)-cyclohexylcarbamoyl]-methyl}-amide | 519.28 |
| 783 | 3-Benzo[1,3]dioxol-5-yl-[1,2,4]oxadiazole-5-carboxylic acid {[4-(1-dimethylamino-3-phenyl-propyl)-cyclohexylcarbamoyl]-methyl}-amide | 533.26 |
| 784 | 3-Thiophen-2-yl-[1,2,4]oxadiazole-5-carboxylic acid {[4-(1-dimethylamino-3-phenyl-propyl)-cyclohexylcarbamoyl]-methyl}-amide | 495.23 |
| 785 | 3-(4-Trifluoromethyl-phenyl)-[1,2,4]oxadiazole-5-carboxylic acid {[4-(1-dimethylamino-3-phenyl-propyl)-cyclohexylcarbamoyl]-methyl}-amide | 557.26 |
| 786 | 3-(4-tert-Butyl-phenyl)-[1,2,4]oxadiazole-5-carboxylic acid {[4-(1-dimethylamino-3-phenyl-propyl)-cyclohexylcarbamoyl]-methyl}-amide | 545.34 |
| 787 | 3-(2-Methoxy-phenyl)-[1,2,4]oxadiazole-5-carboxylic acid [({4-[dimethylamino-(3-fluoro-phenyl)-methyl]-cyclohexylmethyl}-carbamoyl)-methyl]-amide | 523.26 |
| 788 | 3-(2,4-Dichloro-phenyl)-[1,2,4]oxadiazole-5-carboxylic acid {2-[4-(1-dimethylamino-3-phenyl-propyl)-cyclohexylcarbamoyl]-ethyl}-amide | 571.21 |
| 789 | 3-(3,4-Dimethoxy-phenyl)-[1,2,4]oxadiazole-5-carboxylic acid {2-[4-(1-dimethylamino-3-phenyl-propyl)-cyclohexylcarbamoyl]-ethyl}-amide | 563.31 |
| 790 | 3-(3,5-Dichloro-phenyl)-[1,2,4]oxadiazole-5-carboxylic acid {[4-(1-dimethylamino-3-phenyl-propyl)-cyclohexylcarbamoyl]-methyl}-amide | 557.20 |
| 791 | 3-Pyridin-2-yl-[1,2,4]oxadiazole-5-carboxylic acid {[4-(1-dimethylamino-3-phenyl-propyl)-cyclohexylcarbamoyl]-methyl}-amide | 490.27 |
| 792 | 3-Benzo[1,3]dioxol-5-yl-[1,2,4]oxadiazole-5-carboxylic acid {2-[4-(1-dimethylamino-3-phenyl-propyl)-cyclohexylcarbamoyl]-ethyl}-amide | 547.28 |
| 793 | 3-(2,6-Dichloro-phenyl)-[1,2,4]oxadiazole-5-carboxylic acid {[4-(1-dimethylamino-3-phenyl-propyl)-cyclohexylcarbamoyl]-methyl}-amide | 557.20 |

TABLE 4-continued

Example compounds synthesized by method K

| Example | Name | Mass |
|---|---|---|
| 794 | 3-(3,4-Dimethoxy-phenyl)-[1,2,4]oxadiazole-5-carboxylic acid {[4-(1-dimethylamino-3-phenyl-propyl)-cyclohexylcarbamoyl]-methyl}-amide | 549.30 |
| 795 | 3-(2,4-Dichloro-phenyl)-[1,2,4]oxadiazole-5-carboxylic acid {[4-(1-dimethylamino-3-phenyl-propyl)-cyclohexylcarbamoyl]-methyl}-amide | 557.20 |
| 796 | 3-(5-Fluoro-2-methyl-phenyl)-[1,2,4]oxadiazole-5-carboxylic acid {[4-(1-dimethylamino-3-phenyl-propyl)-cyclohexylcarbamoyl]-methyl}-amide | 521.28 |
| 797 | 3-Thiophen-2-yl-[1,2,4]oxadiazole-5-carboxylic acid {2-[4-(1-dimethylamino-3-phenyl-propyl)-cyclohexylcarbamoyl]-ethyl}-amide | 509.25 |

Investigation of the Activity of the Compounds of the Invention
Method for Determining the Affinity for the Human μ Opiate Receptor The receptor affinity for the human p opiate receptor is determined in a homogeneous set-up in microtitre plates. For this, dilution series of the substances to be tested are incubated with a receptor membrane preparation (15-40 μg of protein/250 μl of incubation batch) of CHO-K1 cells which express the human p opiate receptor (RB-HOM receptor membrane preparation from PerkinElmer Life Sciences, Zaventem, Belgium) in the presence of 1 nmol/l of the radioactive ligand [$^3$H]-naloxone (NET719, PerkinElmer Life Sciences, Zaventem, Belgium) and 1 mg of WGA-SPA-Beads (wheat germ agglutinin SPA beads from Amersham/Pharmacia, Freiburg, Germany) in a total volume of 250 μl for 90 minutes at room temperature. 50 mmol/l of Tris-HCl supplemented with 0.06% of bovine serum albumin is used as the incubation buffer. 100 μmol/l of naloxone are additionally added for determination of the non-specific binding. After the end of the ninety-minute incubation time, the microtitre plates are centrifuged for 20 minutes at 1,000 g and the radioactivity is measured in a β-counter (Microbeta-Trilux, PerkinElmer Wallac, Freiburg, Germany). The percentage displacement of the radioactive ligand from its binding to the human p opiate receptor is determined at a concentration of the test substances of 1 μmol/l and stated as the percentage inhibition of the specific binding. Starting from the percentage displacement by various concentrations of the test substances, $IC_{50}$ inhibitory concentrations which cause a 50 percent displacement of the radioactive ligand are calculated. By conversion by means of the Cheng-Prusoff relationship, $K_i$ values for the test substances are obtained.

Inhibition of Serotonin (5HT) Reuptake

In order to be able to carry out these in vitro studies, synaptosomes are freshly isolated from areas of the rat brain. In each case a so-called "$P_2$" fraction prepared in accordance with the instructions of Gray and Whittaker (E. G. Gray and V. P. Whittaker (1962) J. Anat. 76, 79-88) is prepared. For the NA uptake, these vesicular particles are isolated from the hypothalamus of male rat brains.

A detailed description of the method can be found in the literature (M. Ch. Frink, H.-H. Hennies, W. Englberger, M. Haurand and B. Wilffert (1996) Arzneim.-Forsch./Drug Res. 46 (III), 11, 1029-1036).

Functional Investigation on the Human Bradykinin 1 Receptor (B1R)

The agonistic or antagonistic action of substances can be determined on the bradykinin 1 receptor (B1R) of the human species and rats with the following assay. In accordance with this assay, the $Ca^{2+}$ inflow through the channel is quantified with the aid of a $Ca^{2+}$-sensitive dyestuff (type Fluo-4, Molecular Probes Europe BV, Leiden, Holland) in a fluorescent imaging plate reader (FLIPR, Molecular Devices, Sunnyvale, USA).

Method:

Chinese hamster ovary cells (CHO K1 cells) transfected stably with the human B1R gene (hB1R cells) or the B1R gene of the rat (rB1R cells) are used. For functional studies, these cells are plated out on black 96-well plates with a clear base (BD Biosciences, Heidelberg, Germany or Greiner, Frickenhausen, Germany) in a density of 20,000-35,000 cells/well. The cells are left overnight at 37° C. and 5% $CO_2$ in culture medium (hB1R cells: Nutrient Mixture Ham's F12, Gibco Invitrogen GmbH, Karlsruhe, Germany or DMEM, Sigma-Aldrich, Taufkirchen, Germany; rB1R cells: D-MEM/F12, Gibco Invitrogen GmbH, Karlsruhe, Germany) with 10 vol. % of FBS (foetal bovine serum, Gibco Invitrogen GmbH, Karlsruhe, Germany or PAN Biotech GmbH, Aidenbach, Germany).

On the following day, the cells are loaded for 60 min at 37° C. with 2.13 μM Fluo-4 (Molecular Probes Europe BV, Leiden, The Netherlands) in HBSS buffer (Hank's buffered saline solution, Gibco Invitrogen GmbH, Karlsruhe, Germany) with 2.5 mM probenecid (Sigma-Aldrich, Taufkirchen, Germany) and 10 mM HEPES (Sigma-Aldrich, Taufkirchen, Germany). The plates are then washed 2× with HBSS buffer, and HBSS buffer which additionally contains 0.1% of BSA (bovine serum albumin; Sigma-Aldrich, Taufkirchen, Germany), 5.6 mM glucose and 0.05% of gelatine (Merck KGaA, Darmstadt, Germany) is added. After a further incubation of 20 minutes at room temperature, the plates are inserted into the FLIPR for the $Ca^{2+}$ measurement. Alternatively, the plates are washed with buffer A (15 mM HEPES, 80 mM NaCl, 5 mM KCl, 1.2 mM $CaCl_2$, 0.7 mM $MgSO_4$, 2 g/l glucose, 2.5 mM probenecid), buffer A is added and the plates are loaded with 2.5 μM Fluo-4 and 0.025% of Pluronic F127 (Sigma-Aldrich, Taufkirchen, Germany). Thereafter, the cells are washed 2× with buffer A and incubated for 30 minutes with buffer A, which additionally contains 0.05% of BSA and 0.05% of gelatine, at room temperature and thereafter inserted into the FLIPR for the $Ca^{2+}$ measurement.

The $Ca^{2+}$-dependent fluorescence is measured before and after addition of substances ($\lambda_{ex}$=488 nm, $\lambda_{em}$=540 nm). Quantification is by measurement of the highest fluorescence intensity (FC, fluorescence counts) over time.

FLIPR Assay:

The FLIPR protocol consists of 2 additions of substance. Test substances (10 μM) are first pipetted on to the cells and the $Ca^{2+}$ inflow is compared with the control (hB1R: Lys-Des-Arg$^9$-bradykinin >=50 nM; rB1R: Des-Arg$^9$-bradykinin 10 μM). This gives the information in % activation based on the $Ca^{2+}$ signal after addition of Lys-Des-Arg$^9$-bradykinin (>=50 nM) or Des-Arg$^9$-bradykinin (10 μM).

After incubation for 10-20 minutes, Lys-Des-Arg$^9$-bradykinin (hB1R) or Des-Arg$^9$-bradykinin (rB1R) is applied in the concentration of the $EC_{80}$ and the inflow of $Ca^{2+}$ is likewise determined.

Antagonists lead to a suppression of the $Ca^{2+}$ inflow. % inhibition compared with the maximum achievable inhibition is calculated.

To determine the $IC_{50}$ value, the substances are added in various concentrations. Duplicate or triplicate determinations (n=2 or n=3) are carried out, and these are repeated in at least one further independent experiment (N>=2).

Preferably, the compounds have a B1R antagonistic action on the human receptor and/or on the rat receptor. The following data are given by way of example in the following table: (In this, "B1R Ant. h" represents "B1R antagonism human" and "B1R Ant. r" represents "B1R antagonism rat")

| Example | B1R Ant. h [10 µM] % Inhibition | B1R Ant. r [10 µM] % Inhibition |
| --- | --- | --- |
| 1 | 46 | −5 |
| 2 | | |
| 3 | 69 | |
| 4 | 2 | 18 |
| 5 | 24 | −3 |
| 6 | 24 | 34 |
| 7 | 47 | 27 |
| 8 | 101 | 62 |
| 9 | 97 | 43 |
| 10 | −17 | 9 |
| 11 | −16 | 36 |
| 12 | 41 | 30 |
| 13 | 99 | 44 |
| 14 | 104 | 40 |
| 15 | 11 | −18 |
| 16 | 86 | 59 |
| 17 | 81 | 22 |
| 18 | 62 | 11 |
| 19 | 63 | 4 |
| 20 | 101 | −9 |
| 21 | 88 | 50 |
| 22 | 0 | 26 |
| 23 | −25 | 7 |
| 24 | 99 | |
| 25 | −6 | 30 |
| 26 | 51 | 38 |
| 27 | 60 | 60 |
| 28 | −7 | 17 |
| 29 | 35 | 17 |
| 30 | 81 | 72 |
| 31 | 10 | 11 |
| 32 | 32 | 14 |
| 33 | 77 | 9 |
| 34 | 102 | 24 |
| 35 | 50 | 0 |
| 36 | −11 | 3 |
| 37 | 40 | 21 |
| 38 | 45 | 46 |
| 39 | 89 | −8 |
| 40 | 99 | |
| 41 | 91 | 54 |
| 42 | −14 | −17 |
| 43 | 37 | 21 |
| 44 | 46 | 22 |
| 45 | 70 | 65 |
| 46 | 86 | 77 |
| 47 | 24 | 36 |
| 48 | 33 | 22 |
| 49 | 2 | 23 |
| 50 | | |
| 51 | 9 | |
| 52 | 103 | 53 |
| 53 | 19 | 41 |
| 54 | 10 | −20 |
| 55 | 11 | 34 |
| 56 | 22 | −4 |
| 57 | 82 | 35 |
| 58 | 52 | 5 |
| 59 | 56 | 70 |
| 60 | 28 | 11 |
| 61 | 63 | 25 |
| 62 | 40 | 32 |
| 63 | 92 | 8 |
| 64 | 60 | 16 |
| 65 | 12 | 18 |
| 66 | −1 | 30 |
| 67 | 48 | 46 |
| 68 | 18 | 39 |
| 69 | 104 | 100 |
| 70 | 98 | 31 |
| 71 | 84 | 54 |
| 72 | 94 | 38 |
| 73 | 11 | 29 |
| 74 | 66 | 27 |
| 75 | 15 | 15 |
| 76 | 52 | −7 |
| 77 | 41 | 44 |
| 78 | 51 | 2 |
| 79 | | |
| 80 | 98 | 6 |
| 81 | −10 | 5 |
| 82 | −2 | −1 |
| 83 | 7 | 11 |
| 84 | 104 | 103 |
| 85 | 7 | 12 |
| 86 | 98 | 100 |
| 87 | 57 | 9 |
| 88 | 80 | 68 |
| 89 | 42 | 50 |
| 90 | 49 | 37 |
| 91 | 42 | 34 |
| 92 | 31 | 1 |
| 93 | −2 | 6 |
| 94 | −5 | 21 |
| 95 | 22 | |
| 96 | 4 | 26 |
| 97 | 1 | 28 |
| 98 | 64 | 69 |
| 99 | −8 | −8 |
| 100 | −3 | 27 |
| 101 | 0 | 27 |
| 102 | −4 | −12 |
| 103 | 90 | 84 |
| 104 | 24 | −10 |
| 105 | 33 | 24 |
| 106 | 4 | 13 |
| 107 | −4 | 49 |
| 108 | | |
| 109 | 26 | |
| 110 | 21 | 10 |
| 111 | 102 | 104 |
| 112 | −1 | 5 |
| 113 | −1 | 28 |
| 114 | −17 | 8 |
| 115 | 10 | 21 |
| 116 | 28 | 14 |
| 117 | 76 | 77 |
| 118 | 23 | −4 |
| 119 | 67 | −6 |
| 120 | −12 | −14 |
| 121 | | |
| 122 | | |
| 123 | −6 | |
| 124 | 9 | |
| 125 | 26 | 6 |
| 126 | 103 | 59 |
| 127 | −13 | 21 |
| 128 | 28 | 46 |
| 129 | −5 | 0 |
| 130 | 30 | 15 |
| 131 | 15 | −20 |
| 132 | 40 | 2 |
| 133 | −23 | 7 |
| 134 | | |
| 135 | 79 | 29 |
| 136 | 87 | −2 |
| 137 | 102 | 100 |
| 138 | 2 | 30 |
| 139 | −5 | 21 |
| 140 | 43 | 30 |
| 141 | 54 | 26 |
| 142 | 50 | 41 |
| 143 | 11 | 19 |
| 144 | 20 | 4 |

-continued

| Example | B1R Ant. h [10 μM] % Inhibition | B1R Ant. r [10 μM] % Inhibition |
|---|---|---|
| 145 | 12 | 33 |
| 146 | 23 | 26 |
| 147 | 52 | 27 |
| 148 | 92 | 46 |
| 149 | 72 | 10 |
| 150 | 4 | 10 |
| 151 | 24 | 23 |
| 152 | 16 | 4 |
| 153 | | |
| 154 | 69 | |
| 155 | −8 | 1 |
| 156 | 5 | 20 |
| 157 | 5 | −1 |
| 158 | 20 | 5 |
| 159 | 91 | |
| 160 | 98 | |
| 161 | 1 | 3 |
| 162 | −5 | 21 |
| 163 | 40 | 36 |
| 164 | 14 | 17 |
| 165 | 98 | 38 |
| 166 | 74 | |
| 167 | −12 | 40 |
| 168 | −5 | 16 |
| 169 | −4 | −15 |
| 170 | 8 | 38 |
| 171 | 68 | 43 |
| 172 | −12 | 18 |
| 173 | 94 | 104 |
| 174 | 103 | 44 |
| 175 | −6 | 5 |
| 176 | 64 | 47 |
| 177 | 10 | 45 |
| 178 | 24 | 12 |
| 179 | 65 | 67 |
| 180 | 62 | 68 |
| 181 | | |
| 182 | 9 | 25 |
| 183 | 104 | 28 |
| 184 | −29 | 38 |
| 185 | 9 | 28 |
| 186 | 23 | 35 |
| 187 | −6 | |
| 188 | 102 | 13 |
| 189 | 47 | 16 |
| 190 | 29 | 18 |
| 191 | −16 | −14 |
| 192 | 30 | 10 |
| 193 | 97 | 6 |
| 194 | −17 | 14 |
| 195 | −13 | 24 |
| 196 | 6 | 27 |
| 197 | 104 | 105 |
| 198 | −12 | |
| 199 | 104 | 100 |
| 200 | 73 | −3 |
| 201 | 76 | 7 |
| 202 | 48 | −15 |
| 203 | 42 | 55 |
| 204 | 2 | −13 |
| 205 | −11 | 5 |
| 206 | −5 | 20 |
| 207 | 104 | 52 |
| 208 | 89 | 25 |
| 209 | 64 | 60 |
| 210 | 46 | 55 |
| 211 | 33 | 10 |
| 212 | 49 | 41 |
| 213 | 78 | 49 |
| 214 | −2 | 19 |
| 215 | 1 | 22 |
| 216 | 20 | 12 |
| 217 | 85 | 47 |
| 218 | 7 | 28 |
| 219 | −1 | 14 |
| 220 | 6 | 7 |
| 221 | 21 | 17 |
| 222 | 54 | 10 |
| 223 | 52 | −5 |
| 224 | 34 | 47 |
| 225 | 51 | 17 |
| 226 | −4 | 24 |
| 227 | 6 | 12 |
| 228 | 104 | 99 |
| 229 | 7 | 8 |
| 230 | −16 | −1 |
| 231 | 9 | 29 |
| 232 | 17 | 5 |
| 233 | 84 | 55 |
| 234 | 50 | 20 |
| 235 | 31 | −8 |
| 236 | | |
| 237 | | |
| 238 | | |
| 239 | 104 | 97 |
| 240 | 2 | −14 |
| 241 | 29 | 8 |
| 242 | 39 | 22 |
| 243 | 16 | 27 |
| 244 | 21 | −5 |
| 245 | | |
| 246 | 10 | 15 |
| 247 | 4 | 8 |
| 248 | 104 | 102 |
| 249 | 104 | 55 |
| 250 | 12 | 38 |
| 251 | 81 | 87 |
| 252 | 59 | 4 |
| 253 | 47 | 18 |
| 254 | 27 | −1 |
| 255 | 37 | 47 |
| 256 | 52 | 1 |
| 257 | 26 | |
| 258 | −12 | 12 |
| 259 | 72 | 25 |
| 260 | −7 | 9 |
| 261 | −28 | −3 |
| 262 | −6 | 36 |
| 263 | 18 | 32 |
| 264 | 77 | 59 |
| 265 | 93 | 97 |
| 266 | 4 | 24 |
| 267 | 68 | −13 |
| 268 | 7 | 25 |
| 269 | 7 | −3 |
| 270 | | |
| 271 | −7 | −13 |
| 272 | 20 | 32 |
| 273 | 25 | 37 |
| 274 | 100 | 61 |
| 275 | 15 | 17 |
| 276 | −12 | 14 |
| 277 | 4 | 4 |
| 278 | 16 | 7 |
| 279 | 23 | 7 |
| 280 | 51 | 36 |
| 281 | 0 | 18 |
| 282 | −31 | 20 |
| 283 | 50 | 24 |
| 284 | 48 | 32 |
| 285 | 97 | 75 |
| 286 | 37 | −2 |
| 287 | 1 | −1 |
| 288 | 62 | 20 |
| 289 | 51 | 13 |
| 290 | 37 | 37 |
| 291 | 105 | 36 |
| 292 | 20 | 34 |
| 293 | −7 | 2 |
| 294 | −3 | 32 |
| 295 | 7 | 44 |
| 296 | −1 | 24 |

| Example | B1R Ant. h [10 μM] % Inhibition | B1R Ant. r [10 μM] % Inhibition |
|---|---|---|
| 297 | 15 | 16 |
| 298 | 103 | 14 |
| 299 | −15 | −13 |
| 300 | −35 | 7 |
| 301 | 2 | 18 |
| 302 | 38 | 0 |
| 303 | −19 | 29 |
| 304 | 22 | 19 |
| 305 | 30 | 29 |
| 306 | 38 | 14 |
| 307 | 105 | 94 |
| 308 | −1 | 17 |
| 309 | −4 | −2 |
| 310 | 89 | 33 |
| 311 | 69 | 64 |
| 312 | 71 | 31 |
| 313 | 34 | 31 |
| 314 | 74 | 13 |
| 315 | | |
| 316 | | |
| 317 | 103 | 18 |
| 318 | 104 | 3 |
| 319 | 0 | 11 |
| 320 | 73 | −8 |
| 321 | 94 | 77 |
| 322 | −14 | 6 |
| 323 | −14 | 23 |
| 324 | 42 | 48 |
| 325 | 45 | 6 |
| 326 | −5 | −6 |
| 327 | 101 | 68 |
| 328 | 71 | 15 |
| 329 | −17 | 9 |
| 330 | −6 | 16 |
| 331 | 30 | 44 |
| 332 | 57 | 32 |
| 333 | 17 | 15 |
| 334 | 103 | 83 |
| 335 | −8 | 2 |
| 336 | 20 | 8 |
| 337 | 51 | −23 |
| 338 | −3 | 27 |
| 339 | −9 | 31 |
| 340 | 39 | 23 |
| 341 | −1 | 18 |
| 342 | 28 | −20 |
| 343 | 12 | −15 |
| 344 | 65 | 12 |
| 345 | 76 | 77 |
| 346 | 52 | 45 |
| 347 | 85 | 56 |
| 348 | 103 | 99 |
| 349 | 68 | 77 |
| 350 | 57 | 35 |
| 351 | 52 | 34 |
| 352 | −18 | −13 |
| 353 | | |
| 354 | 104 | 44 |
| 355 | −7 | 28 |
| 356 | 92 | 43 |
| 357 | 7 | 27 |
| 358 | 66 | 27 |
| 359 | 42 | −4 |
| 360 | | |
| 361 | 3 | 31 |
| 362 | 7 | 3 |
| 363 | 80 | 29 |
| 364 | 0 | −9 |
| 365 | 48 | 2 |
| 366 | 55 | 16 |
| 367 | −9 | 2 |
| 368 | 39 | 17 |
| 369 | 21 | |
| 370 | −14 | 3 |
| 371 | 7 | 5 |
| 372 | 65 | 22 |
| 373 | 98 | 12 |
| 374 | 18 | 11 |
| 375 | 2 | 6 |
| 376 | −17 | 12 |
| 377 | 28 | 25 |
| 378 | 104 | 101 |
| 379 | −5 | 49 |
| 380 | 86 | |
| 381 | −19 | 12 |
| 382 | 103 | 30 |
| 383 | 77 | 33 |
| 384 | 31 | 25 |
| 385 | 15 | |
| 386 | 104 | 20 |
| 387 | 75 | −2 |
| 388 | 74 | 16 |
| 389 | 36 | 21 |
| 390 | 55 | 16 |
| 391 | 71 | 32 |
| 392 | 104 | 103 |
| 393 | 97 | 39 |
| 394 | 2 | 21 |
| 395 | 27 | 15 |
| 396 | 70 | 68 |
| 397 | 2 | −11 |
| 398 | 80 | 56 |
| 399 | 20 | 29 |
| 400 | 3 | 9 |
| 401 | −19 | 1 |
| 402 | 0 | 45 |
| 403 | 106 | 84 |
| 404 | 104 | 33 |
| 405 | 5 | 24 |
| 406 | 5 | 12 |
| 407 | 4 | 10 |
| 408 | −16 | 1 |
| 409 | 45 | 48 |
| 410 | 1 | 6 |
| 411 | 41 | 3 |
| 412 | 40 | −5 |
| 413 | 96 | 83 |
| 414 | 28 | 10 |
| 415 | 96 | 39 |
| 416 | 104 | 30 |
| 417 | 100 | |
| 418 | 53 | 6 |
| 419 | 37 | 34 |
| 420 | −7 | 2 |
| 421 | | |
| 422 | 104 | 104 |
| 423 | 4 | −20 |
| 424 | −12 | 20 |
| 425 | 12 | 30 |
| 426 | −7 | 9 |
| 427 | 76 | 8 |
| 428 | 48 | 8 |
| 429 | 75 | 13 |
| 430 | −7 | 21 |
| 431 | 25 | 34 |
| 432 | 61 | 45 |
| 433 | −4 | −12 |
| 434 | 47 | 58 |
| 435 | 15 | 14 |
| 436 | 8 | 10 |
| 437 | 103 | 32 |
| 438 | 9 | −10 |
| 439 | 44 | 16 |
| 440 | 8 | 31 |
| 441 | 94 | 84 |
| 442 | 84 | 11 |
| 443 | 21 | −1 |
| 444 | −20 | −5 |
| 445 | 66 | 46 |
| 446 | 19 | 33 |
| 447 | 24 | 3 |
| 448 | 0 | 12 |

| Example | B1R Ant. h [10 μM] % Inhibition | B1R Ant. r [10 μM] % Inhibition |
|---|---|---|
| 449 | 25 | −7 |
| 450 | 40 | 52 |
| 451 | 87 | 11 |
| 452 | 37 | 18 |
| 453 | 97 | |
| 454 | 45 | 10 |
| 455 | | |
| 456 | 80 | 48 |
| 457 | 14 | 11 |
| 458 | 103 | 104 |
| 459 | 29 | 26 |
| 460 | 50 | 71 |
| 461 | 13 | 20 |
| 462 | −8 | −13 |
| 463 | −7 | 17 |
| 464 | −2 | −6 |
| 465 | −3 | |
| 466 | 7 | 22 |
| 467 | 67 | 47 |
| 468 | 50 | 33 |
| 469 | 91 | 87 |
| 470 | 4 | 23 |
| 471 | 7 | 15 |
| 472 | 1 | 26 |
| 473 | 52 | −3 |
| 474 | 17 | 10 |
| 475 | 103 | 40 |
| 476 | 103 | 74 |
| 477 | −16 | 17 |
| 478 | −3 | 23 |
| 479 | 18 | 22 |
| 480 | 23 | 4 |
| 481 | 9 | 49 |
| 482 | | |
| 483 | 34 | |
| 484 | −21 | 19 |
| 485 | 5 | 6 |
| 486 | 28 | 20 |
| 487 | 9 | 9 |
| 488 | 4 | −6 |
| 489 | 34 | 22 |
| 490 | 45 | 12 |
| 491 | 5 | 16 |
| 492 | 105 | 78 |
| 493 | −13 | 4 |
| 494 | 86 | 36 |
| 495 | | |
| 496 | 98 | 35 |
| 497 | −4 | 17 |
| 498 | 17 | 2 |
| 499 | 25 | −10 |
| 500 | 3 | 23 |
| 501 | 77 | 38 |
| 502 | −3 | 21 |
| 503 | 105 | 37 |
| 504 | 69 | 48 |
| 505 | | |
| 506 | 83 | 23 |
| 507 | −19 | 3 |
| 508 | 46 | 42 |
| 509 | 104 | 94 |
| 510 | 15 | 27 |
| 511 | 38 | 17 |
| 512 | −4 | 38 |
| 513 | 100 | 40 |
| 514 | −6 | 22 |
| 515 | 101 | 54 |
| 516 | | |
| 517 | −13 | 38 |
| 518 | −2 | 26 |
| 519 | 38 | 44 |
| 520 | −4 | 24 |
| 521 | 66 | 11 |
| 522 | 1 | 12 |
| 523 | 50 | 26 |
| 524 | −11 | 26 |
| 525 | 99 | 93 |
| 526 | 10 | −30 |
| 527 | 57 | 68 |
| 528 | 98 | 14 |
| 529 | | |
| 530 | −18 | 27 |
| 531 | 2 | −1 |
| 532 | 5 | −14 |
| 533 | 35 | 12 |
| 534 | −18 | −4 |
| 535 | 77 | 72 |
| 536 | 105 | 95 |
| 537 | −15 | 8 |
| 538 | 7 | 5 |
| 539 | 27 | 32 |
| 540 | −19 | 19 |
| 541 | 100 | 104 |
| 542 | 103 | 45 |
| 543 | −31 | 15 |
| 544 | 22 | 38 |
| 545 | | |
| 546 | 34 | 59 |
| 547 | 76 | 30 |
| 548 | 6 | 11 |
| 549 | 13 | 40 |
| 550 | 62 | 50 |
| 551 | 94 | 36 |
| 552 | 49 | 26 |
| 553 | −21 | −14 |
| 554 | 23 | −11 |
| 555 | −14 | 0 |
| 556 | 82 | 20 |
| 557 | 20 | 29 |
| 558 | 14 | 12 |
| 559 | 2 | −12 |
| 560 | 16 | −5 |
| 561 | −1 | −12 |
| 562 | 91 | 23 |
| 563 | 54 | −16 |
| 564 | | |
| 565 | 102 | 104 |
| 566 | 1 | 22 |
| 567 | 75 | 42 |
| 568 | −20 | 12 |
| 569 | 14 | 9 |
| 570 | −18 | 4 |
| 571 | −10 | 15 |
| 572 | 50 | 62 |
| 573 | −4 | 14 |
| 574 | 2 | 26 |
| 575 | −4 | 26 |
| 576 | −6 | 3 |
| 577 | | |
| 578 | −14 | 12 |
| 579 | | |
| 580 | 95 | 44 |
| 581 | 2 | 8 |
| 582 | | |
| 583 | −27 | 20 |
| 584 | −20 | 41 |
| 585 | −10 | |
| 586 | 95 | 76 |
| 587 | −14 | 16 |
| 588 | 6 | |
| 589 | 28 | |
| 590 | −1 | |
| 591 | 0 | |
| 592 | 1 | |
| 593 | 56 | |
| 594 | 20 | |
| 595 | 15 | |
| 596 | 32 | |
| 597 | 72 | −22 |
| 598 | 86 | |
| 599 | −6 | |
| 600 | 101 | |

-continued

| Example | B1R Ant. h [10 μM] % Inhibition | B1R Ant. r [10 μM] % Inhibition |
|---|---|---|
| 601 | 78 | |
| 602 | 81 | |
| 603 | 86 | 85 |
| 604 | −18 | 33 |
| 605 | 40 | 38 |
| 606 | 77 | 37 |
| 607 | 12 | 3 |
| 608 | 78 | 34 |
| 609 | 64 | 32 |
| 610 | 12 | 5 |
| 611 | 97 | 68 |
| 612 | 103 | 64 |
| 613 | 66 | 34 |
| 614 | 102 | 29 |
| 615 | 95 | 26 |
| 616 | 100 | 43 |
| 617 | 86 | 48 |
| 618 | 95 | 3 |
| 619 | 56 | 12 |
| 620 | 103 | 73 |
| 621 | 88 | 0 |
| 622 | 106 | 68 |
| 623 | 84 | 41 |
| 624 | 104 | 81 |
| 625 | 100 | 57 |
| 626 | 105 | 47 |
| 627 | 75 | 35 |
| 628 | 105 | 89 |
| 629 | 96 | 67 |
| 630 | 50 | −11 |
| 631 | 92 | 87 |
| 632 | 105 | 75 |
| 633 | 55 | 63 |
| 634 | 92 | 38 |
| 635 | 67 | 22 |
| 636 | 41 | 16 |
| 637 | 85 | 45 |
| 638 | 37 | 21 |
| 639 | 53 | 41 |
| 640 | 101 | 63 |
| 641 | 96 | 45 |
| 642 | 105 | 105 |
| 643 | 102 | 62 |
| 644 | 73 | 52 |
| 645 | 101 | 100 |
| 646 | 60 | 15 |
| 647 | 92 | 94 |
| 648 | 95 | 98 |
| 649 | 105 | 106 |
| 650 | 96 | 99 |
| 651 | 103 | 105 |
| 652 | 101 | 105 |
| 653 | 101 | 95 |
| 654 | 80 | 46 |
| 655 | 71 | 74 |
| 656 | 76 | 42 |
| 657 | 104 | 105 |
| 658 | 104 | 105 |
| 659 | 50 | 100 |
| 660 | 30 | 12 |
| 661 | 73 | 25 |
| 662 | 104 | 101 |
| 663 | 103 | 95 |
| 664 | 70 | 11 |
| 665 | 94 | 28 |
| 666 | 11 | 5 |
| 667 | 57 | 17 |
| 668 | 88 | 64 |
| 669 | 103 | 95 |
| 670 | 12 | 58 |
| 671 | 43 | 4 |
| 672 | 18 | 11 |
| 673 | 57 | 20 |
| 674 | 61 | 45 |
| 675 | 97 | 89 |
| 676 | 93 | 106 |

-continued

| Example | B1R Ant. h [10 μM] % Inhibition | B1R Ant. r [10 μM] % Inhibition |
|---|---|---|
| 677 | 104 | 107 |
| 678 | 45 | 73 |
| 679 | 39 | 34 |
| 680 | 21 | 23 |
| 681 | 98 | 98 |
| 682 | 104 | 103 |
| 683 | 32 | 48 |
| 684 | 95 | 61 |
| 685 | 13 | 18 |
| 686 | 80 | 29 |
| 687 | 48 | 88 |
| 688 | 103 | 94 |
| 689 | 22 | 39 |
| 690 | 54 | 30 |
| 691 | 10 | 6 |
| 692 | 78 | 41 |
| 693 | 26 | 50 |
| 694 | 54 | 104 |
| 695 | 103 | 103 |
| 696 | 43 | 91 |
| 697 | 71 | 97 |
| 698 | 39 | 86 |
| 699 | 90 | 104 |
| 700 | 38 | 89 |
| 701 | 16 | 49 |
| 702 | 70 | 74 |
| 703 | −4 | 37 |
| 704 | 75 | 39 |
| 705 | 49 | −9 |
| 706 | 77 | 52 |
| 707 | 2 | 25 |
| 708 | 100 | 91 |
| 709 | 82 | 104 |
| 710 | 42 | 92 |
| 711 | 86 | 103 |
| 712 | 46 | 100 |
| 713 | −15 | 16 |
| 714 | 104 | 64 |
| 715 | 55 | 24 |
| 716 | 59 | 31 |
| 717 | 100 | 88 |
| 718 | 105 | 96 |
| 719 | 103 | 101 |
| 720 | 101 | 101 |
| 721 | 94 | 57 |
| 722 | 101 | 89 |
| 723 | 90 | 40 |
| 724 | 55 | 50 |
| 725 | 96 | 63 |
| 726 | 103 | 94 |
| 727 | 16 | 29 |
| 728 | −9 | 9 |
| 729 | 92 | 22 |
| 730 | 46 | 38 |
| 731 | 101 | 80 |
| 732 | 100 | 84 |
| 733 | 87 | 100 |
| 734 | 104 | 104 |
| 735 | 103 | 103 |
| 736 | 103 | 102 |
| 737 | 23 | 56 |
| 738 | 75 | 62 |
| 739 | 104 | 87 |
| 740 | 79 | 70 |
| 741 | −5 | 46 |
| 742 | 36 | 53 |
| 743 | −3 | 10 |
| 744 | 18 | 40 |
| 745 | 45 | 44 |
| 746 | 98 | 51 |
| 747 | 24 | 32 |
| 748 | 92 | 78 |
| 749 | 103 | 109 |
| 750 | 101 | 94 |
| 751 | 45 | 73 |
| 752 | 103 | 104 |

-continued

| Example | B1R Ant. h [10 μM] % Inhibition | B1R Ant. r [10 μM] % Inhibition |
|---|---|---|
| 753 | 104 | 103 |
| 754 | 47 | 76 |
| 755 | 103 | 102 |
| 756 | 64 | 43 |
| 757 | 103 | 100 |
| 758 | 41 | 107 |
| 759 | 100 | 56 |
| 760 | 66 | -4 |
| 761 | 34 | 15 |
| 762 | 73 | 25 |
| 763 | -10 | 22 |
| 764 | 17 | -31 |
| 765 | 15 | 29 |
| 766 | 6 | -9 |
| 767 | 43 | 17 |
| 768 | -3 | -2 |
| 769 | 15 | 39 |
| 770 | 53 | 16 |
| 771 | -16 | 8 |
| 772 | 11 | 41 |
| 773 | 20 | 17 |
| 774 | -8 | 2 |
| 775 | -7 | 20 |
| 776 | -22 | 30 |
| 777 | -1 | 27 |
| 778 | -1 | 12 |
| 779 | -10 | -13 |
| 780 | -12 | -2 |
| 781 | -4 | -35 |
| 782 | -6 | -11 |
| 783 | 45 | -28 |
| 784 | 76 | -1 |
| 785 | 76 | 32 |
| 786 | 35 | -4 |
| 787 | 19 | 11 |
| 788 | 90 | 11 |
| 789 | -11 | -6 |
| 790 | 35 | 11 |
| 791 | -3 | 16 |
| 792 | 9 | 2 |
| 793 | 104 | 6 |
| 794 | 1 | |
| 795 | 103 | |
| 796 | 94 | |
| 797 | 0 | |
| 798 | 110 | 100 |
| 799 | 110 | 100 |
| 800 | 108 | 97 |
| 801 | 106 | 97 |
| 802 | 106 | 97 |
| 803 | 108 | 99 |
| 804 | 105 | 100 |
| 805 | 103 | 99 |
| 806 | 109 | 99 |
| 807 | 105 | 98 |
| 808 | 122 | 75 |
| 809 | 109 | 87 |
| 810 | 102 | 97 |
| 811 | 104 | 96 |
| 812 | 105 | 98 |

The foregoing description and examples have been set forth merely to illustrate the invention and are not intended to be limiting. Since modifications of the described embodiments incorporating the spirit and substance of the invention may occur to persons skilled in the art, the invention should be construed broadly to include all variations within the scope of the appended claims and equivalents thereof.

What is claimed is:

1. A substituted amide compound corresponding to formula I:

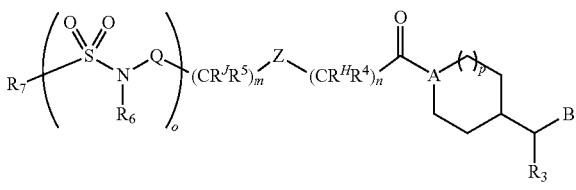

wherein
m represents 0, 1, 2 or 3
n represents 1 or 2
o represents 0 or 1
p represents 0, 1 or 2
A represents N, CH—NH—, CH—CH$_2$—NH—, CH—CH$_2$—CH$_2$—NH— or CH—CH$_2$—CH$_2$—CH$_2$—NH—, wherein individual H atoms can also be replaced by C$_{1-5}$-alkyl,
B represents NR$^1$R$^2$ or CN
R$^1$ and R$^2$ each independently represent H; C$_{1-6}$-alkyl, in each case saturated or unsaturated, branched or unbranched, unsubstituted or mono- or polysubstituted; or aryl, linked via a C$_{1-3}$-alkyl chain and unsubstituted or mono- or polysubstituted, with the proviso that R$^1$ and R$^2$ are not both H, or
R$^1$ and R$^2$ together denote CH$_2$CH$_2$OCH$_2$CH$_2$, CH$_2$CH$_2$NR$^8$CH$_2$CH$_2$ or (CH$_2$)$_{3-6}$, wherein
R$^8$ denotes H; C$_{1-6}$-alkyl, in each case saturated or unsaturated, branched or unbranched, unsubstituted or mono- or polysubstituted; aryl, heteroaryl, in each case unsubstituted or mono- or polysubstituted, or aryl or heteroaryl, linked via a C$_{1-3}$-alkyl chain and in each case unsubstituted or mono- or polysubstituted;
R$^3$ represents C$_{1-8}$-alkyl, in each case saturated or unsaturated, branched or unbranched, unsubstituted or mono- or polysubstituted; aryl or heteroaryl, in each case unsubstituted or mono- or polysubstituted; or aryl or heteroaryl, linked via a C$_{1-3}$-alkyl chain and in each case unsubstituted or mono- or polysubstituted;
R$^4$ represents H, C$_{1-6}$-alkyl, in each case saturated or unsaturated, branched or unbranched, unsubstituted or mono- or polysubstituted; aryl, in each case unsubstituted or mono- or polysubstituted; or aryl, linked via a C$_{1-3}$-alkyl chain and in each case unsubstituted or mono- or polysubstituted;
R$^H$ represents H, or
R$^4$ and R$^H$ together denote =O;
Z represents O or NH;
R$^5$ represents H; or C$_{1-6}$-alkyl, in each case saturated or unsaturated, branched or unbranched, unsubstituted or mono- or polysubstituted;
R$^J$ represents H, or
R$^5$ and R$^J$ together denote =O;
Q denotes a single bond, —CH$_2$—, —CH$_2$—CH$_2$—, or

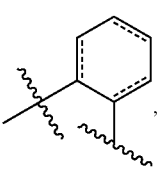 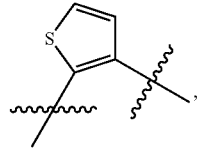

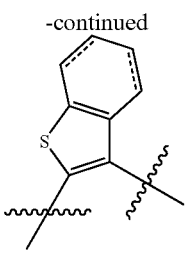

wherein ----- represents a single bond or a double bond;
$R^6$ represents H; $C_{1-6}$-alkyl, in each case saturated or unsaturated, branched or unbranched, unsubstituted or mono- or polysubstituted; $C_{3-8}$-cycloalkyl, saturated or unsaturated, unsubstituted or mono- or polysubstituted; aryl or heteroaryl, unsubstituted or mono- or polysubstituted; aryl or $C_{3-8}$-cycloalkyl, linked via a $C_{1-3}$-alkyl chain; or $R^6$ together with Q, including the adjacent nitrogen, forms a four-, five-, six- or seven-membered carbocyclic ring, which can be saturated or unsaturated and can contain a further hetero atom O, S or N and on to which a further five- or six-membered ring, saturated or unsaturated, can be fused; wherein, in the case of the common ring closure, Q represents

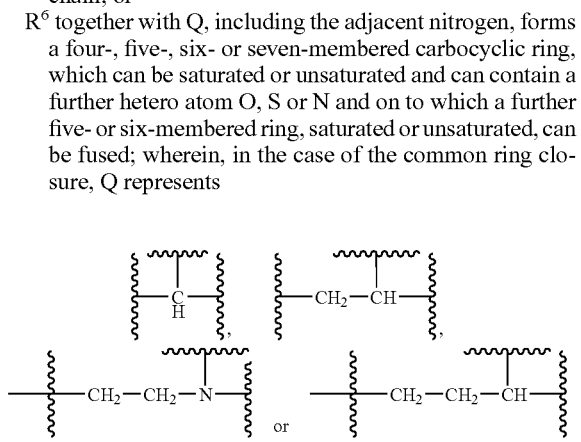

and the ring can be substituted in any position by phenyl, =O, OH; $OR^N$ where $R^N$=$C_{1-3}$-alkyl; F, Cl, $CF_3$ or $C_{1-6}$-alkyl; and $R^7$ represents aryl or heteroaryl, in each case unsubstituted or mono- or polysubstituted; $SO_2$-aryl, $SO_2$-heteroaryl, aryl or heteroaryl, linked via a $C_{1-3}$-alkyl group and in each case unsubstituted or mono- or polysubstituted;

or a salt thereof with a physiologically acceptable acid.

2. A compound according to claim 1, wherein said compound is in the form of an isolated stereoisomer.

3. A compound according to claim 1, wherein said compound is in the form of a mixture of stereoisomers in any mixing ratio.

4. A compound according to claim 1, wherein said compound is in the form of a racemic mixture.

5. A substituted amide compound according to claim 1, wherein:

"alkyl substituted" and "cycloalkyl substituted" mean the replacement of one or more hydrogen atoms independently of one another by F, Cl, Br, I, —CN, $NH_2$, NH—$C_{1-6}$-alkyl, NH—$C_{1-6}$-alkyl-OH, $C_{1-6}$-alkyl, N($C_{1-6}$-alkyl)$_2$, N($C_{1-6}$-alkyl-OH)$_2$, $NO_2$, SH, S—$C_{1-6}$-alkyl, S-benzyl, O—$C_{1-6}$-alkyl, OH, O—$C_{1-6}$-alkyl-OH, =O, O-benzyl, C(=O)$C_{1-6}$-alkyl, $CO_2H$, $CO_2$—$C_{1-6}$-alkyl or benzyl, and "aryl substituted" and "heteroaryl substituted" mean the replacement, of one or more hydrogen atoms of the ring system independently of one another by F, Cl, Br, I, CN, $NH_2$, NH—$C_{1-6}$-alkyl, NH—$C_{1-6}$-alkyl-OH, N($C_{1-6}$-alkyl)$_2$, N($C_{1-6}$-alkyl-OH)$_2$, $NO_2$, SH, S—$C_{1-6}$-alkyl, OH, O—$C_{1-6}$-alkyl, O—$C_{1-6}$-alkyl-OH, C(=O)$C_{1-6}$-alkyl, $CO_2H$, $CH_2SO_2$-phenyl, $CO_2$—$C_{1-6}$-alkyl, $OCF_3$, $CF_3$,

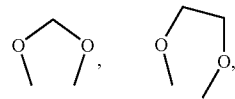

$C_{1-6}$-alkyl, phenyl, pyridyl, thienyl or furyl.

6. A substituted amide compound according to claim 1, wherein A represents CH—NH—, CH—$CH_2$—NH—, CH—$CH_2$—$CH_2$—NH— or CH—$CH_2$—$CH_2$—$CH_2$—NH—, wherein individual H atoms can also be replaced by $C_{1-5}$-alkyl.

7. A substituted amide compound according to claim 1, wherein B represents $NR^1R^2$.

8. A substituted amide compound according to claim 7, wherein $R^1$ and $R^2$ independently of one another denote H; $CH_3$; or phenyl linked via a $C_{1-3}$-alkyl chain, with the proviso that $R^1$ and $R^2$ are not both H, or $R^1$ and $R^2$ together denote $CH_2CH_2OCH_2CH_2$, $CH_2CH_2NR^8CH_2CH_2$ or $(CH_2)_{4-5}$.

9. A substituted amide compound according to claim 1, wherein $R^3$ represents aryl or heteroaryl, in each case unsubstituted or mono- or polysubstituted; or aryl, linked via a $C_{1-3}$-alkyl chain and in each case unsubstituted or mono- or polysubstituted.

10. A substituted amide compound according to claim 1, wherein Z represents O.

11. A substituted amide compound according to claim 1, wherein $R^6$ represents methyl, ethyl, cyclopropyl or benzyl, and Q represents a single bond.

12. A substituted amide compound according to claim 1, wherein the group

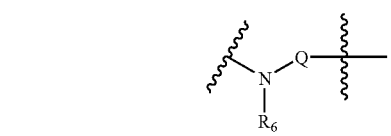

of formula I represents:

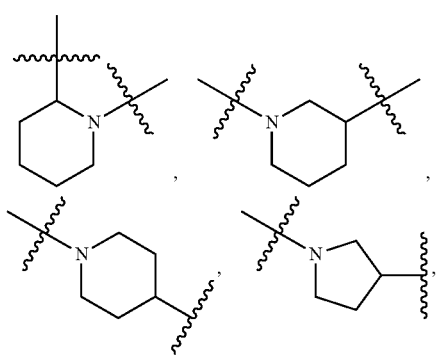

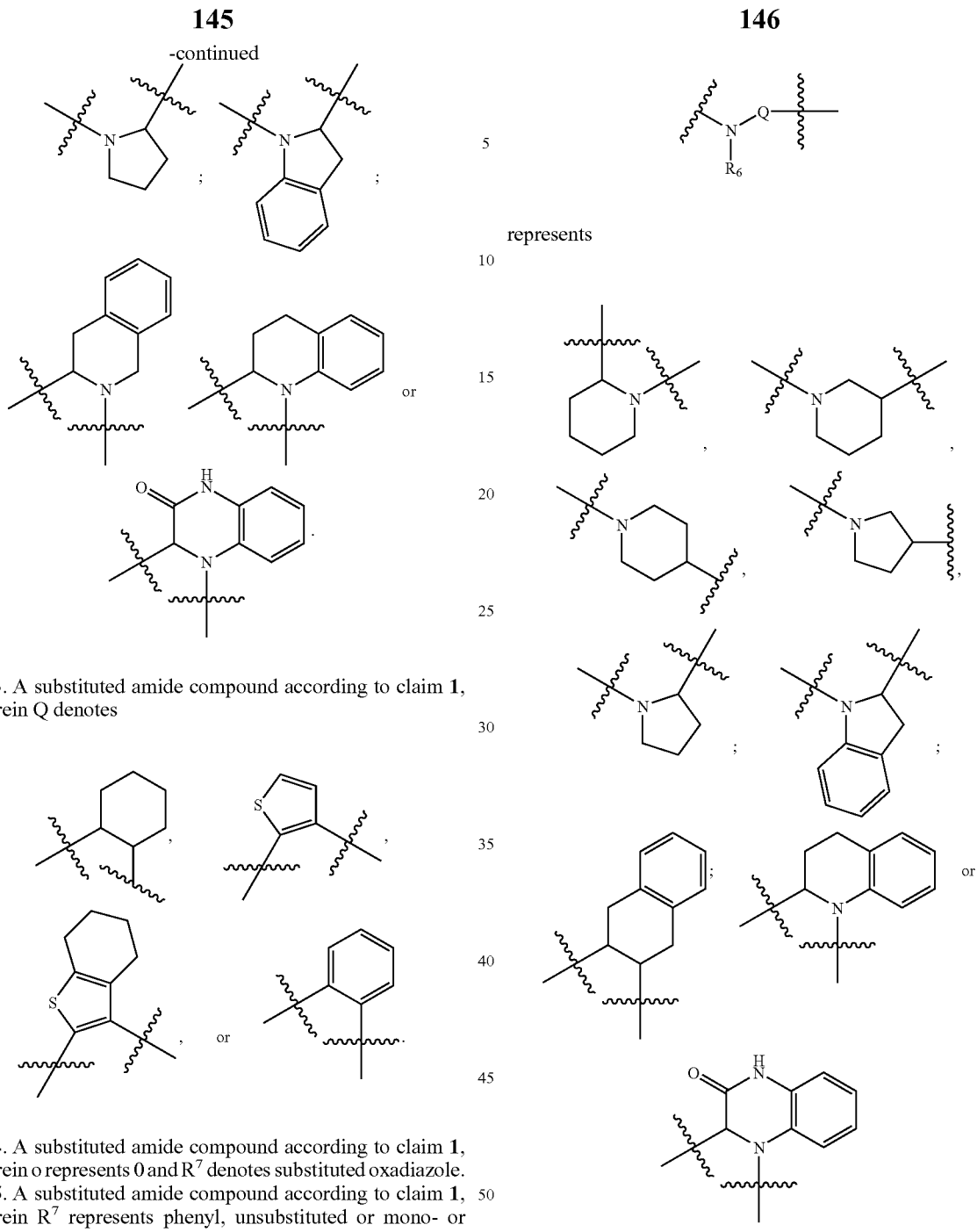

13. A substituted amide compound according to claim 1, wherein Q denotes

14. A substituted amide compound according to claim 1, wherein o represents 0 and $R^7$ denotes substituted oxadiazole.

15. A substituted amide compound according to claim 1, wherein $R^7$ represents phenyl, unsubstituted or mono- or polysubstituted.

16. A substituted amide compound according to claim 1, wherein o represents 1, and $R^7$ represents aryl or heteroaryl, in each case unsubstituted or mono- or polysubstituted.

17. A substituted amide compound according to claim 1, wherein
 o represents 1;
 Z represents O;
 m represents 1 or 2;
 $R^J$ and $R^5$ each represent H;
 n represents 1; and
 $R^H$ and $R^4$ each represent H.

18. A substituted amide compound according to claim 1, wherein
 o represents 1;
 and the group Q represents a single bond or —CH$_2$—; and
$R^6$ represents C$_{1-6}$-alkyl or C$_{3-8}$-cycloalkyl.

19. A substituted amide compound according to claim 18, wherein the group

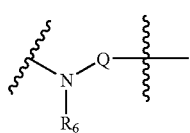

represents

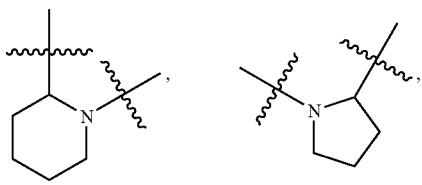

or in the group

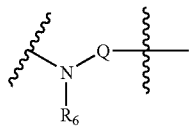

Q represents a single bond or —CH$_2$—; and
R$^6$ represents methyl, ethyl or cyclopropyl.

20. A substituted amide compound according to claim 1, wherein o represents 1;
m represents 1 or 2;
R$^J$ and R$^5$ each represent H;
Z represents O;
n represents 1;
R$^H$ and R$^4$ each represent H;
the group

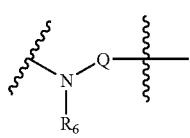

represents

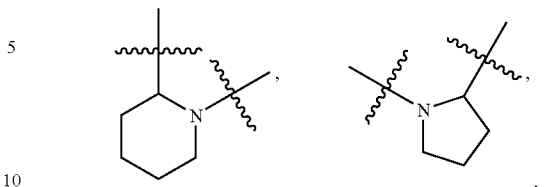

or in the group

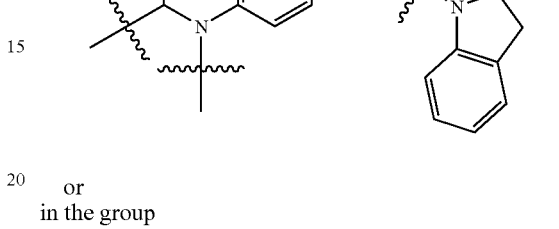

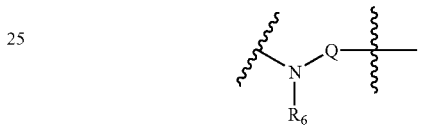

Q represents a single bond and
R$^6$ represents C$_{1-6}$-alkyl, or C$_{3-8}$-cycloalkyl, and
(i) A represents CH—CH$_2$—NH— or CH—CH$_2$—CH$_2$—NH, wherein individual H atoms can also be replaced by C$_{1-5}$-alkyl;
B represents NR$^1$R$^2$, wherein
R$^1$ and R$^2$ each independently represent H; C$_{1-6}$-alkyl, in each case saturated or unsaturated, branched or unbranched, unsubstituted or mono- or polysubstituted; with the proviso that R$^1$ and R$^2$ are not both H, or
R$^1$ and R$^2$ together denote (CH$_2$)$_{3-6}$, and
R$^3$ represents aryl or heteroaryl, in each case unsubstituted or mono- or polysubstituted; or aryl linked via a C$_{1-3}$-alkyl chain, in each case unsubstituted or mono- or polysubstituted; or
(ii) A represents N,
B represents NR$^1$R$^2$, wherein R$^1$ and R$^2$ together form CH$_2$CH$_2$NR$^8$CH$_2$CH$_2$ and R$^8$ represents C$_{1-6}$-alkyl; and
R$^3$ represents aryl or heteroaryl, in each case unsubstituted or mono- or polysubstituted, or aryl linked via a C$_{1-3}$-alkyl chain, in each case unsubstituted or mono- or polysubstituted.

21. A substituted amide compound according to claim 20, wherein R$^3$ represents phenyl, 2-thienyl, 4-fluorophenyl, 3-fluorophenyl, 4-chlorophenyl, 2-, 3- or 4-pyridinyl; phenethyl or benzyl.

22. A substituted amide compound according to claim 1, wherein said compound is selected from the group consisting of:

(1) N-(4-((dimethylamino)(thiophen-2-yl)methyl)cyclohexyl)-2-(1-(4-methoxy-2,3,6-trimethylphenylsulfonyl)piperidin-4-yloxy)acetamide;
(2) N-((4-((dimethylamino)(thiophen-2-yl)methyl)cyclohexyl)methyl)-2-phenoxypropanamide;
(3) N-(4-((dimethylamino)(phenyl)methyl)cyclohexyl)-2-(2-(1-(4-methoxyphenylsulfonyl)piperidin-2-yl)ethoxy)acetamide;

(4) N-((4-((dimethylamino)(thiophen-2-yl)methyl)cyclohexyl)methyl)-2-(2-(N,4-dimethylphenylsulfonamido)ethoxy)acetamide;

(5) N-(4-((dimethylamino)(thiophen-2-yl)methyl)cyclohexyl)-2-(2-(1-(4-methoxy-2,3,6-trimethylphenylsulfonyl)piperidin-4-yl)ethoxy)acetamide;

(6) N-(4-((dimethylamino)(thiophen-2-yl)methyl)cyclohexyl)-2-(2-(1-(4-methoxyphenylsulfonyl)piperidin-2-yl)ethoxy)acetamide;

(7) N-((4-((dimethylamino)(thiophen-2-yl)methyl)cyclohexyl)methyl)-2-((2-(4-methoxyphenylsulfonyl)-1,2,3,4-tetrahydroisoquinolin-3-yl)methoxy)acetamide;

(8) 2-(2-(2,4-dichloro-N-methylphenylsulfonamido)ethoxy)-N-((4-((dimethylamino)(thiophen-2-yl)methyl)cyclohexyl)methyl)acetamide;

(9) 2-(2-(2,4-dichloro-N-methylphenylsulfonamido)ethoxy)-N-(2-(4-((dimethylamino)(thiophen-2-yl)methyl)cyclohexyl)ethyl)acetamide;

(10) N-(4-((dimethylamino)(thiophen-2-yl)methyl)cyclohexyl)-2-(2-(4-fluoro-N-methylphenylsulfonamido)ethoxy)acetamide;

(11) N-(4-((dimethylamino)(thiophen-2-yl)methyl)cyclohexyl)-2-(1-(3-(trifluoromethyl)phenylsulfonyl)pyrrolidin-3-yloxy)acetamide;

(12) N-(4-((dimethylamino)(thiophen-2-yl)methyl)cyclohexyl)-2-(1-(mesitylsulfonyl)pyrrolidin-3-yloxy)acetamide;

(13) 2-(2-(2,6-dichloro-N-methylphenylsulfonamido)ethoxy)-N-((4-((dimethylamino)(phenyl)methyl)cyclohexyl)methyl)acetamide;

(14) N-((4-((dimethylamino)(phenyl)methyl)cyclohexyl)methyl)-2-(2-(2,4,6-trichloro-N-methylphenylsulfonamido)ethoxy)acetamide;

(15) 2-(2-(N-benzylphenylsulfonamido)ethoxy)-N-((4-((dimethylamino)(phenyl)methyl)cyclohexyl)methyl)acetamide;

(16) N-((4-((dimethylamino)(thiophen-2-yl)methyl)cyclohexyl)methyl)-2-(2-(N-ethyl-4-methoxy-2,3,6-trimethylphenylsulfonamido)ethoxy)acetamide;

(17) 2-((1-(3,4-dichlorophenylsulfonyl)piperidin-2-yl)methoxy)-N-((4-((dimethylamino)(phenyl)methyl)cyclohexyl)methyl)acetamide;

(18) 2-((1-(3,4-dichlorophenylsulfonyl)pyrrolidin-2-yl)methoxy)-N-((4-((dimethylamino)(phenyl)methyl)cyclohexyl)methyl)acetamide;

(19) N-((4-((dimethylamino)(phenyl)methyl)cyclohexyl)methyl)-2-((2-(4-methoxyphenylsulfonyl)-1,2,3,4-tetrahydroisoquinolin-3-yl)methoxy)acetamide;

(20) N-(4-((dimethylamino)(phenyl)methyl)cyclohexyl)-2-(2-(4-(4-methoxy-2,3,6-trimethylphenylsulfonyl)piperazin-1-yl)ethoxy)acetamide;

(21) 2-(1-(2,4-dichlorophenylsulfonyl)pyrrolidin-3-yloxy)-N-(2-(4-((dimethylamino)(thiophen-2-yl)methyl)cyclohexyl)ethyl)acetamide;

(22) 2-(1-(3,4-dimethoxyphenylsulfonyl)pyrrolidin-3-yloxy)-N-((4-((dimethylamino)(phenyl)methyl)cyclohexyl)methyl)acetamide;

(23) 2-(1-(3,4-dimethoxyphenylsulfonyl)pyrrolidin-3-yloxy)-N-((4-((dimethylamino)(thiophen-2-yl)methyl)cyclohexyl)methyl)acetamide;

(24) 2-((1-(2,3-dichlorophenylsulfonyl)piperidin-2-yl)methoxy)-N-(4-((dimethylamino)(phenyl)methyl)cyclohexyl)acetamide;

(25) N-((4-((dimethylamino)(thiophen-2-yl)methyl)cyclohexyl)methyl)-2-(1-(3-(trifluoromethyl)phenylsulfonyl)pyrrolidin-3-yloxy)acetamide;

(26) N-((4-((dimethylamino)(phenyl)methyl)cyclohexyl)methyl)-2-(1-(mesitylsulfonyl)pyrrolidin-3-yloxy)acetamide;

(27) N-((4-((dimethylamino)(thiophen-2-yl)methyl)cyclohexyl)methyl)-2-(1-(mesitylsulfonyl)pyrrolidin-3-yloxy)acetamide;

(28) N-(4-((dimethylamino)(thiophen-2-yl)methyl)cyclohexyl)-2-(1-(4-fluorophenylsulfonyl)pyrrolidin-3-yloxy)acetamide;

(29) N-((4-((dimethylamino)(phenyl)methyl)cyclohexyl)methyl)-2-(1-(4-methoxy-2,3,6-trimethylphenylsulfonyl)piperidin-3-yloxy)acetamide;

(30) N-(2-(4-((dimethylamino)(thiophen-2-yl)methyl)cyclohexyl)ethyl)-2-((1-(4-methoxyphenylsulfonyl)piperidin-2-yl)methoxy)acetamide;

(31) 2-(2-(3,4-dichloro-N-methylphenylsulfonamido)cyclohexyloxy)-N-((4-((dimethylamino)(thiophen-2-yl)methyl)cyclohexyl)methyl)acetamide;

(32) N-(2-(4-((dimethylamino)(thiophen-2-yl)methyl)cyclohexyl)ethyl)-2-(2-(N-methyl-3-(trifluoromethyl)phenylsulfonamido)ethoxy)acetamide;

(33) 2-(2-(2,4-dichloro-N-methylphenylsulfonamido)ethoxy)-N-(4-((dimethylamino)(phenyl)methyl)cyclohexyl)acetamide;

(34) N-(4-((dimethylamino)(phenyl)methyl)cyclohexyl)-2-(2-(2,4,6-trichloro-N-methylphenylsulfonamido)ethoxy)acetamide;

(35) N-((4-((dimethylamino)(thiophen-2-yl)methyl)cyclohexyl)methyl)-2-(2-(4-methoxy-N,2,3,6-tetramethylphenylsulfonamido)ethoxy)acetamide;

(36) N-((4-((dimethylamino)(thiophen-2-yl)methyl)cyclohexyl)methyl)-2-(1-(phenylsulfonyl)pyrrolidin-3-yloxy)acetamide;

(37) 2-(2-(4-chloro-N-methylphenylsulfonamido)ethoxy)-N-(2-(4-((dimethylamino)(thiophen-2-yl)methyl)cyclohexyl)ethyl)acetamide;

(38) N-(4-((dimethylamino)(phenyl)methyl)cyclohexyl)-2-((2-(4-methoxyphenylsulfonyl)-1,2,3,4-tetrahydroisoquinolin-3-yl)methoxy)acetamide;

(39) 2-(2-(3,4-dichloro-N-methylphenylsulfonamido)cyclohexyloxy)-N-(4-((dimethylamino)(phenyl)methyl)cyclohexyl)acetamide;

(40) N-((4-((dimethylamino)(phenyl)methyl)cyclohexyl)methyl)-2-(2-(4-methoxy-N,2,3,6-tetramethylphenylsulfonamido)ethoxy)acetamide;

(41) 2-(2-(2,6-dichloro-N-methylphenylsulfonamido)ethoxy)-N-(2-(4-((dimethylamino)(3-fluorophenyl)methyl)cyclohexyl)ethyl)acetamide;

(42) N-(4-((dimethylamino)(thiophen-2-yl)methyl)cyclohexyl)-2-(1-(phenylsulfonyl)piperidin-3-yloxy)acetamide;

(43) N-(4-((dimethylamino)(thiophen-2-yl)methyl)cyclohexyl)-2-(1-(4-methoxy-2,3,6-trimethylphenylsulfonyl)pyrrolidin-3-yloxy)acetamide;

(44) N-((4-((dimethylamino)(phenyl)methyl)cyclohexyl)methyl)-2-(1-(4-methoxy-2,3,6-trimethylphenylsulfonyl)pyrrolidin-3-yloxy)acetamide;

(45) N-((4-((dimethylamino)(thiophen-2-yl)methyl)cyclohexyl)methyl)-2-((1-(4-methoxyphenylsulfonyl)piperidin-2-yl)methoxy)acetamide;

(46) N-(2-(4-((dimethylamino)(thiophen-2-yl)methyl)cyclohexyl)ethyl)-2-(1-(4-methoxyphenylsulfonyl)piperidin-2-yloxy)acetamide;

(47) N-(4-((dimethylamino)(thiophen-2-yl)methyl)cyclohexyl)-2-((2-(4-methoxyphenylsulfonyl)-1,2,3,4-tetrahydroisoquinolin-3-yl)methoxy)acetamide;

(48) N-(2-(4-((dimethylamino)(thiophen-2-yl)methyl)cyclohexyl)ethyl)-2-((2-(4-methoxyphenylsulfonyl)-1,2,3,4-tetrahydroisoquinolin-3-yl)methoxy)acetamide;
(49) 2-((1-(2,4-dimethoxyphenylsulfonyl)piperidin-2-yl)methoxy)-N-((4-((dimethylamino)(thiophen-2-yl)methyl)cyclohexyl)methyl)acetamide;
(50) N-((4-((dimethylamino)(phenyl)methyl)cyclohexyl)methyl)-2-phenoxypropanamide
(51) 2-(2-(N-benzylphenylsulfonamido)ethoxy)-N-(4-((dimethylamino)(phenyl)methyl)cyclohexyl)acetamide;
(52) N-(2-(4-((dimethylamino)(thiophen-2-yl)methyl)cyclohexyl)ethyl)-2-(2-(4-methoxy-N,2,3,6-tetramethylphenylsulfonamido)ethoxy)acetamide;
(53) N-((4-((dimethylamino)(phenyl)methyl)cyclohexyl)methyl)-2-(2-(N-methyl-4-(trifluoromethoxy)phenylsulfonamido)ethoxy)acetamide;
(54) 2-(1-(4-chlorophenylsulfonyl)pyrrolidin-3-yloxy)-N-((4-((dimethylamino)(thiophen-2-yl)methyl)cyclohexyl)methyl)acetamide;
(55) 2-(2-(4-chloro-N-methylphenylsulfonamido)ethoxy)-N-((4-((dimethylamino)(thiophen-2-yl)methyl)cyclohexyl)methyl)acetamide;
(56) N-((4-((dimethylamino)(thiophen-2-yl)methyl)cyclohexyl)methyl)-2-(2-(4-fluoro-N-methylphenylsulfonamido)ethoxy)acetamide;
(57) N-((4-((dimethylamino)(thiophen-2-yl)methyl)cyclohexyl)methyl)-2-(2-(N,2,4,6-tetramethylphenylsulfonamido)ethoxy)acetamide;
(58) N-((4-((dimethylamino)(thiophen-2-yl)methyl)cyclohexyl)methyl)-2-(1-(4-methoxy-2,3,6-trimethylphenylsulfonyl)pyrrolidin-3-yloxy)acetamide;
(59) N-(4-((dimethylamino)(thiophen-2-yl)methyl)cyclohexyl)-2-(2-(N-ethyl-4-methoxy-2,3,6-trimethylphenylsulfonamido)ethoxy)acetamide;
(60) N-((4-((dimethylamino)(thiophen-2-yl)methyl)cyclohexyl)methyl)-2-(1-(4-methoxy-2,3,6-trimethylphenylsulfonyl)piperidin-3-yloxy)acetamide;
(61) N-((4-((dimethylamino)(phenyl)methyl)cyclohexyl)methyl)-2-(2-(4-(4-methoxy-2,3,6-trimethylphenylsulfonyl)piperazin-1-yl)ethoxy)acetamide;
(62) N-(4-((dimethylamino)(3-fluorophenyl)methyl)cyclohexyl)-2-(2-(1-(4-methoxyphenylsulfonyl)piperidin-2-yl)ethoxy)acetamide;
(63) N-(4-((dimethylamino)(phenyl)methyl)cyclohexyl)-2-(2-(N,2,4,6-tetramethylphenylsulfonamide)ethoxy)acetamide;
(64) N-(4-((dimethylamino)(phenyl)methyl)cyclohexyl)-2-(1-(mesitylsulfonyl)pyrrolidin-3-yloxy)acetamide;
(65) N-(2-(4-((dimethylamino)(thiophen-2-yl)methyl)cyclohexyl)ethyl)-2-(2-(N -methyl-4-(trifluoromethoxy)phenylsulfonamido)ethoxy)acetamide;
(66) 2-(1-(4-chlorophenylsulfonyl)pyrrolidin-3-yloxy)-N-(2-(4-((dimethylamino)(thiophen-2-yl)methyl)cyclohexyl)ethyl)acetamide;
(67) 2-(1-(2,4-dichlorophenylsulfonyl)pyrrolidin-3-yloxy)-N-((4-((dimethylamino)(phenyl)methyl)cyclohexyl)methyl)acetamide;
(68) N-((4-((dimethylamino)(thiophen-2-yl)methyl)cyclohexyl)methyl)-2-(1-tosylpyrrolidin-3-yloxy)acetamide;
(69) N-((4-((dimethylamino)(thiophen-2-yl)methyl)cyclohexyl)methyl)-2-(2-(4-methoxy-N,2,6-trimethylphenylsulfonamido)ethoxy)acetamide;
(70) 2-(2-(2,4-dichloro-N-methylphenylsulfonamido)ethoxy)-N-((4-((dimethylamino)(3-fluorophenyl)methyl)cyclohexyl)methyl)acetamide;
(71) N-(2-(4-((dimethylamino)(thiophen-2-yl)methyl)cyclohexyl)ethyl)-2-(1-(mesitylsulfonyl)pyrrolidin-3-yloxy)acetamide;
(72) 2-(2-(2,6-dichloro-N-methylphenylsulfonamido)ethoxy)-N-((4-((dimethylamino)(3-fluorophenyl)methyl)cyclohexyl)methyl)acetamide;
(73) N-(4-((dimethylamino)(thiophen-2-yl)methyl)cyclohexyl)-2-(2-(4-methoxy-N-methylphenylsulfonamido)ethoxy)acetamide;
(74) N-(2-(4-((dimethylamino)(thiophen-2-yl)methyl)cyclohexyl)ethyl)-2-(1-(4-methoxy-2,3,6-trimethylphenylsulfonyl)pyrrolidin-3-yloxy)acetamide;
(75) N-(2-(4-((dimethylamino)(thiophen-2-yl)methyl)cyclohexyl)ethyl)-2-(2-(1-(4-methoxy-2,3,6-trimethylphenylsulfonyl)piperidin-4-yl)ethoxy)acetamide;
(76) N-(4-((dimethylamino)(3-fluorophenyl)methyl)cyclohexyl)-2-(2-(4-(4-methoxy-2,3,6-trimethylphenylsulfonyl)piperazin-1-yl)ethoxy)acetamide;
(77) N-(2-(4-((dimethylamino)(thiophen-2-yl)methyl)cyclohexyl)ethyl)-2-((1-(4-methoxyphenylsulfonyl)pyrrolidin-2-yl)methoxy)acetamide;
(78) 2-(2-(3,4-dichloro-N-methylphenylsulfonamido)cyclohexyloxy)-N-((4-((dimethylamino)(phenyl)methyl)cyclohexyl)methyl)acetamide;
(79) N-((4-((dimethylamino)(3-fluorophenyl)methyl)cyclohexyl)methyl)-2-phenoxypropanamide
(80) N-(4-((dimethylamino)(phenyl)methyl)cyclohexyl)-2-(2-(4-methoxy-N,2,3,6-tetramethylphenylsulfonamido)ethoxy)acetamide;
(81) 2-(1-(4-chlorophenylsulfonyl)pyrrolidin-3-yloxy)-N-((4-((dimethylamino)(phenyl)methyl)cyclohexyl)methyl)acetamide;
(82) N-(2-(4-((dimethylamino)(thiophen-2-yl)methyl)cyclohexyl)ethyl)-2-(2-(N,4-dimethylphenylsulfonamido)ethoxy)acetamide;
(83) 2-(2-(4-chloro-N-methylphenylsulfonamido)ethoxy)-N-(4-((dimethylamino)(thiophen-2-yl)methyl)cyclohexyl)acetamide;
(84) N-(2-(4-((dimethylamino)(thiophen-2-yl)methyl)cyclohexyl)ethyl)-2-(4-methoxy-N,2,6-trimethylphenylsulfonamido)ethoxy)acetamide;
(85) N-(2-(4-((dimethylamino)(thiophen-2-yl)methyl)cyclohexyl)ethyl)-2-(2-(4-fluoro-N-methylphenylsulfonamido)ethoxy)acetamide;
(86) N-((4-((dimethylamino)(thiophen-2-yl)methyl)cyclohexyl)methyl)-2-(1-(4-methoxy-2,6-dimethylphenylsulfonyl)pyrrolidin-3-yloxy)acetamide;
(87) 2-((1-(3,4-dichlorophenylsulfonyl)piperidin-2-yl)methoxy)-N-((4-((dimethylamino)(3-fluorophenyl)methyl)cyclohexyl)methyl)acetamide;
(88) N-((4-((dimethylamino)(phenyl)methyl)cyclohexyl)methyl)-2-((1-(4-methoxyphenylsulfonyl)piperidin-2-yl)methoxy)acetamide;
(89) N-((4-((dimethylamino)(phenyl)methyl)cyclohexyl)methyl)-2-(2-(1-(4-methoxyphenylsulfonyl)piperidin-2-yl)ethoxy)acetamide;
(90) N-((4-((dimethylamino)(thiophen-2-yl)methyl)cyclohexyl)methyl)-2-(2-(1-(4-methoxyphenylsulfonyl)piperidin-2-yl)ethoxy)acetamide;
(91) N-((4-((dimethylamino)(phenyl)methyl)cyclohexyl)methyl)-2-(2-(N-methyl-3-(trifluoromethyl)phenylsulfonamido)ethoxy)acetamide;
(92) N-((4-((dimethylamino)(thiophen-2-yl)methyl)cyclohexyl)methyl)-2-(2-(N-methyl-3-(trifluoromethyl)phenylsulfonamido)ethoxy)acetamide;

(93) N-((4-((dimethylamino)(thiophen-2-yl)methyl)cyclohexyl)methyl)-2-(2-(N-methyl-4-(trifluoromethoxy)phenylsulfonamido)ethoxy)acetamide;

(94) 2-(1-(3,4-dimethoxyphenylsulfonyl)pyrrolidin-3-yloxy)-N-(2-(4-((dimethylamino)(thiophen-2-yl)methyl)cyclohexyl)ethyl)acetamide;

(95) 2-((1-(4-chlorophenylsulfonyl)piperidin-2-yl)methoxy)-N-(4-((dimethylamino)(phenyl)methyl)cyclohexyl)acetamide;

(96) N-(2-(4-((dimethylamino)(thiophen-2-yl)methyl)cyclohexyl)ethyl)-2-(1-(3-(trifluoromethyl)phenylsulfonyl)pyrrolidin-3-yloxy)acetamide;

(97) N-((4-((dimethylamino)(thiophen-2-yl)methyl)cyclohexyl)methyl)-2-(1-(4-fluorophenylsulfonyl)pyrrolidin-3-yloxy)acetamide;

(98) N-(4-((dimethylamino)(thiophen-2-yl)methyl)cyclohexyl)-2-(1-(4-methoxy-2,6-dimethylphenylsulfonyl)pyrrolidin-3-yloxy)acetamide;

(99) N-(2-(4-((dimethylamino)(thiophen-2-yl)methyl)cyclohexyl)ethyl)-2-(2-(4-(phenylsulfonyl)piperazin-1-yl)ethoxy)acetamide;

(100) N-(2-(4-((dimethylamino)(thiophen-2-yl)methyl)cyclohexyl)ethyl)-2-(1-(phenylsulfonyl)piperidin-3-yloxy)acetamide;

(101) N-((4-((dimethylamino)(thiophen-2-yl)methyl)cyclohexyl)methyl)-2-((1-(phenylsulfonyl)piperidin-3-yl)methoxy)acetamide;

(102) 2-(2-(N-benzylphenylsulfonamido)ethoxy)-N-((4-((dimethylamino)(thiophen-2-yl)methyl)cyclohexyl)methyl)acetamide;

(103) N-(2-(4-((dimethylamino)(thiophen-2-yl)methyl)cyclohexyl)ethyl)-2-(2-(N-ethyl-4-methoxy-2,3,6-trimethylphenylsulfonamido)ethoxy)acetamide;

(104) N-((4-((dimethylamino)(thiophen-2-yl)methyl)cyclohexyl)methyl)-2-(1-(4-methoxy-2,3,6-trimethylphenylsulfonyl)piperidin-4-yloxy)acetamide;

(105) N-((4-((dimethylamino)(thiophen-2-yl)methyl)cyclohexyl)methyl)-2-((1-(4-methoxyphenylsulfonyl)pyrrolidin-2-yl)methoxy)acetamide;

(106) 2-((1-(2,4-dimethoxyphenylsulfonyl)piperidin-2-yl)methoxy)-N-((4-((dimethylamino)(phenyl)methyl)cyclohexyl)methyl)acetamide;

(107) 2-((1-(2,4-dimethoxyphenylsulfonyl)piperidin-2-yl)methoxy)-N-(2-(4-((dimethylamino)(thiophen-2-yl)methyl)cyclohexyl)ethyl)acetamide;

(108) N-((4-((dimethylamino)(3-fluorophenyl)methyl)cyclohexyl)methyl)-2-phenoxypropanamide (109) N-(4-((dimethylamino)(phenyl)methyl)cyclohexyl)-2-(1-(phenylsulfonyl)piperidin-3-yloxy)acetamide;

(110) 2-(2-(4-chloro-N-methylphenylsulfonamido)ethoxy)-N-((4-((dimethylamino)(phenyl)methyl)cyclohexyl)methyl)acetamide;

(111) N-(4-((dimethylamino) (thiophen-2-yl)methyl)cyclohexyl)-2-(2-(4-methoxy-N,2,6-trimethylphenylsulfonamido)ethoxy)acetamide;

(112) N-((4-((dimethylamino)(phenyl)methyl)cyclohexyl)methyl)-2-(2-(4-fluoro-N-methylphenylsulfonamido)ethoxy)acetamide;

(113) N-((4-((dimethylamino)(phenyl)methyl)cyclohexyl)methyl)-2-(1-(3-(trifluoromethyl)phenylsulfonyl)pyrrolidin-3-yloxy)acetamide;

(114) N-((4-((dimethylamino)(phenyl)methyl)cyclohexyl)methyl)-2-(1-(phenylsulfonyl)piperidin-3-yloxy)acetamide;

(115) N-(2-(4-((dimethylamino)(thiophen-2-yl)methyl)cyclohexyl)ethyl)-2-((1-(phenyl sulfonyl)piperidin-3-yl)methoxy)acetamide;

(116) 2-(2-(N-benzylphenylsulfonamido)ethoxy)-N-(2-(4-((dimethylamino)(thiophen-2-yl)methyl)cyclohexyl)ethyl)acetamide;

(117) N-((4-((dimethylamino)(3-fluorophenyl)methyl)cyclohexyl)methyl)-2-(2-(N-ethyl-4-methoxy-2,3,6-trimethylphenylsulfonamido)ethoxy)acetamide;

(118) N-(4-((dimethylamino)(3-fluorophenyl)methyl)cyclohexyl)-2-(2-(1-(4-methoxy-2,3,6-trimethylphenylsulfonyl)piperidin-4-yl)ethoxy)acetamide;

(119) 2-((1-(3,4-dichlorophenylsulfonyl)pyrrolidin-2-yl)methoxy)-N-((4-((dimethylamino)(3-fluorophenyl)methyl)cyclohexyl)methyl)acetamide;

(120) 2-((1-(3,4-dimethoxyphenylsulfonyl)piperidin-2-yl)methoxy)-N-(2-(4-((dimethylamino) (thiophen-2-yl)methyl)cyclohexyl)ethyl)acetamide;

(121) N-(4-((dimethylamino)(3-fluorophenyl)methyl)cyclohexyl)-2-phenoxypropanamide (122) N-((4-((dimethylamino)(3-fluorophenyl)methyl)cyclohexyl)methyl)-2-phenoxypropanamide (123) N-(4-((dimethylamino)(phenyl)methyl)cyclohexyl)-2-(1-tosylpyrrolidin-3-yloxy)acetamide;

(124) N-(4-((dimethylamino)(phenyl)methyl)cyclohexyl)-2-(2-(1-(phenylsulfonyl)piperidin-4-yl)ethoxy)acetamide;

(125) N-((4-((dimethylamino)(phenyl)methyl)cyclohexyl)methyl)-2-(1-tosylpyrrolidin-3-yloxy)acetamide;

(126) 2-(2-(2,4-dichloro-N-methylphenylsulfonamido)ethoxy)-N-(2-(4-((dimethylamino)(3-fluorophenyl)methyl)cyclohexyl)ethyl)acetamide;

(127) 2-(2-(3,4-dimethoxy-N-methylphenylsulfonamido)ethoxy)-N-((4-((dimethylamino)(thiophen-2-yl)methyl)cyclohexyl)methyl)acetamide;

(128) N-(2-(4-((dimethylamino)(thiophen-2-yl)methyl)cyclohexyl)ethyl)-2-(2-(4-methoxy-N-methylphenylsulfonamido)ethoxy)acetamide;

(129) N-((4-((dimethylamino)(phenyl)methyl)cyclohexyl)methyl)-2-((1-(phenylsulfonyl)piperidin-3-yl)methoxy)acetamide;

(130) N-(2-(4-((dimethylamino)(thiophen-2-yl)methyl)cyclohexyl)ethyl)-2-(1-(4-methoxy-2,3,6-trimethylphenylsulfonyl)piperidin-3-yloxy)acetamide;

(131) N-((4-((dimethylamino)(thiophen-2-yl)methyl)cyclohexyl)methyl)-2-(2-(1-(4-methoxy-2,3,6-trimethylphenylsulfonyl)piperidin-4-yl)ethoxy)acetamide;

(132) 2-(2-(3,4-dichloro-N-methylphenylsulfonamido)cyclohexyloxy)-N-(4-((dimethylamino)(3-fluorophenyl)methyl)cyclohexyl)acetamide;

(133) 2-((1-(3,4-dimethoxyphenylsulfonyl)piperidin-2-yl)methoxy)-N-((4-((dimethylamino)(thiophen-2-yl)methyl)cyclohexyl)methyl)acetamide;

(134) 2-(benzyloxy)-N-(2-(4-((dimethylamino)(phenyl)methyl)cyclohexyl)ethyl)acetamide;

(135) 2-(2-(2,6-dichloro-N-methylphenylsulfonamido)ethoxy)-N-(4-((dimethylamino)(phenyl)methyl)cyclohexyl)acetamide;

(136) N-(4-((dimethylamino)(phenyl)methyl)cyclohexyl)-2-(2-(2,3,4,5,6-pentafluoro-N-methylphenylsulfonamido)ethoxy)acetamide;

(137) N-((4-((dimethylamino)(phenyl)methyl)cyclohexyl)methyl)-2-(2-(4-methoxy-N,2,6-trimethylphenylsulfonamido)ethoxy)acetamide;

(138) N-(2-(4-((dimethylamino)(thiophen-2-yl)methyl)cyclohexyl)ethyl)-2-(1-(4-fluorophenylsulfonyl)pyrrolidin-3-yloxy)acetamide;
(139) N-(4-((dimethylamino)(3-fluorophenyl)methyl)cyclohexyl)-2-(1-(3-(trifluoromethyl)phenylsulfonyl)pyrrolidin-3-yloxy)acetamide;
(140) N-(4-((dimethylamino)(3-fluorophenyl)methyl)cyclohexyl)-2-(1-(mesitylsulfonyl)pyrrolidin-3-yloxy)acetamide;
(141) N-((4-((dimethylamino)(3-fluorophenyl)methyl)cyclohexyl)methyl)-2-(1-(mesitylsulfonyl)pyrrolidin-3-yloxy)acetamide;
(142) N-((4-((dimethylamino)(thiophen-2-yl)methyl)cyclohexyl)methyl)-2-(2-(4-methoxy-N-methylphenylsulfonamido)ethoxy)acetamide;
(143) N-((4-((dimethylamino)(phenyl)methyl)cyclohexyl)methyl)-2-(1-(4-methoxy-2,3,6-trimethylphenylsulfonyl)piperidin-4-yloxy)acetamide;
(144) N-(4-((dimethylamino)(thiophen-2-yl)methyl)cyclohexyl)-2-(1-(4-methoxy-2,3,6-trimethylphenylsulfonyl)piperidin-3-yloxy)acetamide;
(145) N-((4-((dimethylamino)(3-fluorophenyl)methyl)cyclohexyl)methyl)-2-(1-(4-methoxy-2,3,6-trimethylphenylsulfonyl)piperidin-3-yloxy)acetamide;
(146) N-((4-((dimethylamino)(phenyl)methyl)cyclohexyl)methyl)-2-(2-(1-(4-methoxy-2,3,6-trimethylphenylsulfonyl)piperidin-4-yl)ethoxy)acetamide;
(147) 2-((1-(3,4-dichlorophenylsulfonyl)piperidin-2-yl)methoxy)-N-(2-(4-((dimethylamino)(3-fluorophenyl)methyl)cyclohexyl)ethyl)acetamide;
(148) 2-(2-(N-benzyl-4-methoxy-2,6-dimethylphenylsulfonamido)ethoxy)-N-((4-((dimethylamino)(phenyl)methyl)cyclohexyl)methyl)acetamide;
(149) 2-(2-(N-benzyl-4-methoxy-2,6-dimethylphenylsulfonamido)ethoxy)-N-(2-(4-((dimethylamino)(thiophen-2-yl)methyl)cyclohexyl)ethyl)acetamide;
(150) 2-((1-(3,4-dimethoxyphenylsulfonyl)piperidin-2-yl)methoxy)-N-((4-((dimethylamino)(phenyl)methyl)cyclohexyl)methyl)acetamide;
(151) 2-((1-(2,4-dimethoxyphenylsulfonyl)piperidin-2-yl)methoxy)-N-((4-((dimethylamino) (3-fluorophenyl)methyl)cyclohexyl)methyl)acetamide;
(152) N-(4-((dimethylamino)(thiophen-2-yl)methyl)cyclohexyl)-2-(2-(N-methyl-3-(trifluoromethyl)phenylsulfonamido)ethoxy)acetamide;
(153) N-(4-((dimethylamino)(3-fluorophenyl)methyl)cyclohexyl)-2-phenoxypropanamide
(154) N-(4-((dimethylamino)(phenyl)methyl)cyclohexyl)-2-((1-(4-methoxyphenylsulfonyl)piperidin-2-yl)methoxy)acetamide;
(155) 2-(1-(3,4-dimethoxyphenylsulfonyl)pyrrolidin-3-yloxy)-N-(4-((dimethylamino)(thiophen-2-yl)methyl)cyclohexyl)acetamide;
(156) N-(4-((dimethylamino)(thiophen-2-yl)methyl)cyclohexyl)-2-(1-tosylpyrrolidin-3-yloxy)acetamide;
(157) N-((4-((dimethylamino)(phenyl)methyl)cyclohexyl)methyl)-2-(2-(N,4-dimethylphenylsulfonamido)ethoxy)acetamide;
(158) 2-(2-(4-chloro-N-methylphenylsulfonamido)ethoxy)-N-((4-((dimethylamino)(3-fluorophenyl)methyl)cyclohexyl)methyl)acetamide;
(159) N-(4-((dimethylamino)(3-fluorophenyl)methyl)cyclohexyl)-2-(2-(4-methoxy-N,2,3,6-tetramethylphenylsulfonamido)ethoxy)acetamide;
(160) N-((4-((dimethylamino)(3-fluorophenyl)methyl)cyclohexyl)methyl)-2-(2-(4-methoxy-N,2,3,6-tetramethylphenylsulfonamido)ethoxy)acetamide;
(161) 2-(2-(N-benzylphenylsulfonamido)ethoxy)-N-(4-((dimethylamino)(thiophen-2-yl)methyl)cyclohexyl)acetamide;
(162) N-(4-((dimethylamino)(thiophen-2-yl)methyl)cyclohexyl)-2-((1-(4-methoxyphenylsulfonyl)pyrrolidin-2-yl)methoxy)acetamide;
(163) N-((4-((dimethylamino)(3-fluorophenyl)methyl)cyclohexyl)methyl)-2-((2-(4-methoxy phenylsulfonyl)-1,2,3,4-tetrahydroisoquinolin-3-yl)methoxy)acetamide;
(164) 2-(2-(3,4-dichloro-N-methylphenylsulfonamido)cyclohexyloxy)-N-((4-((dimethylamino)(3-fluorophenyl)methyl)cyclohexyl)methyl)acetamide;
(165) N-(4-((dimethylamino)(phenyl)methyl)cyclohexyl)-2-(1-(4-methoxy-2,6-dimethyl phenylsulfonyl)pyrrolidin-3-yloxy)acetamide;
(166) 2-(2-(3,4-dichloro-N-methylphenylsulfonamido)phenoxy)-N-(4-((dimethylamino)(phenyl)methyl)cyclohexyl)acetamide;
(167) N-(4-((dimethylamino)(3-fluorophenyl)methyl)cyclohexyl)-2-(1-tosylpyrrolidin-3-yloxy)acetamide;
(168) N-(4-((dimethylamino)(thiophen-2-yl)methyl)cyclohexyl)-2-(2-(N,4-dimethylphenylsulfonamide)ethoxy)acetamide;
(169) 2-(2-(3,4-dimethoxy-N-methylphenylsulfonamido)ethoxy)-N-((4-((dimethylamino)(phenyl)methyl)cyclohexyl)methyl)acetamide;
(170) N-((4-((dimethylamino)(3-fluorophenyl)methyl)cyclohexyl)methyl)-2-(1-(3-(trifluoromethyl)phenylsulfonyl)pyrrolidin-3-yloxy)acetamide;
(171) 2-(2-(2,6-dichloro-N-methylphenylsulfonamido)ethoxy)-N-(4-((dimethylamino)(3-fluorophenyl)methyl)cyclohexyl)acetamide;
(172) N-(4-((dimethylamino)(3-fluorophenyl)methyl)cyclohexyl)-2-(1-(4-fluorophenylsulfonyl)pyrrolidin-3-yloxy)acetamide;
(173) N-((4-((dimethylamino)(phenyl)methyl)cyclohexyl)methyl)-2-(1-(4-methoxy-2,6-dimethylphenylsulfonyl)pyrrolidin-3-yloxy)acetamide;
(174) N-(2-(4-((dimethylamino)(3-fluorophenyl)methyl)cyclohexyl)ethyl)-2-(2-(2,4,6-trichloro-N-methylphenylsulfonamido)ethoxy)acetamide;
(175) 2-(2-(N-benzylphenylsulfonamido)ethoxy)-N-(4-((dimethylamino)(3-fluorophenyl)methyl)cyclohexyl)acetamide;
(176) N-(4-((dimethylamino)(3-fluorophenyl)methyl)cyclohexyl)-2-(2-(N-ethyl-4-methoxy-2,3,6-trimethylphenylsulfonamido)ethoxy)acetamide;
(177) N-(2-(4-((dimethylamino)(thiophen-2-yl)methyl)cyclohexyl)ethyl)-2-(1-(4-methoxy-2,3,6-trimethylphenylsulfonyl)piperidin-4-yloxy)acetamide;
(178) N-(4-((dimethylamino)(4-fluorophenyl)methyl)cyclohexyl)-2-(2-(1-(4-methoxy-2,3,6-trimethylphenylsulfonyl)piperidin-4-yl)ethoxy)acetamide;
(179) N-((4-((dimethylamino)(3-fluorophenyl)methyl)cyclohexyl)methyl)-2-((1-(4-methoxyphenylsulfonyl)piperidin-2-yl)methoxy)acetamide;
(180) N-(2-(4-((dimethylamino)(3-fluorophenyl)methyl)cyclohexyl)ethyl)-2-((1-(4-methoxyphenylsulfonyl)piperidin-2-yl)methoxy)acetamide;
(181) N-(4-((dimethylamino)(phenyl)methyl)cyclohexyl)-2-phenoxypropanamide
(182) N-(4-((dimethylamino)(phenyl)methyl)cyclohexyl)-2-((1-(4-methoxyphenylsulfonyl)pyrrolidin-2-yl)methoxy)acetamide;
(183) N-(2-(4-((dimethylamino)(3-fluorophenyl)methyl)cyclohexyl)ethyl)-2-(2-(4-methoxy-N,2,3,6-tetramethylphenylsulfonamido)ethoxy)acetamide;

(184) 2-(1-(3,4-dimethoxyphenylsulfonyl)pyrrolidin-3-yloxy)-N-((4-((dimethylamino)(3-fluorophenyl)methyl)cyclohexyl)methyl)acetamide;
(185) N-((4-((dimethylamino)(3-fluorophenyl)methyl)cyclohexyl)methyl)-2-(1-tosylpyrrolidin-3-yloxy)acetamide;
(186) 2-(2-(4-chloro-N-methylphenylsulfonamido)ethoxy)-N-(2-(4-((dimethylamino)(3-fluorophenyl)methyl)cyclohexyl)ethyl)acetamide;
(187) 2-((1-(2,4-dimethoxyphenylsulfonyl)piperidin-2-yl)methoxy)-N-(4-((dimethylamino)(phenyl)methyl)cyclohexyl)acetamide;
(188) N-((4-((dimethylamino)(3-fluorophenyl)methyl)cyclohexyl)methyl)-2-(2-(2,4,6-trichloro-N-methylphenylsulfonamido)ethoxy)acetamide;
(189) N-(4-((dimethylamino)(3-fluorophenyl)methyl)cyclohexyl)-2-(1-(4-methoxy-2,3,6-trimethylphenylsulfonyl)pyrrolidin-3-yloxy)acetamide;
(190) N-(2-(4-((dimethylamino)(3-fluorophenyl)methyl)cyclohexyl)ethyl)-2-((2-(4-methoxyphenylsulfonyl)-1,2,3,4-tetrahydroisoquinolin-3-yl)methoxy)acetamide;
(191) 2-((1-(3,4-dimethoxyphenylsulfonyl)piperidin-2-yl)methoxy)-N-(2-(4-((dimethylamino)(3-fluorophenyl)methyl)cyclohexyl)ethyl)acetamide;
(192) N-(2-(4-((dimethylamino)(3-fluorophenyl)methyl)cyclohexyl)ethyl)-2-(2-(N-methyl-3-(trifluoromethyl)phenylsulfonamido)ethoxy)acetamide;
(193) 2-(2-(N-benzyl-4-methoxy-2,3,6-trimethylphenylsulfonamido)ethoxy)-N-(4-((dimethylamino)(phenyl)methyl)cyclohexyl)acetamide;
(194) N-(4-((dimethylamino)(thiophen-2-yl)methyl)cyclohexyl)-2-(1-(phenylsulfonyl)pyrrolidin-3-yloxy)acetamide;
(195) N-((4-((dimethylamino)(phenyl)methyl)cyclohexyl)methyl)-2-(1-(phenylsulfonyl)pyrrolidin-3-yloxy)acetamide;
(196) 2-(2-(4-chloro-N-methylphenylsulfonamido)ethoxy)-N-(4-((dimethylamino)(3-fluorophenyl)methyl)cyclohexyl)acetamide;
(197) N-(2-(4-((dimethylamino)(3-fluorophenyl)methyl)cyclohexyl)ethyl)-2-(2-(4-methoxy-N,2,6-trimethylphenylsulfonamido)ethoxy)acetamide;
(198) 2-((1-(3,4-dimethoxyphenylsulfonyl)piperidin-2-yl)methoxy)-N-(4-((dimethylamino)(phenyl)methyl)cyclohexyl)acetamide;
(199) N-(2-(4-((dimethylamino)(thiophen-2-yl)methyl)cyclohexyl)ethyl)-2-(1-(4-methoxy-2,6-dimethylphenylsulfonyl)pyrrolidin-3-yloxy)acetamide;
(200) N-(2-(4-((dimethylamino)(3-fluorophenyl)methyl)cyclohexyl)ethyl)-2-(2-(4-(4-methoxy-2,3,6-trimethylphenylsulfonyl)piperazin-1-yl)ethoxy)acetamide;
(201) 2-(2-(N-benzyl-4-methoxy-2,3,6-trimethylphenylsulfonamido)ethoxy)-N-((4-((dimethylamino)(phenyl)methyl)cyclohexyl)methyl)acetamide;
(202) 2-((1-(3,4-dichlorophenylsulfonyl)pyrrolidin-2-yl)methoxy)-N-(2-(4-((dimethylamino)(3-fluorophenyl)methyl)cyclohexyl)ethyl)acetamide;
(203) N-((4-((dimethylamino)(3-fluorophenyl)methyl)cyclohexyl)methyl)-2-(2-(1-(4-methoxyphenylsulfonyl)piperidin-2-yl)ethoxy)acetamide;
(204) 2-(1-(4-chlorophenylsulfonyl)pyrrolidin-3-yloxy)-N-(4-((dimethylamino)(3-fluorophenyl)methyl)cyclohexyl)acetamide;
(205) N-(4-((dimethylamino)(3-fluorophenyl)methyl)cyclohexyl)-2-(2-(4-fluoro-N-methylphenylsulfonamido)ethoxy)acetamide;
(206) 2-(2-(3,4-dimethoxy-N-methylphenylsulfonamido)ethoxy)-N-(4-((dimethylamino)(thiophen-2-yl)methyl)cyclohexyl)acetamide;
(207) N-((4-((4-chlorophenyl)(dimethylamino)methyl)cyclohexyl)methyl)-2-(2-(2,6-dichloro-N-methylphenylsulfonamido)ethoxy)acetamide;
(208) N-(4-((dimethylamino)(3-fluorophenyl)methyl)cyclohexyl)-2-(2-(2,4,6-trichloro-N-methylphenylsulfonamido)ethoxy)acetamide;
(209) N-(2-(4-((dimethylamino)(3-fluorophenyl)methyl)cyclohexyl)ethyl)-2-(2-(N-ethyl-4-methoxy-2,3,6-trimethylphenylsulfonamido)ethoxy)acetamide;
(210) 2-((1-(3,4-dichlorophenylsulfonyl)piperidin-2-yl)methoxy)-N-(4-((dimethylamino)(3-fluorophenyl)methyl)cyclohexyl)acetamide;
(211) 2-((1-(3,4-dichlorophenylsulfonyl)pyrrolidin-2-yl)methoxy)-N-(4-((dimethylamino)(3-fluorophenyl)methyl)cyclohexyl)acetamide;
(212) N-(4-((dimethylamino)(4-fluorophenyl)methyl)cyclohexyl)-2-(2-(1-(4-methoxyphenylsulfonyl)piperidin-2-yl)ethoxy)acetamide;
(213) N-(2-(4-((dimethylamino)(3-fluorophenyl)methyl)cyclohexyl)ethyl)-2-(2-(1-(4-methoxyphenylsulfonyl)piperidin-2-yl)ethoxy)acetamide;
(214) 2-(2-(3,4-dichloro-N-methylphenylsulfonamido)cyclohexyloxy)-N-(2-(4-((dimethylamino)(thiophen-2-yl)methyl)cyclohexyl)ethyl)acetamide;
(215) N-(2-(4-((dimethylamino)(3-fluorophenyl)methyl)cyclohexyl)ethyl)-2-(2-(N-methyl-4-(trifluoromethoxy)phenylsulfonamido)ethoxy)acetamide;
(216) N-(2-(4-((dimethylamino)(3-fluorophenyl)methyl)cyclohexyl)ethyl)-2-(1-tosylpyrrolidin-3-yloxy)acetamide;
(217) 2-(2-(2,4-dichloro-N-methylphenylsulfonamido)ethoxy)-N-(4-((dimethylamino)(3-fluorophenyl)methyl)cyclohexyl)acetamide;
(218) N-(2-(4-((dimethylamino)(3-fluorophenyl)methyl)cyclohexyl)ethyl)-2-(2-(4-fluoro-N-methylphenylsulfonamido)ethoxy)acetamide;
(219) N-((4-((dimethylamino)(phenyl)methyl)cyclohexyl)methyl)-2-(1-(4-fluorophenylsulfonyl)pyrrolidin-3-yloxy)acetamide;
(220) N-((4-((dimethylamino)(3-fluorophenyl)methyl)cyclohexyl)methyl)-2-((1-(phenylsulfonyl)piperidin-3-yl)methoxy)acetamide;
(221) N-(2-(4-((dimethylamino)(3-fluorophenyl)methyl)cyclohexyl)ethyl)-2-(1-(4-methoxy-2,3,6-trimethylphenylsulfonyl)piperidin-3-yloxy)acetamide;
(222) N-(4-((dimethylamino)(4-fluorophenyl)methyl)cyclohexyl)-2-(2-(4-(4-methoxy-2,3,6-trimethylphenylsulfonyl)piperazin-1-yl)ethoxy)acetamide;
(223) N-((4-((dimethylamino)(3-fluorophenyl)methyl)cyclohexyl)methyl)-2-(2-(4-(4-methoxy-2,3,6-trimethylphenylsulfonyl)piperazin-1-yl)ethoxy)acetamide;
(224) N-(2-(4-((dimethylamino)(3-fluorophenyl)methyl)cyclohexyl)ethyl)-2-((1-(4-methoxyphenylsulfonyl)pyrrolidin-2-yl)methoxy)acetamide;
(225) 2-(1-(2,4-dichlorophenylsulfonyl)pyrrolidin-3-yloxy)-N-((4-((dimethylamino)(3-fluorophenyl)methyl)cyclohexyl)methyl)acetamide;
(226) N-(4-((dimethylamino)(3-fluorophenyl)methyl)cyclohexyl)-2-(2-(N,4-dimethylphenylsulfonamido)ethoxy)acetamide;
(227) N-((4-((dimethylamino)(3-fluorophenyl)methyl)cyclohexyl)methyl)-2-(2-(N,4-dimethylphenylsulfonamido)ethoxy)acetamide;

(228) N-(4-((dimethylamino)(3-fluorophenyl)methyl)cyclohexyl)-2-(2-(4-methoxy-N,2,6-trimethylphenylsulfonamido)ethoxy)acetamide;
(229) N-((4-((dimethylamino)(3-fluorophenyl)methyl)cyclohexyl)ethyl)-2-(2-(4-fluoro-N-methylphenylsulfonamido)ethoxy)acetamide;
(230) N-(2-(4-((dimethylamino)(thiophen-2-yl)methyl)cyclohexyl)ethyl)-2-(1-(phenylsulfonyl)piperidin-4-yloxy)acetamide;
(231) N-((4-((dimethylamino)(phenyl)methyl)cyclohexyl)methyl)-2-(2-(N-ethyl-4-methoxy-2,3,6-trimethylphenylsulfonamido)ethoxy)acetamide;
(232) N-(2-(4-((dimethylamino)(3-fluorophenyl)methyl)cyclohexyl)ethyl)-2-(1-(4-methoxy-2,3,6-trimethylphenylsulfonyl)piperidin-4-yloxy)acetamide;
(233) 2-((1-(3,4-dichlorophenylsulfonyl)piperidin-2-yl)methoxy)-N-((4-((dimethylamino)(4-fluorophenyl)methyl)cyclohexyl)methyl)acetamide;
(234) N-(4-((dimethylamino)(4-fluorophenyl)methyl)cyclohexyl)-2-((2-(4-methoxyphenylsulfonyl)-1,2,3,4-tetrahydroisoquinolin-3-yl)methoxy)acetamide;
(235) N-(4-((dimethylamino)(thiophen-2-yl)methyl)cyclohexyl)-2-(2-(N,2,4,6-tetramethylphenylsulfonamido)ethoxy)acetamide;
(236) N-((4-((dimethylamino)(4-fluorophenyl)methyl)cyclohexyl)methyl)-2-phenoxypropanamide
(237) N-((4-((4-chlorophenyl)(dimethylamino)methyl)cyclohexyl)methyl)-2-phenoxypropanamide
(238) N-((4-((4-chlorophenyl)(dimethylamino)methyl)cyclohexyl)methyl)-2-phenoxypropanamide
(239) N-(4-((dimethylamino)(phenyl)methyl)cyclohexyl)-2-(2-(4-methoxy-N,2,6-trimethylphenylsulfonamido)ethoxy)acetamide;
(240) N-(2-(4-((dimethylamino)(3-fluorophenyl)methyl)cyclohexyl)ethyl)-2-(2-(N,4-dimethylphenylsulfonamido)ethoxy)acetamide;
(241) N-(2-(4-((4-chlorophenyl)(dimethylamino)methyl)cyclohexyl)ethyl)-2-(2-(4-fluoro-N-methylphenylsulfonamido)ethoxy)acetamide;
(242) N-((4-((dimethylamino)(phenyl)methyl)cyclohexyl)methyl)-2-(2-(4-methoxy-N-methylphenylsulfonamido)ethoxy)acetamide;
(243) N-(4-((dimethylamino)(thiophen-2-yl)methyl)cyclohexyl)-2-((1-(4-methoxyphenylsulfonyl)piperidin-2-yl)methoxy)acetamide;
(244) 2-(2-(3,4-dichloro-N-methylphenylsulfonamido)cyclohexyloxy)-N-(2-(4-((dimethylamino)(4-fluorophenyl)methyl)cyclohexyl)ethyl)acetamide;
(245) 2-(benzyloxy)-N-(4-((dimethylamino)(phenyl)methyl)cyclohexyl)acetamide;
(246) N-(4-((dimethylamino)(3-fluorophenyl)methyl)cyclohexyl)-2-(2-(N-methyl-4-(trifluoromethoxy)phenylsulfonamido)ethoxy)acetamide;
(247) 2-(1-(4-chlorophenylsulfonyl)pyrrolidin-3-yloxy)-N-(2-(4-((dimethylamino)(3-fluorophenyl)methyl)cyclohexyl)ethyl)acetamide;
(248) N-((4-((dimethylamino)(3-fluorophenyl)methyl)cyclohexyl)methyl)-2-(2-(4-methoxy-N,2,6-trimethylphenylsulfonamido)ethoxy)acetamide;
(249) 2-(2-(2,4-dichloro-N-methylphenylsulfonamido)ethoxy)-N-((4-((dimethylamino)(4-fluorophenyl)methyl)cyclohexyl)methyl)acetamide;
(250) N-(4-((dimethylamino)(3-fluorophenyl)methyl)cyclohexyl)-2-(2-(4-methoxy-N-methylphenylsulfonamido)ethoxy)acetamide;
(251) N-(4-((dimethylamino)(3-fluorophenyl)methyl)cyclohexyl)-2-(1-(4-methoxy-2,6-dimethylphenylsulfonyl)pyrrolidin-3-yloxy)acetamide;
(252) N-((4-((dimethylamino)(3-fluorophenyl)methyl)cyclohexyl)methyl)-2-(1-(4-methoxy-2,3,6-trimethylphenylsulfonyl)pyrrolidin-3-yloxy)acetamide;
(253) N-(2-(4-((dimethylamino)(3-fluorophenyl)methyl)cyclohexyl)ethyl)-2-(1-(4-methoxy-2,3,6-trimethylphenylsulfonyl)pyrrolidin-3-yloxy)acetamide;
(254) 2-(2-(N-benzyl-4-methoxy-2,3,6-trimethylphenylsulfonamido)ethoxy)-N-(2-(4-((dimethylamino)(thiophen-2-yl)methyl)cyclohexyl)ethyl)acetamide;
(255) N-(4-((dimethylamino)(3-fluorophenyl)methyl)cyclohexyl)-2-((1-(4-methoxyphenylsulfonyl)piperidin-2-yl)methoxy)acetamide;
(256) 2-(2-(3,4-dichloro-N-methylphenylsulfonamido)cyclohexyloxy)-N-(4-((dimethylamino)(4-fluorophenyl)methyl)cyclohexyl)acetamide;
(257) N-(4-((dimethylamino)(phenyl)methyl)cyclohexyl)-2-(1-(phenylsulfonyl)piperidin-4-yloxy)acetamide;
(258) 2-(1-(4-chlorophenylsulfonyl)pyrrolidin-3-yloxy)-N-((4-((dimethylamino)(3-fluorophenyl)methyl)cyclohexyl)methyl)acetamide;
(259) 2-(1-(2,4-dichlorophenylsulfonyl)pyrrolidin-3-yloxy)-N-(2-(4-((dimethylamino)(3-fluorophenyl)methyl)cyclohexyl)ethyl)acetamide;
(260) N-((4-((4-chlorophenyl)(dimethylamino)methyl)cyclohexyl)methyl)-2-(1-(3,4-dimethoxyphenylsulfonyl)pyrrolidin-3-yloxy)acetamide;
(261) 2-((1-(3,4-dimethoxyphenylsulfonyl)piperidin-2-yl)methoxy)-N-(4-((dimethylamino)(thiophen-2-yl)methyl)cyclohexyl)acetamide;
(262) 2-(1-(3,4-dimethoxyphenylsulfonyl)pyrrolidin-3-yloxy)-N-(2-(4-((dimethylamino)(3-fluorophenyl)methyl)cyclohexyl)ethyl)acetamide;
(263) N-((4-((4-chlorophenyl)(dimethylamino)methyl)cyclohexyl)methyl)-2-(2-(4-fluoro-N-methylphenylsulfonamido)ethoxy)acetamide;
(264) N-(2-(4-((dimethylamino)(3-fluorophenyl)methyl)cyclohexyl)ethyl)-2-(1-(mesitylsulfonyl)pyrrolidin-3-yloxy)acetamide;
(265) N-((4-((dimethylamino)(3-fluorophenyl)methyl)cyclohexyl)methyl)-2-(1-(4-methoxy-2,6-dimethylphenylsulfonyl)pyrrolidin-3-yloxy)acetamide;
(266) N-(4-((dimethylamino)(3-fluorophenyl)methyl)cyclohexyl)-2-((1-(phenylsulfonyl)piperidin-3-yl)methoxy)acetamide;
(267) 2-((1-(3,4-dichlorophenylsulfonyl)pyrrolidin-2-yl)methoxy)-N-((4-((dimethylamino)(4-fluorophenyl)methyl)cyclohexyl)methyl)acetamide;
(268) N-(4-((dimethylamino)(3-fluorophenyl)methyl)cyclohexyl)-2-((1-(4-methoxyphenylsulfonyl)pyrrolidin-2-yl)methoxy)acetamide;
(269) N-((4-((4-chlorophenyl)(dimethylamino)methyl)cyclohexyl)methyl)-2-(2-(3,4-dichloro-N-methylphenylsulfonamido)cyclohexyloxy)acetamide;
(270) N-(2-(4-((dimethylamino)(phenyl)methyl)cyclohexyl)ethyl)-2-phenoxypropanamide
(271) N-(4-((dimethylamino)(3-fluorophenyl)methyl)cyclohexyl)-2-(1-(phenylsulfonyl)pyrrolidin-3-yloxy)acetamide;
(272) N-(2-(4-((dimethylamino)(thiophen-2-yl)methyl)cyclohexyl)ethyl)-2-(1-tosylpyrrolidin-3-yloxy)acetamide;

(273) N-((4-((4-chlorophenyl)(dimethylamino)methyl)cyclohexyl)methyl)-2-(2-(N,4-dimethylphenylsulfonamido)ethoxy)acetamide;
(274) N-(2-(4-((4-chlorophenyl)(dimethylamino)methyl)cyclohexyl)ethyl)-2-(2-(2,6-dichloro-N-methylphenylsulfonamido)ethoxy)acetamide;
(275) N-((4-((dimethylamino)(3-fluorophenyl)methyl)cyclohexyl)methyl)-2-(1-(4-fluorophenylsulfonyl)pyrrolidin-3-yloxy)acetamide;
(276) N-((4-((dimethylamino)(thiophen-2-yl)methyl)cyclohexyl)methyl)-2-(1-(phenylsulfonyl)piperidin-4-yloxy)acetamide;
(277) N-(4-((dimethylamino)(3-fluorophenyl)methyl)cyclohexyl)-2-(1-(phenylsulfonyl)piperidin-3-yloxy)acetamide;
(278) 2-(2-(N-benzylphenylsulfonamido)ethoxy)-N-(2-(4-((dimethylamino)(3-fluorophenyl)methyl)cyclohexyl)ethyl)acetamide;
(279) N-(4-((dimethylamino)(3-fluorophenyl)methyl)cyclohexyl)-2-(1-(4-methoxy-2,3,6-trimethylphenylsulfonyl)piperidin-3-yloxy)acetamide;
(280) N-((4-((4-chlorophenyl)(dimethylamino)methyl)cyclohexyl)methyl)-2-((1-(2,4-dimethoxyphenylsulfonyl)piperidin-2-yl)methoxy)acetamide;
(281) 2-((1-(2,4-dimethoxyphenylsulfonyl)piperidin-2-yl)methoxy)-N-(2-(4-((dimethylamino)(3-fluorophenyl)methyl)cyclohexyl)ethyl)acetamide;
(282) N-(4-((dimethylamino)(thiophen-2-yl)methyl)cyclohexyl)-2-(2-(N-methyl-4-(trifluoromethoxy)phenylsulfonamido)ethoxy)acetamide;
(283) 2-(1-(2,4-dichlorophenylsulfonyl)pyrrolidin-3-yloxy)-N-(4-((dimethylamino)(3-fluorophenyl)methyl)cyclohexyl)acetamide;
(284) 2-(2-(4-chloro-N-methylphenylsulfonamido)ethoxy)-N-((4-((4-chlorophenyl)(dimethylamino)methyl)cyclohexyl)methyl)acetamide;
(285) 2-(2-(2,6-dichloro-N-methylphenylsulfonamido)ethoxy)-N-(2-(4-((dimethylamino)(4-fluorophenyl)methyl)cyclohexyl)ethyl)acetamide;
(286) N-(4-((dimethylamino)(3-fluorophenyl)methyl)cyclohexyl)-2-(1-(4-methoxy-2,3,6-trimethylphenylsulfonyl)piperidin-4-yloxy)acetamide;
(287) N-((4-((dimethylamino)(3-fluorophenyl)methyl)cyclohexyl)methyl)-2-(1-(4-methoxy-2,3,6-trimethylphenylsulfonyl)piperidin-4-yloxy)acetamide;
(288) N-((4-((dimethylamino)(4-fluorophenyl)methyl)cyclohexyl)methyl)-2-((2-(4-methoxyphenylsulfonyl)-1,2,3,4-tetrahydroisoquinolin-3-yl)methoxy)acetamide;
(289) N-(2-(4-((4-chlorophenyl)(dimethylamino)methyl)cyclohexyl)ethyl)-2-(2-(N-methyl-3-(trifluoromethyl)phenylsulfonamido)ethoxy)acetamide;
(290) 2-(1-(2,4-dichlorophenylsulfonyl)pyrrolidin-3-yloxy)-N-(4-((dimethylamino)(4-fluorophenyl)methyl)cyclohexyl)acetamide;
(291) N-(2-(4-((4-chlorophenyl)(dimethylamino)methyl)cyclohexyl)ethyl)-2-(2-(2,4-dichloro-N-methylphenylsulfonamido)ethoxy)acetamide;
(292) N-(2-(4-((dimethylamino)(3-fluorophenyl)methyl)cyclohexyl)ethyl)-2-(2-(4-methoxy-N-methylphenylsulfonamido)ethoxy)acetamide;
(293) 2-(2-(3,4-dimethoxy-N-methylphenylsulfonamido)ethoxy)-N-(2-(4-((dimethylamino)(3-fluorophenyl)methyl)cyclohexyl)ethyl)acetamide;
(294) N-((4-((4-chlorophenyl)(dimethylamino)methyl)cyclohexyl)methyl)-2-((1-(phenylsulfonyl)piperidin-3-yl)methoxy)acetamide;
(295) N-(2-(4-((dimethylamino)(3-fluorophenyl)methyl)cyclohexyl)ethyl)-2-((1-(phenylsulfonyl)piperidin-3-yl)methoxy)acetamide;
(296) 2-(2-(N-benzylphenylsulfonamido)ethoxy)-N-((4-((dimethylamino)(3-fluorophenyl)methyl)cyclohexyl)methyl)acetamide;
(297) N-(4-((dimethylamino)(3-fluorophenyl)methyl)cyclohexyl)-2-(2-(N-methyl-3-(trifluoromethyl)phenylsulfonamido)ethoxy)acetamide;
(298) N-((4-((4-chlorophenyl)(dimethylamino)methyl)cyclohexyl)methyl)-2-(2-(4-methoxy-N,2,3,6-tetramethylphenylsulfonamido)ethoxy)acetamide;
(299) N-((4-((4-chlorophenyl)(dimethylamino)methyl)cyclohexyl)methyl)-2-(1-(phenylsulfonyl)pyrrolidin-3-yloxy)acetamide;
(300) N-((4-((dimethylamino)(phenyl)methyl)cyclohexyl)methyl)-2-(1-(phenylsulfonyl)piperidin-4-yloxy)acetamide;
(301) N-((4-((4-chlorophenyl)(dimethylamino)methyl)cyclohexyl)methyl)-2-(1-(phenylsulfonyl)piperidin-3-yloxy)acetamide;
(302) N-((4-((dimethylamino)(3-fluorophenyl)methyl)cyclohexyl)methyl)-2-(2-(N-methyl-3-(trifluoromethyl)phenylsulfonamido)ethoxy)acetamide;
(303) N-((4-((dimethylamino)(3-fluorophenyl)methyl)cyclohexyl)methyl)-2-(2-(N-methyl-4-(trifluoromethoxy)phenylsulfonamido)ethoxy)acetamide;
(304) N-((4-((4-chlorophenyl)(dimethylamino)methyl)cyclohexyl)methyl)-2-(1-tosylpyrrolidin-3-yloxy)acetamide;
(305) N-(2-(4-((4-chlorophenyl)(dimethylamino)methyl)cyclohexyl)ethyl)-2-(1-tosylpyrrolidin-3-yloxy)acetamide;
(306) N-(2-(4-((4-chlorophenyl)(dimethylamino)methyl)cyclohexyl)ethyl)-2-(2-(N,4-dimethylphenylsulfonamido)ethoxy)acetamide;
(307) N-(2-(4-((dimethylamino)(3-fluorophenyl)methyl)cyclohexyl)ethyl)-2-(1-(4-methoxy-2,6-dimethylphenylsulfonyl)pyrrolidin-3-yloxy)acetamide;
(308) N-((4-((dimethylamino)(3-fluorophenyl)methyl)cyclohexyl)methyl)-2-(2-(4-(phenylsulfonyl)piperazin-1-yl)ethoxy)acetamide;
(309) N-((4-((dimethylamino)(3-fluorophenyl)methyl)cyclohexyl)methyl)-2-(1-(phenylsulfonyl)piperidin-3-yloxy)acetamide;
(310) N-((4-((4-chlorophenyl)(dimethylamino)methyl)cyclohexyl)methyl)-2-(2-(N-ethyl-4-methoxy-2,3,6-trimethylphenylsulfonamido)ethoxy)acetamide;
(311) N-(2-(4-((4-chlorophenyl)(dimethylamino)methyl)cyclohexyl)ethyl)-2-((1-(4-methoxyphenylsulfonyl)piperidin-2-yl)methoxy)acetamide;
(312) N-((4-((4-chlorophenyl)(dimethylamino)methyl)cyclohexyl)methyl)-2-(2-(1-(4-methoxyphenylsulfonyl)piperidin-2-yl)ethoxy)acetamide;
(313) N-((4-((dimethylamino)(3-fluorophenyl)methyl)cyclohexyl)methyl)-2-((1-(4-methoxyphenylsulfonyl)pyrrolidin-2-yl)methoxy)acetamide;
(314) N-((4-((4-chlorophenyl)(dimethylamino)methyl)cyclohexyl)methyl)-2-(2-(N-methyl-3-(trifluoromethyl)phenylsulfonamido)ethoxy)acetamide;
(315) N-(2-(4-((dimethylamino)(thiophen-2-yl)methyl)cyclohexyl)ethyl)-2-phenoxypropanamide
(316) 2-(4-chlorophenoxy)-N-(4-((dimethylamino)(phenyl)-methyl)cyclohexyl)acetamide;
(317) N-(2-(4-((4-chlorophenyl)(dimethylamino)methyl)cyclohexyl)ethyl)-2-(2-(4-methoxy-N,2,3,6-tetramethylphenylsulfonamido)ethoxy)acetamide;

(318) N-((4-((4-chlorophenyl)(dimethylamino)methyl)cyclohexyl)methyl)-2-(2-(2,4,6-trichloro-N-methylphenylsulfonamido)ethoxy)acetamide;
(319) N-((4-((dimethylamino)(3-fluorophenyl)methyl)cyclohexyl)methyl)-2-(2-(1-(4-methoxy-2,3,6-trimethylphenylsulfonyl)piperidin-4-yl)ethoxy)acetamide;
(320) N-(2-(4-((4-chlorophenyl)(dimethylamino)methyl)cyclohexyl)ethyl)-2-(2-(4-(4-methoxy-2,3,6-trimethylphenylsulfonyl)piperazin-1-yl)ethoxy)acetamide;
(321) N-((4-((4-chlorophenyl)(dimethylamino)methyl)cyclohexyl)methyl)-2-((1-(4-methoxyphenylsulfonyl)piperidin-2-yl)methoxy)acetamide;
(322) 2-((1-(2,4-dimethoxyphenylsulfonyl)piperidin-2-yl)methoxy)-N-(4-((dimethylamino)(3-fluorophenyl)methyl)cyclohexyl)acetamide;
(323) 2-(1-(3,4-dimethoxyphenylsulfonyl)pyrrolidin-3-yloxy)-N-(4-((dimethylamino)(3-fluorophenyl)methyl)cyclohexyl)acetamide;
(324) N-((4-((4-chlorophenyl)(dimethylamino)methyl)cyclohexyl)methyl)-2-(2-(4-methoxy-N-methylphenylsulfonamido)ethoxy)acetamide;
(325) N-(2-(4-((dimethylamino)(3-fluorophenyl)methyl)cyclohexyl)ethyl)-2-(2-(4-(phenylsulfonyl)piperazin-1-yl)ethoxy)acetamide;
(326) N-(2-(4-((dimethylamino)(3-fluorophenyl)methyl)cyclohexyl)ethyl)-2-(1-(phenylsulfonyl)piperidin-3-yloxy)acetamide;
(327) N-((4-((dimethylamino)(4-fluorophenyl)methyl)cyclohexyl)methyl)-2-(2-(N-ethyl-4-methoxy-2,3,6-trimethylphenylsulfonamido)ethoxy)acetamide;
(328) 2-((1-(3,4-dichlorophenylsulfonyl)piperidin-2-yl)methoxy)-N-(4-((dimethylamino)(4-fluorophenyl)methyl)cyclohexyl)acetamide;
(329) 2-((1-(3,4-dimethoxyphenylsulfonyl)piperidin-2-yl)methoxy)-N-((4-((dimethylamino)(3-fluorophenyl)methyl)cyclohexyl)methyl)acetamide;
(330) N-(4-((dimethylamino)(4-fluorophenyl)methyl)cyclohexyl)-2-(1-(3-(trifluoromethyl)phenylsulfonyl)pyrrolidin-3-yloxy)acetamide;
(331) N-((4-((4-chlorophenyl)(dimethylamino)methyl)cyclohexyl)methyl)-2-(1-(3-(trifluoromethyl)phenylsulfonyl)pyrrolidin-3-yloxy)acetamide;
(332) N-(4-((dimethylamino)(4-fluorophenyl)methyl)cyclohexyl)-2-(1-(mesitylsulfonyl)pyrrolidin-3-yloxy)acetamide;
(333) N-((4-((dimethylamino)(3-fluorophenyl)methyl)cyclohexyl)methyl)-2-(2-(1-(phenylsulfonyl)piperidin-4-yl)ethoxy)acetamide;
(334) 2-(2-(2,6-dichloro-N-methylphenylsulfonamido)ethoxy)-N-((4-((dimethylamino) (4-fluorophenyl)methyl)cyclohexyl)methyl)acetamide;
(335) N-(4-((dimethylamino)(3-fluorophenyl)methyl)cyclohexyl)-2-(1-(phenylsulfonyl)piperidin-4-yloxy)acetamide;
(336) 2-(2-(N-benzylphenylsulfonamido)ethoxy)-N-(4-((dimethylamino)(4-fluorophenyl)methyl)cyclohexyl)acetamide;
(337) 2-((1-(3,4-dichlorophenylsulfonyl)piperidin-2-yl)methoxy)-N-(2-(4-((dimethylamino)(4-fluorophenyl)methyl)cyclohexyl)ethyl)acetamide;
(338) N-(2-(4-((4-chlorophenyl)(dimethylamino)methyl)cyclohexyl)ethyl)-2-(1-(3,4-dimethoxyphenylsulfonyl)pyrrolidin-3-yloxy)acetamide;
(339) N-(2-(4-((4-chlorophenyl)(dimethylamino)methyl)cyclohexyl)ethyl)-2-(2-(3,4-dimethoxy-N-methylphenylsulfonamido)ethoxy)acetamide;
(340) N-((4-((dimethylamino)(3-fluorophenyl)methyl)cyclohexyl)methyl)-2-(2-(4-methoxy-N-methylphenylsulfonamido)ethoxy)acetamide;
(341) N-(4-((dimethylamino)(thiophen-2-yl)methyl)cyclohexyl)-2-(2-(4-(phenylsulfonyl)piperazin-1-yl)ethoxy)acetamide;
(342) 2-(2-(N-benzylphenylsulfonamido)ethoxy)-N-((4-((dimethylamino)(4-fluorophenyl)methyl)cyclohexyl)methyl)acetamide;
(343) 2-(2-(N-benzylphenylsulfonamido)ethoxy)-N-((4-((4-chlorophenyl)(dimethylamino)methyl)cyclohexyl)methyl)acetamide;
(344) 2-((1-(3,4-dichlorophenylsulfonyl)pyrrolidin-2-yl)methoxy)-N-(4-((dimethylamino)(4-fluorophenyl)methyl)cyclohexyl)acetamide;
(345) N-((4-((dimethylamino)(4-fluorophenyl)methyl)cyclohexyl)methyl)-2-((1-(4-methoxyphenylsulfonyl)piperidin-2-yl)methoxy)acetamide;
(346) N-(2-(4-((4-chlorophenyl)(dimethylamino)methyl)cyclohexyl)ethyl)-2-((1-(4-methoxyphenylsulfonyl)pyrrolidin-2-yl)methoxy)acetamide;
(347) 2-(2-(4-chloro-N-methylphenylsulfonamido)ethoxy)-N-(2-(4-((4-chlorophenyl)(dimethylamino)methyl)cyclohexyl)ethyl)acetamide;
(348) N-((4-((4-chlorophenyl)(dimethylamino)methyl)cyclohexyl)methyl)-2-(2-(4-methoxy-N,2,6-trimethylphenylsulfonamido)ethoxy)acetamide;
(349) N-(2-(4-((dimethylamino)(4-fluorophenyl)methyl)cyclohexyl)ethyl)-2-((1-(4-methoxyphenylsulfonyl)piperidin-2-yl)methoxy)acetamide;
(350) N-((4-((dimethylamino)(4-fluorophenyl)methyl)cyclohexyl)methyl)-2-(2-(1-(4-methoxyphenylsulfonyl)piperidin-2-yl)ethoxy)acetamide;
(351) N-((4-((4-chlorophenyl)(dimethylamino)methyl)cyclohexyl)methyl)-2-((1-(4-methoxyphenylsulfonyl)pyrrolidin-2-yl)methoxy)acetamide;
(352) 2-((1-(3,4-dimethoxyphenylsulfonyl)piperidin-2-yl)methoxy)-N-(4-((dimethylamino)(3-fluorophenyl)methyl)cyclohexyl)acetamide;
(353) 2-(benzyloxy)-N-(4-((dimethylamino)(3-fluorophenyl)methyl)cyclohexyl)acetamide;
(354) N-(2-(4-((dimethylamino)(4-fluorophenyl)methyl)cyclohexyl)ethyl)-2-(2-(4-methoxy-N,2,3,6-tetramethylphenylsulfonamido)ethoxy)acetamide;
(355) N-((4-((dimethylamino)(3-fluorophenyl)methyl)cyclohexyl)methyl)-2-(1-(phenylsulfonyl)pyrrolidin-3-yloxy)acetamide;
(356) 2-(2-(2,4-dichloro-N-methylphenylsulfonamido)ethoxy)-N-(4-((dimethylamino)(4-fluorophenyl)methyl)cyclohexyl)acetamide;
(357) N-(4-((dimethylamino)(4-fluorophenyl)methyl)cyclohexyl)-2-(2-(4-fluoro-N-methylphenylsulfonamido)ethoxy)acetamide;
(358) 2-(2-(N-benzyl-4-methoxy-2,6-dimethylphenylsulfonamido)ethoxy)-N-(2-(4-((dimethylamino)(3-fluorophenyl)methyl)cyclohexyl)ethyl)acetamide;
(359) 2-(2-(3,4-dichloro-N-methylphenylsulfonamido)cyclohexyloxy)-N-((4-((dimethylamino)(4-fluorophenyl)methyl)cyclohexyl)methyl)acetamide;
(360) 2-((4-((4-chlorophenyl)(dimethylamino)methyl)cyclohexyl)methylamino)-2-oxo-1-phenylethyl acetate
(361) N-(4-((dimethylamino)(4-fluorophenyl)methyl)cyclohexyl)-2-(2-(N-methyl-4-(trifluoromethoxy)phenylsulfonamido)ethoxy)acetamide;
(362) N-((4-((dimethylamino)(4-fluorophenyl)methyl)cyclohexyl)methyl)-2-(2-(N,4-dimethylphenylsulfonamido)ethoxy)acetamide;

(363) 2-(2-(2,6-dichloro-N-methylphenylsulfonamido) ethoxy)-N-(4-(((dimethylamino)(4-fluorophenyl)methyl)cyclohexyl)acetamide;

(364) N-(4-((dimethylamino)(3-fluorophenyl)methyl)cyclohexyl)-2-(2-(4-(phenylsulfonyl)piperazin-1-yl)ethoxy)acetamide;

(365) N-(4-((dimethylamino)(4-fluorophenyl)methyl)cyclohexyl)-2-(1-(4-methoxy-2,3,6-trimethylphenylsulfonyl)pyrrolidin-3-yloxy)acetamide;

(366) N-((4-((dimethylamino)(4-fluorophenyl)methyl)cyclohexyl)methyl)-2-(2-(4-(4-methoxy-2,3,6-trimethylphenylsulfonyl)piperazin-1-yl)ethoxy)acetamide;

(367) N-((4-((4-chlorophenyl)(dimethylamino)methyl)cyclohexyl)methyl)-2-((1-(3,4-dimethoxyphenylsulfonyl)piperidin-2-yl)methoxy)acetamide;

(368) N-(2-(4-((dimethylamino)(4-fluorophenyl)methyl)cyclohexyl)ethyl)-2-(2-(N-methyl-3-(trifluoromethyl)phenylsulfonamido)ethoxy)acetamide;

(369) 2-((2-(3,4-dichloro-N-methylphenylsulfonamido)-4,5,6,7-tetrahydrobenzo[b]thiophen-3-yl)methoxy)-N-(4-((dimethylamino)(phenyl)methyl)cyclohexyl)acetamide;

(370) 2-(1-(4-chlorophenylsulfonyl)pyrrolidin-3-yloxy)-N-(4-((dimethylamino)(4-fluorophenyl)methyl)cyclohexyl)acetamide;

(371) N-(4-((dimethylamino) (4-fluorophenyl)methyl)cyclohexyl)-2-(1-tosylpyrrolidin-3-yloxy)acetamide;

(372) 2-(2-(N-benzyl-4-methoxy-2,6-dimethylphenylsulfonamido)ethoxy)-N-(4-((dimethylamino)(3-fluorophenyl)methyl)cyclohexyl)acetamide;

(373) N-((4-(1-(dimethylamino)-3-phenylpropyl)cyclohexyl)methyl)-2-((2-(4-methoxyphenylsulfonyl)-1,2,3,4-tetrahydroisoquinolin-3-yl)methoxy)acetamide;

(374) N-(2-(4-((4-chlorophenyl)(dimethylamino)methyl)cyclohexyl)ethyl)-2-((2-(4-methoxyphenylsulfonyl)-1,2,3,4-tetrahydroisoquinolin-3-yl)methoxy)acetamide;

(375) N-(2-(4-((4-chlorophenyl)(dimethylamino)methyl)cyclohexyl)ethyl)-2-(1-(phenylsulfonyl)pyrrolidin-3-yloxy)acetamide;

(376) N-(2-(4-((dimethylamino)(3-fluorophenyl)methyl)cyclohexyl)ethyl)-2-(1-(phenylsulfonyl)pyrrolidin-3-yloxy)acetamide;

(377) 2-(2-(4-chloro-N-methylphenylsulfonamido)ethoxy)-N-(2-(4-((dimethylamino) (4-fluorophenyl)methyl)cyclohexyl)ethyl)acetamide;

(378) N-(2-(4-((4-chlorophenyl)(dimethylamino)methyl)cyclohexyl)ethyl)-2-(2-(4-methoxy-N,2,6-trimethylphenylsulfonamido)ethoxy)acetamide;

(379) N-((4-((4-chlorophenyl)(dimethylamino)methyl)cyclohexyl)methyl)-2-(2-(3,4-dimethoxy-N-methylphenylsulfonamido)ethoxy)acetamide;

(380) N-(4-((dimethylamino)(4-fluorophenyl)methyl)cyclohexyl)-2-(2-(4-methoxy-N,2,3,6-tetramethylphenylsulfonamido)ethoxy)acetamide;

(381) N-(4-((dimethylamino)(4-fluorophenyl)methyl)cyclohexyl)-2-(1-(4-fluorophenylsulfonyl)pyrrolidin-3-yloxy)acetamide;

(382) N-(4-((dimethylamino)(4-fluorophenyl)methyl)cyclohexyl)-2-(2-(2,4,6-trichloro-N-methylphenylsulfonamido)ethoxy)acetamide;

(383) N-(2-(4-((4-chlorophenyl)(dimethylamino)methyl)cyclohexyl)ethyl)-2-(2-(1-(4-methoxyphenylsulfonyl)piperidin-2-yl)ethoxy)acetamide;

(384) N-((4-((4-chlorophenyl)(dimethylamino)methyl)cyclohexyl)methyl)-2-(1-(4-chlorophenylsulfonyl)pyrrolidin-3-yloxy)acetamide;

(385) N-(2-(4-((dimethylamino)(thiophen-2-yl)methyl)cyclohexyl)ethyl)-2-(2-(N,2,4,6-tetramethylphenylsulfonamido)ethoxy)acetamide;

(386) N-(2-(4-((dimethylamino)(4-fluorophenyl)methyl)cyclohexyl)ethyl)-2-(2-(2,4,6-trichloro-N-methylphenylsulfonamido)ethoxy)acetamide;

(387) N-(2-(4-((dimethylamino)(4-fluorophenyl)methyl)cyclohexyl)ethyl)-2-(2-(4-(4-methoxy-2,3,6-trimethylphenylsulfonyl)piperazin-1-yl)ethoxy)acetamide;

(388) 2-(2-(N-benzyl-4-methoxy-2,6-dimethylphenylsulfonamido)ethoxy)-N-((4-((dimethylamino)(3-fluorophenyl)methyl)cyclohexyl)methyl)acetamide;

(389) N-(2-(4-((dimethylamino)(4-fluorophenyl)methyl)cyclohexyl)ethyl)-2-((2-(4-methoxyphenylsulfonyl)-1,2,3,4-tetrahydroisoquinolin-3-yl)methoxy)acetamide;

(390) N-((4-((dimethylamino)(4-fluorophenyl)methyl)cyclohexyl)methyl)-2-(2-(N-methyl-3-(trifluoromethyl)phenylsulfonamido)ethoxy)acetamide;

(391) 2-(1-(2,4-dichlorophenylsulfonyl)pyrrolidin-3-yloxy)-N-((4-((dimethylamino)(4-fluorophenyl)methyl)cyclohexyl)methyl)acetamide;

(392) N-(2-(4-((dimethylamino)(4-fluorophenyl)methyl)cyclohexyl)ethyl)-2-(2-(4-methoxy-N,2,6-trimethylphenylsulfonamido)ethoxy)acetamide;

(393) N-((4-((4-chlorophenyl)(dimethylamino)methyl)cyclohexyl)methyl)-2-(1-(mesitylsulfonyl)pyrrolidin-3-yloxy)acetamide;

(394) N-((4-((4-chlorophenyl)(dimethylamino)methyl)cyclohexyl)methyl)-2-(1-(4-fluorophenylsulfonyl)pyrrolidin-3-yloxy)acetamide;

(395) N-(2-(4-((4-chlorophenyl)(dimethylamino)methyl)cyclohexyl)ethyl)-2-(1-(phenylsulfonyl)piperidin-3-yloxy)acetamide;

(396) N-(4-((dimethylamino)(4-fluorophenyl)methyl)cyclohexyl)-2-(2-(N-ethyl-4-methoxy-2,3,6-trimethylphenylsulfonamido)ethoxy)acetamide;

(397) N-(2-(4-((dimethylamino)(3-fluorophenyl)methyl)cyclohexyl)ethyl)-2-(2-(1-(4-methoxy-2,3,6-trimethylphenylsulfonyl)piperidin-4-yl)ethoxy)acetamide;

(398) N-(2-(4-((dimethylamino)(4-fluorophenyl)methyl)cyclohexyl)ethyl)-2-(2-(1-(4-methoxyphenylsulfonyl)piperidin-2-yl)ethoxy)acetamide;

(399) 2-(2-(4-chloro-N-methylphenylsulfonamido)ethoxy)-N-((4-((dimethylamino)(4-fluorophenyl)methyl)cyclohexyl)methyl)acetamide;

(400) N-((4-((dimethylamino)(4-fluorophenyl)methyl)cyclohexyl)methyl)-2-(2-(4-fluoro-N-methylphenylsulfonamido)ethoxy)acetamide;

(401) 2-(2-(3,4-dimethoxy-N-methylphenylsulfonamido)ethoxy)-N-(4-((dimethylamino)(3-fluorophenyl)methyl)cyclohexyl)acetamide;

(402) N-((4-((dimethylamino)(4-fluorophenyl)methyl)cyclohexyl)methyl)-2-(1-(3-(trifluoromethyl)phenylsulfonyl)pyrrolidin-3-yloxy)acetamide;

(403) N-((4-((4-chlorophenyl)(dimethylamino)methyl)cyclohexyl)methyl)-2-(1-(4-methoxy-2,6-dimethylphenylsulfonyl)pyrrolidin-3-yloxy)acetamide;

(404) N-((4-((dimethylamino)(4-fluorophenyl)methyl)cyclohexyl)methyl)-2-(2-(2,4,6-trichloro-N-methylphenylsulfonamido)ethoxy)acetamide;

(405) 2-((1-(2,4-dimethoxyphenylsulfonyl)piperidin-2-yl)methoxy)-N-((4-((dimethylamino)(4-fluorophenyl)methyl)cyclohexyl)methyl)acetamide;

(406) 2-(2-(4-chloro-N-methylphenylsulfonamido)ethoxy)-N-(4-((dimethylamino)(4-fluorophenyl)methyl)cyclohexyl)acetamide;

(407) N-(2-(4-((dimethylamino)(3-fluorophenyl)methyl)cyclohexyl)ethyl)-2-(1-(4-fluorophenylsulfonyl)pyrrolidin-3-yloxy)acetamide;

(408) N-(4-((dimethylamino)(4-fluorophenyl)methyl)cyclohexyl)-2-(1-(phenylsulfonyl)piperidin-4-yloxy)acetamide;

(409) N-(2-(4-((dimethylamino)(4-fluorophenyl)methyl)cyclohexyl)ethyl)-2-((1-(4-methoxyphenylsulfonyl)pyrrolidin-2-yl)methoxy)acetamide;

(410) N-(2-(4-((4-chlorophenyl)(dimethylamino)methyl)cyclohexyl)ethyl)-2-(2-(3,4-dichloro-N-methylphenylsulfonamido)cyclohexyloxy)acetamide;

(411) N-((4-((4-chlorophenyl)(dimethylamino)methyl)cyclohexyl)methyl)-2-(2-(N-methyl-4-(trifluoromethoxy)phenylsulfonamido)ethoxy)acetamide;

(412) N-(2-(4-((4-chlorophenyl)(dimethylamino)methyl)cyclohexyl)ethyl)-2-(1-(4-methoxy-2,3,6-trimethylphenylsulfonyl)pyrrolidin-3-yloxy)acetamide;

(413) N-(2-(4-((dimethylamino)(4-fluorophenyl)methyl)cyclohexyl)ethyl)-2-(2-(N-ethyl-4-methoxy-2,3,6-trimethylphenylsulfonamido)ethoxy)acetamide;

(414) 2-(2-(N-benzyl-4-methoxy-2,3,6-trimethylphenylsulfonamido)ethoxy)-N-((4-((dimethylamino)(3-fluorophenyl)methyl)cyclohexyl)methyl)acetamide;

(415) 2-((1-(3,4-dichlorophenylsulfonyl)pyrrolidin-2-yl)methoxy)-N-((4-(1-(dimethylamino)-3-phenylpropyl)cyclohexyl)methyl)acetamide;

(416) N-(2-(4-((4-chlorophenyl)(dimethylamino)methyl)cyclohexyl)ethyl)-2-(2-(N,2,4,6-tetramethylphenylsulfonamido)ethoxy)acetamide;

(417) N-(2-(4-((dimethylamino)(4-fluorophenyl)methyl)cyclohexyl)ethyl)-2-(2-(N,2,4,6-tetramethylphenylsulfonamido)ethoxy)acetamide;

(418) N-((4-((dimethylamino)(4-fluorophenyl)methyl)cyclohexyl)methyl)-2-(1-(4-methoxy-2,3,6-trimethylphenylsulfonyl)piperidin-3-yloxy)acetamide;

(419) 2-(2-(N-benzyl-4-methoxy-2,3,6-trimethylphenylsulfonamido)ethoxy)-N-(4-((dimethylamino)(3-fluorophenyl)methyl)cyclohexyl)acetamide;

(420) 2-((1-(2,4-dimethoxyphenylsulfonyl)piperidin-2-yl)methoxy)-N-((4-(1-(dimethylamino)-3-phenylpropyl)cyclohexyl)methyl)acetamide;

(421) Ethyl 2-((4-(1-(dimethylamino)-3-phenylpropyl)cyclohexyl)methylamino)-2-oxoacetate (422) N-(4-((dimethylamino)(4-fluorophenyl)methyl)cyclohexyl)-2-(4-methoxy-N,2,6-trimethylphenylsulfonamido)ethoxy)acetamide;

(423) N-(4-((dimethylamino)(4-fluorophenyl)methyl)cyclohexyl)-2-(1-(phenylsulfonyl)piperidin-3-yloxy)acetamide;

(424) N-((4-((dimethylamino)(4-fluorophenyl)methyl)cyclohexyl)methyl)-2-((1-(phenylsulfonyl)piperidin-3-yl)methoxy)acetamide;

(425) N-(2-(4-((4-chlorophenyl)(dimethylamino)methyl)cyclohexyl)ethyl)-2-((1-(phenylsulfonyl)piperidin-3-yl)methoxy)acetamide;

(426) 2-(2-(N-benzylphenylsulfonamido)ethoxy)-N-(2-(4-((4-chlorophenyl)(dimethylamino)methyl)cyclohexyl)ethyl)acetamide;

(427) N-((4-((dimethylamino)(4-fluorophenyl)methyl)cyclohexyl)methyl)-2-(1-(4-methoxy-2,3,6-trimethylphenylsulfonyl)pyrrolidin-3-yloxy)acetamide;

(428) N-((4-((4-chlorophenyl)(dimethylamino)methyl)cyclohexyl)methyl)-2-(1-(4-methoxy-2,3,6-trimethylphenylsulfonyl)pyrrolidin-3-yloxy)acetamide;

(429) N-((4-((4-chlorophenyl)(dimethylamino)methyl)cyclohexyl)methyl)-2-(2-(4-(4-methoxy-2,3,6-trimethylphenylsulfonyl)piperazin-1-yl)ethoxy)-acetamide;

(430) 2-(1-(3,4-dimethoxyphenylsulfonyl)pyrrolidin-3-yloxy)-N-(2-(4-((dimethylamino)(4-fluorophenyl)methyl)cyclohexyl)ethyl)acetamide;

(431) N-(2-(4-((4-chlorophenyl)(dimethylamino)methyl)cyclohexyl)ethyl)-2-(1-(3-(trifluoromethyl)phenylsulfonyl)pyrrolidin-3-yloxy)acetamide;

(432) N-((4-((dimethylamino)(4-fluorophenyl)methyl)cyclohexyl)methyl)-2-(1-(mesitylsulfonyl)pyrrolidin-3-yloxy)acetamide;

(433) N-((4-((dimethylamino)(4-fluorophenyl)methyl)cyclohexyl)methyl)-2-(2-(4-(phenylsulfonyl)piperazin-1-yl)ethoxy)acetamide;

(434) N-(2-(4-((4-chlorophenyl)(dimethylamino)methyl)cyclohexyl)ethyl)-2-(2-(N-ethyl-4-methoxy-2,3,6-trimethylphenylsulfonamido)ethoxy)acetamide;

(435) N-(4-((dimethylamino)(4-fluorophenyl)methyl)cyclohexyl)-2-(1-(4-methoxy-2,3,6-trimethylphenylsulfonyl)piperidin-3-yloxy)acetamide;

(436) 2-(2-(N-benzyl-4-methoxy-2,3,6-trimethylphenylsulfonamido)ethoxy)-N-(2-(4-((dimethylamino)(3-fluorophenyl)methyl)cyclohexyl)ethyl)acetamide;

(437) 2-((1-(3,4-dichlorophenylsulfonyl)piperidin-2-yl)methoxy)-N-((4-(1-(dimethylamino)-3-phenylpropyl)cyclohexyl)methyl)acetamide;

(438) N-(4-((dimethylamino)(4-fluorophenyl)methyl)cyclohexyl)-2-(2-(N-methyl-3-(trifluoromethyl)phenylsulfonamido)ethoxy)acetamide;

(439) N-((4-((dimethylamino)(4-fluorophenyl)methyl)cyclohexyl)methyl)-2-(2-(N-methyl-4-(trifluoromethoxy)phenylsulfonamido)ethoxy)acetamide;

(440) N-(2-(4-((4-chlorophenyl)(dimethylamino)methyl)cyclohexyl)ethyl)-2-(1-(4-fluorophenylsulfonyl)pyrrolidin-3-yloxy)acetamide;

(441) N-(4-((dimethylamino)(4-fluorophenyl)methyl)cyclohexyl)-2-(1-(4-methoxy-2,6-dimethylphenylsulfonyl)pyrrolidin-3-yloxy)acetamide;

(442) N-(2-(4-((4-chlorophenyl)(dimethylamino)methyl)cyclohexyl)ethyl)-2-(2-(2,4,6-trichloro-N-methylphenylsulfonamido)ethoxy)acetamide;

(443) N-(2-(4-((4-chlorophenyl)(dimethylamino)methyl)cyclohexyl)ethyl)-2-(1-(phenylsulfonyl)piperidin-4-yloxy)acetamide;

(444) N-(2-(4-((dimethylamino)(3-fluorophenyl)methyl)cyclohexyl)ethyl)-2-(1-(phenylsulfonyl)piperidin-4-yloxy)acetamide;

(445) 2-(2-(4-chloro-N-methylphenylsulfonamido)ethoxy)-N-((4-(1-(dimethylamino)-3-phenylpropyl)cyclohexyl)methyl)acetamide;

(446) N-(2-(4-((dimethylamino)(4-fluorophenyl)methyl)cyclohexyl)ethyl)-2-(2-(N-methyl-4-(trifluoromethoxy)phenylsulfonamido)ethoxy)acetamide;

(447) N-((4-((dimethylamino)(4-fluorophenyl)methyl)cyclohexyl)methyl)-2-(1-tosylpyrrolidin-3-yloxy)acetamide;

(448) N-(4-((dimethylamino)(4-fluorophenyl)methyl)cyclohexyl)-2-(2-(N,4-dimethylphenylsulfonamide)ethoxy)acetamide;

(449) N-((4-((4-chlorophenyl)(dimethylamino)methyl)cyclohexyl)methyl)-2-(1-(4-methoxy-2,3,6-trimethylphenylsulfonyl)piperidin-3-yloxy)acetamide;

(450) N-(4-((dimethylamino)(4-fluorophenyl)methyl)cyclohexyl)-2-((1-(4-methoxyphenylsulfonyl)piperidin-2-yl)methoxy)acetamide;

(451) 2-(2-(3,4-dichloro-N-methylphenylsulfonamido) cyclohexyloxy)-N-((4-(1-(dimethylamino)-3-phenylpropyl)cyclohexyl)methyl)acetamide;
(452) N-((4-(1-(dimethylamino)-3-phenylpropyl)cyclohexyl)methyl)-2-(2-(N,4-dimethylphenylsulfonamido) ethoxy)acetamide;
(453) N-((4-(1-(dimethylamino)-3-phenylpropyl)cyclohexyl)methyl)-2-(2-(4-methoxy-N,2,3,6-tetramethylphenylsulfonamido)ethoxy)acetamide;
(454) N-(4-((dimethylamino)(4-fluorophenyl)methyl)cyclohexyl)-2-(1-(4-methoxy-2,3,6-trimethylphenylsulfonyl)piperidin-4-yloxy)acetamide;
(455) N-(2-(4-((dimethylamino)(4-fluorophenyl)methyl) cyclohexyl)ethyl)-2-phenoxypropanamide
(456) 2-(1-(2,4-dichlorophenylsulfonyl)pyrrolidin-3-yloxy)-N-(2-(4-((dimethylamino)(4-fluorophenyl)methyl)cyclohexyl)ethyl)acetamide;
(457) N-(2-(4-((dimethylamino)(4-fluorophenyl)methyl) cyclohexyl)ethyl)-2-(2-(N,4-dimethylphenylsulfonamido)ethoxy)acetamide;
(458) N-((4-((dimethylamino)(4-fluorophenyl)methyl)cyclohexyl)methyl)-2-(2-(4-methoxy-N,2,6-trimethylphenylsulfonamido)ethoxy)acetamide;
(459) N-((4-((4-chlorophenyl)(dimethylamino)methyl) cyclohexyl)methyl)-2-(2-(2,4-dichloro-N-methylphenylsulfonamido)ethoxy)acetamide;
(460) N-(2-(4-((4-chlorophenyl)(dimethylamino)methyl) cyclohexyl)ethyl)-2-(2-(4-methoxy-N-methylphenylsulfonamido)ethoxy)acetamide;
(461) N-(4-((dimethylamino)(4-fluorophenyl)methyl)cyclohexyl)-2-((1-(4-methoxyphenylsulfonyl)pyrrolidin-2-yl)methoxy)acetamide;
(462) 2-((1-(3,4-dimethoxyphenylsulfonyl)piperidin-2-yl)methoxy)-N-(2-(4-((dimethylamino)(4-fluorophenyl)methyl)cyclohexyl)ethyl)acetamide;
(463) N-(4-((dimethylamino)(4-fluorophenyl)methyl)cyclohexyl)-2-(1-(phenylsulfonyl)pyrrolidin-3-yloxy)acetamide;
(464) 2-(1-(4-chlorophenylsulfonyl)pyrrolidin-3-yloxy)-N-(2-(4-((dimethylamino)(4-fluorophenyl)methyl)cyclohexyl)ethyl)acetamide;
(465) N-(2-(4-(((dimethylamino)(thiophen-2-yl)methyl) cyclohexyl)ethyl)-2-(2-(2,3,4,5,6-pentafluoro-N-methylphenylsulfonamido)ethoxy)acetamide;
(466) N-(2-(4-((dimethylamino)(4-fluorophenyl)methyl) cyclohexyl)ethyl)-2-(1-(3-(trifluoromethyl)phenylsulfonyl)pyrrolidin-3-yloxy)acetamide;
(467) N-(2-(4-((dimethylamino)(4-fluorophenyl)methyl) cyclohexyl)ethyl)-2-(1-(4-methoxy-2,3,6-trimethylphenylsulfonyl)pyrrolidin-3-yloxy)acetamide;
(468) N-(2-(4-((dimethylamino)(4-fluorophenyl)methyl) cyclohexyl)ethyl)-2-(1-(4-methoxy-2,3,6-trimethylphenylsulfonyl)piperidin-3-yloxy)acetamide;
(469) N-((4-(1-(dimethylamino)-3-phenylpropyl)cyclohexyl)methyl)-2-((1-(4-methoxyphenylsulfonyl)piperidin-2-yl)methoxy)acetamide;
(470) N-(2-(4-((dimethylamino)(4-fluorophenyl)methyl) cyclohexyl)ethyl)-2-(2-(1-(phenylsulfonyl)piperidin-4-yl)ethoxy)acetamide;
(471) N-((4-((4-chlorophenyl)(dimethylamino)methyl) cyclohexyl)methyl)-2-(1-(phenylsulfonyl)piperidin-4-yloxy)acetamide;
(472) N-(2-(4-((4-chlorophenyl)(dimethylamino)methyl) cyclohexyl)ethyl)-2-(1-(4-methoxy-2,3,6-trimethylphenylsulfonyl)piperidin-4-yloxy)acetamide;
(473) 2-(2-(N-benzyl-4-methoxy-2,6-dimethylphenylsulfonamido)ethoxy)-N-((4-((4-chlorophenyl)(dimethylamino)methyl)cyclohexyl)methyl)acetamide;
(474) N-(2-(4-((4-chlorophenyl)(dimethylamino)methyl) cyclohexyl)ethyl)-2-((1-(2,4-dimethoxyphenylsulfonyl)piperidin-2-yl)methoxy)acetamide;
(475) N-((4-(1-(dimethylamino)-3-phenylpropyl)cyclohexyl)methyl)-2-(1-(mesitylsulfonyl)pyrrolidin-3-yloxy)acetamide;
(476) 2-(2-(2,6-dichloro-N-methylphenylsulfonamido) ethoxy)-N-((4-(1-(dimethylamino)-3-phenylpropyl)cyclohexyl)methyl)acetamide;
(477) N-((4-((dimethylamino)(3-fluorophenyl)methyl)cyclohexyl)methyl)-2-(1-(phenylsulfonyl)piperidin-4-yloxy)acetamide;
(478) N-(4-((dimethylamino)(4-fluorophenyl)methyl)cyclohexyl)-2-((1-(phenylsulfonyl)piperidin-3-yl)methoxy)acetamide;
(479) N-(2-(4-((dimethylamino)(4-fluorophenyl)methyl) cyclohexyl)ethyl)-2-((1-(phenylsulfonyl)piperidin-3-yl)methoxy)acetamide;
(480) N-(2-(4-((dimethylamino)(4-fluorophenyl)methyl) cyclohexyl)ethyl)-2-(1-(4-methoxy-2,3,6-trimethylphenylsulfonyl)piperidin-4-yloxy)acetamide;
(481) N-((4-((dimethylamino)(4-fluorophenyl)methyl)cyclohexyl)methyl)-2-(2-(1-(4-methoxy-2,3,6-trimethylphenylsulfonyl)piperidin-4-yl)ethoxy)acetamide;
(482) 2-(benzyloxy)-N-(2-(4-((4-chlorophenyl)(dimethylamino)methyl)cyclohexyl)ethyl)acetamide;
(483) 2-(2-(N-benzyl-4-methoxy-2,6-dimethylphenylsulfonamido)ethoxy)-N-(4-((dimethylamino)(phenyl)methyl)cyclohexyl)acetamide;
(484) 2-(2-(3,4-dimethoxy-N-methylphenylsulfonamido) ethoxy)-N-(2-(4-((dimethylamino)(4-fluorophenyl) methyl)cyclohexyl)ethyl)acetamide;
(485) N-(2-(4-((4-chlorophenyl)(dimethylamino)methyl) cyclohexyl)ethyl)-2-(1-(4-methoxy-2,3,6-trimethylphenylsulfonyl)piperidin-3-yloxy)acetamide;
(486) 2-((1-(2,4-dimethoxyphenylsulfonyl)piperidin-2-yl)methoxy)-N-((4-(1-(dimethylamino)-3-phenylpropyl)cyclohexyl)methyl)acetamide;
(487) N-(2-(4-((dimethylamino)(4-fluorophenyl)methyl) cyclohexyl)ethyl)-2-(2-(4-fluoro-N-methylphenylsulfonamido)ethoxy)acetamide;
(488) N-((4-((dimethylamino)(4-fluorophenyl)methyl)cyclohexyl)methyl)-2-(1-(phenylsulfonyl)piperidin-3-yloxy)acetamide;
(489) 2-(2-(N-benzylphenylsulfonamido)ethoxy)-N-(2-(4-((dimethylamino)(4-fluorophenyl)methyl)cyclohexyl)ethyl)acetamide;
(490) N-(4-((dimethylamino) (4-fluorophenyl)methyl)cyclohexyl)-2-(2-(N,2,4,6-tetramethylphenylsulfonamido)ethoxy)acetamide;
(491) N-(2-(4-((dimethylamino)(4-fluorophenyl)methyl) cyclohexyl)ethyl)-2-(1-tosylpyrrolidin-3-yloxy)acetamide;
(492) N-(2-(4-((4-chlorophenyl)(dimethylamino)methyl) cyclohexyl)ethyl)-2-(1-(4-methoxy-2,6-dimethylphenylsulfonyl)pyrrolidin-3-yloxy)acetamide;
(493) N-(2-(4-((dimethylamino)(4-fluorophenyl)methyl) cyclohexyl)ethyl)-2-(2-(4-(phenylsulfonyl)piperazin-1-yl)ethoxy)acetamide;
(494) 2-(2-(N-benzyl-4-methoxy-2,6-dimethylphenylsulfonamido)ethoxy)-N-((4-((dimethylamino)(4-fluorophenyl)methyl)cyclohexyl)methyl)acetamide;
(495) N-((4-(1-(dimethylamino)-3-phenylpropyl)cyclohexyl)methyl)-2-phenoxypropanamide (496) 2-(1-(2,4-dichlorophenylsulfonyl)pyrrolidin-3-yloxy)-N-((4-(1-(dimethylamino)-3-phenylpropyl)cyclohexyl)methyl)acetamide;
(497) 2-(1-(3,4-dimethoxyphenylsulfonyl)pyrrolidin-3-yloxy)-N-((4-((dimethylamino)(4-fluorophenyl)methyl)cyclohexyl)methyl)acetamide;
(498) N-((4-((4-chlorophenyl)(dimethylamino)methyl)cyclohexyl)methyl)-2-(1-(4-methoxy-2,3,6-trimethylphenylsulfonyl)piperidin-4-yloxy)acetamide;
(499) N-((4-((4-chlorophenyl)(dimethylamino)methyl)cyclohexyl)methyl)-2-(2-(1-(4-methoxy-2,3,6-trimethylphenylsulfonyl)piperidin-4-yl)ethoxy)acetamide;
(500) 2-((1-(2,4-dimethoxyphenylsulfonyl)piperidin-2-yl)methoxy)-N-(2-(4-((dimethylamino)(4-fluorophenyl)methyl)cyclohexyl)ethyl)acetamide;
(501) N-(2-(4-((dimethylamino)(4-fluorophenyl)methyl)cyclohexyl)ethyl)-2-(1-(mesitylsulfonyl)pyrrolidin-3-yloxy)acetamide;
(502) N-(4-((dimethylamino)(4-fluorophenyl)methyl)cyclohexyl)-2-(2-(4-(phenylsulfonyl)piperazin-1-yl)ethoxy)acetamide;
(503) N-((4-(1-(dimethylamino)-3-phenylpropyl)cyclohexyl)methyl)-2-(1-(4-methoxy-2,3,6-trimethylphenylsulfonyl)pyrrolidin-3-yloxy)acetamide;
(504) 2-(2-(N-benzyl-4-methoxy-2,6-dimethylphenylsulfonamido)ethoxy)-N-(4-((dimethylamino)(4-fluorophenyl)methyl)cyclohexyl)acetamide;
(505) 2-(4-chlorophenoxy)-N-(4-((dimethylamino)(3-fluorophenyl)methyl)cyclohexyl)acetamide;
(506) N-(2-(4-((4-chlorophenyl)(dimethylamino)methyl)cyclohexyl)ethyl)-2-(1-(mesitylsulfonyl)pyrrolidin-3-yloxy)acetamide;
(507) N-((4-((dimethylamino)(phenyl)methyl)cyclohexyl)methyl)-2-(2-(1-(phenylsulfonyl)piperidin-4-yl)ethoxy)acetamide;
(508) N-((4-((dimethylamino)(4-fluorophenyl)methyl)cyclohexyl)methyl)-2-(2-(4-methoxy-N-methylphenylsulfonamido)ethoxy)acetamide;
(509) N-(2-(4-((dimethylamino)(4-fluorophenyl)methyl)cyclohexyl)ethyl)-2-(1-(4-methoxy-2,6-dimethylphenylsulfonyl)pyrrolidin-3-yloxy)acetamide;
(510) N-(2-(4-((dimethylamino)(4-fluorophenyl)methyl)cyclohexyl)ethyl)-2-(2-(1-(4-methoxy-2,3,6-trimethylphenylsulfonyl)piperidin-4-yl)ethoxy)acetamide;
(511) N-((4-((dimethylamino)(4-fluorophenyl)methyl)cyclohexyl)methyl)-2-((1-(4-methoxyphenylsulfonyl)pyrrolidin-2-yl)methoxy)acetamide;
(512) 2-(1-(3,4-dimethoxyphenylsulfonyl)pyrrolidin-3-yloxy)-N-(4-((dimethylamino)(4-fluorophenyl)methyl)cyclohexyl)acetamide;
(513) 2-(2-(2,4-dichloro-N-methylphenylsulfonamido)ethoxy)-N-((4-(1-(dimethylamino)-3-phenylpropyl)cyclohexyl)methyl)acetamide;
(514) 2-(2-(3,4-dimethoxy-N-methylphenylsulfonamido)ethoxy)-N-((4-((dimethylamino)(4-fluorophenyl)methyl)cyclohexyl)methyl)acetamide;
(515) N-((4-(1-(dimethylamino)-3-phenylpropyl)cyclohexyl)methyl)-2-(2-(2,4,6-trichloro-N-methylphenylsulfonamido)ethoxy)acetamide;
(516) N-(4-((dimethylamino)(4-fluorophenyl)methyl)cyclohexyl)-2-phenoxypropanamide
(517) 2-(1-(4-chlorophenylsulfonyl)pyrrolidin-3-yloxy)-N-(4-((dimethylamino)(4-fluorophenyl)methyl)cyclohexyl)methyl)acetamide;
(518) N-(2-(4-((dimethylamino)(4-fluorophenyl)methyl)cyclohexyl)ethyl)-2-(1-(4-fluorophenylsulfonyl)pyrrolidin-3-yloxy)acetamide;
(519) N-(2-(4-((dimethylamino)(4-fluorophenyl)methyl)cyclohexyl)ethyl)-2-(2-(4-methoxy-N-methylphenylsulfonamido)ethoxy)acetamide;
(520) N-(2-(4-((dimethylamino)(4-fluorophenyl)methyl)cyclohexyl)ethyl)-2-(1-(phenylsulfonyl)piperidin-3-yloxy)acetamide;
(521) N-((4-(1-(dimethylamino)-3-phenylpropyl)cyclohexyl)methyl)-2-(2-(1-(4-methoxy-2,3,6-trimethylphenylsulfonyl)piperidin-4-yl)ethoxy)acetamide;
(522) N-((4-((dimethylamino)(4-fluorophenyl)methyl)cyclohexyl)methyl)-2-(1-(4-fluorophenyl sulfonyl)pyrrolidin-3-yloxy)acetamide;
(523) 2-(2-(N-benzyl-4-methoxy-2,3,6-trimethylphenylsulfonamido)ethoxy)-N-(4-((dimethylamino)(4-fluorophenyl)methyl)cyclohexyl)acetamide;
(524) 2-((1-(2,4-dimethoxyphenylsulfonyl)piperidin-2-yl)methoxy)-N-(4-((dimethylamino)(4-fluorophenyl)methyl)cyclohexyl)acetamide;
(525) N-((4-(1-(dimethylamino)-3-phenylpropyl)cyclohexyl)methyl)-2-(2-(4-methoxy-N,2,6-trimethylphenylsulfonamido)ethoxy)acetamide;
(526) N-((4-(1-(dimethylamino)-3-phenylpropyl)cyclohexyl)methyl)-2-(2-(4-(phenylsulfonyl)piperazin-1-yl)ethoxy)acetamide;
(527) N-((4-((dimethylamino)(4-fluorophenyl)methyl)cyclohexyl)methyl)-2-(1-(4-methoxy-2,3,6-trimethylphenylsulfonyl)piperidin-4-yloxy)acetamide;
(528) N-((4-(1-(dimethylamino)-3-phenylpropyl)cyclohexyl)methyl)-2-(2-(4-(4-methoxy-2,3,6-trimethylphenylsulfonyl)piperazin-1-yl)ethoxy)acetamide;
(529) 2-(benzyloxy)-N-(4-((dimethylamino)(4-fluorophenyl)methyl)cyclohexyl)acetamide;
(530) N-(2-(4-((dimethylamino)(4-fluorophenyl)methyl)cyclohexyl)ethyl)-2-(1-(phenylsulfonyl)pyrrolidin-3-yloxy)acetamide;
(531) N-(2-(4-((4-chlorophenyl)(dimethylamino)methyl)cyclohexyl)ethyl)-2-(2-(1-(phenylsulfonyl)piperidin-4-yl)ethoxy)acetamide;
(532) N-((4-((dimethylamino)(4-fluorophenyl)methyl)cyclohexyl)methyl)-2-(1-(phenylsulfonyl)pyrrolidin-3-yloxy)acetamide;
(533) 2-(2-(N-benzylphenylsulfonamido)ethoxy)-N-((4-(1-(dimethylamino)-3-phenylpropyl)cyclohexyl)methyl)acetamide;
(534) 2-((1-(3,4-dimethoxyphenylsulfonyl)piperidin-2-yl)methoxy)-N-((4-((dimethylamino)(4-fluorophenyl)methyl)cyclohexyl)methyl)acetamide;
(535) N-((4-(1-(dimethylamino)-3-phenylpropyl)cyclohexyl)methyl)-2-(2-(1-(4-methoxyphenylsulfonyl)piperidin-2-yl)ethoxy)acetamide;
(536) N-((4-(1-(dimethylamino)-3-phenylpropyl)cyclohexyl)methyl)-2-(2-(N-ethyl-4-methoxy-2,3,6-trimethylphenylsulfonamido)ethoxy)acetamide;
(537) 2-((1-(3,4-dimethoxyphenylsulfonyl)piperidin-2-yl)methoxy)-N-((4-((dimethylamino)(4-fluorophenyl)methyl)cyclohexyl)methyl)acetamide;
(538) N-((4-(1-(dimethylamino)-3-phenylpropyl)cyclohexyl)methyl)-2-(1-tosylpyrrolidin-3-yloxy)acetamide;
(539) N-((4-(1-(dimethylamino)-3-phenylpropyl)cyclohexyl)methyl)-2-(2-(4-fluoro-N-methylphenylsulfonamido)ethoxy)acetamide;
(540) N-(2-(4-((4-chlorophenyl)(dimethylamino)methyl)cyclohexyl)ethyl)-2-((1-(3,4-dimethoxyphenylsulfonyl)piperidin-2-yl)methoxy)acetamide;

(541) N-((4-((dimethylamino)(4-fluorophenyl)methyl)cyclohexyl)methyl)-2-(1-(4-methoxy-2,6-dimethylphenylsulfonyl)pyrrolidin-3-yloxy)acetamide;
(542) 2-(2-(N-benzyl-4-methoxy-2,6-dimethylphenylsulfonamido)ethoxy)-N-((4-(1-(dimethylamino)-3-phenylpropyl)cyclohexyl)methyl)acetamide;
(543) N-(2-(4-((dimethylamino)(3-fluorophenyl)methyl)cyclohexyl)ethyl)-2-(2-(1-(phenylsulfonyl)piperidin-4-yl)ethoxy)acetamide;
(544) N-((4-(1-(dimethylamino)-3-phenylpropyl)cyclohexyl)methyl)-2-((1-(phenylsulfonyl)piperidin-3-yl)methoxy)acetamide;
(545) N-(4-(1-(dimethylamino)-3-phenylpropyl)cyclohexyl)-2-phenoxypropanamide
(546) N-((4-(1-(dimethylamino)-3-phenylpropyl)cyclohexyl)methyl)-2-(1-(4-methoxy-2,3,6-trimethylphenylsulfonyl)piperidin-4-yloxy)acetamide;
(547) 2-(2-(N-benzyl-4-methoxy-2,6-dimethylphenylsulfonamido)ethoxy)-N-(2-(4-((dimethylamino)(4-fluorophenyl)methyl)cyclohexyl)ethyl)acetamide;
(548) 2-(2-(3,4-dimethoxy-N-methylphenylsulfonamido)ethoxy)-N-(4-((dimethylamino)(4-fluorophenyl)methyl)cyclohexyl)acetamide;
(549) N-(4-((dimethylamino)(4-fluorophenyl)methyl)cyclohexyl)-2-(2-(4-methoxy-N-methylphenylsulfonamido)ethoxy)acetamide;
(550) N-((4-(1-(dimethylamino)-3-phenylpropyl)cyclohexyl)methyl)-2-(2-(4-methoxy-N-methylphenylsulfonamido)ethoxy)acetamide;
(551) N-((4-(1-(dimethylamino)-3-phenylpropyl)cyclohexyl)methyl)-2-(1-(4-methoxy-2,3,6-trimethylphenylsulfonyl)piperidin-3-yloxy)acetamide;
(552) N-((4-(1-(dimethylamino)-3-phenylpropyl)cyclohexyl)methyl)-2-(1-(3-(trifluoromethyl)phenylsulfonyl)pyrrolidin-3-yloxy)acetamide;
(553) N-(2-(4-((dimethylamino)(4-fluorophenyl)methyl)cyclohexyl)ethyl)-2-(1-(phenylsulfonyl)piperidin-4-yloxy)acetamide;
(554) 2-(2-(N-benzyl-4-methoxy-2,3,6-trimethylphenylsulfonamido)ethoxy)-N-(2-(4-((dimethylamino)(4-fluorophenyl)methyl)cyclohexyl)ethyl)acetamide;
(555) 2-((1-(3,4-dimethoxyphenylsulfonyl)piperidin-2-yl)methoxy)-N-(4-((dimethylamino)(4-fluorophenyl)methyl)cyclohexyl)acetamide;
(556) N-((4-(1-(dimethylamino)-3-phenylpropyl)cyclohexyl)methyl)-2-(2-(N-methyl-3-(trifluoromethyl)phenylsulfonamido)ethoxy)acetamide;
(557) 2-(1-(4-chlorophenylsulfonyl)pyrrolidin-3-yloxy)-N-((4-(1-(dimethylamino)-3-phenylpropyl)cyclohexyl)methyl)acetamide;
(558) N-((4-(1-(dimethylamino)-3-phenylpropyl)cyclohexyl)methyl)-2-(1-(phenylsulfonyl)piperidin-3-yloxy)acetamide;
(559) 2-((1-(3,4-dimethoxyphenylsulfonyl)piperidin-2-yl)methoxy)-N-((4-(1-(dimethylamino)-3-phenylpropyl)cyclohexyl)methyl)acetamide;
(560) 2-(2-(N-benzyl-4-methoxy-2,3,6-trimethylphenylsulfonamido)ethoxy)-N-((4-((4-chlorophenyl)(dimethylamino)methyl)cyclohexyl)methyl)acetamide;
(561) N-(2-(4-((4-chlorophenyl)(dimethylamino)methyl)cyclohexyl)ethyl)-2-(2-(1-(4-methoxy-2,3,6-trimethylphenylsulfonyl)piperidin-4-yl)-ethoxy)acetamide;
(562) 2-(2-(N-benzyl-4-methoxy-2,3,6-trimethylphenylsulfonamido)ethoxy)-N-((4-(1-(dimethylamino)-3-phenylpropyl)cyclohexyl)methyl)acetamide;
(563) 2-(2-(N-benzyl-4-methoxy-2,3,6-trimethylphenylsulfonamido)ethoxy)-N-((4-((dimethylamino)(4-fluorophenyl)methyl)cyclohexyl)methyl)acetamide;
(564) 2-(4-chlorophenoxy)-N-(4-(1-(dimethylamino)-3-phenylpropyl)cyclohexyl)acetamide;
(565) N-((4-(1-(dimethylamino)-3-phenylpropyl)cyclohexyl)methyl)-2-(1-(4-methoxy-2,6-dimethylphenylsulfonyl)pyrrolidin-3-yloxy)acetamide;
(566) 2-(1-(3,4-dimethoxyphenylsulfonyl)pyrrolidin-3-yloxy)-N-((4-(1-(dimethylamino)-3-phenylpropyl)cyclohexyl)methyl)acetamide;
(567) N-((4-(1-(dimethylamino)-3-phenylpropyl)cyclohexyl)methyl)-2-(2-(N-methyl-4-(trifluoromethoxy)phenylsulfonamido)ethoxy)acetamide;
(568) N-((4-((dimethylamino)(4-fluorophenyl)methyl)cyclohexyl)methyl)-2-(1-(phenylsulfonyl)piperidin-4-yloxy)acetamide;
(569) 2-(2-(N-benzyl-4-methoxy-2,6-dimethylphenylsulfonamido)ethoxy)-N-(2-(4-((4-chlorophenyl)(dimethylamino)methyl)cyclohexyl)ethyl)acetamide;
(570) 2-((1-(3,4-dimethoxyphenylsulfonyl)piperidin-2-yl)methoxy)-N-((4-(1-(dimethylamino)-3-phenylpropyl)cyclohexyl)methyl)acetamide;
(571) 2-(2-(3,4-dimethoxy-N-methylphenylsulfonamido)ethoxy)-N-((4-(1-(dimethylamino)-3-phenylpropyl)cyclohexyl)methyl)acetamide;
(572) N-((4-(1-(dimethylamino)-3-phenylpropyl)cyclohexyl)methyl)-2-((1-(4-methoxyphenylsulfonyl)pyrrolidin-2-yl)methoxy)acetamide;
(573) N-((4-(1-(dimethylamino)-3-phenylpropyl)cyclohexyl)methyl)-2-(1-(phenylsulfonyl)pyrrolidin-3-yloxy)acetamide;
(574) N-((4-(1-(dimethylamino)-3-phenylpropyl)cyclohexyl)methyl)-2-(1-(4-fluorophenylsulfonyl)pyrrolidin-3-yloxy)acetamide;
(575) N-(2-(4-((4-chlorophenyl)(dimethylamino)methyl)cyclohexyl)ethyl)-2-(2-(N-methyl-4-(trifluoromethoxy)phenylsulfonamido)ethoxy)acetamide;
(576) 2-(2-(N-benzyl-4-methoxy-2,3,6-trimethylphenylsulfonamido)ethoxy)-N-(2-(4-((4-chlorophenyl)(dimethylamino)methyl)cyclohexyl)ethyl)acetamide;
(577) N-(4-(1-(dimethylamino)-3-phenylpropyl)cyclohexyl)-2-phenoxypropanamide
(578) N-((4-(1-(dimethylamino)-3-phenylpropyl)cyclohexyl)methyl)-2-(1-(phenylsulfonyl)piperidin-4-yloxy)acetamide;
(579) methyl 2-(2-(4-((dimethylamino)(phenyl)methyl)cyclohexyl)ethylamino)-2-oxoacetate
(580) 2-(2-(2,6-dichloro-N-methylphenylsulfonamido)ethoxy)-N-((4-(1-(dimethylamino)-3-phenylpropyl)cyclohexyl)methyl)acetamide;
(581) 2-((1-(3,4-dimethoxyphenylsulfonyl)piperidin-2-yl)methoxy)-N-(2-(4-((dimethylamino)(3-fluorophenyl)methyl)cyclohexyl)ethyl)acetamide;
(582) 2-(benzyloxy)-N-(4-(1-(dimethylamino)-3-phenylpropyl)cyclohexyl)acetamide;
(583) N-((4-((dimethylamino)(4-fluorophenyl)methyl)cyclohexyl)methyl)-2-(2-(1-(phenylsulfonyl)piperidin-4-yl)ethoxy)acetamide;
(584) N-((4-((4-chlorophenyl)(dimethylamino)methyl)cyclohexyl)methyl)-2-(2-(1-(phenylsulfonyl)piperidin-4-yl)ethoxy)acetamide;
(585) N-(4-((dimethylamino)(phenyl)methyl)cyclohexyl)-2-(2-(4-fluoro-N-methylphenylsulfonamido)ethoxy)acetamide;

(586) 2-(2-(2,4-dichloro-N-methylphenylsulfonamido)ethoxy)-N-(2-(4-((dimethylamino)(4-fluorophenyl)methyl)cyclohexyl)ethyl)acetamide;
(587) N-(2-(4-((dimethylamino)(3-fluorophenyl)methyl)cyclohexyl)ethyl)-2-(2-(N,2,4,6-tetramethylphenylsulfonamido)ethoxy)acetamide;
(588) N-(4-((dimethylamino)(phenyl)methyl)cyclohexyl)-2-(2-(N-methylphenylsulfonamido)ethoxy)acetamide;
(589) 2-(2-(4-chloro-N-methylphenylsulfonamido)ethoxy)-N-(4-((dimethylamino)(phenyl)methyl)cyclohexyl)acetamide;
(590) N-(4-((dimethylamino)(phenyl)methyl)cyclohexyl)-2-(2-(4-methoxy-N-methylphenylsulfonamido)ethoxy)acetamide;
(591) N-(4-((dimethylamino)(phenyl)methyl)cyclohexyl)-2-(1-(4-fluorophenylsulfonyl)pyrrolidin-3-yloxy)acetamide;
(592) 2-(2-(3,4-dimethoxy-N-methylphenylsulfonamido)ethoxy)-N-(4-((dimethylamino)(phenyl)methyl)cyclohexyl)acetamide;
(593) N-(4-((dimethylamino)(phenyl)methyl)cyclohexyl)-2-(2-(N-methyl-3-(trifluoromethyl)phenylsulfonamido)ethoxy)acetamide;
(594) N-(4-((dimethylamino)(phenyl)methyl)cyclohexyl)-2-(2-(N-methyl-4-(trifluoromethoxy)phenylsulfonamido)ethoxy)acetamide;
(595) N-(4-((dimethylamino)(phenyl)methyl)cyclohexyl)-2-(1-(phenylsulfonyl)pyrrolidin-3-yloxy)acetamide;
(596) 2-(1-(2,4-dichlorophenylsulfonyl)pyrrolidin-3-yloxy)-N-(4-((dimethylamino)(phenyl)methyl)cyclohexyl)acetamide;
(597) N-[4-(dimethylaminophenylmethyl)-cyclohexyl]-2-{2-[(4-methoxy-2,3,6-trimethylbenzenesulfonyl)-methylamino]-ethoxy}-acetamide;
(598) N-[4-(dimethylaminophenylmethyl)-cyclohexyl]-2-{2-[methyl-(2,4,6-trichlorobenzenesulfonyl)-amino]-ethoxy}-acetamide;
(599) N-{4-[(benzylmethylamino)-phenylmethyl]-cyclohexyl}-2-{2-[methyl-(2,4,6-trichlorobenzenesulfonyl)-amino]-ethoxy}-acetamide;
(600) 2-{2-[cyclopropyl-(2,4,6-trichlorobenzenesulfonyl)-amino]-ethoxy}-N-[4-(dimethylaminophenylmethyl)-cyclohexyl]-acetamide;
(601) 2-{2-[methyl-(2,4,6-trichlorobenzenesulfonyl)-amino]-ethoxy}-N-[4-(phenylpiperidin-1-yl-methyl)-cyclohexyl]-acetamide;
(602) 2-{2-[cyclopropyl-(2,4,6-trichlorobenzenesulfonyl)-amino]-ethoxy}-N-[4-(phenylpiperidin-1-ylmethyl)-cyclohexyl]-acetamide;
(603) 2-{2-[cyclopropyl-(2,4,6-trichlorobenzenesulfonyl)-amino]-ethoxy}-N-[4-(phenylpyrrolidin-1-ylmethyl)-cyclohexyl]-acetamide;
(604) N-{4-[(b enzylmethylamino)-phenylmethyl]-cyclohexyl}-2-{2-[cyclopropyl-(2,4,6-trichlorobenzenesulfonyl)-amino]-ethoxy}-acetamide;
(605) 2-{2-[cyclopropyl-(2,4,6-trichlorobenzenesulfonyl)-amino]-ethoxy}-N-[4-(morpholin-4-yl-phenylmethyl)-cyclohexyl]-acetamide;
(606) 2-{2-[methyl-(2,4,6-trichlorobenzenesulfonyl)-amino]-ethoxy}-N-[4-(phenylpyrrolidin-1-yl-methyl)-cyclohexyl]-acetamide;
(607) 2-{2-[methyl-(2,4,6-trichlorobenzenesulfonyl)-amino]-ethoxy}-N-[4-(morpholin-4-ylphenylmethyl)-cyclohexyl]-acetamide;
(608) N-[4-(dimethylaminophenylmethyl)-cyclohexyl]-2-[1-(2,4,6-trichlorobenzenesulfonyl)-piperidin-3-yloxy]-acetamide;
(609) N-[4-(dimethylaminophenylmethyl)-cyclohexyl]-2-[1-(2,4,6-trichlorobenzenesulfonyl)-pyrrolidin-3-yloxy]-acetamide
(610) N-[4-(morpholin-4-ylphenylmethyl)-cyclohexyl]-2-[1-(2,4,6-trichlorobenzenesulfonyl)-pyrrolidin-3-yloxy]-acetamide;
(611) N-[4-(dimethylaminophenylmethyl)-cyclohexyl]-2-[1-(2,4,6-trichlorobenzenesulfonyl)-pyrrolidin-2-yl-methoxy]-acetamide;
(612) N-[4-(dimethylaminophenylmethyl)-cyclohexyl]-2-[1-(2,4,6-trichlorobenzenesulfonyl)-pyrrolidin-2-yl-methoxy]-acetamide;
(613) N-[4-(dimethylaminophenylmethyl)-cyclohexyl]-2-[1-(2,4,6-trichlorobenzenesulfonyl)-pyrrolidin-2-yl-methoxy]-acetamide;
(614) N-[4-(dimethylaminophenylmethyl)-cyclohexylmethyl]-2-{2-[(2,4,6-trichlorobenzenesulfonyl)-methylamino]-ethoxy}-acetamide;
(615) N-[3-(dimethylaminophenylmethyl)-cyclopentyl]-2-{2-[(2,4,6-trichlorobenzenesulfonyl)-methylamino]-ethoxy}-acetamide;
(616) N-[4-(1-dimethylamino-2-phenylethyl)-cyclohexyl]-2-{2-[methyl-(2,4,6-trichlorobenzenesulfonyl)-amino]-ethoxy}-acetamide;
(617) 2-{2-[(4-methoxy-2,3,6-trimethylbenzenesulfonyl)-methylamino]-ethoxy}-N-[4-(phenylpiperidin-1-yl-methyl)-cyclohexyl]-acetamide;
(618) 2-{2-[(4-methoxy-2,3,6-trimethylbenzenesulfonyl)-methylamino]-ethoxy}-N-[4-(phenylpyrrolidin-1-yl-methyl)-cyclohexyl]-acetamide;
(619) 2-{2-[(4-methoxy-2,3,6-trimethylbenzenesulfonyl)-methylamino]-ethoxy}-N-[4-(morpholin-4-yl-phenyl-methyl)-cyclohexyl]-acetamide;
(620) N-[4-(dimethylaminophenylmethyl)-cyclohexyl]-3-{[methyl-(2,4,6-trichlorobenzenesulfonyl)-amino]-methoxy}-propionamide;
(621) N-[4-(dimethylaminophenylmethyl)-cyclohexylmethyl]-2-[1-(2,4,6-trichlorobenzenesulfonyl)-piperidin-3-yloxy]-acetamide;
(622) N-[4-(dimethylaminophenylmethyl)-cyclohexylmethyl]-2-[1-(2,4,6-trichlorobenzenesulfonyl)-pyrrolidin-2-ylmethoxy]-acetamide;
(623) N-[4-(dimethylaminophenylmethyl)-cyclohexylmethyl]-2-{2-[(4-methoxy-2,3,6-trimethylbenzenesulfonyl)-methylamino]-ethoxy}-acetamide;
(624) N-[4-(dimethylaminophenylmethyl)-cyclohexylmethyl]-3-{[methyl-(2,4,6-trichlorobenzenesulfonyl)-amino]-methoxy}-propionamide;
(625) N-(4-(phenyl(pyrrolidin-1-yl)methyl)cyclohexyl)-2-(2-(2,4,6-trichloro-N-methylphenylsulfonamido)ethoxy)acetamide;
(626) N-((4-(phenyl(pyrrolidin-1-yl)methyl)cyclohexyl)methyl)-2-(2-(2,4,6-trichloro-N-methylphenylsulfonamido)ethoxy)acetamide;
(627) 2-(2-(2,4-dichloro-N-methylphenylsulfonamido)ethoxy)-N-(4-(phenyl(pyrrolidin-1-yl)methyl)cyclohexyl)acetamide;
(628) 2-(2-(4-methoxy-N,2,6-trimethylphenylsulfonamido)ethoxy)-N-(4-(phenyl(pyrrolidin-1-yl)methyl)cyclohexyl)acetamide
(629) 2-(1-(4-methoxy-2,6-dimethylphenylsulfonyl)pyrrolidin-3-yloxy)-N-(4-(phenyl(pyrrolidin-1-yl)methyl)cyclohexyl)acetamide;

(630) 2-(2-(2,6-dichloro-N-methyl-4-(trifluoromethyl)-phenylsulfonamido)ethoxy)-N-(4-(phenyl(pyrrolidin-1-yl)methyl)cyclohexyl)acetamide;

(631) N-(4-(phenyl(pyrrolidin-1-yl)methyl)cyclohexyl)-2-(1-(2,4,6-trichlorophenylsulfonyl)piperidin-3-yloxy)acetamide;

(632) 2-((1-(4-methoxy-2,6-dimethylphenylsulfonyl)pyrrolidin-2-yl)methoxy)-N-(4-(phenyl(pyrrolidin-1-yl)methyl)cyclohexyl)acetamide;

(633) N-(4-(phenyl(pyrrolidin-1-yl)methyl)cyclohexyl)-2-((1-(2,4,6-trichlorophenylsulfonyl)piperidin-3-yl)methoxy)acetamide;

(634) 2-(2-(2,6-dichloro-N-methylphenylsulfonamido)ethoxy)-N-(4-(phenyl(pyrrolidin-1-yl)methyl)cyclohexyl)acetamide;

(635) N-(4-(phenyl(pyrrolidin-1-yl)methyl)cyclohexyl)-2-(1-(2,4,6-trichlorophenylsulfonyl)pyrrolidin-3-yloxy)acetamide;

(636) N-(4-(1-morpholino-3-phenylpropyl)cyclohexyl)-2-(2-(2,4,6-trichloro-N-methylphenylsulfonamido)ethoxy)acetamide;

(637) N-(4-(3-phenyl-1-(piperidin-1-yl)propyl)cyclohexyl)-2-(2-(2,4,6-trichloro-N-methylphenylsulfonamido)ethoxy)acetamide;

(638) N-(4-(morpholino(phenyl)methyl)cyclohexyl)-2-(2-(2,4,6-trichloro-N-methylphenylsulfonamido)ethoxy)acetamide;

(639) N-((4-(morpholino(phenyl)methyl)cyclohexyl)methyl)-2-(2-(2,4,6-trichloro-N-methylphenylsulfonamido)ethoxy)acetamide;

(640) N-((4-(3-phenyl-1-(pyrrolidin-1-yl)propyl)cyclohexyl)methyl)-2-(2-(2,4,6-trichloro-N-methylphenylsulfonamido)ethoxy)acetamide;

(641) 2-(2-(2,4-dichloro-N-methylphenylsulfonamido)ethoxy)-N-((4-(phenyl(pyrrolidin-1-yl)methyl)cyclohexyl)methyl)acetamide;

(642) 2-(2-(4-methoxy-N,2,6-trimethylphenylsulfonamido)ethoxy)-N-((4-(phenyl(pyrrolidin-1-yl)methyl)cyclohexyl)methyl)acetamide;

(643) 2-(2-(2,6-dichloro-N-methylphenylsulfonamido)ethoxy)-N-((4-(phenyl(pyrrolidin-1-yl)methyl)cyclohexyl)methyl)acetamide;

(644) N-((4-(phenyl(pyrrolidin-1-yl)methyl)cyclohexyl)methyl)-2-(1-(2,4,6-trichlorophenylsulfonyl)pyrrolidin-3-yloxy)acetamide;

(645) 2-(1-(4-methoxy-2,6-dimethylphenylsulfonyl)pyrrolidin-3-yloxy)-N-((4-(phenyl(pyrrolidin-1-yl)methyl)cyclohexyl)methyl)acetamide;

(646) 2-(2-(2,6-dichloro-N-methyl-4-(trifluoromethyl)phenylsulfonamido)ethoxy)-N-((4-(phenyl(pyrrolidin-1-yl)methyl)cyclohexyl)methyl)acetamide;

(647) 2-(1-(4-methoxy-2,6-dimethylphenylsulfonyl)piperidin-3-yloxy)-N-(4-(phenyl(pyrrolidin-1-yl)methyl)cyclohexyl)acetamide;

(648) 2-(1-(4-methoxy-2,6-dimethylphenylsulfonyl)piperidin-3-yloxy)-N-((4-(phenyl(pyrrolidin-1-yl)methyl)cyclohexyl)methyl)acetamide;

(649) 2-((1-(4-methoxy-2,6-dimethylphenylsulfonyl)pyrrolidin-2-yl)methoxy)-N-((4-(phenyl(pyrrolidin-1-yl)methyl)cyclohexyl)methyl)acetamide;

(650) N-(4-(phenyl(pyrrolidin-1-yl)methyl)cyclohexyl)-2-((1-(2,4,6-trichlorophenylsulfonyl)pyrrolidin-2-yl)methoxy)acetamide;

(651) N-((4-(phenyl(pyrrolidin-1-yl)methyl)cyclohexyl)methyl)-2-((1-(2,4,6-trichlorophenylsulfonyl)pyrrolidin-2-yl)methoxy)acetamide;

(652) 2-((1-(4-methoxy-2,6-dimethylphenylsulfonyl)piperidin-2-yl)methoxy)-N-(4-(phenyl(pyrrolidin-1-yl)methyl)cyclohexyl)acetamide;

(653) N-(4-(phenyl(pyrrolidin-1-yl)methyl)cyclohexyl)-2-((1-(2,4,6-trichlorophenylsulfonyl)piperidin-2-yl)methoxy)acetamide;

(654) 2-((1-(4-methoxy-2,6-dimethylphenylsulfonyl)piperidin-3-yl)methoxy)-N-(4-(phenyl(pyrrolidin-1-yl)methyl)cyclohexyl)acetamide;

(655) 2-((1-(4-methoxy-2,6-dimethylphenylsulfonyl)piperidin-3-yl)methoxy)-N-((4-(phenyl(pyrrolidin-1-yl)methyl)cyclohexyl)methyl)acetamide;

(656) N-((4-(phenyl(pyrrolidin-1-yl)methyl)cyclohexyl)methyl)-2-(1-(2,4,6-trichlorophenylsulfonyl)piperidin-3-yloxy)acetamide;

(657) 2-((1-(4-methoxy-2,6-dimethylphenylsulfonyl)piperidin-2-yl)methoxy)-N-((4-(phenyl(pyrrolidin-1-yl)methyl)cyclohexyl)methyl)acetamide;

(658) N-((4-(phenyl(pyrrolidin-1-yl)methyl)cyclohexyl)methyl)-2-((1-(2,4,6-trichlorophenylsulfonyl)piperidin-2-yl)methoxy)acetamide;

(659) N-((4-(phenyl(pyrrolidin-1-yl)methyl)cyclohexyl)methyl)-2-((1-(2,4,6-trichlorophenylsulfonyl)piperidin-3-yl)methoxy)acetamide;

(660) 2-(2-(2,4-dichloro-N-methylphenylsulfonamido)ethoxy)-N-(4-(1-morpholino-3-phenylpropyl)cyclohexyl)acetamide;

(661) 2-(2-(2,4-dichloro-N-methylphenylsulfonamido)ethoxy)-N-(4-(3-phenyl-1-(piperidin-1-yl)propyl)cyclohexyl)acetamide;

(662) 2-(2-(4-methoxy-N,2,6-trimethylphenylsulfonamido)ethoxy)-N-(4-(1-morpholino-3-phenylpropyl)cyclohexyl)acetamide;

(663) 2-(2-(4-methoxy-N,2,6-trimethylphenylsulfonamido)ethoxy)-N-(4-(3-phenyl-1-(piperidin-1-yl)propyl)cyclohexyl)acetamide;

(664) 2-(2-(2,6-dichloro-N-methylphenylsulfonamido)ethoxy)-N-(4-(1-morpholino-3-phenylpropyl)cyclohexyl)acetamide;

(665) 2-(2-(2,6-dichloro-N-methylphenylsulfonamido)ethoxy)-N-(4-(3-phenyl-1-(piperidin-1-yl)propyl)cyclohexyl)acetamide;

(666) N-(4-(1-morpholino-3-phenylpropyl)cyclohexyl)-2-(1-(2,4,6-trichlorophenylsulfonyl)pyrrolidin-3-yloxy)acetamide;

(667) N-(4-(3-phenyl-1-(piperidin-1-yl)propyl)cyclohexyl)-2-(1-(2,4,6-trichlorophenylsulfonyl)pyrrolidin-3-yloxy)acetamide;

(668) 2-(1-(4-methoxy-2,6-dimethylphenylsulfonyl)pyrrolidin-3-yloxy)-N-(4-(1-morpholino-3-phenylpropyl)cyclohexyl)acetamide;

(669) 2-(1-(4-methoxy-2,6-dimethylphenylsulfonyl)pyrrolidin-3-yloxy)-N-(4-(3-phenyl-1-(piperidin-1-yl)propyl)cyclohexyl)acetamide;

(670) 2-(2-(2,6-dichloro-N-methyl-4-(trifluoromethyl)phenylsulfonamido)ethoxy)-N-(4-(1-morpholino-3-phenylpropyl)cyclohexyl)acetamide;

(671) 2-(2-(2,6-dichloro-N-methyl-4-(trifluoromethyl)phenylsulfonamido)ethoxy)-N-(4-(3-phenyl-1-(piperidin-1-yl)propyl)cyclohexyl)acetamide;

(672) N-(4-(1-morpholin-3-phenylpropyl)cyclohexyl)-2-(1-(2,4,6-trichlorophenylsulfonyl)piperidin-3-yloxy)acetamide;

(673) N-(4-(3-phenyl-1-(piperidin-1-yl)propyl)cyclohexyl)-2-(1-(2,4,6-trichlorophenylsulfonyl)piperidin-3-yloxy)acetamide;

(674) 2-(1-(4-methoxy-2,6-dimethylphenylsulfonyl)piperidin-3-yloxy)-N-(4-(1-morpholino-3-phenylpropyl)cyclohexyl)acetamide;
(675) 2-(1-(4-methoxy-2,6-dimethylphenylsulfonyl)piperidin-3-yloxy)-N-(4-(3-phenyl-1-(piperidin-1-yl)propyl)cyclohexyl)acetamide;
(676) 2-((1-(4-methoxy-2,6-dimethylphenylsulfonyl)pyrrolidin-2-yl)methoxy)-N-(4-(1-morpholino-3-phenylpropyl)cyclohexyl)acetamide;
(677) 2-((1-(4-methoxy-2,6-dimethylphenylsulfonyl)pyrrolidin-2-yl)methoxy)-N-(4-(3-phenyl-1-(piperidin-1-yl)propyl)cyclohexyl)acetamide;
(678) 2-((1-(4-methoxy-2,6-dimethylphenylsulfonyl)piperidin-3-yl)methoxy)-N-(4-(1-morpholino-3-phenylpropyl)cyclohexyl)acetamide;
(679) N-(4-(3-phenyl-1-(piperidin-1-yl)propyl)cyclohexyl)-2-((1-(2,4,6-trichlorophenylsulfonyl)piperidin-3-yl)methoxy)acetamide;
(680) 2-(2-(2,4-dichloro-N-methylphenylsulfonamido)ethoxy)-N-(4-(morpholino(phenyl)methyl)cyclohexyl)acetamide;
(681) 2-(2-(4-methoxy-N,2,6-trimethylphenylsulfonamido)ethoxy)-N-(4-(morpholino(phenyl)methyl)cyclohexyl)acetamide;
(682) 2-(2-(4-methoxy-N,2,6-trimethylphenylsulfonamido)ethoxy)-N-(4-((4-methylpiperazin-1-yl)(phenyl)methyl)cyclohexyl)acetamide;
(683) 2-(2-(2,6-dichloro-N-methylphenylsulfonamido)ethoxy)-N-(4-(morpholino(phenyl)methyl)cyclohexyl)acetamide;
(684) 2-(2-(2,6-dichloro-N-methylphenylsulfonamido)ethoxy)-N-(4-((4-methylpiperazin-1-yl)(phenyl)methyl)cyclohexyl)acetamide;
(685) N-(4-(morpholin(phenyl)methyl)cyclohexyl)-2-(1-(2,4,6-trichlorophenylsulfonyl)pyrrolidin-3-yloxy)acetamide;
(686) N-(4-((4-methylpiperazin-1-yl)(phenyl)methyl)cyclohexyl)-2-(1-(2,4,6-trichlorophenylsulfonyl)pyrrolidin-3-yloxy)acetamide;
(687) 2-(1-(4-methoxy-2,6-dimethylphenylsulfonyl)pyrrolidin-3-yloxy)-N-(4-(morpholino(phenyl)methyl)cyclohexyl)acetamide;
(688) 2-(1-(4-methoxy-2,6-dimethylphenylsulfonyl)pyrrolidin-3-yloxy)-N-(4-((4-methylpiperazin-1-yl)(phenyl)methyl)cyclohexyl)acetamide;
(689) 2-(2-(2,6-dichloro-N-methyl-4-(trifluoromethyl)phenylsulfonamido)ethoxy)-N-(4-(morpholino(phenyl)-methyl)cyclohexyl)acetamide;
(690) 2-(2-(2,6-dichloro-N-methyl-4-(trifluoromethyl)phenylsulfonamido)ethoxy)-N-(4-((4-methylpiperazin-1-yl)(phenyl)methyl)cyclohexyl)acetamide;
(691) N-(4-(morpholino(phenyl)methyl)cyclohexyl)-2-(1-(2,4,6-trichlorophenylsulfonyl)piperidin-3-yloxy)acetamide;
(692) N-(4-((4-methylpiperazin-1-yl)(phenyl)methyl)cyclohexyl)-2-(1-(2,4,6-trichlorophenylsulfonyl)piperidin-3-yloxy)acetamide;
(693) 2-(1-(4-methoxy-2,6-dimethylphenylsulfonyl)piperidin-3-yloxy)-N-(4-(morpholino(phenyl)methyl)cyclohexyl)acetamide;
(694) 2-((1-(4-methoxy-2,6-dimethylphenylsulfonyl)pyrrolidin-2-yl)methoxy)-N-(4-(morpholino(phenyl)methyl)cyclohexyl)acetamide;
(695) 2-((1-(4-methoxy-2,6-dimethylphenylsulfonyl)pyrrolidin-2-yl)methoxy)-N-(4-((4-methylpiperazin-1-yl)(phenyl)methyl)cyclohexyl)acetamide;
(696) N-(4-(1-morpholino-3-phenylpropyl)cyclohexyl)-2-((1-(2,4,6-trichlorophenylsulfonyl)pyrrolidin-2-yl)methoxy)acetamide;
(697) N-(4-(3-phenyl-1-(piperidin-1-yl)propyl)cyclohexyl)-2-((1-(2,4,6-trichlorophenylsulfonyl)pyrrolidin-2-yl)methoxy)acetamide;
(698) N-(4-(morpholino(phenyl)methyl)cyclohexyl)-2-((1-(2,4,6-trichlorophenylsulfonyl)pyrrolidin-2-yl)methoxy)acetamide;
(699) 2-((1-(4-methoxy-2,6-dimethylphenylsulfonyl)piperidin-2-yl)methoxy)-N-(4-(morpholino(phenyl)methyl)cyclohexyl)acetamide;
(700) N-(4-(morpholino(phenyl)methyl)cyclohexyl)-2-((1-(2,4,6-trichlorophenylsulfonyl)piperidin-2-yl)methoxy)acetamide;
(701) 2-((1-(4-methoxy-2,6-dimethylphenylsulfonyl)piperidin-3-yl)methoxy)-N-(4-(morpholino(phenyl)methyl)cyclohexyl)acetamide;
(702) 2-((1-(4-methoxy-2,6-dimethylphenylsulfonyl)piperidin-3-yl)methoxy)-N-(4-((4-methylpiperazin-1-yl)(phenyl)methyl)cyclohexyl)acetamide;
(703) N-(4-(morpholino(phenyl)methyl)cyclohexyl)-2-((1-(2,4,6-trichlorophenylsulfonyl)piperidin-3-yl)methoxy)acetamide;
(704) 2-(2-(2,4-dichloro-N-methylphenylsulfonamido)ethoxy)-N-(4-((4-methylpiperazin-1-yl)(phenyl)methyl)cyclohexyl)acetamide;
(705) 2-(2-(2,4-dichloro-N-methylphenylsulfonamido)ethoxy)-N-((4-(morpholino(phenyl)methyl)cyclohexyl)methyl)acetamide;
(706) 2-(2-(2,6-dichloro-N-methylphenylsulfonamido)ethoxy)-N-((4-(morpholino(phenyl)methyl)cyclohexyl)methyl)acetamide;
(707) N-((4-(morpholino(phenyl)methyl)cyclohexyl)methyl)-2-(1-(2,4,6-trichlorophenylsulfonyl)piperidin-3-yloxy)acetamide;
(708) 2-(1-(4-methoxy-2,6-dimethylphenylsulfonyl)piperidin-3-yloxy)-N-(4-((4-methylpiperazin-1-yl)(phenyl)methyl)cyclohexyl)acetamide;
(709) 2-((1-(4-methoxy-2,6-dimethylphenylsulfonyl)pyrrolidin-2-yl)methoxy)-N-((4-(morpholino(phenyl)methyl)cyclohexyl)methyl)acetamide;
(710) N-((4-(morpholino(phenyl)methyl)cyclohexyl)methyl)-2-((1-(2,4,6-trichlorophenylsulfonyl)pyrrolidin-2-yl)methoxy)acetamide;
(711) 2-((1-(4-methoxy-2,6-dimethylphenylsulfonyl)piperidin-2-yl)methoxy)-N-((4-(morpholino(phenyl)methyl)cyclohexyl)methyl)acetamide;
(712) N-((4-(morpholino(phenyl)methyl)cyclohexyl)methyl)-2-((1-(2,4,6-trichlorophenylsulfonyl)piperidin-2-yl)methoxy)acetamide;
(713) N-((4-(morpholino(phenyl)methyl)cyclohexyl)methyl)-2-((1-(2,4,6-trichlorophenylsulfonyl)piperidin-3-yl)methoxy)acetamide;
(714) N-(4-((4-methylpiperazin-1-yl)(phenyl)methyl)cyclohexyl)-2-(2-(2,4,6-trichloro-N-methylphenylsulfonamido)ethoxy)acetamide;
(715) N-((4-(1-morpholino-3-phenylpropyl)cyclohexyl)methyl)-2-(2-(2,4,6-trichloro-N-methylphenylsulfonamido)ethoxy)acetamide;
(716) 2-(2-(2,4-dichloro-N-methylphenylsulfonamido)ethoxy)-N-((4-(1-morpholino-3-phenylpropyl)cyclohexyl)methyl)acetamide;
(717) 2-(2-(2,4-dichloro-N-methylphenylsulfonamido)ethoxy)-N-((4-(3-phenyl-1-(pyrrolidin-1-yl)propyl)cyclohexyl)methyl)acetamide;

(718) 2-(2-(4-methoxy-N,2,6-trimethylphenylsulfonamido)ethoxy)-N-((4-(morpholino(phenyl)methyl)cyclohexyl)methyl)acetamide;

(719) 2-(2-(4-methoxy-N,2,6-trimethylphenylsulfonamido)ethoxy)-N-((4-(1-morpholino-3-phenylpropyl)cyclohexyl)methyl)acetamide;

(720) 2-(2-(4-methoxy-N,2,6-trimethylphenylsulfonamido)ethoxy)-N-((4-(3-phenyl-1-(pyrrolidin-1-yl)propyl)cyclohexyl)methyl)acetamide;

(721) 2-(2-(2,6-dichloro-N-methylphenylsulfonamido)ethoxy)-N-((4-(1-morpholino-3-phenylpropyl)cyclohexyl)methyl)acetamide;

(722) 2-(2-(2,6-dichloro-N-methylphenylsulfonamido)ethoxy)-N-((4-(3-phenyl-1-(pyrrolidin-1-yl)propyl)cyclohexyl)methyl)acetamide;

(723) N-((4-(3-phenyl-1-(pyrrolidin-1-yl)propyl)cyclohexyl)methyl)-2-(1-(2,4,6-trichlorophenylsulfonyl)pyrrolidin-3-yloxy)acetamide;

(724) 2-(1-(4-methoxy-2,6-dimethylphenylsulfonyl)pyrrolidin-3-yloxy)-N-((4-(morpholino(phenyl)methyl)cyclohexyl)methyl)acetamide;

(725) 2-(1-(4-methoxy-2,6-dimethylphenylsulfonyl)pyrrolidin-3-yloxy)-N-((4-(1-morpholino-3-phenylpropyl)cyclohexyl)methyl)acetamide;

(726) 2-(1-(4-methoxy-2,6-dimethylphenylsulfonyl)pyrrolidin-3-yloxy)-N-((4-(3-phenyl-1-(pyrrolidin-1-yl)propyl)cyclohexyl)methyl)acetamide;

(727) 2-(2-(2,6-dichloro-N-methyl-4-(trifluoromethyl)-phenylsulfonamido)ethoxy)-N-((4-(morpholino(phenyl)-methyl)cyclohexyl)methyl)acetamide;

(728) 2-(2-(2,6-dichloro-N-methyl-4-(trifluoromethyl)-phenylsulfonamido)ethoxy)-N-((4-(1-morpholino-3-phenylpropyl)cyclohexyl)methyl)acetamide;

(729) N-((4-(3-phenyl-1-(pyrrolidin-1-yl)propyl)cyclohexyl)methyl)-2-(1-(2,4,6-trichlorophenylsulfonyl)piperidin-3-yloxy)acetamide;

(730) 2-(1-(4-methoxy-2,6-dimethylphenylsulfonyl)piperidin-3-yloxy)-N-((4-(morpholino(phenyl)methyl)cyclohexyl)methyl)acetamide;

(731) 2-(1-(4-methoxy-2,6-dimethylphenylsulfonyl)piperidin-3-yloxy)-N-((4-(3-phenyl-1-(pyrrolidin-1-yl)propyl)cyclohexyl)methyl)acetamide;

(732) N-(4-((4-methylpiperazin-1-yl)(phenyl)methyl)cyclohexyl)-2-((1-(2,4,6-trichlorophenylsulfonyl)pyrrolidin-2-yl)methoxy)acetamide;

(733) 2-((1-(4-methoxy-2,6-dimethylphenylsulfonyl)piperidin-2-yl)methoxy)-N-(4-(1-morpholino-3-phenylpropyl)cyclohexyl)acetamide;

(734) 2-((1-(4-methoxy-2,6-dimethylphenylsulfonyl)piperidin-2-yl)methoxy)-N-(4-(3-phenyl-1-(piperidin-1-yl)propyl)cyclohexyl)acetamide;

(735) 2-((1-(4-methoxy-2,6-dimethylphenylsulfonyl)piperidin-2-yl)methoxy)-N-(4-((4-methylpiperazin-1-yl)(phenyl)methyl)cyclohexyl)acetamide;

(736) 2-((1-(4-methoxy-2,6-dimethylphenylsulfonyl)piperidin-2-yl)methoxy)-N-((4-(3-phenyl-1-(pyrrolidin-1-yl)propyl)cyclohexyl)methyl)acetamide;

(737) N-(4-(1-morpholino-3-phenylpropyl)cyclohexyl)-2-((1-(2,4,6-trichlorophenylsulfonyl)piperidin-2-yl)methoxy)acetamide;

(738) N-(4-(3-phenyl-1-(piperidin-1-yl)propyl)cyclohexyl)-2-((1-(2,4,6-trichlorophenylsulfonyl)piperidin-2-yl)methoxy)acetamide;

(739) N-(4-((4-methylpiperazin-1-yl)(phenyl)methyl)cyclohexyl)-2-((1-(2,4,6-trichlorophenylsulfonyl)piperidin-2-yl)methoxy)acetamide;

(740) 2-((1-(4-methoxy-2,6-dimethylphenylsulfonyl)piperidin-3-yl)methoxy)-N-(4-(3-phenyl-1-(piperidin-1-yl)propyl)cyclohexyl)acetamide;

(741) N-(4-(1-morpholino-3-phenylpropyl)cyclohexyl)-2-((1-(2,4,6-trichlorophenylsulfonyl)piperidin-3-yl)methoxy)acetamide;

(742) N-(4-((4-methylpiperazin-1-yl)(phenyl)methyl)cyclohexyl)-2-((1-(2,4,6-trichlorophenylsulfonyl)piperidin-3-yl)methoxy)acetamide;

(743) N-((4-(morpholino(phenyl)methyl)cyclohexyl)methyl)-2-(1-(2,4,6-trichlorophenylsulfonyl)pyrrolidin-3-yloxy)acetamide;

(744) 2-((1-(4-methoxy-2,6-dimethylphenylsulfonyl)piperidin-3-yl)methoxy)-N-((4-(morpholino(phenyl)methyl)cyclohexyl)methyl)acetamide;

(745) N-((4-(1-morpholino-3-phenylpropyl)cyclohexyl)methyl)-2-(1-(2,4,6-trichlorophenylsulfonyl)pyrrolidin-3-yloxy)acetamide;

(746) 2-(2-(2,6-dichloro-N-methyl-4-(trifluoromethyl)-phenylsulfonamido)ethoxy)-N-((4-(3-phenyl-1-(pyrrolidin-1-yl)propyl)cyclohexyl)methyl)acetamide;

(747) N-((4-(1-morpholino-3-phenylpropyl)cyclohexyl)methyl)-2-(1-(2,4,6-trichlorophenylsulfonyl)piperidin-3-yloxy)acetamide;

(748) 2-(1-(4-methoxy-2,6-dimethylphenylsulfonyl)piperidin-3-yloxy)-N-((4-(1-morpholino-3-phenylpropyl)cyclohexyl)methyl)acetamide;

(749) 2-((1-(4-methoxy-2,6-dimethylphenylsulfonyl)pyrrolidin-2-yl)methoxy)-N-((4-(1-morpholino-3-phenylpropyl)cyclohexyl)methyl)acetamide;

(750) 2-((1-(4-methoxy-2,6-dimethylphenylsulfonyl)pyrrolidin-2-yl)methoxy)-N-((4-(3-phenyl-1-(pyrrolidin-1-yl)propyl)cyclohexyl)methyl)acetamide;

(751) N-((4-(1-morpholino-3-phenylpropyl)cyclohexyl)methyl)-2-((1-(2,4,6-trichlorophenylsulfonyl)pyrrolidin-2-yl)methoxy)acetamide;

(752) N-((4-(3-phenyl-1-(pyrrolidin-1-yl)propyl)cyclohexyl)methyl)-2-((1-(2,4,6-trichlorophenylsulfonyl)pyrrolidin-2-yl)methoxy)acetamide;

(753) 2-((1-(4-methoxy-2,6-dimethylphenylsulfonyl)piperidin-2-yl)methoxy)-N-((4-(1-morpholino-3-phenylpropyl)cyclohexyl)methyl)acetamide;

(754) N-((4-(1-morpholino-3-phenylpropyl)cyclohexyl)methyl)-2-((1-(2,4,6-trichlorophenylsulfonyl)piperidin-2-yl)methoxy)acetamide;

(755) N-((4-(3-phenyl-1-(pyrrolidin-1-yl)propyl)cyclohexyl)methyl)-2-((1-(2,4,6-trichlorophenylsulfonyl)piperidin-2-yl)methoxy)acetamide;

(756) 2-((1-(4-methoxy-2,6-dimethylphenylsulfonyl)piperidin-3-yl)methoxy)-N-((4-(1-morpholino-3-phenylpropyl)cyclohexyl)methyl)acetamide;

(757) 2-((1-(4-methoxy-2,6-dimethylphenylsulfonyl)piperidin-3-yl)methoxy)-N-((4-(3-phenyl-1-(pyrrolidin-1-yl)propyl)cyclohexyl)methyl)acetamide;

(758) N-((4-(1-morpholino-3-phenylpropyl)cyclohexyl)methyl)-2-((1-(2,4,6-trichlorophenylsulfonyl)piperidin-3-yl)methoxy)acetamide;

(759) N-((4-(3-phenyl-1-(pyrrolidin-1-yl)propyl)cyclohexyl)methyl)-2-((1-(2,4,6-trichlorophenylsulfonyl)piperidin-3-yl)methoxy)acetamide;

(760) 3-(3,5-dichloro-phenyl)-[1,2,4]oxadiazole-5-carboxylic acid {[4-(dimethylamino-phenyl-methyl)-cyclohexylcarbamoyl]-methyl}-amide;

(761) 3-(3,5-dichloro-phenyl)-[1,2,4]oxadiazole-5-carboxylic acid {2-[4-(dimethylamino-phenyl-methyl)-cyclohexylcarbamoyl]-ethyl}-amide;

(762) 3-(2,4-dichloro-6-methyl-phenyl)-[1,2,4]oxadiazole-5-carboxylic acid {[4-(dimethylamino-phenyl-methyl)-cyclohexylcarbamoyl]-methyl}-amide;
(763) 3-(2-methoxy-phenyl)-[1,2,4]oxadiazole-5-carboxylic acid {[4-(dimethylamino-phenyl-methyl)-cyclohexylcarbamoyl]-methyl}-amide;
(764) 3-thiophen-2-yl-[1,2,4]oxadiazole-5-carboxylic acid {[4-(dimethylamino-phenyl-methyl)-cyclohexylcarbamoyl]-methyl}-amide;
(765) 3-(4-trifluoromethyl-phenyl)-[1,2,4]oxadiazole-5-carboxylic acid {[4-(dimethylamino-phenyl-methyl)-cyclohexylcarbamoyl]-methyl}-amide;
(766) 3-(4-tert-butyl-phenyl)-[1,2,4]oxadiazole-5-carboxylic acid {[4-(dimethylamino-phenyl-methyl)-cyclohexylcarbamoyl]-methyl}-amide;
(767) 3-(5-fluoro-2-methyl-phenyl)-[1,2,4]oxadiazole-5-carboxylic acid {[4-(dimethylamino-phenyl-methyl)-cyclohexylcarbamoyl]-methyl}-amide;
(768) 3-benzo[1,3]dioxol-5-yl-[1,2,4]oxadiazole-5-carboxylic acid {2-[4-(dimethylamino-phenyl-methyl)-cyclohexylcarbamoyl]-ethyl}-amide;
(769) 3-benzenesulfonylmethyl-[1,2,4]oxadiazole-5-carboxylic acid {[4-(dimethylamino-phenyl-methyl)-cyclohexylcarbamoyl]-methyl}-amide;
(770) 3-(2,6-dichloro-phenyl)-[1,2,4]oxadiazole-5-carboxylic acid {[4-(dimethylamino-phenyl-methyl)-cyclohexylcarbamoyl]-methyl}-amide;
(771) 3-pyridin-2-yl-[1,2,4]oxadiazole-5-carboxylic acid {2-[4-(dimethylamino-phenyl-methyl)-cyclohexylcarbamoyl]-ethyl}-amide;
(772) 3-(2,4,6-trimethyl-phenyl)-[1,2,4]oxadiazole-5-carboxylic acid {[4-(dimethylamino-phenyl-methyl)-cyclohexylcarbamoyl]-methyl}-amide;
(773) 3-(2,4-dichloro-phenyl)-[1,2,4]oxadiazole-5-carboxylic acid {2-[4-(dimethylamino-phenyl-methyl)-cyclohexylcarbamoyl]-ethyl}-amide;
(774) 3-(3,4-dimethoxy-phenyl)-[1,2,4]oxadiazole-5-carboxylic acid {2-[4-(dimethylamino-phenyl-methyl)-cyclohexylcarbamoyl]-ethyl}-amide;
(775) 3-(3,4-dimethoxy-phenyl)-[1,2,4]oxadiazole-5-carboxylic acid {[4-(dimethylamino-phenyl-methyl)-cyclohexylcarbamoyl]-methyl}-amide;
(776) 3-thiophen-2-yl-[1,2,4]oxadiazole-5-carboxylic acid {2-[4-(dimethylamino-phenyl-methyl)-cyclohexylcarbamoyl]-ethyl}-amide;
(777) 3-(4-trifluoromethyl-phenyl)-[1,2,4]oxadiazole-5-carboxylic acid {[4-(dimethylamino-thiophen-2-yl-methyl)-cyclohexylcarbamoyl]-methyl}-amide;
(778) 3-(4-trifluoromethyl-phenyl)-[1,2,4]oxadiazole-5-carboxylic acid [({4-[dimethylamino-(3-fluoro-phenyl)-methyl]-cyclohexylmethyl}-carbamoyl)-methyl]-amide;
(779) 3-(4-tert-butyl-phenyl)-[1,2,4]oxadiazole-5-carboxylic acid {[4-(dimethylamino-thiophen-2-yl-methyl)-cyclohexylcarbamoyl]-methyl}-amide;
(780) 3-thiophen-2-yl-[1,2,4]oxadiazole-5-carboxylic acid [2-({4-[dimethylamino-(3-fluoro-phenyl)-methyl]-cyclohexylmethyl}-carbamoyl)-ethyl]-amide;
(781) 3-benzenesulfonylmethyl-[1,2,4]oxadiazole-5-carboxylic acid [({4-[dimethylamino-(3-fluoro-phenyl)-methyl]-cyclohexylmethyl}-carbamoyl)-methyl]-amide;
(782) 3-(2-methoxy-phenyl)-[1,2,4]oxadiazole-5-carboxylic acid {[4-(1-dimethylamino-3-phenyl-propyl)-cyclohexylcarbamoyl]-methyl}-amide;
(783) 3-benzo[1,3]dioxol-5-yl-[1,2,4]oxadiazole-5-carboxylic acid {[4-(1-dimethylamino-3-phenyl-propyl)-cyclohexylcarbamoyl]-methyl}-amide;
(784) 3-thiophen-2-yl-[1,2,4]oxadiazole-5-carboxylic acid {[4-(1-dimethylamino-3-phenyl-propyl)-cyclohexylcarbamoyl]-methyl}-amide;
(785) 3-(4-trifluoromethyl-phenyl)-[1,2,4]oxadiazole-5-carboxylic acid {[4-(1-dimethylamino-3-phenyl-propyl)-cyclohexylcarbamoyl]-methyl}-amide;
(786) 3-(4-tert-butyl-phenyl)-[1,2,4]oxadiazole-5-carboxylic acid {[4-(1-dimethylamino-3-phenyl-propyl)-cyclohexylcarbamoyl]-methyl}-amide;
(787) 3-(2-methoxy-phenyl)-[1,2,4]oxadiazole-5-carboxylic acid [({4-[dimethylamino-(3-fluoro-phenyl)-methyl]-cyclohexylmethyl}-carbamoyl)-methyl]-amide;
(788) 3-(2,4-dichloro-phenyl)-[1,2,4]oxadiazole-5-carboxylic acid {2-[4-(1-dimethylamino-3-phenyl-propyl)-cyclohexylcarbamoyl]-ethyl}-amide;
(789) 3-(3,4-dimethoxy-phenyl)-[1,2,4]oxadiazole-5-carboxylic acid {2-[4-(1-dimethylamino-3-phenyl-propyl)-cyclohexylcarbamoyl]-ethyl}-amide;
(790) 3-(3,5-dichloro-phenyl)-[1,2,4]oxadiazole-5-carboxylic acid {[4-(1-dimethylamino-3-phenyl-propyl)-cyclohexylcarbamoyl]-methyl}-amide;
(791) 3-pyridin-2-yl-[1,2,4]oxadiazole-5-carboxylic acid {[4-(1-dimethylamino-3-phenyl-propyl)-cyclohexylcarbamoyl]-methyl}-amide;
(792) 3-benzo[1,3]dioxol-5-yl-[1,2,4]oxadiazole-5-carboxylic acid {2-[4-(1-dimethylamino-3-phenyl-propyl)-cyclohexylcarbamoyl]-ethyl}-amide;
(793) 3-(2,6-dichloro-phenyl)-[1,2,4]oxadiazole-5-carboxylic acid {[4-(1-dimethylamino-3-phenyl-propyl)-cyclohexylcarbamoyl]-methyl}-amide;
(794) 3-(3,4-dimethoxy-phenyl)-[1,2,4]oxadiazole-5-carboxylic acid {[4-(1-dimethylamino-3-phenyl-propyl)-cyclohexylcarbamoyl]-methyl}-amide;
(795) 3-(2,4-dichloro-phenyl)-[1,2,4]oxadiazole-5-carboxylic acid {[4-(1-dimethylamino-3-phenyl-propyl)-cyclohexylcarbamoyl]-methyl}-amide;
(796) 3-(5-fluoro-2-methyl-phenyl)-[1,2,4]oxadiazole-5-carboxylic acid {[4-(1-dimethylamino-3-phenyl-propyl)-cyclohexylcarbamoyl]-methyl}-amide;
(797) 3-thiophen-2-yl-[1,2,4]oxadiazole-5-carboxylic acid {2-[4-(1-dimethylamino-3-phenyl-propyl)-cyclohexylcarbamoyl]-ethyl}-amide;
(798) 4-methoxy-N,2,6-trimethyl-N-(2-(2-(4-((4-methylpiperazin-1-yl)(phenyl)methyl)piperidin-1-yl)-2-oxoethoxy)ethyl)benzenesulfonamide;
(799) N-(2-(2-(4-((3-fluorophenyl)(4-methylpiperazin-1-yl)methyl)piperidin-1-yl)-2-oxoethoxy)ethyl)-4-methoxy-N,2,6-trimethylbenzenesulfonamide;
(800) 1-(4-((3-fluorophenyl)(4-methylpiperazin-1-yl)methyl)piperidin-1-yl)-2-((1-(4-methoxy-2,6-dimethylphenylsulfonyl)piperidin-2-yl)methoxy)ethanone;
(801) 4-methoxy-N,2,6-trimethyl-N-(2-(2-(4-(1-(4-methylpiperazin-1-yl)-3-phenylpropyl)piperidin-1-yl)-2-oxoethoxy)ethyl)benzenesulfonamide;
(802) 2-((1-(4-methoxy-2,6-dimethylphenylsulfonyl)piperidin-2-yl)methoxy)-1-(4-(1-(4-methylpiperazin-1-yl)-2-phenylethyl)piperidin-1-yl)ethanone;
(803) 4-methoxy-N,2,6-trimethyl-N-(2-(2-(4-(1-(4-methylpiperazin-1-yl)-2-phenylethyl)piperidin-1-yl)-2-oxoethoxy)ethyl)benzenesulfonamide;
(804) N-(2-(2-(4-((4-fluorophenyl)(4-methylpiperazin-1-yl)methyl)piperidin-1-yl)-2-oxoethoxy)ethyl)-4-methoxy-N,2,6-trimethylbenzenesulfonamide;

(805) 1-(4-((4-fluorophenyl)(4-methylpiperazin-1-yl)methyl)piperidin-1-yl)-2-((1-(4-methoxy-2,6-dimethylphenylsulfonyl)piperidin-2-yl)methoxy)ethanone;
(806) 2-((1-(4-methoxy-2,6-dimethylphenylsulfonyl)piperidin-2-yl)methoxy)-1-(4-(1-(4-methylpiperazin-1-yl)-3-phenylpropyl)piperidin-1-yl)ethanone;
(807) 2-((1-(4-methoxy-2,6-dimethylphenylsulfonyl)piperidin-2-yl)methoxy)-1-(4-((4-methylpiperazin-1-yl)(phenyl)methyl)piperidin-1-yl)ethanone;
(808) 2-((1-(3,4-dichlorophenylsulfonyl)-1,2,3,4-tetrahydroquinolin-2-yl)methoxy)-1-(4-((4-fluorophenyl)(4-methylpiperazin-1-yl)methyl)piperidin-1-yl)ethanone;
(809) 2-((1-(3,4-dichlorophenylsulfonyl)-1,2,3,4-tetrahydroquinolin-2-yl)methoxy)-1-(4-((3-fluorophenyl)(4-methylpiperazin-1-yl)methyl)piperidin-1-yl)ethanone;
(810) 2-((1-(3,4-dichlorophenylsulfonyl)-1,2,3,4-tetrahydroquinolin-2-yl)methoxy)-1-(4-((4-methylpiperazin-1-yl)(phenyl)methyl)piperidin-1-yl)ethanone;
(811) 2-((1-(3,4-dichlorophenylsulfonyl)-1,2,3,4-tetrahydroquinolin-2-yl)methoxy)-1-(4-(1-(4-methylpiperazin-1-yl)-3-phenylpropyl)piperidin-1-yl)ethanone;
(812) 2-((1-(3,4-dichlorophenylsulfonyl)-1,2,3,4-tetrahydroquinolin-2-yl)methoxy)-1-(4-(1-(4-methylpiperazin-1-yl)-2-phenylethyl)piperidin-1-yl)ethanone, and salts thereof with physiologically acceptable acids.

23. A pharmaceutical composition comprising a compound according to claim 1, and at least one pharmaceutically acceptable carrier or agent.

24. A process for preparing a substituted amide compound according to claim 1, said process comprising reacting a carboxylic acid K with a primary or secondary amine corresponding to formula II

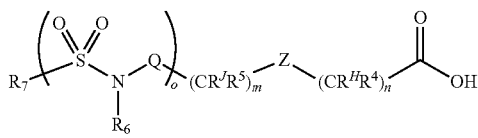

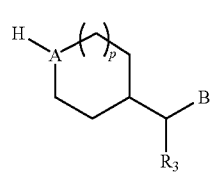

in the presence of a dehydrating agent, optionally in the presence of HOAt or HOBt and an organic base, and in an organic solvent, or in a polar or nonpolar aprotic solvent, and in the presence of an organic or inorganic auxiliary base, at −30 to +40 °C.

25. A process according to claim 24, wherein
the dehydrating agent is sodium sulphate, magnesium sulfate, phosphorus oxide or a reagents selected from the group consisting of CDI, DCC optionally bonded to a polymer, TBTU, EDCI, PyBOP and PFPTFA; or
the organic base is DIPEA or pyridine; or
the organic solvent is THF, methylene chloride, diethyl ether, dioxane, DMF or acetonitrile.

26. A process according to claim 24, wherein:
said solvent ia methlene chloride or chloroform; or
said base is an amine selected from the group consisting of triethylamine, diisopropylethylamine, pyridine and DMAP.

27. A method of treating or inhibiting pain in a subject, said method comprising administering to said subject a pharmacologically effective amount of a compound according to claim 1.

28. A method according to claim 27, wherein said pain is selected from the group consisting of acute pain, neuropathic pain and chronic pain.

29. A method of treating a disorder or diesease state selected from the group consisting of disease of the respiratory tract, inflammatory intestinal diseases, inflammations of the skin, and rheumatic diseases, in a subject, said method comprising administering to said subject a pharmacologically effective amount of compound according to claim 1.

* * * * *